(12) United States Patent
Konradi et al.

(10) Patent No.: US 11,059,786 B2
(45) Date of Patent: Jul. 13, 2021

(54) AMINOPYRIDINE COMPOUNDS AND METHODS FOR THE PREPARATION AND USE THEREOF

(71) Applicant: Cortexyme, Inc., South San Francisco, CA (US)

(72) Inventors: Andrei W. Konradi, Burlingame, CA (US); Robert A. Galemmo, Jr., South San Francisco, CA (US); Casey C. Lynch, San Francisco, CA (US)

(73) Assignee: CORTEXYME, INC., South San Francisco, CA (US)

( * ) Notice: Subject to any disclaimer, the term of this patent is extended or adjusted under 35 U.S.C. 154(b) by 61 days.

(21) Appl. No.: 16/678,700

(22) Filed: Nov. 8, 2019

(65) Prior Publication Data

US 2020/0148642 A1 May 14, 2020

Related U.S. Application Data

(63) Continuation of application No. PCT/US2018/032139, filed on May 10, 2018.

(60) Provisional application No. 62/504,442, filed on May 10, 2017, provisional application No. 62/504,480, filed on May 10, 2017.

(51) Int. Cl.
| | | |
|---|---|---|
| *C07D 213/73* | (2006.01) | |
| *C07D 217/22* | (2006.01) | |
| *C07D 401/04* | (2006.01) | |
| *C07D 401/06* | (2006.01) | |
| *C07D 401/12* | (2006.01) | |
| *C07D 413/12* | (2006.01) | |
| *C07D 491/048* | (2006.01) | |
| *A61P 25/28* | (2006.01) | |

(52) U.S. Cl.
CPC ............ *C07D 213/73* (2013.01); *A61P 25/28* (2018.01); *C07D 217/22* (2013.01); *C07D 401/04* (2013.01); *C07D 401/06* (2013.01); *C07D 401/12* (2013.01); *C07D 413/12* (2013.01); *C07D 491/048* (2013.01)

(58) Field of Classification Search
CPC .. C07D 213/73; C07D 217/22; C07D 401/04; C07D 401/06; C07D 401/12; C07D 413/12; C07D 491/048; C07D 403/04; A61P 25/28
See application file for complete search history.

(56) References Cited

U.S. PATENT DOCUMENTS

| | | | |
|---|---|---|---|
| 2003/0008829 A1 | 1/2003 | Costanzo et al. | |
| 2016/0096830 A1 | 4/2016 | Konradi et al. | |
| 2016/0347715 A1 | 12/2016 | David et al. | |
| 2017/0014468 A1* | 1/2017 | Dominy | ................ A61K 31/27 |

FOREIGN PATENT DOCUMENTS

| | | |
|---|---|---|
| WO | 00/53172 A1 | 9/2000 |
| WO | 2016/046530 A1 | 3/2016 |
| WO | 2017/083433 A1 | 5/2017 |
| WO | 2018/053353 A1 | 3/2018 |
| WO | 2018/209132 A1 | 11/2018 |

OTHER PUBLICATIONS

Matzno, S., "A possible mechanism of action of a new potassium channel opener, AL0671, on lipid metabolism in obese Zucker rats." Journal of Pharmacology and Experimental Therapeutics 271.3 (1994): 1666-1671.*
Bialas et al., Exploring the Sn Binding Pockets in Gingipains by Newly Developed Inhibitors: Structure-Based Design, Chemistry, and Activity, J. Med. Chem., 2006, vol. 49, pp. 1744-1753.
PCT/US2018/032139, International Search Report dated Aug. 1, 2018, 2 pages.
PUBCHEM 104185245 deposited on Jan. 13, 2016, pp. 1-9.
PUBCHEM 106640197 deposited Jan. 15, 2016, pp. 1-9.

* cited by examiner

*Primary Examiner* — John M Mauro
(74) *Attorney, Agent, or Firm* — Kilpatrick Townsend & Stockton LLP

(57) ABSTRACT

The present invention relates generally to therapeutics targeting the bacterium *Porphyromonas gingivalis*, including its proteases arginine gingipain A/B (Rgp), and their use for the treatment of disorders associated with *P. gingivalis* infection, including brain disorders such as Alzheimer's disease. In certain embodiments, the invention provides compounds according to Formula I and Formula III, as described herein, and pharmaceutically acceptable salts thereof.

23 Claims, No Drawings

AMINOPYRIDINE COMPOUNDS AND METHODS FOR THE PREPARATION AND USE THEREOF

CROSS-REFERENCES TO RELATED APPLICATIONS

The present application is a continuation of International Patent Application No. PCT/US2018/032139, filed on May 10, 2018, which claims priority to U.S. Provisional Pat. Appl. No. 62/504,442, filed on May 10, 2017, and U.S. Provisional Pat. Appl. No. 62/504,480, filed on May 10, 2017, which applications are incorporated herein by reference in their entirety.

BACKGROUND OF THE INVENTION

Infection with the bacterium *Porphyromonas gingivalis* has been linked to the development of periodontal disease, Alzheimer's disease and other brain disorders, cardiovascular disease, diabetes, cancer, liver disease, kidney disease, preterm birth, arthritis, pneumonia and other disorders. *P. gingivalis* is an anaerobic asaccharolytic gram-negative rod bacterium that is known to infect the oral cavity and translocate systemically into coronary arteries, aorta, placental tissue, the brain, the kidneys, and the liver. The bacterium has also been identified in cancerous tissues and a mechanism has been proposed by which gingipains can trigger immortalization and metastasis. See: Gandhimadhi, et al. *Journal of Indian Society of Periodontology.* 2010; 14(2): 114-120; Liao, et al., *Med Hypotheses,* 2009. 72(6): 732-5; Byrne, et al., *Oral Microbiol Immunol,* 2009. 24(6): 469-77; Mahendra, et al., *J Maxillofac Oral Surg,* 2009. 8(2): 108-13; Stelzel, et al., *J Periodontol,* 2002. 73(8): 868-70; Katz, et al., *Journal of Dental Research,* 2009. 88(6): 575-578; Poole, et al., *J Alzheimers Dis,* 2015, 43(1): 67-80; Ishikawa, et al., *Biochim Biophys Acta,* 2013. 1832(12): 2035-2043; Inaba, et al., *Cellular Microbiology,* 2014. 16(1): 131-145.

*P. gingivalis* produces proteases called gingipains, including Arginine Gingipain A (RgpA), Arginine Gingipain B (RgpB) and Lysine Gingipain (Kgp). Gingipains contribute to many functions of the organism including its survival and virulence. Gingipains can be secreted, transported to outer membrane surfaces of *P. gingivalis*, or released in outer membrane vesicles by the bacterium. Gingipains degrade a broad range of proteins (e.g., immunoglobulins, proteinase inhibitors, actin, and collagen) which can lead to cytoskeleton collapse and apoptosis in many types of cells. Recent research has demonstrated that inhibitors of gingipains can prevent *P. gingivalis*-induced cell death. See: Travis, et al., *Adv Exp Med Biol,* 2000. 477: 455-65; Sheets, et al., *Infect Immun,* 2005. 73(3): 1543-52; Sheets, et al., *Infect Immun,* 2006. 74(10): 5667-78; Stathopoulou, et al., *BMC Microbiol,* 2009. 9: 107. New compounds for the inhibition of gingipain activity and the treatment of diseases associated with gingipain activity and *P. gingivalis* infection are needed. The present invention addresses this and other needs.

BRIEF SUMMARY OF THE INVENTION

In one embodiment, the invention provides a compound according to Formula I:

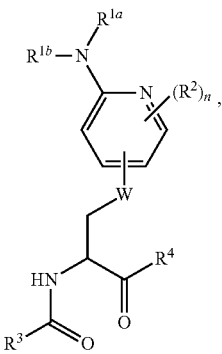

or a pharmaceutically acceptable salt thereof, wherein

W is selected from the group consisting of a bond, $CH_2$, and O;

$R^{1a}$ and $R^{1b}$ are independently selected from the group consisting of H and $C_{1-6}$ alkyl;

$R^2$ is selected from the group consisting of $C_{1-6}$ alkyl and halogen;

subscript n is 0 or 1;

$R^3$ is selected from the group consisting of $C_{3-8}$ alkyl, $C_{3-8}$ cycloalkyl, $C_{3-12}$ heterocyclyl, $C_{6-10}$ aryl, and $C_{5-12}$ heteroaryl wherein $R^3$ is optionally substituted with one or more $R^{3a}$ substituents;

each $R^{3a}$ is independently selected from the group consisting of halogen, —CN, —$NO_2$, —$N_3$, —OH, $C_{1-4}$ alkyl, $C_{1-4}$ haloalkyl, $C_{1-4}$ alkoxy, $C_{1-4}$ haloalkoxy, —$N(R^c)_2$, —$(CH_2)_kC(O)R^b$, —$NR(CH_2)_uC(O)R^b$, —$O(CH_2)C(O)R^b$, —$(CH_2)_kCONR^cR^c$, —$(CH_2)_k NR^cC(O)R^b$, —$NR^c(CH_2)_uCONR^cR^c$, —$NR^c(CH_2)_u NR^c$—$(O)R^b$, —$O(CH_2)_uCONR^cR^c$, and —$O(CH_2)_u NR^cC(O)R^b$, and optionally substituted triazolyl;

each $R^b$ is independently selected from the group consisting of $C_{1-4}$ alkyl, $C_{1-4}$ haloalkyl, and $C_{1-4}$ deuteroalkyl;

each $R^c$ is independently selected from the group consisting of hydrogen and Cis alkyl;

each subscript k is independently selected from 0, 1, 2, 3, 4, 5, and 6;

each subscript u is independently selected from 1, 2, 3, 4, 5, and 6;

$R^4$ is selected from the group consisting of —$CH_2R^{4a}$ and $C_{1-6}$ haloalkyl;

$R^{4a}$ is selected from the group consisting of —O—$R^5$, —S—$R^6$, —SO—$R^6$, —$SO_2$—$R^6$, —$N(R^7)_2$, and $C_{5-12}$ heteroaryl;

$R^5$ is selected from the group consisting of phenyl, $C_{1-6}$ alkyl, $C_{1-6}$ haloalkyl, and $C_{5-12}$ heteroaryl, wherein phenyl is substituted with 1-5 halogens, and wherein $C_{5-12}$ heteroaryl is optionally substituted with halogen or $C_{1-3}$ haloalkyl;

$R^6$ is selected from the group consisting of phenyl, $C_{1-6}$ alkyl, $C_{1-6}$ haloalkyl, and $C_{5-12}$ heteroaryl, wherein phenyl is optionally substituted with 1-5 halogens, and wherein $C_{5-12}$ heteroaryl is optionally substituted with halogen or $C_{1-3}$ haloalkyl; and each $R^7$ is independently selected $C_{1-6}$ alkyl.

In one embodiment, the invention provides a compound according to Formula III:

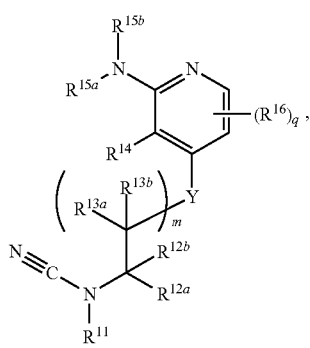

(III)

or a pharmaceutically acceptable salt thereof, wherein:
$R^{11}$ is selected from $C_{1-6}$ alkyl and $C_{3-8}$ cycloalkyl;
$R^{12a}$ and $R^{12b}$ are independently selected from H, $C_{1-6}$ alkyl, and $C_{6-10}$ aryl, or
  $R^{12a}$ and $R^{12b}$ are taken together to form $C_{3-6}$ cycloalkyl, or
  $R^{12a}$ and $R^{11}$ are taken together to form 4- to 10-membered heterocyclyl which is optionally substituted with one or more $R^{17}$;
each $R^{13a}$ and each $R^{13b}$ is independently selected from H, —OH, and $C_{1-6}$ alkyl, or
  one $R^{13a}$ and $R^{11}$ are taken together to form 4- to 10-membered heterocyclyl, or
  one $R^{13b}$ and $R^{12b}$ are taken together to form a 5- or 6-membered ring;
$R^{14}$ is selected from H and halogen, or
  $R^{14}$, $R^{12a}$, and $R^{12b}$ are taken together to form a 6- to 8-membered ring, which is optionally substituted with one or more $R^{18}$, or
  $R^{14}$ and one $R^{13a}$ are taken together to form a 5- to 8-membered ring, which is optionally substituted with one or more $R^{18}$, or
  $R^{14}$ is taken together with one $R^{13a}$ and one $R^{13b}$ on the same carbon atom to form a 5- to 8-membered ring, which is optionally substituted with one or more $R^{18}$, or
  $R^{14}$, $R^{11}$, and $R^{12a}$ are taken together to form a 6- to 10-membered bicyclic ring, which is optionally substituted with one or more $R^{18}$;
$R^{15a}$ and $R^{15b}$ are independently selected from H and $C_{1-6}$ alkyl;
$R^{16}$ is independently selected from $C_{1-6}$ alkyl and halogen;
each $R^{17}$ is independently selected from $C_{1-6}$ alkyl, $C_{1-6}$ alkoxy, $C_{1-6}$ haloalkyl, $C_{1-6}$ haloalkoxy, —OH, and —N($R^{17a}$)$_2$, wherein each $R^{17a}$ is independently selected from H and $C_{1-6}$ alkyl;
each $R^{18}$ is independently selected from $C_{1-6}$ alkyl and halogen;
Y is selected from O, S, C($R^{19a}$)$_2$, and N$R^{19}$b;
each $R^{19a}$ is selected from H and $C_{1-6}$ alkyl, or
  one $R^{19a}$ and one $R^{13b}$ on adjacent atoms are taken together to form a double bond;
$R^{19b}$ is selected from H and $C_{1-6}$ alkyl, or
  $R^{19b}$ and $R^{11}$ are taken together to form a 4- to 6-membered ring;
subscript m is 0, 1, 2, or 3; and
subscript q is 0 or 1.

In a related embodiment, the invention provides a pharmaceutical composition containing a compound as described herein, or a pharmaceutically acceptable salt thereof, and one or more pharmaceutically acceptable excipients.

In another embodiment, the invention provides a method of inhibiting a gingipain. The method includes contacting the gingipain with an effective amount of a compound as described herein.

In another embodiment, the invention provides a method of treating a disease or condition associated with *P. gingivalis* infection. The method includes administering to a subject in need thereof an effective amount of a compound or pharmaceutical composition as described herein.

DETAILED DESCRIPTION OF THE INVENTION

I. General

Inhibition of gingipains has been shown to protect cells, prevent bacterial growth, increase immune system surveillance of *P. gingivalis*, and protect against bacterial reinfection. The present invention provides potent nonpeptidic compounds for inhibition of arginine gingipains. The compounds can be used to prevent cell death, inflammation, and other pathology in a variety of diseases associated with *P. gingivalis* infection, including aging-related conditions such as Alzheimer's disease.

II. Definitions

As used herein, the term "alkyl," by itself or as part of another substituent, refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. For example, "substituted alkyl" groups can be substituted with one or more groups selected from halo, hydroxy, amino, alkylamino, amido, acyl, nitro, cyano, and alkoxy.

As used herein, the term "alkoxy," by itself or as part of another substituent, refers to a group having the formula —OR, wherein R is alkyl.

As used herein, the term "cycloalkyl," by itself or as part of another substituent, refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. For example, "substituted cycloalkyl" groups can be substituted with one or more groups selected from halo, hydroxy, amino, alkylamino, amido, acyl, nitro, cyano, and alkoxy.

As used herein, the term "alkylene" refers to an alkyl group, as defined above, linking at least two other groups (i.e., a divalent alkyl radical). The two moieties linked to the alkylene group can be linked to the same carbon atom or different carbon atoms of the alkylene group.

As used herein, the term "alkylthio," by itself or as part of another substituent, refers to a group having the formula —SR, wherein R is alkyl.

As used herein, the term "heteroalkyl," by itself or as part of another substituent, refers to an alkyl group of any suitable length and having from 1 to 3 heteroatoms such as N, O and S. For example, heteroalkyl can include ethers, thioethers and alkyl-amines. Additional heteroatoms can also be useful, including, but not limited to, B, Al, Si and P. The heteroatoms can be oxidized to form moieties such as, but not limited to, —S(O)— and —S(O)$_2$—. The heteroatom portion of the heteroalkyl can replace a hydrogen of the alkyl group to form a hydroxy, thio, or amino group. Alternatively, the heteroatom portion can be the connecting atom, or be inserted between two carbon atoms.

As used herein, the terms "halo" and "halogen," by themselves or as part of another substituent, refer to a fluorine, chlorine, bromine, or iodine atom.

As used herein, the term "haloalkyl," by itself or as part of another substituent, refers to an alkyl group where some or all of the hydrogen atoms are replaced with halogen atoms. As for alkyl groups, haloalkyl groups can have any suitable number of carbon atoms, such as $C_{1-6}$. For example, haloalkyl includes trifluoromethyl, fluoromethyl, etc. In some instances, the term "perfluoro" can be used to define a compound or radical where all the hydrogens are replaced with fluorine. For example, perfluoromethyl refers to 1,1,1-trifluoromethyl.

As used herein, the term "haloalkoxy," by itself or as part of another substituent, refers to an alkoxy group where some or all of the hydrogen atoms are replaced with halogen atoms.

As used herein, the term "halocycloalkyl," by itself or as part of another substituent, refers to a cycloalkyl group where some or all of the hydrogen atoms are replaced with halogen atoms.

As used herein, the term "deuteroalkyl," by itself or as part of another substituent, refers to an alkyl group where some or all of the hydrogen atoms are replaced with deuterium atoms. As for alkyl groups, deuteroalkyl groups can have any suitable number of carbon atoms, such as $C_{1-6}$. In some instances, the term "perdeutero" can be used to define a compound or radical where all the hydrogens are replaced with deuterium.

As used herein, the term "aryl," by itself or as part of another substituent, refers to an aromatic ring system having any suitable number of carbon ring atoms and any suitable number of rings. Aryl groups can include any suitable number of carbon ring atoms, such as $C_6$, $C_7$, $C_8$, $C_9$, $C_{10}$, $C_{11}$, $C_{12}$, $C_{13}$, $C_{14}$, $C_{15}$ or $C_{16}$, as well as $C_{6-10}$, $C_{6-12}$, or $C_{6-14}$. Aryl groups can be monocyclic, fused to form bicyclic (e.g., benzocyclohexyl) or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. For example, "substituted aryl" groups can be substituted with one or more groups selected from halo, hydroxy, amino, alkylamino, amido, acyl, nitro, cyano, and alkoxy.

As used herein, the term "heteroaryl," by itself or as part of another substituent, refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can be oxidized to form moieties such as, but not limited to, —S(O)— and —S(O)$_2$—. Heteroaryl groups can include any number of ring atoms, such as $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of heteroatoms can be included in the heteroaryl groups, such as 1, 2, 3, 4; or 5, or 1 to 2, 1 to 3, 1 to 4, 1 to 5, 2 to 3, 2 to 4, 2 to 5, 3 to 4, or 3 to 5. For example, heteroaryl groups can be $C_{5-8}$ heteroaryl, wherein 1 to 4 carbon ring atoms are replaced with heteroatoms; or $C_{5-8}$ heteroaryl, wherein 1 to 3 carbon ring atoms are replaced with heteroatoms; or $C_{5-6}$ heteroaryl, wherein 1 to 4 carbon ring atoms are replaced with heteroatoms; or $C_{5-6}$ heteroaryl, wherein 1 to 3 carbon ring atoms are replaced with heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. For example, "substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the term "heterocyclyl," by itself or as part of another substituent, refers to a saturated ring system having from 3 to 12 ring members and from 1 to 4 heteroatoms of N, O and S. Additional heteroatoms can also be useful, including, but not limited to, B, Al, Si and P. The heteroatoms can be oxidized to form moieties such as, but not limited to, —S(O)— and —S(O)$_2$—. Heterocyclyl groups can include any number of ring atoms, such as, $C_{3-6}$, $C_4$-6, $C_{5-6}$, $C_{3-8}$, $C_{4-8}$, $C_{5-8}$, $C_{6-8}$, $C_{3-9}$, $C_{3-10}$, $C_{3-11}$, or $C_{3-12}$, wherein at least one of the carbon atoms is replaced by a heteroatom. Any suitable number of carbon ring atoms can be replaced with heteroatoms in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. For example, "substituted heterocyclyl" groups can be substituted with one or more groups selected from halo, hydroxy, amino, oxo, alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "protecting group" refers to a chemical moiety that renders a functional group (e.g., an amino group) unreactive, but is also removable so as to restore the amino group. Examples of protecting groups include, but are not limited to, benzyloxycarbonyl (Z or Cbz); 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-sulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other protecting groups are known to those of skill in the art including, for example, those described by Green and Wuts (*Protective Groups in Organic Synthesis*, 4$^{th}$ Ed. 2007, Wiley-Interscience, New York).

As used herein, the term "carbonyl," by itself or as part of another substituent, refers to —C(O)—, i.e., a carbon atom double-bonded to oxygen and bound to two other groups in the moiety having the carbonyl.

As used herein, the term "amino" refers to a moiety —NR$_2$, wherein each R group is H or alkyl. An amino moiety can be ionized to form the corresponding ammonium cation. "Dialkylamino" refers to an amino moiety wherein each R group is alkyl.

As used herein, the term "sulfonyl" refers to a moiety —SO$_2$R, wherein the R group is alkyl, haloalkyl, or aryl. An amino moiety can be ionized to form the corresponding ammonium cation. "Alkylsulfonyl" refers to an amino moiety wherein the R group is alkyl.

As used herein, the term "hydroxy" refers to the moiety —OH.

As used herein, the term "cyano" refers to a carbon atom triple-bonded to a nitrogen atom (i.e., the moiety —C≡N).

As used herein, the term "carboxy" refers to the moiety —C(O)OH. A carboxy moiety can be ionized to form the corresponding carboxylate anion.

As used herein, the term "amido" refers to a moiety —NR$^c$(O)R or —C(O)NR$_2$, wherein each R group is H or alkyl.

As used herein, the term "nitro" refers to the moiety —NO$_2$.

As used herein, the term "oxo" refers to an oxygen atom that is double-bonded to a compound (i.e., O=).

In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In general, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., a cyclohexyl group.

Examples of suitable monovalent substituents on a substitutable carbon atom of an "optionally substituted" group are independently halogen; —$(CH_2)_{0-4}R^\alpha$; —$(CH_2)_{0-4}OR^\alpha$; —$O(CH_2)_{0-4}R^\alpha$, —O—$(CH_2)_{0-4}C(O)OR^\alpha$; —$(CH_2)_{0-4}CH(OR^\alpha)_2$; —$(CH_2)_{0-4}SR^\alpha$; —$(CH_2)_{0-4}Ph$, wherein Ph is phenyl which may be substituted with $R^\alpha$; —$(CH_2)_{0-4}O(CH_2)_{0-1}$phenyl, which phenyl may be substituted with $R^\alpha$; —CH=CHPh, wherein Ph is phenyl which may be substituted with $R^\alpha$; —$(CH_2)_{0-4}O(CH_2)_{0-1}$-Py, wherein Py is pyridyl which may be substituted with $R^\alpha$; —$NO_2$; —CN; —$N_3$; —$(CH_2)_{0-4}N(R^\alpha)_2$; —$(CH_2)_{0-4}N(R^\alpha)C(O)R^\alpha$; —$N(R^\alpha)C(S)R^\alpha$; —$(CH_2)_{0-4}N(R^\alpha)C(O)NR^\alpha_2$; —$N(R^\alpha)C(S)NR^\alpha_2$; —$(CH_2)_{0-4}N(R^\alpha)C(O)OR^\alpha$; —$N(R^\alpha)N(R^\alpha)C(O)R^\alpha$; —$N(R^\alpha)N(R^\alpha)C(O)NR^\alpha_2$; —$N(R^\alpha)N(R^\alpha)C(O)OR^\alpha$; —$(CH_2)_{0-4}C(O)R^\alpha$; —$C(S)R^\alpha$; —$(CH_2)_{0-4}C(O)OR^\alpha$; —$(CH_2)_{0-4}C(O)SR^\alpha$; —$(CH_2)_{0-4}C(O)OSiR^\alpha_3$; —$(CH_2)_{0-4}OC(O)R^\alpha$; —$OC(O)(CH_2)_{0-4}SR$—$SC(S)SR^\alpha$; —$(CH_2)_{0-4}SC(O)R^\alpha$; —$(CH_2)_{0-4}C(O)NR^\alpha_2$; —$C(S)NR^\alpha_2$, —$C(S)SR^\alpha$; —$SC(S)SR^\alpha$, —$(CH_2)_{0-4}OC(O)NR^\alpha_2$; —$C(O)N(OR^\alpha)R^\alpha$; —$C(O)C(O)R^\alpha$; —$C(O)CH_2C(O)R^\alpha$; —$C(NOR^\alpha)R^\alpha$; —$(CH_2)_{0-4}SSR^\alpha$; —$(CH_2)_{0-4}S(O)_2R^\alpha$; —$(CH_2)_{0-4}S(O)_2OR^\alpha$; —$(CH_2)_{0-4}OS(O)_2R^\alpha$; —$S(O)_2NR^\alpha_2$; —$(CH_2)_{0-4}S(O)R^\alpha$; —$N(R^\alpha)S(O)_2NR^\alpha_2$; —$N(R^\alpha)S(O)_2R^\alpha$; —$N(OR^\alpha)R^\alpha$; —$C(NH)NR^\alpha_2$; —$P(O)_2R^\alpha$; —$P(O)R^\alpha_2$; —$OP(O)R^\alpha_2$; —$OP(O)(OR^\alpha)_2$; $SiR^\alpha_3$; —$(C_{1-4}$ straight or branched)alkylene)-O—$N(R^\alpha)_2$; or —$(C_{1-4}$ straight or branched)alkylene)C(O)O—$N(R^\alpha)_2$. Each $R^1$ is independently hydrogen; $C_{1-6}$ alkyl; —$CH_2Ph$, —$O(CH_2)_{0-1}Ph$; —$CH_2$-(5- to 6-membered heteroaryl); $C_{3-8}$ cycloalkyl; $C_{6-10}$ aryl; 4- to 10-membered heterocyclyl; or 6- to 10-membered heteroaryl; and each $R^\alpha$ may be further substituted as described below.

Examples of suitable monovalent substituents on $R^\alpha$ are independently halogen, —$(CH_2)_{0-2}R^\beta$; —$(CH_2)_{0-2}OH$; —$(CH_2)_{0-2}OR^\beta$; —$(CH_2)_{0-2}CH(OR)_2$; —CN; —$N_3$; —$(CH_2)_{0-2}C(O)R^\beta$; —$(CH_2)_{0-2}C(O)OH$; —$(CH_2)_{0-2}C(O)OR^\beta$; —$(CH_2)_{0-2}SR^\beta$; —$(CH_2)_{0-2}SH$; —$(CH_2)_{0-2}NH_2$; —$(CH_2)_{0-2}NHR^\beta$; —$(CH_2)_{0-2}NR^\beta_2$; —$NO_2$; $SiR^\beta_3$; —$OSiR^\beta_3$; —$C(O)SR^\beta$; —$(C_{1-4}$ straight or branched alkylene)C(O)OR$^\beta$; or —$SSR^\beta$; wherein each RR is independently selected from $C_{1-4}$ alkyl; —$CH_2Ph$; —$O(CH_2)_{0-1}$Ph; $C_{3-8}$ cycloalkyl; $C_{6-10}$ aryl; 4- to 10-membered heterocyclyl; or 6- to 10-membered heteroaryl. Suitable divalent substituents on a saturated carbon atom of $R^\alpha$ include =O and =S.

Examples of suitable divalent substituents on a saturated carbon atom of an "optionally substituted" group include the following: =O; =S; =$NNR^\gamma_2$; =$NNHC(O)R^\gamma$; =$NNHC(O)OR^\gamma$; =$NNHS(O)_2R^\gamma$; =$NR^\gamma$; =$NOR^\gamma$; —$O(C(R^\gamma_2))_{2-3}$O—; or —$S(C(R^\gamma_2))_{2-3}$S—; wherein each independent occurrence of $R^\gamma$ is selected from hydrogen; $C_{1-6}$ alkyl, which may be substituted as defined below; $C_{3-8}$ cycloalkyl; $C_{6-10}$ aryl; 4- to 10-membered heterocyclyl; or 6- to 10-membered heteroaryl. Suitable divalent substituents that are bound to vicinal substitutable carbons of an "optionally substituted" group include: —$O(CR^\beta_2)_{2-3}O$—; wherein each independent occurrence of RR is selected from hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Examples of suitable substituents on the alkyl group of Rγinclude halogen; —$R^\delta$; —OH; —$OR^\delta$; —CN; —C(O)OH; —$C(O)OR^\delta$; —$NH_2$; —$NHR^\delta$; —$NR^\delta_2$; or —$NO_2$; wherein each $R^\delta$ is independently $C_{1-4}$ alkyl; —$CH_2Ph$; —$O(CH_2)_{0-1}Ph$; 4- to 10-membered heterocyclyl; or 6- to 10-membered heteroaryl.

Examples of suitable substituents on a substitutable nitrogen of an "optionally substituted" group include —$R^\epsilon$; —$NR^\epsilon_2$; —$C(O)R^\epsilon$; —$C(O)OR^\epsilon$; —$C(O)C(O)R^\epsilon$; —$C(O)CH_2C(O)R^\epsilon$; —$S(O)_2R^\epsilon$; —$S(O)_2NR^\epsilon_2$; —$C(S)NR^\epsilon_2$; —$C(NH)NR^\epsilon_2$; or —$N(R^\epsilon)S(O)_2R^\epsilon$; wherein each $R^\epsilon$ is independently hydrogen; $C_{1-6}$ alkyl which may be substituted as defined below; $C_{3-8}$ cycloalkyl; $C_{6-10}$ aryl; 4- to 10-membered heterocyclyl; or 6- to 10-membered heteroaryl.

Examples of suitable substituents on the alkyl group of $R^\epsilon$ are independently halogen; —$R^\delta$; —OH; —$OR^\delta$; —CN; —C(O)OH; —$C(O)OR^\delta$; —$NH_2$; —$NHR^\delta$; —$NR^\delta_2$; or —$NO_2$; wherein each $R^\delta$ is independently $C_{1-4}$ alkyl; —$CH_2Ph$; —$O(CH_2)_{0-1}Ph$; $C_{6-10}$ aryl; 4- to 10-membered heterocyclyl; or 6- to 10-membered heteroaryl.

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Pharmaceutical excipients useful in the present invention include, but are not limited to, binders, fillers, disintegrants, lubricants, glidants, coatings, sweeteners, flavors and colors.

As used herein, the term "salt" refers to acid or base salts of the compounds of the invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic.

Pharmaceutically acceptable salts of the acidic compounds of the present invention are salts formed with bases, namely cationic salts such as alkali and alkaline earth metal salts (such as sodium, lithium, potassium, calcium, and magnesium salts), as well as ammonium salts (such as ammonium, trimethyl-ammonium, diethylammonium, and tris-(hydroxymethyl)-methyl-ammonium salts).

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are eq to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

As used herein, the terms "*Porphyromonas gingivalis*" and "*P. gingivalis*" refer to the gram-negative asaccharolytic bacterium that is recognized as a key causative microbe in the pathogenesis of periodontitis and related conditions. "*P. gingivalis* infection" refers to the invasion and colonization of *P. gingivalis* in a bodily tissue such as the gums or the brain. *P. gingivalis* infection is frequently characterized by subsequent tissue injury and disease.

As used herein, the term "gingipain" refers to cysteine proteases expressed by *P. gingivalis* having trypsin-like specificity (i.e., Lys-Xaa and Arg-Xaa). Gingipains are recognized as the major virulence factors of *P. gingivalis* and contribute to bacterial attachment and colonization, nutrient acquisition, evasion of host defenses, and tissue invasion. The terms "arginine gingipain" and "Rgp" are used interchangeably to refer to the *P. gingivalis* arginine-specific gingipains RgpA and RgpB, classified under EC number EC 3.4.22.37. The rgpA and rgpB gene-translation products, RgpA and RgpB, share a caspase-like protease domain (specific for Arg-Xaa peptide bonds) and an immunoglobulin-like domain. In RgpA, the protease and immunoglobulin-like domains are followed by a large C-terminal extension containing hemagglutinin-adhesin domains.

As used herein, the term "inhibiting" refers to reducing the level of activity (e.g., proteolytic activity) of an enzyme such as a gingipain which can be assessed, for example, using an in vitro assay or other suitable assay. Inhibition of enzyme activity caused by a particular substance (e.g., a gingipain inhibitor as described herein) can be expressed as the percentage of the enzyme activity measured in the absence of the substance under similar conditions. The ability of a particular substance to inhibit an enzyme can be expressed as an $IC_{50}$ value, i.e., the concentration of the compound required to reduce the activity of the enzyme to 50% of its maximum activity.

As used herein, the terms "treat," "treatment," and "treating" refer to any indicia of success in the treatment or amelioration of an injury, pathology, condition, or symptom (e.g., cognitive impairment), including any objective or subjective parameter such as abatement; remission; diminishing of symptoms or making the symptom, injury, pathology or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, e.g., the result of a physical examination.

As used herein, the terms "effective amount" and "therapeutically effective amount" refer to a dose of a compound such as an Rgp inhibitor that inhibits the activity of a gingipain and/or produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, *The Art, Science and Technology of Pharmaceutical Compounding* (1999); Pickar, Dosage Calculations (1999); *Goodman & Gilman's The Pharmacological Basis of Therapeutics*, $11^{th}$ Edition, 2006, Brunton, Ed., McGraw-Hill; and *Remington: The Science and Practice of Pharmacy*, $21^{st}$ Edition, 2005, Hendrickson, Ed., Lippincott, Williams & Wilkins).

As used herein, the term "Alzheimer's disease" refers to a progressive disease of the central nervous system in humans and other mammals. It is manifested by dementia (especially in the elderly); disorientation; loss of memory; difficulty with language, calculation, or visual-spatial skills; and psychiatric manifestations. Alzheimer's disease is associated with progressive neurodegeneration and characteristic pathology, namely beta amyloid plaques and tau tangles.

As used herein, the term "osteoarthritis" refers to a chronic degenerative joint disease that results from breakdown of joint cartilage, synovial tissue, and underlying bone.

As used herein, the term "subject" refers to animals such as mammals, including, but not limited to, primates (e.g., humans), cows, sheep, goats, horses, dogs, cats, rabbits, rats, mice and the like.

III. Gingipain Inhibitors

In one embodiment, the invention provides a compound according to Formula I:

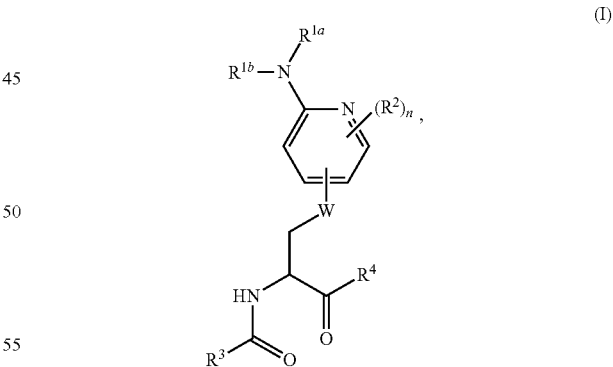

or a pharmaceutically acceptable salt thereof, wherein
W is selected from a bond, $CH_2$, and O;
$R^{1a}$ and $R^{1b}$ are independently selected from H and $C_{1-6}$ alkyl;
$R^2$ is selected from $C_{1-6}$ alkyl and halogen;
subscript n is 0 or 1;
$R^3$ is selected from $C_{3-8}$ alkyl, $C_{3-8}$ cycloalkyl, $C_{3-12}$ heterocyclyl, $C_{6-10}$ aryl, and $C_{5-12}$ heteroaryl wherein $R^3$ is optionally substituted with one or more $R^{3a}$ substituents;

each $R^{3a}$ is independently selected from halogen, —CN, —NO$_2$, —N$_3$, —OH, C$_{1-4}$ alkyl, C$_{1-4}$ haloalkyl, C$_{1-4}$ alkoxy, C$_{1-4}$ haloalkoxy, —N(R$^c$)$_2$, —(CH$_2$)$_k$C(O)R$^b$, —NR(CH$_2$)$_u$C(O)R$^b$, —O(CH$_2$)C(O)R$^b$, —(CH$_2$)$_k$CONR$^c$R$^c$, —(CH$_2$)$_k$NR$^c$C(O)R$^b$, —NR$^c$(CH$_2$)$_u$CONR$^c$R$^c$, 13 NR$^c$(CH$_2$)NR$^c$—(O)R$^b$, —O(CH$_2$)$_u$CONR$^c$R$^c$, and —O(CH$_2$)NR$^c$C(O)R$^b$, and optionally substituted triazolyl;

each $R^b$ is independently selected from C$_{1-4}$ alkyl, C$_{14}$ haloalkyl, and C$_{1-4}$ deuteroalkyl;

each R is independently selected from hydrogen and C$_{1-8}$ alkyl;

each subscript k is independently selected from 0, 1, 2, 3, 4, 5, and 6;

each subscript u is independently selected from 1, 2, 3, 4, 5, and 6;

$R^4$ is selected from —CH$_2$R$^{4a}$ and C$_{1-6}$ haloalkyl;

$R^{4a}$ is selected from —O—R$^5$, —S—R$^6$, —SO—R$^6$, —SO$_2$—R$^6$, —N(R$^7$)$_2$, and C$_{5-12}$ heteroaryl;

$R^5$ is selected from phenyl, C$_{1-6}$ alkyl, C$_{1-6}$ haloalkyl, and C$_{5-12}$ heteroaryl,
  wherein phenyl is substituted with 1-5 halogens, and
  wherein C$_{5-12}$ heteroaryl is optionally substituted with halogen or C$_{1-3}$ haloalkyl;

$R^6$ is selected from phenyl, C$_{1-6}$ alkyl, C$_{1-6}$ haloalkyl, and C$_{5-12}$ heteroaryl,
  wherein phenyl is optionally substituted with 1-5 halogens, and
  wherein C$_{5-2}$ heteroaryl is optionally substituted with halogen or C$_{1-3}$ haloalkyl; and each $R^7$ is independently selected C$_{1-6}$ alkyl.

In some embodiments, each of $R^{1a}$ and $R^{1b}$ is independently selected from H, methyl, ethyl, n-propyl, isopropyl, n-butyl, sec-butyl, isobutyl, tert-butyl, n-pentyl, branched pentyl, n-hexyl, and branched hexyl. In some embodiments, each of $R^{1a}$ is H and $R^{1b}$ is selected from H, methyl, ethyl, n-propyl, isopropyl, n-butyl, sec-butyl, isobutyl, tert-butyl, n-pentyl, branched pentyl, n-hexyl, and branched hexyl. In some embodiments, $R^{1b}$ is independently selected from H, methyl, ethyl, n-propyl, isopropyl, n-butyl, sec-butyl, isobutyl, tert-butyl, n-pentyl, branched pentyl, n-hexyl, and branched hexyl and $R^{1a}$ is H. In some embodiments, $R^{1a}$ and $R^{1b}$ are H.

Compounds of the invention can be prepared in protected form (e.g., protected compounds wherein at least one of $R^{1a}$ and $R^{1b}$ is an amine protecting group). A number of suitable protecting groups—as described, for example, by Green and Wuts (*Protective Groups in Organic Synthesis*, 4$^{th}$ Ed. 2007, Wiley-Interscience, New York)—can be used. In some embodiments, $R^{1a}$ is H and $R^b$ is selected from benzyloxycarbonyl; 9-fluorenylmethyl-oxycarbonyl; tert-butyloxycarbonyl; and allyloxycarbonyl. In some embodiments, $R^{1a}$ and $R^{1b}$ are selected from benzyloxycarbonyl; 9-fluorenylmethyl-oxycarbonyl; tert-butyloxycarbonyl; and allyloxycarbonyl. In some embodiments, $R^{1a}$ is H and $R^b$ is tert-butyloxycarbonyl. Compounds can also be prepared in alkylated form (i.e., compounds wherein at least one of $R^{1a}$ and $R^b$ is an alkyl group). One or both of $R^{1a}$ and $R^{1b}$ can be, for example, methyl, ethyl, n-propyl, isopropyl, n-butyl, or t-butyl.

In some embodiments, subscript n is 0. In some embodiments, subscript p is 1. In some embodiments, subscript n is 1 and $R^2$ is selected from fluoro, chloro, bromo, iodo, methyl, ethyl, n-propyl, isopropyl, n-butyl, sec-butyl, isobutyl, tert-butyl, n-pentyl, branched pentyl, n-hexyl, and branched hexyl. In some embodiments, subscript n is 1 and $R^2$ is selected from fluoro, chloro, and methyl. In some embodiments, subscript n is 2 or 3.

In some embodiments, W is a bond. In some embodiments, W is selected from CH$_2$ and O.

In some embodiments, the compound has a structure according to Formula IIa:

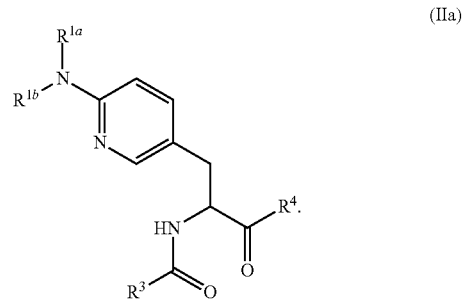

(IIa)

In some embodiments, the compound has a structure according to Formula IIb:

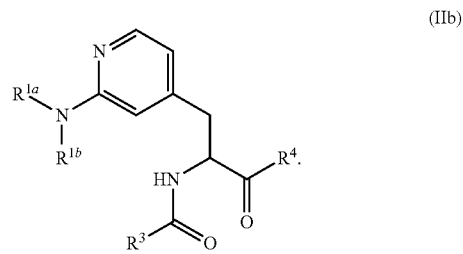

(IIb)

In some embodiments, the invention provides compounds of Formula I, Formula IIa, and/or Formula IIb, and pharmaceutically acceptable salts thereof, wherein $R^3$ is selected from C$_{3-8}$ cycloalkyl, C$_{6-10}$ aryl, C$_{5-12}$ heteroaryl, and C$_{3-12}$ heterocyclyl, each of which is optionally substituted with one or more $R^{3a}$ substituents. For example, $R^3$ can be cyclopropyl, cyclobutyl, cyclopentyl, cyclohexyl, cycloheptyl, cyclooctyl. In some embodiments, $R^3$ is selected from cyclobutyl, cyclopentyl, and cyclohexyl. In some embodiments, $R^3$ is selected from phenyl and naphthyl. In some embodiments, $R^3$ is selected from pyrrolyl, pyridinyl, imidazolyl, pyrazolyl, triazolyl, pyrazinyl, triazinyl, indolyl, isoindolyl, and quinolinyl. In some such embodiments, $R^3$ is selected from cyclopentyl and phenyl, each of which is optionally substituted with one or more $R^{3a}$ substituents. In some such embodiments, each $R^{3a}$ is independently selected from halogen, —N$_3$, C$_{1-4}$ alkyl, C$_{1-4}$ haloalkyl, C$_{1-4}$ alkoxy, C$_{1-4}$ haloalkoxy, and —NR$^c$C(O)R$^b$. In some embodiments, $R^3$ is cyclopentyl.

In some embodiments, the invention provides compounds of Formula I, Formula IIa, and/or Formula IIb, and pharmaceutically acceptable salts thereof, wherein $R^3$ is selected from C$_{3-8}$ cycloalkyl, C$_{6-10}$ aryl, C$_{5-12}$ heteroaryl, and C$_{3-12}$ heterocyclyl, each of which is optionally substituted with one or more $R^{3a}$ substituents. In some such embodiments, $R^3$ is selected from cyclopentyl and phenyl, each of which is optionally substituted with one or more $R^{3a}$ substituents. In some such embodiments, each $R^{3a}$ is independently selected from halogen, —N$_3$, C$_{1-4}$ alkyl, C$_{1-4}$ haloalkyl, C$_{1-4}$ alkoxy, C$_{1-4}$ haloalkoxy, and —NR$^c$C(O)R$^b$. In some embodiments, $R^3$ is cyclopentyl.

One of skill in the art will appreciate that compounds containing azide groups (e.g., compounds wherein $R^{3a}$ is $—N_3$) can be modified with further functional groups via reaction with a complementary reaction partner such as an alkyne-bearing compound or a phosphine-bearing compound. Reaction of azides and alkynes via [3+2] cycloaddition, commonly referred to as "click chemistry," can be used to install a variety of substituted triazole groups in the compounds of the invention. Accordingly, some embodiments of the invention provide compounds wherein $R^{3a}$ is an optionally substituted triazolyl moiety according to the formula:

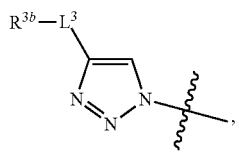

wherein $R^{3b}$ is a functional moiety and $L^3$ is a linking moiety.

In some embodiments, the linking moiety $L^3$ has a structure $—L^{3a}$-$L^{3b}$-, wherein $L^{3a}$ and $L^{3b}$ are independently selected from a bond, a divalent polymer moiety, and linear or branched, saturated or unsaturated $C_{1-30}$ alkyl; wherein:
  one or more carbon atoms in the $C_{1-30}$ alkyl is optionally and independently replaced by O, S, $NR^a$;
  two or more groupings of adjacent carbon atoms in the $C_{1-30}$ alkyl are optionally and independently replaced by $—NR^a(CO)—$ or $—(CO)NR^a—$; and
  two or more groupings of adjacent carbon atoms in the $C_{1-30}$ alkyl are optionally and independently replaced by a 4- to 8-membered, divalent carbocycle or a 4- to 8-membered, divalent heterocycle having one to four heteroatoms selected from O, S, and N; and
  each $R^a$ is independently selected from H and $C_{1-6}$ alkyl.

In some embodiments, the functional group $R^{3b}$ is selected from a chromophore, a fluorophore, and a binding moiety (e.g., biotin, glutathione, and the like).

In some embodiments, $R^3$ is selected from $C_{3-8}$ alkyl and $C_{3-8}$ cycloalkyl, each of which is optionally substituted with one or more $R^{3a}$ substituents. In some embodiments, $R^3$ is selected from cyclopentyl and isopropyl. In some embodiments, $R^3$ is unsubstituted cyclopentyl. In some embodiments, $R^3$ is isopropyl and $R^{3a}$ is methoxy.

In certain embodiments, $R^3$ and the carbonyl to which it is bonded form a moiety other than a naturally-occurring amino acid residue (an L amino acid residue) or an isomer of a naturally-occurring amino acid residue (a D amino acid residue). In some embodiments, $R^3$ and the carbonyl to which it is bonded form a moiety other than asparaginyl, substituted asparaginyl, glutaminyl (i.e., a glutamine residue), substituted glutaminyl (i.e., a substituted glutamine residue), glutamyl (i.e., a glutamic acid residue), substituted glutamyl (i.e., a substituted glutamic acid residue), isoleucinyl, substituted isoleucinyl, leucinyl, substituted leucinyl, lysinyl, substituted lysinyl, methioninyl, substituted methioninyl, prolinyl, substituted prolinyl, threoninyl, substituted threoninyl, valinyl, or substituted valinyl. The substituted amino acid residues may be present in larger peptide groups having two or more amino acid residues linked via amine bonds.

In some embodiments, the invention provides compounds of Formula I, Formula IIa, and/or Formula IIb, and pharmaceutically acceptable salts thereof, wherein $R^{4a}$ is selected from $—S—R^6$, $—SO—R^6$, $—SO_2—R^6$, $C_{5-12}$ heteroaryl, and $—N—R^7$. In some embodiments, $R^{4a}$ is selected from $—O—R^5$, $C_{5-12}$ heteroaryl, and $—N—(R^7)_2$. In some embodiments, $R^{4a}$ is selected from $—O—R^5$, $—S—R^6$, $—SO—R^6$, $—SO_2—R^6$, and $—N—(R^7)_2$. In some embodiments, $R^{4a}$ is selected from $—O—R^5$, $—S—R^6$, $—SO—R^6$, $—SO_2—R^6$, and $C_{5-12}$ heteroaryl.

In some embodiments, the invention provides compounds of Formula I, Formula IIa, and/or Formula IIb, and pharmaceutically acceptable salts thereof, wherein $R^{4a}$ is selected from $C_{1-6}$ haloalkoxy, $C_{1-6}$ alkylthio, $C_{1-6}$ haloalkythio, $C_{1-6}$ alkylsufonyl, ($C_{1-6}$ dialkyl)amino, $C_{5-12}$ heteroaryl, —O-phenyl wherein phenyl is substituted with 1-5 halogens, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ alkylthio, $C_{1-6}$ haloalkythio, $C_{1-6}$ alkylsufonyl, ($C_{1-6}$ dialkyl)amino, $C_{5-12}$ heteroaryl, —O-phenyl wherein phenyl is substituted with 1-5 halogens, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ haloalkoxy, $C_{1-6}$ haloalkythio, $C_{1-6}$ alkylsufonyl, ($C_{1-6}$ dialkyl)amino, $C_{5-12}$ heteroaryl, —O-phenyl wherein phenyl is substituted with 1-5 halogens, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ haloalkoxy, $C_{1-6}$ alkylthio, $C_{1-6}$ alkylsufonyl, ($C_{1-6}$ dialkyl)amino, $C_{5-12}$ heteroaryl, —O-phenyl wherein phenyl is substituted with 1-5 halogens, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ haloalkoxy, $C_{1-6}$ alkylthio, $C_{1-6}$ haloalkythio, ($C_{1-6}$ dialkyl)amino, $C_{5-12}$ heteroaryl, —O-phenyl wherein phenyl is substituted with 1-5 halogens, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, $C_{5-12}$ heteroaryl, —O-phenyl wherein phenyl is substituted with 1-5 halogens, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, ($C_{1-6}$ dialkyl)amino, —O-phenyl wherein phenyl is substituted with 1-5 halogens, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, $(C_{1-6}$ dialkyl)amino, $C_{5-12}$ heteroaryl, and —S-phenyl wherein phenyl is optionally substituted with 1-5 halogens.

In some embodiments, the invention provides compounds of Formula I, Formula IIa, and/or Formula IIb, and pharmaceutically acceptable salts thereof, wherein $R^{4a}$ is selected from $C_{1-6}$ alkoxy, $C_{1-6}$ haloalkoxy, $C_{1-6}$ alkylthio, $C_{1-6}$ haloalkythio, $C_{1-6}$ alkylsufonyl, $(C_{1-6}$ dialkyl)amino, $C_{5-12}$ heteroaryl, and —O-phenyl wherein phenyl is substituted with 1-5 halogens.

In some embodiments, the invention provides compounds of Formula I, Formula IIa, and/or Formula IIb, and pharmaceutically acceptable salts thereof, wherein $R^4$ is —CH$_2$—O—$R^5$ and $R^5$ is selected from 1,1,1,3,3,3-hexafluoroprop-2-yl, isoxazolyl, and phenyl, wherein phenyl is substituted with 1-5 halogens.

In some embodiments, the invention provides compounds of Formula I, Formula IIa, and/or Formula IIb, and pharmaceutically acceptable salts thereof, wherein $R^5$ is phenyl substituted with 1-5 halogens. In some embodiments, each halogen in $R^5$ is selected from F and Cl. In some embodiments, each halogen in $R^5$ is F.

In some embodiments, the invention provides compounds of Formula I, Formula IIa, and/or Formula IIb, and pharmaceutically acceptable salts thereof, wherein $R^{4a}$ is —O$R^5$, such that $R^4$ is a moiety having the structure:

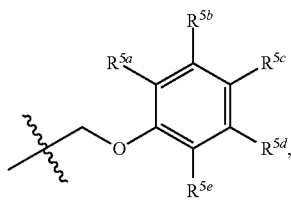

wherein $R^{5a}$, $R^{5b}$, $R^{5c}$, $R^{5d}$, and $R^{5e}$ are independently selected from hydrogen and halogen, and the wavy line represents the point of connection to the compound.

In some embodiments:
$R^{5a}$ is halogen, $R^{5b}$ is H, $R^{5c}$ is H, $R^{5d}$ is H, and $R^{5e}$ is H; or
$R^{5a}$ is H, $R^{5b}$ is halogen, $R^{5c}$ is H, $R^{5d}$ is H, and $R^{5e}$ is H; or
$R^{5a}$ is H, $R^{5b}$ is H, $R^{5c}$ is halogen, $R^{5d}$ is H, and $R^{5e}$ is H; or
$R^{5a}$ is H, $R^{5b}$ is H, $R^{5c}$ is H, $R^{5d}$ is halogen, and $R^{5e}$ is H; or
$R^{5a}$ is H, $R^{5b}$ is H, $R^{5c}$ is H, $R^{5d}$ is H, and $R^{5e}$ is halogen; or
$R^{5a}$ is halogen, $R^{5b}$ is halogen, $R^{5c}$ is H, $R^{5d}$ is H, and $R^{5e}$ is H; or
$R^{5a}$ is halogen, $R^{5b}$ is H, $R^{5c}$ is halogen, $R^{5d}$ is H, and $R^{5e}$ is H; or
$R^{5a}$ is halogen, $R^{5b}$ is H, $R^{5c}$ is H, $R^{5d}$ is halogen, and $R^{5e}$ is H; or
$R^{5a}$ is halogen, $R^{5b}$ is H, $R^{5c}$ is H, $R^{5d}$ is H, and $R^{5e}$ is halogen; or
$R^{5a}$ is H, $R^{5b}$ is halogen, $R^{5c}$ is halogen, $R^{5d}$ is H, and $R^{5e}$ is H; or
$R^{5a}$ is H, $R^{5b}$ is halogen, $R^{5c}$ is H, $R^{5d}$ is halogen, and $R^{5e}$ is H; or
$R^{5a}$ is H, $R^{5b}$ is halogen, $R^{5c}$ is H, $R^{5d}$ is H, and $R^{5e}$ is halogen; or
$R^{5a}$ is H, $R^{5b}$ is H, $R^{5c}$ is halogen, $R^{5d}$ is halogen, and $R^{5e}$ is H; or
$R^{5a}$ is H, $R^{5b}$ is H, $R^{5c}$ is halogen, $R^{5d}$ is H, and $R^{5e}$ is halogen; or
$R^{5a}$ is H, $R^{5b}$ is H, $R^{5c}$ is H, $R^{5d}$ is halogen, and $R^{5e}$ is halogen; or
$R^{5a}$ is halogen, $R^{5b}$ is halogen, $R^{5c}$ is halogen, $R^{5d}$ is H, and $R^{5e}$ is H; or
$R^{5a}$ is halogen, $R^{5b}$ is halogen, $R^{5c}$ is H, $R^{5d}$ is halogen, and $R^{5e}$ is H; or
$R^{5a}$ is halogen, $R^{5b}$ is halogen, $R^{5c}$ is H, $R^{5d}$ is H, and $R^{5e}$ is halogen; or
$R^{5a}$ is halogen, $R^{5b}$ is H, $R^{5c}$ is halogen, $R^{5d}$ is halogen, and $R^{5e}$ is H; or
$R^{5a}$ is halogen, $R^{5b}$ is H, $R^{5c}$ is halogen, $R^{5d}$ is H, and $R^{5e}$ is halogen; or $R^{5a}$ is H, $R^{5b}$ is halogen, $R^{5c}$ is halogen, $R^{5d}$ is halogen, and $R^{5e}$ is H; or
$R^{5a}$ is H, $R^{5b}$ is halogen, $R^{5c}$ is halogen, $R^{5d}$ is H, and $R^{5e}$ is halogen; or
$R^{5a}$ is H, $R^{5b}$ is halogen, $R^{5c}$ is H, $R^{5d}$ is halogen, and $R^{5e}$ is halogen; or
$R^{5a}$ is H, $R^{5b}$ is H, $R^{5c}$ is halogen, $R^{5d}$ is halogen, and $R^{5e}$ is halogen; or
$R^{5a}$ is H, $R^{5b}$ is halogen, $R^{5c}$ is halogen, $R^{5d}$ is halogen, and $R^{5e}$ is halogen; or
$R^{5a}$ is halogen, $R^{5b}$ is H, $R^{5c}$ is halogen, $R^{5d}$ is halogen, and $R^{5e}$ is halogen; or
$R^{5a}$ is halogen, $R^{5b}$ is halogen, $R^{5c}$ is halogen, $R^{5d}$ is H, and $R^{5e}$ is halogen; or
$R^{5a}$ is halogen, $R^{5b}$ is halogen, $R^{5c}$ is halogen, $R^{5d}$ is halogen, and $R^{5e}$ is H; or
$R^{5a}$ is halogen, $R^{5b}$ is halogen, $R^{5c}$ is H, $R^{5d}$ is halogen, and $R^{5e}$ is halogen.

In some embodiments:
$R^{5a}$ is F or Cl, $R^{5b}$ is H, $R^{5c}$ is H, $R^{5d}$ is H, and $R^{5e}$ is H; or
$R^{5a}$ is H, $R^{5b}$ is F or Cl, $R^{5c}$ is H, $R^{5d}$ is H, and $R^{5e}$ is H; or
$R^{5a}$ is H, $R^{5b}$ is H, $R^{5c}$ is F or Cl, $R^{5d}$ is H, and $R^{5e}$ is H; or
$R^{5a}$ is H, $R^{5b}$ is H, $R^{5c}$ is H, $R^{5d}$ is F or Cl, and $R^{5e}$ is H; or
$R^{5a}$ is H, $R^{5b}$ is H, $R^{5c}$ is H, $R^{5d}$ is H, and $R^{5e}$ is F or Cl; or
$R^{5a}$ is F or Cl, $R^{5b}$ is F or Cl, $R^{5c}$ is H, $R^{5d}$ is H, and $R^{5e}$ is H; or
$R^{5a}$ is F or Cl, $R^{5b}$ is H, $R^{5c}$ is F or Cl, $R^{5d}$ is H, and $R^{5e}$ is H; or
$R^{5a}$ is F or Cl, $R^{5b}$ is H, $R^{5c}$ is H, $R^{5d}$ is F or Cl, and $R^{5e}$ is H; or
$R^{5a}$ is F or Cl, $R^{5b}$ is H, $R^{5c}$ is H, $R^{5d}$ is H, and $R^{5e}$ is F or Cl; or
$R^{5a}$ is H, $R^{5b}$ is F or Cl, $R^{5c}$ is F or Cl, $R^{5d}$ is H, and $R^{5e}$ is H; or
$R^{5a}$ is H, $R^{5b}$ is F or Cl, $R^{5c}$ is H, $R^{5d}$ is F or Cl, and $R^{5e}$ is H; or
$R^{5a}$ is H, $R^{5b}$ is F or Cl, $R^{5c}$ is H, $R^{5d}$ is H, and $R^{5e}$ is F or Cl; or
$R^{5a}$ is H, $R^{5b}$ is H, $R^{5c}$ is F or Cl, $R^{5d}$ is F or Cl, and $R^{5e}$ is H; or
$R^{5a}$ is H, $R^{5b}$ is H, $R^{5c}$ is F or Cl, $R^{5d}$ is H, and $R^{5e}$ is F or Cl; or
$R^{5a}$ is H, $R^{5b}$ is H, $R^{5c}$ is H, $R^{5d}$ is F or Cl, and $R^{5e}$ is F or Cl; or
$R^{5a}$ is F or Cl, $R^{5b}$ is F or Cl, $R^{5c}$ is F or Cl, $R^{5d}$ is H, and $R^{5e}$ is H; or $R^{5a}$ is F or Cl, $R^{5b}$ is F or Cl, $R^{5c}$ is H, $R^{5d}$ is F or Cl, and $R^{5e}$ is H; or
$R^{5a}$ is F or Cl, $R^{5b}$ is F or Cl, $R^{5c}$ is H, $R^{5d}$ is H, and $R^{5e}$ is F or Cl; or
$R^{5a}$ is F or Cl, $R^{5b}$ is H, $R^{5c}$ is F or Cl, $R^{5d}$ is F or Cl, and $R^{5e}$ is H; or
$R^{5a}$ is F or Cl, $R^{5b}$ is H, $R^{5c}$ is F or Cl, $R^{5d}$ is H, and $R^{5e}$ is F or Cl; or
$R^{5a}$ is F or Cl, $R^{5b}$ is H, $R^{5c}$ is H, $R^{5d}$ is F or Cl, and $R^{5e}$ is F or Cl; or
$R^{5a}$ is H, $R^{5b}$ is F or Cl, $R^{5c}$ is F or Cl, $R^{5d}$ is F or Cl, and $R^{5e}$ is H; or
$R^{5a}$ is H, $R^{5b}$ is F or Cl, $R^{5c}$ is F or Cl, $R^{5d}$ is H, and $R^{5e}$ is F or Cl; or
$R^{5a}$ is H, $R^{5b}$ is F or Cl, $R^{5c}$ is H, $R^{5d}$ is F or Cl, and $R^{5e}$ is F or Cl; or
$R^{5a}$ is H, $R^{5b}$ is H, $R^{5c}$ is F or Cl, $R^{5d}$ is F or Cl, and $R^{5e}$ is F or Cl; or
$R^{5a}$ is H, $R^{5b}$ is F or Cl, $R^{5c}$ is F or Cl, $R^{5d}$ is F or Cl, and $R^{5e}$ is F or Cl; or
$R^{5a}$ is F or Cl, $R^{5b}$ is H, $R^{5c}$ is F or Cl, $R^{5d}$ is F or Cl, and $R^{5e}$ is F or Cl; or
$R^{5a}$ is F or Cl, $R^{5b}$ is F or Cl, $R^{5c}$ is F or Cl, $R^{5d}$ is H, and $R^{5e}$ is F or Cl; or
$R^{a}$ is F or Cl, $R^{5b}$ is F or Cl, $R^{5c}$ is F or Cl, $R^{5d}$ is H, and $R^{5e}$ is F or Cl; or
$R^{5a}$ is F or Cl, $R^{5b}$ is F or Cl, $R^{5c}$ is H, $R^{5d}$ is F or Cl, and $R^{5e}$ is F or Cl.

In some embodiments:
$R^{5a}$ is F, $R^{5b}$ is H, $R^{5c}$ is H, $R^{5d}$ is H, and $R^{5e}$ is H; or
$R^{5a}$ is H, $R^{5b}$ is F, $R^{5c}$ is H, $R^{5d}$ is H, and $R^{5e}$ is H; or
$R^{5a}$ is H, $R^{5b}$ is H, $R^{5c}$ is F, $R^{5d}$ is H, and $R^{5e}$ is H; or
$R^{5a}$ is H, $R^{5b}$ is H, $R^{5c}$ is H, $R^{5d}$ is F, and $R^{5e}$ is H; or
$R^{5a}$ is H, $R^{5b}$ is H, $R^{5c}$ is H, $R^{5d}$ is H, and $R^{5e}$ is F; or
$R^{5a}$ is F, $R^{5b}$ is F, $R^{5c}$ is H, $R^{5d}$ is H, and $R^{5e}$ is H; or
$R^{5a}$ is F, $R^{5b}$ is H, $R^{5c}$ is F, $R^{5d}$ is H, and $R^{5e}$ is H; or
$R^{5a}$ is F, $R^{5b}$ is H, $R^{5c}$ is H, $R^{5d}$ is F, and $R^{5e}$ is H; or
$R^{5a}$ is F, $R^{5b}$ is H, $R^{5c}$ is H, $R^{5d}$ is H, and $R^{5e}$ is F; or
$R^{5a}$ is H, $R^{5b}$ is F, $R^{5c}$ is F, $R^{5d}$ is H, and $R^{5e}$ is H; or
$R^{5a}$ is H, $R^{5b}$ is F, $R^{5c}$ is H, $R^{5d}$ is F, and $R^{5e}$ is H; or
$R^{5a}$ is H, $R^{5b}$ is F, $R^{5c}$ is H, $R^{5d}$ is H, and $R^{5e}$ is F; or
$R^{5a}$ is H, $R^{5b}$ is H, $R^{5c}$ is F, $R^{5d}$ is F, and $R^{5e}$ is H; or
$R^{5a}$ is H, $R^{5b}$ is H, $R^{5c}$ is F, $R^{5d}$ is H, and $R^{5e}$ is F; or
$R^{5a}$ is H, $R^{5b}$ is H, $R^{5c}$ is H, $R^{5d}$ is F, and $R^{5e}$ is F; or
$R^{5a}$ is F, $R^{5b}$ is F, $R^{5c}$ is F, $R^{5d}$ is H, and $R^{5e}$ is H; or
$R^{5a}$ is F, $R^{5b}$ is F, $R^{5c}$ is H, $R^{5d}$ is F, and $R^{5e}$ is H; or
$R^{5a}$ is F, $R^{5b}$ is F, $R^{5c}$ is H, $R^{5d}$ is F, and $R^{5e}$ is F; or
$R^{5a}$ is F, $R^{5b}$ is H, $R^{5c}$ is F, $R^{5d}$ is F, and $R^{5e}$ is H; or
$R^{5a}$ is F, $R^{5b}$ is H, $R^{5c}$ is F, $R^{5d}$ is H, and $R^{5e}$ is F; or
$R^{5a}$ is F, $R^{5b}$ is H, $R^{5c}$ is H, $R^{5d}$ is F, and $R^{5e}$ is F; or
$R^{5a}$ is H, $R^{5b}$ is F, $R^{5c}$ is F, $R^{5d}$ is F, and $R^{5e}$ is H; or
$R^{5a}$ is H, $R^{5b}$ is F, $R^{5c}$ is F, $R^{5d}$ is H, and $R^{5e}$ is F; or
$R^{5a}$ is H, $R^{5b}$ is F, $R^{5c}$ is H, $R^{5d}$ is F, and $R^{5e}$ is F; or
$R^{5a}$ is H, $R^{5b}$ is H, $R^{5c}$ is F, $R^{5d}$ is F, and $R^{5e}$ is F; or
$R^{5a}$ is H, $R^{5b}$ is F, $R^{5c}$ is F, $R^{5d}$ is F, and $R^{5e}$ is F; or
$R^{5a}$ is F, $R^{5b}$ is H, $R^{5c}$ is F, $R^{5d}$ is F, and $R^{5e}$ is F; or
$R^{5a}$ is F, $R^{5b}$ is F, $R^{5c}$ is F, $R^{5d}$ is H, and $R^{5e}$ is F; or
$R^{5a}$ is F, $R^{5b}$ is F, $R^{5c}$ is F, $R^{5d}$ is H, and $R^{5e}$ is F; or
$R^{5a}$ is F, $R^{5b}$ is F, $R^{5c}$ is H, $R^{5d}$ is F, and $R^{5e}$ is F.

In certain embodiments, $R^4$ is not 2,3,5,6-tetrafluorophenoxymethyl.

In some embodiments, the invention provides compounds of Formula I, Formula IIa, and/or Formula IIb, and pharmaceutically acceptable salts thereof, wherein $R^5$ is selected from 2-fluorophenyl; 3-fluorophenyl; 4-fluorophenyl; 2,3-difluorophenyl; 2,4-difluorophenyl; 2,5-difluorophenyl; 2,6-difluorophenyl; 3,4-difluorophenyl; 3,5-difluorophenyl; 2,3,4-trifluorophenyl; 3,4,5-trifluorophenyl; 2,3,6-trifluorophenyl; 2,3,5-trifluorophenyl; and 2,3,5,6-tetrafluorophenyl.

In some embodiments, the invention provides compounds of Formula I, Formula IIa, and/or Formula IIb, and pharmaceutically acceptable salts thereof, wherein $R^5$ is selected from 2,6-difluorophenyl; 2,3,6-trifluorophenyl; and 2,3,5,6-tetrafluorophenyl.

In some embodiments, the invention provides compounds of Formula I, Formula IIa, and/or Formula IIb, and pharmaceutically acceptable salts thereof, wherein $R^{4a}$ is $C_{5-12}$ heteroaryl. $R^{4a}$ can be, for example, pyrrolyl, pyridinyl, imidazolyl, pyrazolyl, triazolyl, tetrazolyl, pyrazinyl, triazinyl, indolyl, isoindolyl, or quinolinyl. In some embodiments, $R^{4a}$ is isoxazolyl.

In some embodiments, the invention provides compounds of Formula I, Formula IIa, and/or Formula IIb, and pharmaceutically acceptable salts thereof, wherein $R^{4a}$ is —O—$R^5$, wherein $R^5$ is $C_{1-6}$ haloalkyl. In such embodiments, $R^5$ can be, e.g., chloromethyl, dichloromethyl, trichloromethyl, fluoromethyl, difluoromethyl, trifluoromethyl, 2,2,2-trichloroethyl, 2,2,2-trifluoroethyl, pentachloroethyl, pentafluoroethyl, 1,1,1,3,3,3-hexachloropropyl, 1,1,1,3,3,3-hexafluoropropyl, or the like. In some embodiments, $R^5$ is 1,1,1,3,3,3-hexafluoroprop-2-yl.

In some embodiments, the invention provides compounds of Formula I, Formula IIa, and/or Formula IIb, and pharmaceutically acceptable salts thereof, wherein $R^{4a}$ is selected from —S—$R^6$ and —SO$_2$—$R^6$, wherein $R^6$ is $C_{1-6}$ alkyl. In such embodiments, $R^6$ can be, e.g., methyl, ethyl, propyl, isopropyl, butyl, isobutyl, sec butyl, tert butyl, pentyl, isopentyl, or hexyl.

In some embodiments, the invention provides compounds of Formula I, Formula IIa, and/or Formula IIb, and pharmaceutically acceptable salts thereof, wherein $R^{4a}$ is —N($R^7$)$_2$, wherein each $R^7$ is independently selected $C_{1-6}$ alkyl. In such embodiments, each $R^7$ can independently be, e.g., methyl, ethyl, propyl, isopropyl, butyl, isobutyl, sec butyl, tert butyl, pentyl, isopentyl, or hexyl.

In some embodiments, the invention provides compounds of Formula I, Formula IIa, and/or Formula IIb, and pharmaceutically acceptable salts thereof, wherein $R^4$ is haloalkyl. For example, $R^5$ can be chloromethyl, dichloromethyl, trichloromethyl, difluoromethyl, or trifluoromethyl.

The compounds of the invention can be further substituted; a compound according to Formula I may contain, for example, an optionally substituted $R^{1a}$ and/or $R^{1b}$ group, one or more optionally substituted $R^2$ groups, an optionally substituted $R^3$ group, and/or an optionally substituted $R^4$ group (including, an optionally substituted $R^5$ group, an optionally substituted $R^6$ group, and/or one or more optionally substituted $R^7$ groups).

In some embodiments, the aminopyridyl ketone compound is selected from:

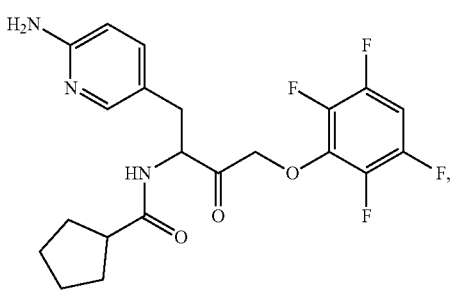

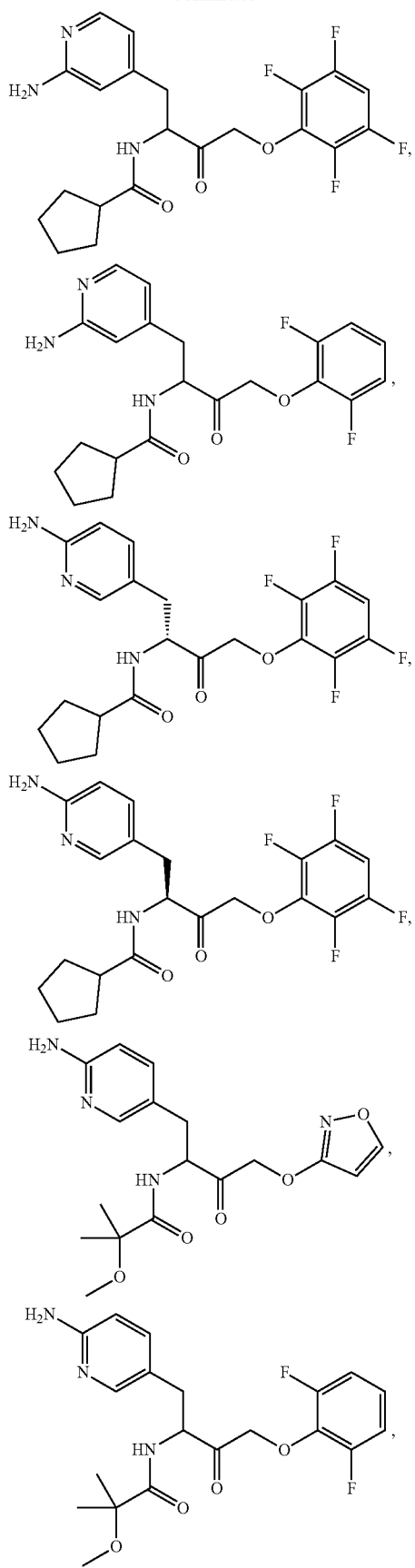
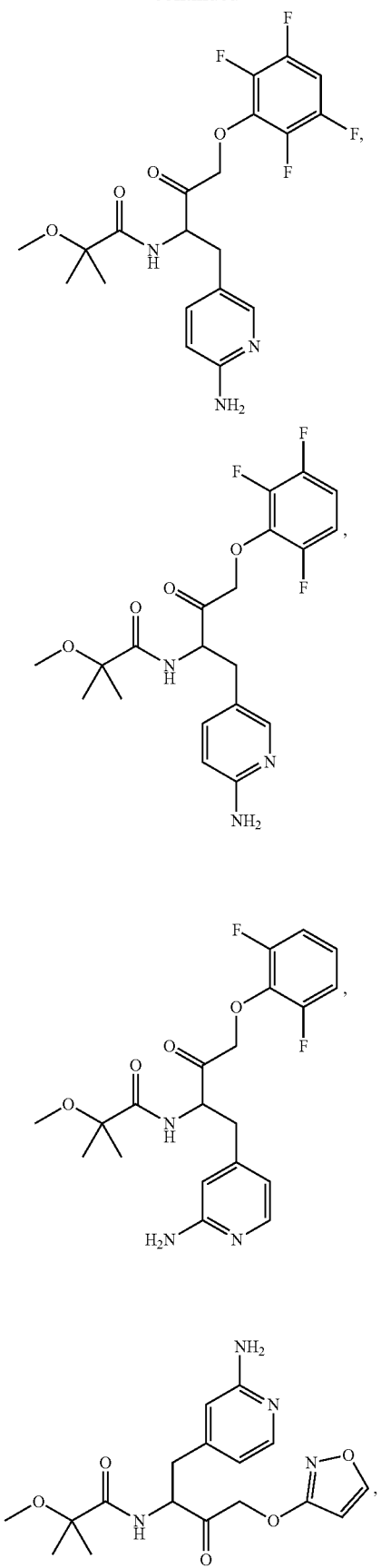

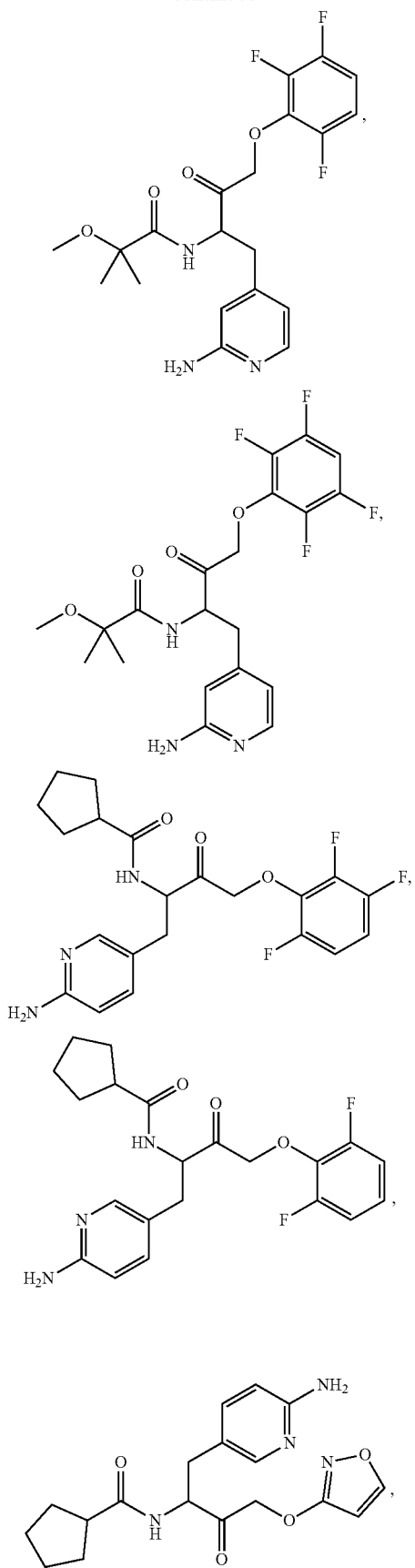
and pharmaceutically acceptable salts thereof.
Aminopyridyl ketones may be prepared by the following approaches, summarized in Scheme 1 and described below. As shown in Scheme 1, aminopyridines (e.g., 2-amino-4- formylpyridine and 2-amino-5-formylpyridine (xi)) can be reacted with a suitable protecting reagent (e.g., di-tert-butyl dicarbonate) to prepare the corresponding mono- and/or di-protected formylpyridines (xii), wherein $P^1$ is H or a protecting group and $P^2$ is a protecting group. Any of these aldehydes (xii) may be reacted with a protected phosphonate (xiii) (wherein $Q^1$ is H or a protecting group; $Q^2$ is a protecting group; and each R is independently $C_{1-6}$ alkyl; e.g., $ZHNCH(CO_2Me)PO_3Me_2$) and a strong base to prepare dehydro-aminopyridylalanine methyl esters (xiv).

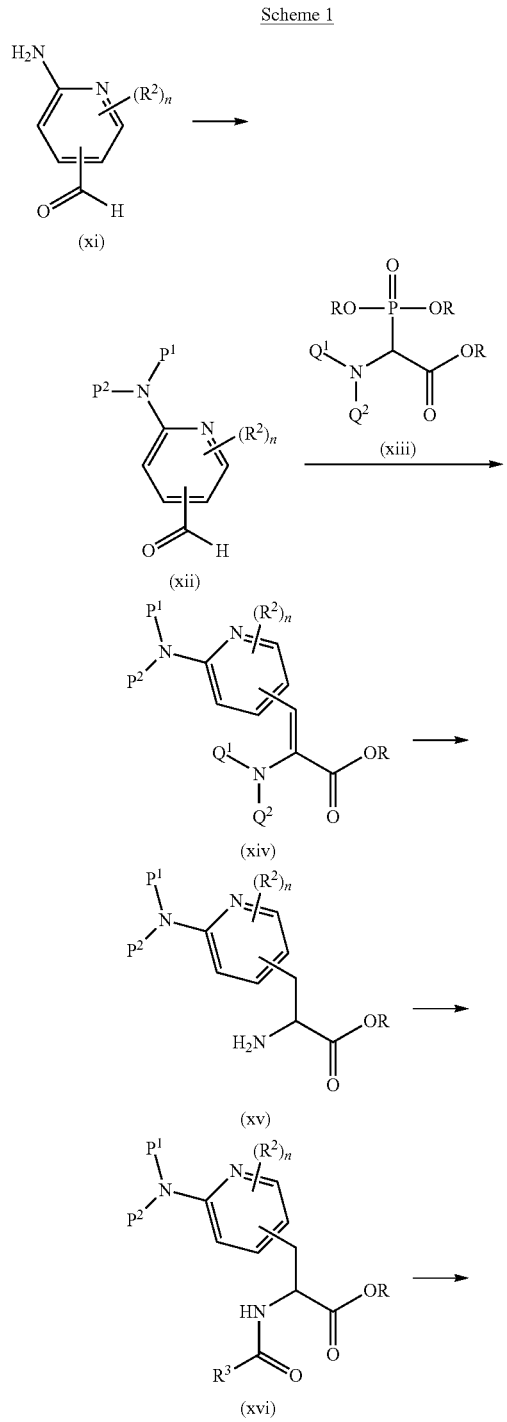

Scheme 1

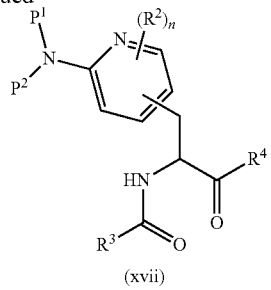

(xvii)

When $Q^1$ and/or $Q^2$ is a Z group (or another protecting group which can be removed by hydrogenation), dehydro-aminopyridylalanines (xiv) may be hydrogenated in the presence of palladium on carbon, providing aminoesters (xv) by simultaneously saturating the olefins and deprotecting the α-amino group. The free amino groups may be reacted with carboxylic acids ($R^3C(O)OH$) and dehydrating agents to form amidoesters (xvi). The dehydrating agent may be HATU or any of many other reagents suitable for carboxamide formation. The amidoesters may be converted to protected products (xvii) by various routes. In one non-limiting example, the amidoesters are hydrolyzed using a strong based such as NaOH. The resulting carboxylic acids are then reacted with $ClCO_2Et$, a tertiary amine, and diazo methane to form diazomethyl ketones, which can then be treated with HBr to give bromomethyl ketones. In another sequence, the methyl esters may be treated with $ClCH_2I$ and $LiN(iPr)_2$ to provide chloromethyl ketones in one step. The bromomethyl ketones or chloromethyl ketones can be heated with substituted phenols and KF in DMF to give aryloxymethyl ketones. In another non-limiting example, the bromomethyl or chloromethyl ketones are treated with isoxazole-5-one and KF in DMF to give isoxazolyloxymethyl ketones. Lastly, the protecting groups $P^1$ and $P^2$ (e.g., Boc groups) may be removed under suitable conditions (e.g., via treatment with trifluoroacetic acid), to afford the desired final products.

The starting materials and reagents used in preparing the compounds of the invention are either available from commercial suppliers or are prepared by methods known to those skilled in the art following procedures set forth in references such as Fieser and Fieser's Reagents for Organic Synthesis, Vol. 1-28 (Wiley, 2016); March's Advanced Organic Chemistry, $7^{th}$ Ed. (Wiley, 2013); and Larock's Comprehensive Organic Transformations, $2^{nd}$ Ed. (Wiley, 1999). The starting materials and the intermediates of the reaction can be isolated and purified if desired using conventional techniques including, but not limited to, filtration, distillation, crystallization, chromatography and the like. Such materials can be characterized using conventional means, including measuring physical constants and obtaining spectral data.

Unless specified to the contrary, the reactions described herein take place at atmospheric pressure over a temperature range of from about −78° C. to about 250° C. For example, reactions can be conducted at from about 0° C. to about 125° C., or at about room (or ambient) temperature, e.g., about 20° C. In some embodiments, reactions are conducted at about 0° C., 20° C., 25° C., 90° C., 10° C., 110° C., 125° C., 150° C., 175° C., or 200° C. In some embodiments, reactions are conducted starting at a first temperature (e.g., about −78° C. or about 0° C.), and allowed to warm to a higher second temperature (e.g., about 20° C. or about 25° C.). One of skill in the art will appreciate that various modifications to the procedures described herein can be made.

The invention provides a number of useful aminopyridinecyanamide compounds having various aminopyridine moieties such as aminopyridines (e.g., 2-aminopyridines), aminoisoquinolines (e.g., 1-aminoisoquinolines and 1-amino-6,7,8,9-tetrahydrobenzo[g]iso-quinolines), aminofuropyridines (e.g., 7-aminofuro[2,3-c]pyridines and 4-aminofuro[3,2-c]pyridines), and aminonapthyridines (e.g., 3-amino-1,7-naphthyridines and 8-amino-2,7-naphthyridines).

In one embodiment, the invention provides a compound according to Formula III:

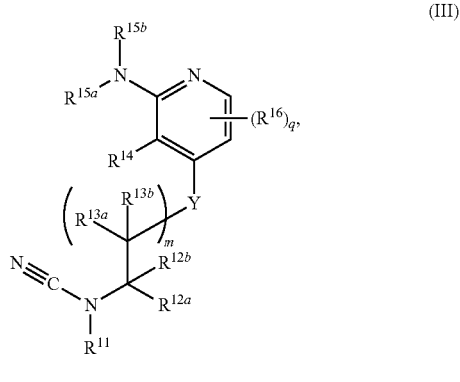

(III)

or a pharmaceutically acceptable salt thereof, wherein:
$R^{11}$ is selected from $C_{1-6}$ alkyl and $C_{3-8}$ cycloalkyl;
$R^{12a}$ and $R^{12b}$ are independently selected from H, $C_{1-6}$ alkyl, and $C_{6-10}$ aryl, or
  $R^{12a}$ and $R^{12b}$ are taken together to form $C_{3-6}$ cycloalkyl, or
  $R^{12a}$ and $R^{11}$ are taken together to form 4- to 10-membered heterocyclyl which is optionally substituted with one or more $R^{17}$;
each $R^{13a}$ and each $R^{13b}$ is independently selected from H, —OH, and $C_{1-6}$ alkyl, or one $R^{13a}$ and $R^{11}$ are taken together to form 4- to 10-membered heterocyclyl, or one $R^{13b}$ and $R^{12b}$ are taken together to form a 5- or 6-membered ring;
$R^{14}$ is selected from H and halogen, or
  $R^{14}$, $R^{12a}$, and $R^{12b}$ are taken together to form a 6- to 8-membered ring, which is optionally substituted with one or more $R^{18}$, or
  $R^{14}$ and one $R^{13a}$ are taken together to form a 5- to 8-membered ring, which is optionally substituted with one or more $R^{18}$, or
  $R^{14}$ is taken together with one $R^{13a}$ and one $R^{13b}$ on the same carbon atom to form a 5- to 8-membered ring, which is optionally substituted with one or more $R^{18}$, or
  $R^{14}$, $R^{11}$, and $R^{12a}$ are taken together to form a 6- to 10-membered bicyclic ring, which is optionally substituted with one or more $R^{18}$;
$R^{15a}$ and $R^{15b}$ are independently selected from H and $C_{1-6}$ alkyl;
$R^{16}$ is independently selected from $C_{1-6}$ alkyl and halogen;
each $R^{17}$ is independently selected from $C_{1-6}$ alkyl, $C_{1-6}$ alkoxy, $C_{1-6}$ haloalkyl, $C_{1-6}$ haloalkoxy, —OH, and —N($R^{17a}$)$_2$, wherein each $R^{17a}$ is independently selected from H and $C_{1-6}$ alkyl;

each $R^{18}$ is independently selected from $C_{1-6}$ alkyl and halogen;
Y is selected from O, S, C($R^{19a}$)$_2$, and N$R^{19b}$;
each $R^{19a}$ is selected from H and $C_{1-6}$ alkyl, or
  one $R^{19a}$ and one $R^{13b}$ on adjacent atoms are taken together to form a double bond;
$R^{19b}$ is selected from H and $C_{1-6}$ alkyl, or
  $R^{19b}$ and $R^{11}$ are taken together to form a 4- to 6-membered ring;
subscript m is 0, 1, 2, or 3; and
subscript q is 0 or 1.

In some embodiments, the invention provides compounds according to Formula

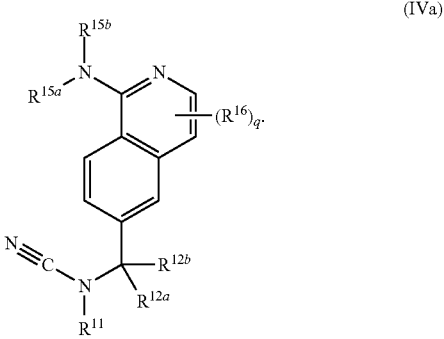

(IVa)

In some embodiments, the invention provides compounds according to Formula IVb:

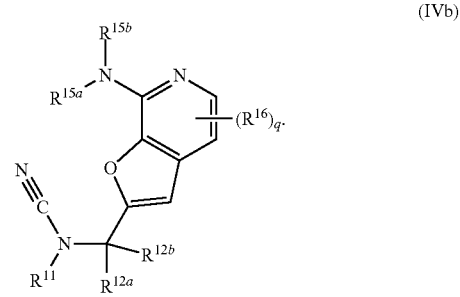

(IVb)

In some embodiments, the invention provides compounds according to Formula

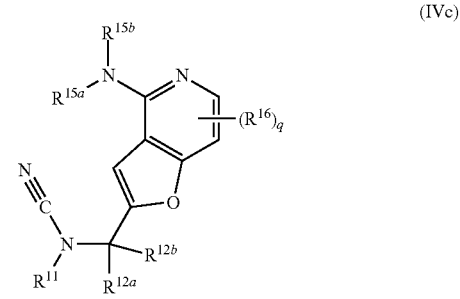

(IVc)

In some embodiments, the invention provides compounds according to Formula V:

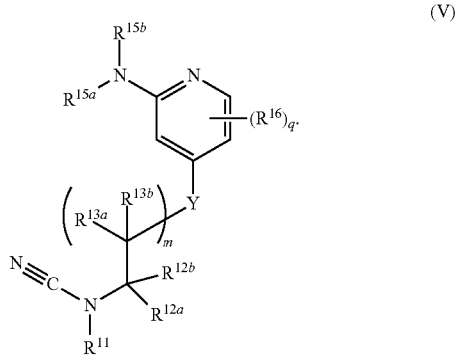

(V)

In some embodiments, the invention provides compounds according to Formula III or Formula V wherein Y is O or S. In some embodiments, the invention provides compounds according to Formula III or Formula V wherein Y is $CH_2$. In some embodiments, W is selected from O, S, and $CH_2$, and each $R^{13a}$ and each $R^{13b}$ is selected from H and $C_{1-6}$ alkyl.

In some embodiments, Y is O and each $R^{13a}$ and each $R^{13b}$ is independently selected from H, —OH, methyl, ethyl, n-propyl, isopropyl, n-butyl, sec-butyl, isobutyl, tert-butyl, n-pentyl, branched pentyl, n-hexyl, and branched hexyl. In some embodiments, Y is S and each $R^{13a}$ and each $R^{13b}$ is independently selected from H, —OH, methyl, ethyl, n-propyl, isopropyl, n-butyl, sec-butyl, isobutyl, tert-butyl, n-pentyl, branched pentyl, n-hexyl, and branched hexyl. In some embodiments, Y is $CH_2$ and each $R^{13a}$ and each $R^{13b}$ is independently selected from H, —OH, methyl, ethyl, n-propyl, isopropyl, n-butyl, sec-butyl, isobutyl, tert-butyl, n-pentyl, branched pentyl, n-hexyl, and branched hexyl.

In some embodiments, Y is selected from O, S, and $CH_2$, and one of $R^{13a}$ and $R^{13b}$ is selected from H and —OH, and the remaining $13^{3a}$ and $R^{13b}$ groups are selected from H and $C_{1-6}$ alkyl.

In some embodiments, Y is $CH(R^{19a})$, and $R^{19a}$ and one $R^{13b}$ are taken together to form a double bond. In some embodiments, the grouping —$CH(R^{19a})(CR^{13a}R^{13b})_m$— is selected from ethen-diyl, prop-1-en-1,3-diyl, and but-1-en-1,4-diyl.

In some embodiments, Y is $CH(R^{19a})$, subscript m is 1, and $R^{19a}$ and $R^{13b}$ are taken together to form a double bond. In some such embodiments, $R^{13a}$ is selected from H, —OH, methyl, ethyl, n-propyl, isopropyl, n-butyl, sec-butyl, isobutyl, tert-butyl, n-pentyl, branched pentyl, n-hexyl, and branched hexyl H. In some such embodiments, $R^{13}$ is H.

In some embodiments, Y is $NR^{19b}$, and $R^{19b}$ and $R^{11}$ are taken together to form a 5- or 6-membered ring. For example, $R^{19b}$ and $R^{11}$ can form imidazolidin-diyl or piperazin-diyl. In some embodiments, $R^{19b}$ and $R^{11}$ are taken together to form 1,4-piperazin-diyl.

In some embodiments, $R^{12a}$ and $R^{11}$ are taken together to form 4- to 10-membered heterocyclyl in the compounds according to Formula III, Formula IVa, Formula IVb, Formula IVc, or Formula V. For example, $R^{12a}$ and $R^{11}$ can be taken together to form aziridin-diyl, azetidin-diyl, diazetidin-diyl, pyrrolidin-diyl, imidazolidin-diyl, pyrazolidin-diyl, piperidin-diyl, piperazin-diyl, morpholin-diyl, azepan-diyl, diazepan-diyl, azocan-diyl, or indolin-diyl. In some embodiments, $R^{12a}$ and $R^{11}$ are taken together to form azetidin-1,2-diyl, pyrrolidin-1,2-diyl, piperidin-1,2-diyl, indolin-1,2-diyl, or isoindolin-1,2-diyl.

In some embodiments, the compound has a structure according to Formula III, Formula IVa, Formula IVb, Formula IVc, or Formula V, and $R^{12a}$ and $R^{11}$ are taken together to form pyrrolidin-1,2-diyl or piperidin-1,2-diyl. In some embodiments, the pyrrolidin-1,2-diyl or piperidin-1,2-diyl is subsisted with one or two $R^{17}$. In some embodiments, the pyrrolidin-1,2-diyl or piperidin-1,2-diyl is subsisted with one $R^{17}$. In some embodiments, $R^{17}$ is selected from $C_{1-6}$ alkoxy, $C_{1-6}$ haloalkoxy, —OH, and —$N(R^{17a})_2$. In some embodiments, $R^{17}$ is selected from —OH, —$NH_2$, methoxy, and dimethylamino.

In some embodiments, the compound has a structure according to Formula V, and $R^{12a}$ and $R^{11}$ are taken together to form azetidin-1,2-diyl, pyrrolidin-1,2-diyl, piperidin-1,2-diyl, indolin-1,2-diyl, or isoindolin-1,2-diyl. In some embodiments, the azetidin-1,2-diyl, pyrrolidin-1,2-diyl, piperidin-1,2-diyl, indolin-1,2-diyl, or isoindolin-1,2-diyl is substituted with one or two $R^7$. In some embodiments, the azetidin-1,2-diyl, pyrrolidin-1,2-diyl, piperidin-1,2-diyl, indolin-1,2-diyl, or isoindolin-1,2-diyl is substituted with one $R^{17}$. In some embodiments, $R^{17}$ is $C_{1-6}$ alkoxy, $C_{1-6}$ haloalkoxy, —OH, or —$N(R^{17a})_2$. In some embodiments, $R^{17}$ is selected from —OH, —$NH_2$, methoxy, and dimethylamino.

In some embodiments, the invention provides compounds according Formula III, Formula IVa, Formula IVb, Formula IVc, and/or Formula V, wherein $R^{12a}$ is H and $R^{12b}$ is selected from H, $C_{1-6}$ alkyl, and $C_{6-10}$ aryl. For example, $R^{12b}$ can be methyl, ethyl, n-propyl, isopropyl, n-butyl, tert-butyl, or phenyl.

In some embodiments, the invention provides compounds according to Formula III, Formula IVa, Formula IVb, Formula IVc, and/or Formula V, wherein $R^{11}$ is $C_{1-6}$ alkyl. For example, $R^{11}$ can be methyl, ethyl, n-propyl, isopropyl, n-butyl, sec-butyl, isobutyl, tert-butyl, n-pentyl, branched pentyl, n-hexyl, or branched hexyl. In some embodiments, $R^{11}$ is $C_{3-8}$ cycloalkyl. In some embodiments, $R^{11}$ is cyclopropyl, cyclobutyl, cyclopentyl, cyclohexyl, cycloheptyl, or cyclooctyl. In some embodiments, the invention provides compounds of Formula III, Formula IVa, Formula IVb, Formula IVc, or Formula V as described above, wherein $R^{11}$ is selected from methyl, ethyl, isopropyl, cyclopentyl, and cyclohexyl. In some such embodiments, $R^{11}$ is selected from methyl, isopropyl, and cyclohexyl.

In some embodiments, the invention provides compounds according to Formula III, Formula IVa, Formula IVb, Formula IVc, and/or Formula V, wherein each of $R^{15a}$ and $R^{15b}$ is independently selected from H, methyl, ethyl, n-propyl, isopropyl, n-butyl, sec-butyl, isobutyl, tert-butyl, n-pentyl, branched pentyl, n-hexyl, and branched hexyl. In some embodiments, $R^{15a}$ is H and $R^{15b}$ is selected from H, methyl, ethyl, n-propyl, isopropyl, n-butyl, sec-butyl, isobutyl, tert-butyl, n-pentyl, branched pentyl, n-hexyl, and branched hexyl. In some embodiments, $R^{15b}$ is selected from H, methyl, ethyl, n-propyl, isopropyl, n-butyl, sec-butyl, isobutyl, tert-butyl, n-pentyl, branched pentyl, n-hexyl, and branched hexyl and $R^{15a}$ is H. In some embodiments, $R^{15a}$ and $R^{15b}$ are H.

The aminopyridinecyanamide compounds of the invention can be prepared in protected form (e.g., protected compounds wherein at least one of $R^{15a}$, $R^{15b}$, $R^{17a}$, and $R^{19b}$ is an amine protecting group). A number of suitable protecting groups—as described, for example, by Green and Wuts (*Protective Groups in Organic Synthesis*, 4th Ed. 2007, Wiley-Interscience, New York)—can be used. In some embodiments, $R^{15a}$ is H and $R^{15b}$ is selected from benzyloxycarbonyl; 9-fluorenylmethyl-oxycarbonyl; tert-butyloxycarbonyl; and allyloxycarbonyl. In some embodiments, $R^{15a}$ and $R^{15b}$ are selected from benzyloxycarbonyl; 9-fluorenylmethyl-oxycarbonyl; tert-butyloxycarbonyl; and allyloxycarbonyl. In some embodiments, $R^{15a}$ is H and $R^{15b}$ is tert-butyloxycarbonyl. Compounds can also be prepared in alkylated form (i.e., compounds wherein at least one of $R^{15a}$, $R^{15b}$, $R^{17a}$, and $R^{19b}$ is an alkyl group). One or both of $R^{17a}$ and $R^{19b}$ can be, for example, methyl, ethyl, n-propyl, isopropyl, n-butyl, or t-butyl.

In some embodiments, the invention provides compounds according to Formula III, Formula IVa, Formula IVb, Formula IVc, and/or Formula V, wherein subscript q is 0. In some embodiments, the invention provides compounds according to Formula III, Formula IVa, Formula IVb, Formula IVc, and/or Formula V, wherein subscript q is 1. In some such embodiments, subscript q is 1 and $R^{16}$ is selected from fluoro, chloro, bromo, iodo, methyl, ethyl, n-propyl, isopropyl, n-butyl, sec-butyl, isobutyl, tert-butyl, n-pentyl, branched pentyl, n-hexyl, and branched hexyl. In some embodiments, subscript q is 1 and $R^{16}$ is selected from fluoro, chloro, and methyl. In some embodiments, subscript q is 2.

The compounds of the invention can be further substituted; a compound according to Formula III may contain, for example, an optionally substituted $R^{11}$ group, an optionally substituted $R^{12a}$ and/or $R^{12b}$ group, one or more optionally substituted $R^{13a}$ and/or $R^{13b}$ groups, an optionally substituted $R^{14}$ group, an optionally substituted $R^{15a}$ and/or $R^{15b}$ group, one or more optionally substituted $R^{16}$ groups, one or more optionally substituted $R^{17}$ groups, one or more optionally substituted $R^{18}$ groups, one or more optionally substituted $R^{19a}$ groups, and/or an optionally substituted $R^{19b}$ group.

In some embodiments, the aminopyridinecyanamide compound is selected from:

-continued

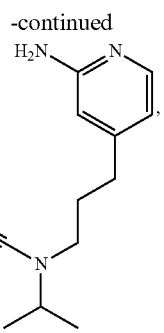

and pharmaceutically acceptable salts thereof.

In some embodiments, the aminopyridinecyanamide compound is selected from:

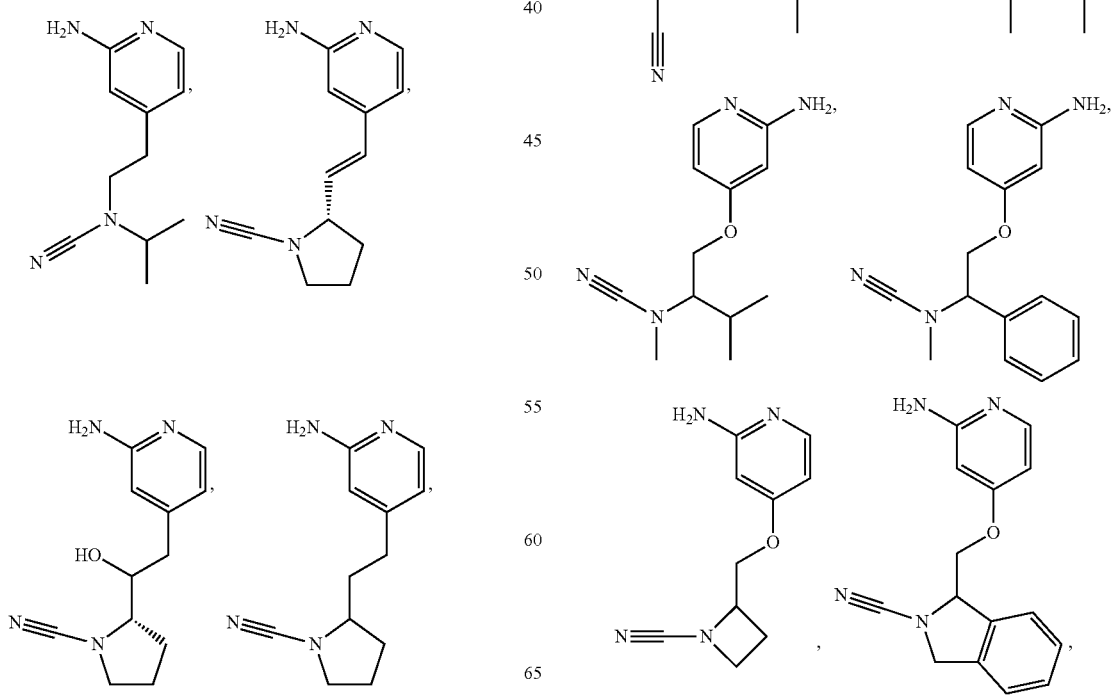

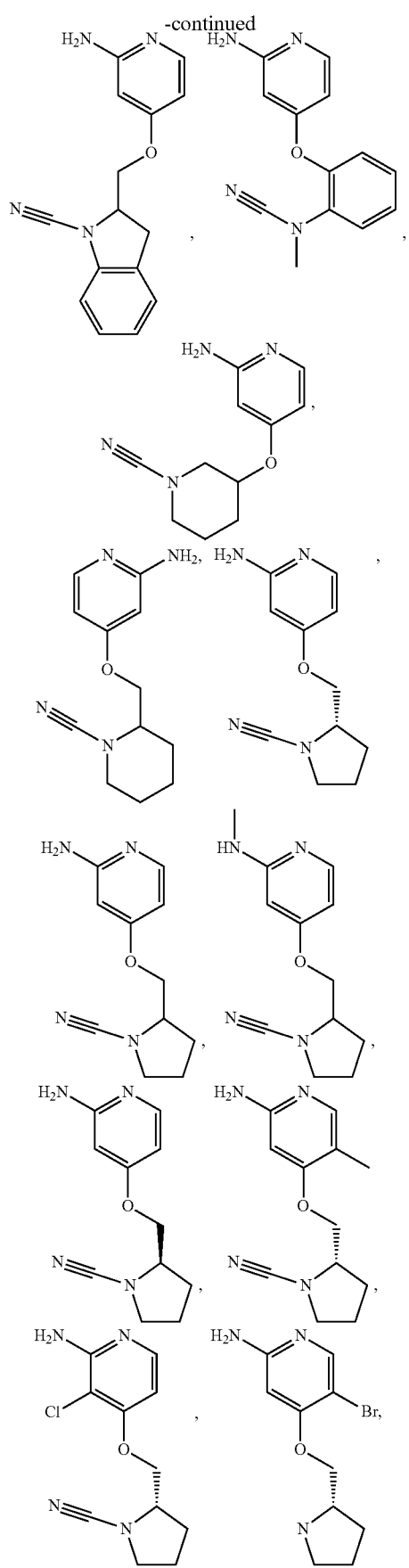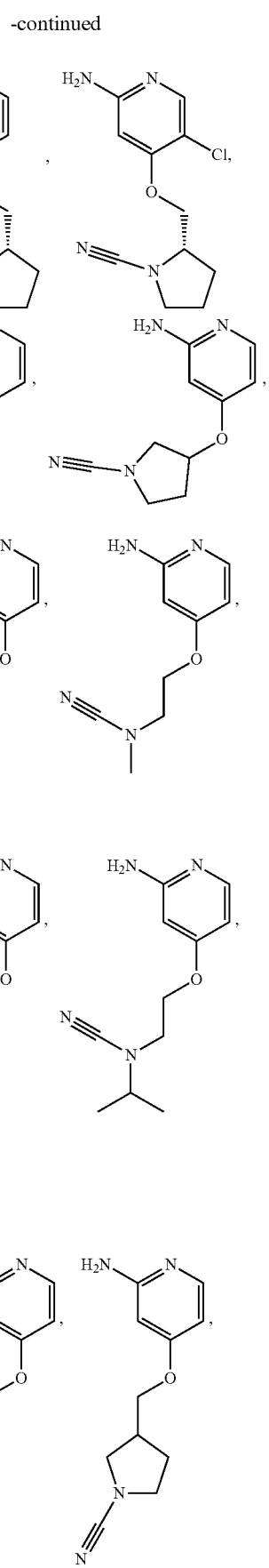

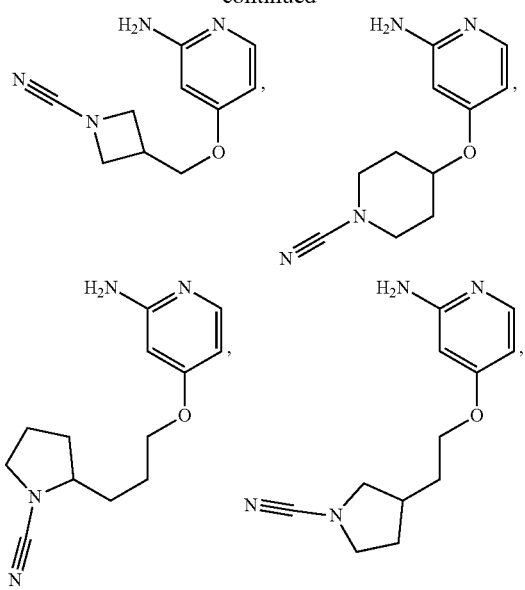
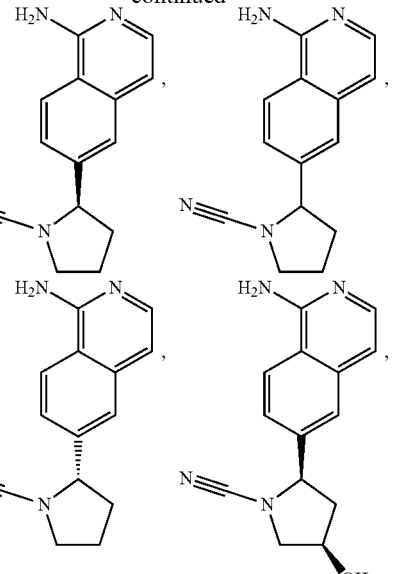
and pharmaceutically acceptable salts thereof.
In some embodiments, the aminopyridinecyanamide compound is selected from:
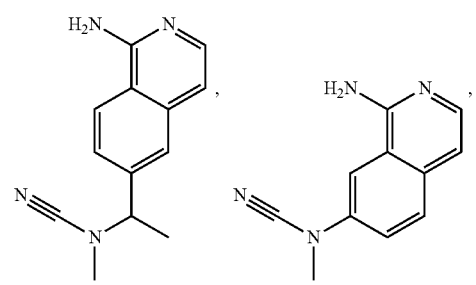
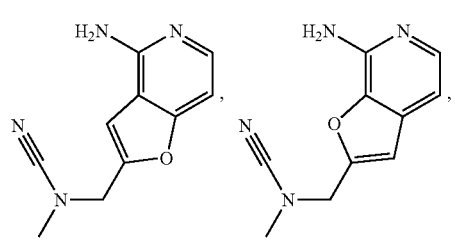
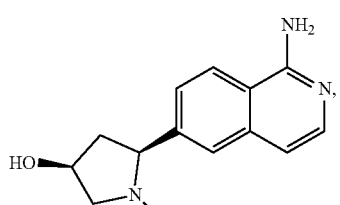
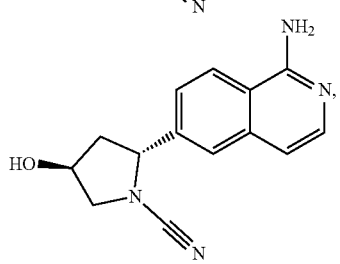
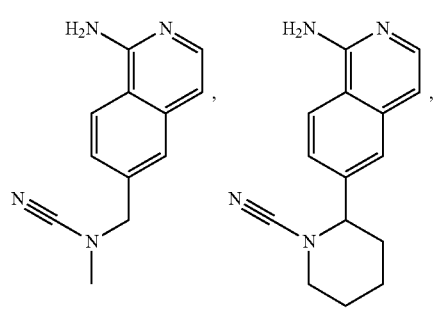
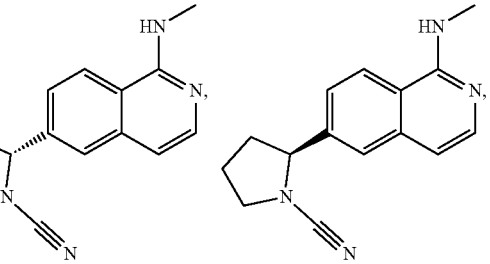
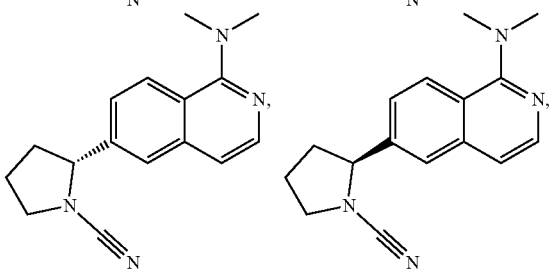
and pharmaceutically acceptable salts thereof.
The aminopyridinecyanamide compounds of the invention may be prepared by the approaches summarized in Scheme 2 and described below. As shown in Scheme 2, an amine (i), bearing a reactive group $G^1$, can be reacted with an amino-heterocycle (ii), bearing a reactive group $G^2$. This reaction involves transformation of reactive groups $G^1$ and $G^2$ to form intermediate (iii) containing a linkage Y between the amine and the amino-heterocycle structures. Prior to this reaction, the amine is usually protected and the amino-heterocycle is sometimes protected. In general, $P^{11}$ is selected from $R^{11}$ as described above, hydrogen, and a protecting group; $P^{12}$ is selected from hydrogen and a protecting group; and $Q^{11}$ and $Q^{12}$ are independently selected from hydrogen, $R^{15a}$ as described above, $R^{15b}$ as described above, and a protecting group. Any suitable protecting group (e.g., tert-butoxy carbonyl (Boc), benzyloxycarbonyl (Z), trifluoroacetyl, or another easily removed group) can be used for protecting the amine and the amino-heterocycle, and the protecting groups are typically chosen so that either may be removed without removing the other. For example, Boc may be removed by treatment with trifluoroacetic acid, which does not remove Z. Meanwhile, Z may be removed by hydrogenolysis in the presence of palladium on carbon, which does not remove Boc.

A wide variety of reactive groups $G^1$ and $G^2$ are suitable for forming the linkage Y between the amine and amino-heterocycle structures. A halide $G^1$ group or a sulfonate ester $G^1$ group can undergo a Williamson reaction with a phenol $G^2$ group or thiophenol $G^2$ group on the amino-heterocycle to form a linking ether or thioether. Employing a phosphine (e.g., $Ph_3P$) and an azodicarboxylate (e.g., DEAD) as co-reagents, an alcohol $G^1$ group can undergo a Mitsunobu reaction with a phenol $G^2$ group or thiophenol $G^2$ group to form a linking ether

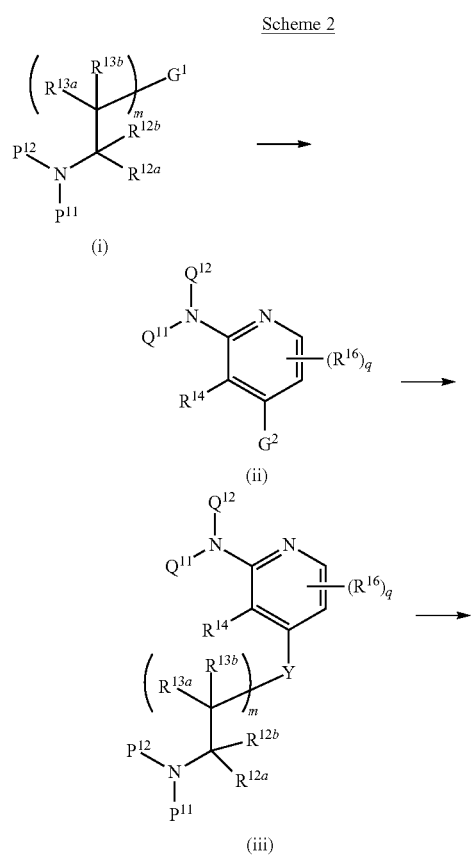

Scheme 2

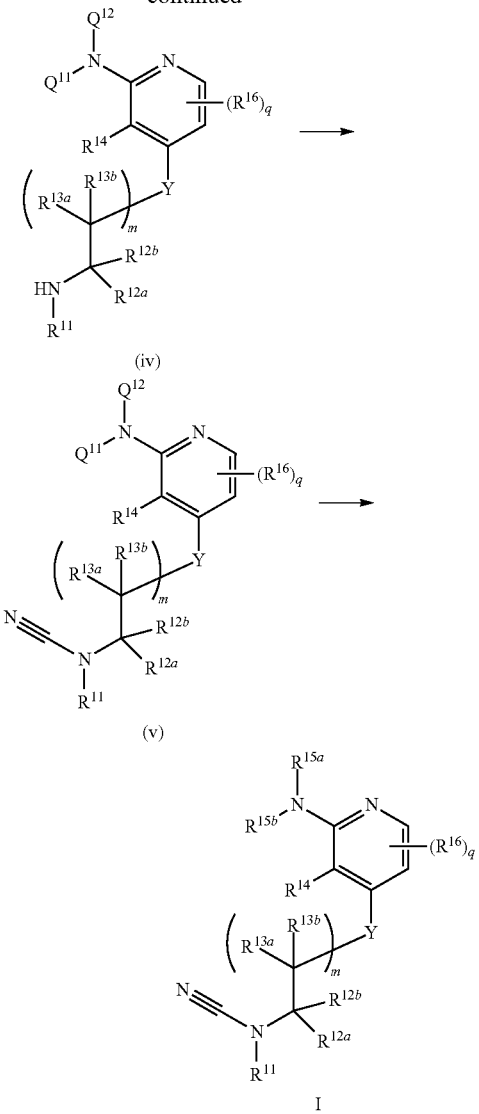

or thioether. An unprotected primary amine $G^1$ group or unprotected secondary amine $G^1$ group can undergo an Ullmann reaction with a halide $G^2$ group to form a secondary or tertiary linking amine. The Ullmann reaction can be catalyzed with a homogeneous copper or palladium catalyst, as described by Buchwald, Hartwig, Fu, and others.

An olefin $G^1$ group can undergo a Heck reaction with a halide $G^2$ group to form a linking olefin. An alkyne $G^1$ group can undergo a Sonagashira reaction with a halide $G^2$ group to form a linking alkyne. A boronic acid $G^1$ group can undergo a Suzuki reaction with a halide $G^2$ group or triflate $G^2$ group to form a biaryl linkage. A stannane $G^1$ group can undergo a Stille reaction with a halide $G^2$ group or triflate $G^2$ group to form a biaryl linkage. After a Heck, Sonagashira, Suzuki, or Stille reaction, certain intermediates (iii) (e.g., interemdiates wherein $P^{11}$ and $R^{12a}$ are taken together to form unsaturated heterocyclyl) can be hydrogenated to achieve partial or full saturation.

An aldehyde $G^1$ group on the amine may undergo a Grignard or "Grignard-like" reaction with an organomagnesium or organolithium $G^2$ group on the amino-heterocycle, to form a linkage bearing a secondary alcohol. A carboxylic acid $G^1$ group on the amine may undergo a decarboxylating photoreaction with a halide $G^2$ group on the amino-heterocycle to form a carbon-carbon bond between the decarboxylated amine and the amino-heterocycle.

After the reaction involving reactive groups $G^1$ and $G^2$, and formation of the linkage Y between the amine and amino-heterocycle, the protecting group on the amine can be removed to provide an amine (iv), and the amine can be reacted with cyanogen bromide to form a cyanamide (v). After formation of the cyanamide, any protecting group on the amino-heterocycle can be removed to provide products according to Formula III.

Other methods can also be used for preparing an amine (iv) for the corresponding cyanamide (v). In some instances, the amine precursor can be obtained via reductive amination of a ketone or aldehyde on the amino-heterocycle. In some instances, the amine precursor can be obtained via reduction of a nitro group on the amino-heterocycle and subsequent mono-alkylation of the resulting amino $G^2$ group. In some instances, the amine precursor can be obtained via reduction of a cyano group on the amino-heterocycle and subsequent monoalkylation of the resulting amino $G^2$ group. In some instances, the amine precursor can be obtained via simultaneous reduction of a nitro group and an olefin on the amino-heterocycle, and subsequent mono-alkylation of the resulting amino $G^2$ group. In some instances, the amine precursor can be obtained via simultaneous reduction of a cyano group and an olefin on the amino-heterocycle, and subsequent mono-alkylation of the resulting amino $G^2$ group. In some instances, the amine precursor can be obtained via a Schmidt reaction of a carboxylic acid on the amino-heterocycle, and subsequent mono-alkylation of the resulting amino $G^2$ group.

The compounds of the invention are highly active Rgp inhibitors, typically exhibiting Rgp $IC_{50}$ values in the nanomolar and micromolar range.

The term "$IC_{50}$" indicates how much of a compound is needed to inhibit a given biological process (or component of a process, e.g., an enzyme, cell, cell receptor, or microorganism) by one half (50%). The $IC_{50}$ value for a particular test compound can be measured as follows. Fifty microliters (µL) of an enzyme such as RgpA or RgpB (1 nM in 50 mM bis-Tris propane [pH 8.0] containing 1% [vol/vol] Triton X-100 and 5 mM 2-mercaptoethanol) is added to columns 1 to 11 of a 96-well plate, and 100 µL is added to column 12. Two µL of the test compound (100 µL in 100% DMSO) is added to column 12, and the sample is mixed three times by pipetting. Then, a doubling dilution is prepared across the plate by serial transfer into adjacent wells. 50 µL of Z-Arg-7-amido-4-methylcoumarin ("Z-Arg-AMC;" 40 µM in buffer) is added to all wells, and the contents are mixed. The reaction is monitored for AMC fluorescence for 15 min at 25° C., and the progress curves are automatically converted to rates by the Fluoroskan Ascent software. The $IC_{50}$ of a compound can then be determined by constructing a dose-response curve and examining the effect of different concentrations of the compound on reversing the activity of the enzyme. From the dose-response curve, $IC_{50}$ values can be calculated for a given compound by determining the concentration needed to inhibit half of the maximum biological response of the enzyme.

The method can also be used to assay enzymes including Kgp, trypsin, and cathepsin B. For Kgp, the substrate can be succinyl-Ala-Phe-Lys-AMC. For trypsin, the buffer can contain 10 mM Tris and 10 mM $CaCl_2$ (pH 8.0), and the substrate can be Z-Gly-Gly-Arg-AMC. For cathepsin B, the buffer can contain 50 mM sodium phosphate, 1 mM EDTA, and 10 mM 2-mercaptoethanol (pH 6.25), and the substrate can be Z-Arg-Arg-AMC.

In general, the Rgp $IC_{50}$ values for compounds of the invention range from about 0.01 nM to about 100 µM. The Rgp $IC_{50}$ value for a compound of the invention can range, for example, from about 0.01 nM to about 0.1 nM, or from about 0.1 nM to about 1 nM, or from about 1 nM to about 100 nM, or from about 100 nM to about 250 nM, or from about 250 nM to about 500 nM, or from about 500 nM to about 750 nM, or from about 750 nM to about 1 µM, or from about 1 µM to about 10 µM, or from about 10 µM to about 25 µM, or from about 25 µM to about 50 µM, or from about 50 µM to about 75 µM, or from about 75 µM to about 100 µM. The Rgp $IC_{50}$ value for a compound of the invention can range from about 0.01 nM to about 1 nM, or from about 0.05 nM to about 0.75 nM, or from about 0.1 nM to about 0.5 nM, from about 1 nM to about 100 nM, or from about 20 nM to about 80 nM, or from about 40 nM to about 60 nM, or from about 1 µM to about 100 µM, or from about 20 µM to about 80 µM, or from about 40 µM to about 60 µM.

In some embodiments, an Rgp inhibitor according to the invention has an RgpB $IC_{50}$ of 75 nM or less. In some embodiments, the Rgp inhibitor has an RgpB $IC_{50}$ of 50 nM or less. In some embodiments, the Rgp inhibitor has an RgpB $IC_{50}$ of 25 nM or less. In some embodiments, the Rgp inhibitor has an RgpB $IC_{50}$ of 10 nM or less. In some embodiments, the Rgp inhibitor has an RgpB $IC_{50}$ of 1 nM or less.

In certain embodiments, Rgp inhibitors according to the invention are selective for Rgp. As used herein, a "selective" Rgp inhibitor is a compound that does not substantially affect the activity of proteases other than RgpA and RgpB when administered at a therapeutically effective dose for treating a disease or condition associated with *P. gingivalis* infection. Typically, a protease that is not substantially affected by a particular compound exhibits at least 90% of its normal enzymatic activity in the presence of the compound under physiological conditions. Selective Rgp inhibitors include those compounds that do not affect the activity of proteases other than Rgp when administered at a therapeutically effective dose for treating a brain disorder, periodontal disease, diabetes, a cardiovascular disease, arthritis, rheumatoid arthritis, osteoarthritis, infectious arthritis, psoriatic arthritis, preterm birth, pneumonia, cancer, a kidney disease, a liver disease, a retinal disorder, or glaucoma associated with *P. gingivalis* infection. Preferably, selective Rgp inhibitors do not adversely affect the coagulation cascade when administered at therapeutically effective levels.

IV. Pharmaceutical Compositions and Administration of Gingipain Inhibitors

In a related embodiment, the invention provides a pharmaceutical composition comprising a compound of Formula I, Formula IIa, Formula IIb, Formula III, Formula IVa, Formula IVb, Formula IVc, or Formula V, and a pharmaceutically acceptable excipient. The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

Pharmaceutical compositions containing compounds of the invention can be formulated for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Rgp inhibitors can also be administered topically as a solution, ointment, cream, gel, or suspension, as well as in mouth washes, eye-drops, and the like. Still further, transdermal delivery of Rgp inhibitors can be accomplished by means of iontophoretic patches and the like.

Pharmaceutical compositions containing Rgp inhibitors can also be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils can be used as a solvent or suspending medium. For this purpose any bland fixed oil can be employed including synthetic monoglycerides, diglycerides, or triglycerides.

In some embodiments, an Rgp inhibitor can be formulated with a polymer such as Pluronic F127 and delivered subcutaneously. Pluronic is a hydrogel that solidifies at body temperature and can provide extended drug delivery over periods of time lasting from days to weeks.

Aqueous suspensions can contain one or more Rgp inhibitors in admixture with excipients including, but not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate. Dispersible powders and granules (suitable for preparation of an aqueous suspension by the addition of water) can contain one or more Rgp inhibitors in admixture with a dispersing agent, wetting agent, suspending agent, or combinations thereof. Oily suspensions can be formulated by suspending an Rgp inhibitor in a vegetable oil (e.g., arachis oil, olive oil, sesame oil or coconut oil), or in a mineral oil (e.g., liquid paraffin). Oily suspensions can contain one or more thickening agents, for example beeswax, hard paraffin, or cetyl alcohol. These compositions can be preserved by the addition of an anti-oxidant such as ascorbic acid.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

The use of hybrid molecules to promote active transport or nanoparticles can be used in certain embodiments to increase blood brain barrier transport. For example liposomes, proteins, engineered peptide compounds or antibodies that bind to the receptors that transport proteins across the blood brain barrier including LPR-1 receptor, transferrin receptor, EGF-like growth factor or glutathione transporter can be used to increase penetration into the brain. Physical techniques including osmotic opening, ultrasound, lasers, sphenopalantine ganglion stimulation, direct intracranial, intrathecal, or intraventricular delivery via a pump can be used.

Pharmaceutical compositions according to the invention can also include one or more additional active agents useful in the treatment of conditions associated with *P. gingivalis* infection. In certain embodiments, the invention provides a pharmaceutical composition comprising one or more Rgp inhibitors as described herein in combination with one or more additional active agents for treatment of Alzheimer's disease. Several therapeutics are in development and in clinical use for treatment of Alzheimer's disease. Therapeutic strategies include lowering circulating levels of β-amyloid and tau (as described in more detail below), stabilizing microtubules, removing atherosclerotic plaques, modulating autophagy, modulating neurotransmitter levels, and inhibiting GABA(A) α5 receptors. Such therapeutics can maintain and/or restore cognitive function in subjects with Alzheimer's disease; slow the decline of cognitive function; and promote neuroplasticity and recovery of the brain.

Active agents that can be combined with Rgp inhibitors in pharmaceutical compositions include, but are not limited to, antibiotics (i.e., bacteriocidal compounds and bacteriostatic compounds), cholinesterase inhibitors, alpha-7 nicotinic receptor modulators, serotonin modulators, NMDA modulators, AP-targeted therapies, ApoE-targeted therapies, microglia-targeted therapies, blood/brain barrier-targeted therapies, tau-targeted therapies, complement-targeted therapies, and anti-inflammatories.

Any suitable antibiotic can be combined with one or more Rgp inhibitors in the pharmaceutical compositions of the invention. In certain embodiments, the invention provides a pharmaceutical composition containing one more Rgp inhibitors and an antibiotic having a *P. gingivalis* MIC$_{50}$ of less than 25 µg/ml. For example, the *P. gingivalis* MIC$_{50}$ of the antibiotic can be less than 20 µg/ml, less than 15 µg/ml, less than 10 µg/ml, less than 8 µg/ml, less than 6 µg/ml, or less than 5 µg/ml. In some embodiments, the *P. gingivalis* MIC$_{50}$ of the antibiotic is less than 1 µg/ml. In some embodiments, the *P. gingivalis* MIC$_{50}$ of the antibiotic is less than 0.2 µg/ml.

Examples of bacteriocidal and bacteriostatic compounds include, but are not limited to: quinolones (e.g., moxifloxacin, gemifloxacin, ciprofloxacin, of laxacin, trovafloxacin, sitafloxacin, and the like), β-lactams (e.g., penicillins such as amoxicillin, amoxacilin-clavulanate, piperacillin-tazobactam, penicillin G, and the like; and cephalosporins such as ceftriaxone and the like), macrolides (e.g., erythromycin, azithromycin, clarithromycin, and the like), carbapenems (e.g., doripenem, imipenem, meropinem, ertapenem, and the like), thiazolides (e.g., tizoxanidine, nitazoxanidine, RM 4807, RM 4809, and the like), tetracyclines (e.g., tetracycline, minocycline, doxycycline, eravacycline, and the like), clindamycin, metronidazole, and satranidazole. Bacteriocidal and bacteriostatic compounds also include agents that inhibit or otherwise interfere with formation of biofilms by anaerobic, gram-negative bacteria; such agents include oxantel, morantel, thiabendazole, and the like. Compositions of the invention can contain one or more Rgp inhibitors with one or more (e.g., two, three, four, five, six, or more) bacteriocidal/bacteriostatic compounds. Compositions containing bacteriocidal/bacteriostatic compounds can further contain a chlorhexidine (e.g., chlorhexidine digluconate) alone or in combination with a zinc compound (e.g., zinc acetate), can also be used in combination with the administered antibiotics.

In some embodiments, a combination of a penicillin (e.g., amoxicillin) and metronidazole or a combination of penicillin (e.g., amoxicillin), metronidazole and a tetracycline is used. In some embodiments, the antibiotic is selected from minocycline, doxycycline, metronidazole, amoxicillin, clindamycin, augmentin, satranidazole, and combinations thereof.

Examples of suitable cholinesterase inhibitors include, but are not limited to, donepezil, donepezil/memantine, galantamine, rivastigmine, and tacrine, as well as pharmaceutically acceptable salts thereof. Examples of suitable serotonin modulators include, but are not limited to, idalopirdine, RVT-101, citalopram, escitalopram, fluoxetine, fluvoxamine, paroxetine, and sertraline, as well as pharmaceutically acceptable salts thereof. Examples of suitable alpha-7 nicotinic receptor modulators include, but are not limited to, alpha-7 agonists such as encenicline and APN1125. Suitable NMDA modulators include, but are not limited to, NMDA receptor antagonists such as memantine and derivatives thereof.

Pharmaceutical compositions of the invention can also contain active agents that are directed to biomolecular targets associated with neurological diseases. Such targets include beta amyloid peptides (also referred to as beta amyloid, abeta, or Aβ), apolipoprotein E (also referred to as ApoE), and microtubule-associated tau (also referred to as tau proteins, or simply as tau).

Aβ-targeted therapies include inhibitors of AP production (such as beta-secretase inhibitors, gamma-secretase inhibitors, alpha-secretase activators), inhibitors of Aβ aggregation, inhibitors of Aβ oligomerization, and up-regulators of Aβ clearance, among others (see, e.g., Jia, et al. *Bio Med Research International,* 2014. Article ID 837157, doi: 10.1155/2014/837157). Examples of Aβ-targeted therapies include but are not limited to, antibodies, pioglitazone, begacestat, atorvastatin, simvastatin, etazolate, and tramiprosate, as well as pharmaceutically acceptable salts thereof.

Examples of ApoE-targeted therapies include, but are not limited to retinoid X receptor agonists (see, Cramer, et al., *Science* 2012. 335(6075): 1503-1506) and others described by Liu et al. (*Nat Rev Neurol.* 2013. 9(2): 106-118). Tau-targeted therapies include, but are not limited to, methylthioninium, leuco-methylthioninium, antibodies and those described by Lee, et al. (*Cold Spring Harb Perspect Med* 2011; 1:a006437).

Pharmaceutical compositions of the invention can also contain complement-targeted therapies. Such therapies target components of the complement system involved in the innate immune response. Complement targeted therapies include, but are not limited to, those described by Ricklin and Lambris (*Nat. Biotechnology* 2007. 25(11): 1265-1275).

Examples of suitable anti-inflammatories include, but are not limited to, NSAIDs such as apazone, diclofenac, ibuprofen, indomethacin, ketoprofen, nabumetone, naproxen, piroxicam, and sulindac, as well as pharmaceutically acceptable salts thereof.

V. Methods for Inhibiting Gingipains and Treating Conditions Associated with *P. Gingivalis* Infection In another embodiment, the invention provides a method of inhibiting a gingipain. The method includes contacting the gingipain with an effective amount of a compound as described herein. In certain embodiments, the gingipain is an arginine gingipain (e.g., RgpA, RgpB, or a variant containing one or more amino acid substitutions, deletions, and/or other peptide sequence variations). Inhibiting the gingipain generally includes contacting the gingipain with an amount of the compound sufficient to reduce the activity of the gingipain as compared to the gingipain activity in the absence of the compound. For example, contacting the gingipain with the gingipain inhibitor can result in from about 1% to about 99% gingipain inhibition (i.e., the activity of the inhibited gingipain ranges from 99% to 1% of the gingipain activity in the absence of the compound). The level of gingipain inhibition can range from about 1% to about 10%, or from about 10% to about 20%, or from about 20% to about 30%, or from about 30% to about 40%, or from about 40% to about 50%, or from about 50% to about 60%, or from about 60% to about 70%, or from about 70% to about 80%, or from about 80% to about 90%, or from about 90% to about 99%. The level of gingipain inhibition can range from about 5% to about 95%, or from about 10% to about 90%, or from about 20% to about 80%, or from about 30% to about 70%, or from about 40% to about 60%. In some embodiments, contacting the gingipain with a compound as described herein will result in complete (i.e., 100%) gingipain inhibition.

As described above, infection with *P. gingivalis* and gingipain activity have been linked to the development of periodontal disease, Alzheimer's and other brain disorders, cardiovascular disease, diabetes, cancer, liver disease, kidney disease, preterm birth, arthritis, pneumonia and other disorders. See: Bostanci, et al. FEMS Microbiol Lett, 2012. 333(1): 1-9; Ghizoni, et al. *J Appl Oral Sci,* 2012. 20(1): 104-12; Gatz, et al. *Alzheimers Dement,* 2006. 2(2): 110-7; Stein, et al. *J Am DentAssoc,* 2007. 138(10): 1314-22; quiz 1381-2; Noble, et al. *J Neurol Neurosurg Psychiatry,* 2009. 80(11): 1206-11; Sparks Stein, et al. *Alzheimers Dement,* 2012. 8(3): 196-203; Velsko, et al. *PLoS ONE,* 2014. 9(5):

e97811; Demmer, et al. *J Dent Res*, 2015. 94(9S): 201-S-11S; Atanasova and Yilmaz. Molecular Oral Microbiology, 2014. 29(2): 55-66; Yoneda, et al. *BMC Gastroenterol*, 2012. 12: 16.

Extracellular proteases produced by *P. gingivalis*, including Arginine Gingipain A (RgpA), Arginine Gingipain B (RgpB), and Lysine Gingipain (Kgp), can also degrade a broad range of proteins in connective tissue and plasma (e.g., collagen, immunoglobulins, and proteinase inhibitors, etc.). Gingipains can enter systemic circulation and/or synoviocytes and chondrocytes, and they can also cause disruption to the kallikrein-kinin cascade, blood coagulation, and host defense systems. Patients with gingipains in their joints and circulatory system may be subject to gingipain-induced death of synovial cells and/or chondrocytes, contributing to osteoarthritis.

It has recently been discovered that RgpB and Kgp can infiltrate human and dog joints, contributing to the development of osteoarthritis. It is believed that *P. gingivalis* and gingipains can infiltrate joint tissues via a number of routes. Gingipains can be secreted, transported to outer membrane surfaces of *P. gingivalis*, or released in outer membrane vesicles by the bacterium. *P. gingivalis* has previously been identified in periodontal tissues, coronary arteries, aorta, and recently, the liver-release of *P. gingivalis* and/or gingipains from any of these niches into the systemic circulation could result in translocation of *P. gingivalis* and/or gingipains to the joints. See: Travis, et al. *Adv Exp Med Biol*, 2000. 477: 455-65; Byme, et al. *Oral Microbiol Immunol*, 2009. 24(6): 469-77; Mahendra, et al. *J Maxillofac Oral Surg*, 2009. 8(2): 108-13; Stelzel. *Periodontol*, 2002. 73(8): 868-70; Ishikawa, et al. *Biochim Biophys Acta*, 2013. 1832(12): 2035-2043.

*P. gingivalis* and/or gingipains may also enter joints by degrading the endothelial cells protecting the blood/joint barrier, or by a traumatic event to the joint, such as a meniscus injury, which permanently or transiently reduces the integrity of the joint tissues. Such a disruption in traumatic joint injury for example, may contribute to the infiltration of *P. gingivalis* and/or gingipains in infected individuals and subsequent development of chronic osteoarthritis. People who are at a high risk of traumatic joint injury, including athletes in contact sports like football, could be preventatively treated with gingipain inhibitors to reduce the risk of trauma-related osteoarthritis.

*P. gingivalis* and gingipains may also reach the joint through other mechanisms including active transport, passive transport or macrophage delivery. Osteoarthritis resulting from any of these mechanisms can be limited to a single joint or present in multiple joints.

Similar to humans, *P. gingivalis* infection and periodontal disease is one of the most common infectious diseases affecting adult dogs and cats. Dogs and cats with *P. gingivalis* infection and gingipains in their joints and circulatory system may experience periodontal disease and osteoarthritis due to gingipain-induced cell death, which could be treated or prevented according to the methods of the invention. Aged dogs spontaneously develop many features of osteoarthritis, including a common inflammatory knee arthritis associated with degeneration of the anterior cruciate ligament (ACL). A study by Muir et al. of dogs with inflammatory knee arthritis and ACL degeneration detected DNA from a range of bacterial species in 37% of knee joints from affected dogs. Muir et al. hypothesized that bacteria may be an important causative factor in the pathogenesis of inflammatory arthritis in dogs. In the Muir et al. study, DNA from *P. gingivalis* was not detected in the dog joints. See, Muir, et al. *Microb Pathog*, 2007. 42(2-3): 47-55. However, similar to humans, *P. gingivalis* is a common oral pathogen affecting adult dogs, and could potentially translocate from the oral cavity to joint tissues as a result of bacteremia. *P. gingivalis* has been demonstrated to infect chondrocytes in vitro causing chondrocyte apoptosis, indicating a pathway for cartilage loss in osteoarthritis of both dogs and humans. See: Rohner, et al. *Calcif Tissue Int*, 2010. 87(4): p. 333-40; Houle, et al. *FEMSMicrobiol Lett*, 2003. 221(2): p. 181-5; Kataoka, et al. *FASEB J*, 2014. 28: 3564-3578; Pischon, et al. *Ann Rheum Dis*, 2009. 68(12): p. 1902-7.

Rgp inhibitors can therefore be used to treat diseases and conditions, such as brain disorders, caused by or otherwise affected by *P. gingivalis*. Accordingly, another aspect of the invention provides a method of treating a disease or condition associated with *P. gingivalis* infection. The method includes administering an effective amount of a compound or a composition of the invention, as described above, to a subject in need thereof.

In certain embodiments, compounds of the invention inhibit active Rgp in the brain of a mammal, e.g., a human or an animal (e.g., a dog), and are cytoprotective or neuroprotective. By "neuroprotective," it is meant that the compounds prevent aberrant changes to neurons or death of neurons. Compounds of the invention are therefore useful, e.g., in treatment of a brain disorder (e.g., a neurodegenerative disease (e.g., Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia and depression, etc.), diabetes, cardiovascular disease, arthritis, rheumatoid arthritis, osteoarthritis, infectious arthritis, psoriatic arthritis, retinal disorders (e.g., age related macular degeneration) and glaucoma.

In some embodiments, the disease or condition is selected from a brain disorder, periodontal disease, diabetes, a cardiovascular disease, arthritis, rheumatoid arthritis, osteoarthritis, preterm birth, pneumonia, cancer, a kidney disease, a liver disease, a retinal disorder, and glaucoma.

In some embodiments, the disease or condition is a brain disorder.

In some embodiments, the brain disorder is selected from Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia, and depression.

In some embodiments, the brain disorder is Alzheimer's disease.

In some embodiments, the method further includes administering to the subject one or more active agents selected from a cholinesterase inhibitor, a serotonin modulator, an NMDA modulator, an Aβ targeted therapy, an ApoE targeted therapy, a microglia targeted therapy, a blood brain barrier targeted therapy, a tau targeted therapy, a complement targeted therapy, and an anti-inflammatory.

In some embodiments, the disease or condition is periodontal disease. In some embodiments, the disease or condition is a liver disease. In some embodiments, the liver disease is non-alcoholic steatohepatitis. In some embodiments, the disease or condition is a retinal disorder. In some embodiments, the retinal disorder is age-related macular degeneration.

In some embodiments, the disease or condition is cancer. In some embodiments, the cancer is breast cancer, oral cancer, pancreatic cancer, or glioblastoma multiforme.

Rgp inhibitors as described herein can be administered at any suitable dose in the methods of the invention. In general, an Rgp inhibitor is administered at a dose ranging from about 0.1 milligrams to about 1000 milligrams per kilogram of a subject's body weight (i.e., about 0.1-1000 mg/kg). The dose of Rgp inhibitor can be, for example, about 0.1-1000 mg/kg, or about 1-500 mg/kg, or about 25-250 mg/kg, or about 50-100 mg/kg. The dose of Rgp inhibitor can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg. The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the disease or condition.

Rgp inhibitors can be administered for periods of time which will vary depending upon the nature of the particular disorder, its severity, and the overall condition of the subject to whom the Rgp inhibitor is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the disorder. The dosage of the Rgp inhibitor can either be increased in the event the subject does not respond significantly to a particular dosage level, or the dose can be decreased if an alleviation of the symptoms of the disorder is observed, or if the disorder has been remedied, or if unacceptable side effects are seen with a particular dosage.

A therapeutically effective amount of an Rgp inhibitor can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 144, 168, 192, 216, or 240 hours (i.e., 3, 4, 5, 6, 7, 8, 9, or 10 days). In certain embodiments, administration of one or more Rgp inhibitors is conducted in a chronic fashion over periods ranging from several months to several years. Accordingly, some embodiments of the invention provide a method of treating a disease or condition associated with *P. gingivalis* infection as described above, wherein the compound is administered to the subject for at least one year. In some embodiments, the compound is administered to the subject for at least 10 years. In some embodiments, the compound is administered to the subject for at least 60 years.

Administration of Rgp inhibitors according to the methods of the invention typically results in the reduction of circulating levels of active Rgp in a subject and/or the reduction of active Rgp in the brain. In certain embodiments, administration of an Rgp inhibitor according to the methods of the invention results in at least a 20% reduction of circulating levels of active Rgp and/or at least a 20% reduction of active Rgp in the brain. For example, the circulating levels of Rgp and/or the levels of Rgp in the brain are preferably reduced by from about 25% to about 95%, or from about 35% to about 95%, or from about 40% to about 85%, or from about 40% to about 80% as compared to the corresponding levels of Rgp 24 hours prior to the first administration of the Rgp inhibitor.

Rgp inhibitors can be administered alone or in combination with one or more additional therapeutically active agents, as described above. The one or more additional therapeutically effective agents include, e.g.; (i) a pharmaceutically acceptable agent which inhibits RgpA, RgpB, and/or Kgp production, translocation of RgpA, RgpB, and/or Kgp into systemic circulation or brain, and/or pathological (e.g., neurotoxic effects) of RgpA, RgpB, and/or Kgp in a mammal; (ii) an antibacterial agent which is bacteriostatic or bacteriocidal with respect to *P. gingivalis*; (iii) one or more antibodies which bind to RgpA, RgpB and/or Kgp (e.g., 18E6, which binds to the first half of the immunoglobulin domain of RgpB; Kgp-specific monoclonal antibody, 7B9, which recognizes an epitope within the Kgp catalytic domain; the RgpA antibody 61Bg 1.3, humanized versions of any of the foregoing, etc.); (iv) epitopes of antibodies which bind to RgpA, RgpB and/or Kgp or other proteins expressed by *P. gingivalis*; and (v) combinations of any of the foregoing.

The additional therapeutically active agents also include Aβ peptides level reducers, pathogenic level tau reducers, microtubule stabilizers, agents capable or removing atherosclerotic plaques, agents that lower circulating levels of β-amyloid and tau, modulators of autophagy, neurotransmitter level regulators, GABA(A) a5 receptors inhibitors, and additional agents that help maintain and/or restore cognitive function and functional deficits of Alzheimer's disease, and/or slow down decline in cognitive functions and functional deficits in Alzheimer's disease.

Pharmaceutical compositions of the invention can contain one or more Rgp inhibitors as described herein in combination with ritonavir (RTV), which can increase bioavailability and increase blood brain barrier penetration. For example, ritonavir is commonly combined with oral peptidic HIV protease inhibitors to increase plasma levels by inhibiting the P450 3A4 enzyme and thus decreasing first-pass metabolism (see, Walmsley, et al., *N Engl J Med,* 2002. 346(26): 2039-46). In addition, RTV binds to P-glycoprotein, a transmembrane efflux pump that is found in many tissues, including the blood brain barrier, allowing co-administered compounds better access to the brain (see, Marzolini, et al., *Mol Pharm,* 2013. 10(6): 2340-9). Therefore, a combination of RTV and Rgp inhibitors can be used to increase plasma concentrations and brain levels of the gingipain inhibitors. As described in U.S. patent application Ser. No. 14/875,416, oral administration of RTV 15 minutes prior to the Kgp inhibitor Kyt-36 increases the half-life therefore it is expected that RTV will also increase the half-life of other gingipain inhibitors.

In some embodiments, compounds of the invention can be administered with natural gingipain inhibitors including melabaricone C, isolated from nutmeg or polyphenolic compounds derived from plants, such as cranberry, green tea, apple, and hops can be administered in conjunction for treatment or prevention of brain disorders. Naturally and unnaturally occurring antimicrobial peptides including: K-casein peptide (109-137) 34, histatin 5, and CL(14-25), CL(K25A) and CL(R24A, K25A), can also be administered in conjunction with the Rgp inhibitors of the invention. (see, e.g., Taniguchi et al., *Biopolymers,* 2014. 102(5): 379-89).

Rgp inhibitors as described herein can be administered with antibodies targeting gingipains or other *P. gingivalis* proteins. Antibodies may rely on damage to the blood brain barrier for access to the brain or peripheral interference with gingipains and *P. gingivalis* propagation. Antibodies can also help to stimulate the efficacy of the immune system in clearing the bacteria. New or existing antibodies to RgpA, RgpB, or Kgp can be utilized including 18E6 and 7B9. An RgpA antibody 61BG 1.3 has previously demonstrated efficacy topically in prevention of recolonization by *P. gingivalis* after periodontal treatment. See, Booth et al., *Infect Immun,* 1996. 64(2): 422-7. Antibodies would preferably be humanized for use in humans. Methods known to those in the field for delivery of biologics to improve half-life and brain penetration can be used including, but not limited to, intravenous delivery, subcutaneous delivery, intranasal delivery, intrathecal delivery, intra-articular delivery, vector transport, and direct brain delivery.

The methods of the invention also encompass administration of Rgp inhibitors as described herein with one or more of the following additional therapeutically active agents or pharmaceutically acceptable salts thereof: an arginine derivative; histatin 5; baculovirus p35; a single point mutant of cowpox viral cytokine-response modifier (CrmA (Asp>Lys)); phenylalanyl-ureido-citrullinyl-valyl-cycloarginal (FA-70C1); (acyloxy)methyl ketone (Cbz-Phe-Lys-CH$_2$OCO-2,4,6-Me$_3$Ph); peptidyl chloro-methyl ketones (e.g., chloromethyl ketone derivatives of arginine, chloromethyl ketone derivatives of lysine, and the like); fluoro-methyl ketones; bromo-methyl ketones; ketopeptides; 1-(3-phenylpropionyl)piperidine-3(R,S)-carboxylic acid [4-amino-1 (S)-(benzothiazole-2-carbonyl)butyl]amide (A71561); azapeptide fumaramide; aza-peptide Michael acceptors; benzamidine compounds; acyclomethylketone; activated factor X inhibitors (e.g., DX-9065a); cranberry nondialyzable fraction; cranberry polyphenol fraction; pancreatic trypsin inhibitor; Cbz-Phe-Lys-CH$_2$O—CO-2,4,6-Me$_3$-Ph; E-64; chlorhexidine; zinc (e.g., zinc acetate); or a combination of two, three or more of any of foregoing. In some of these embodiments, Zn can enhance potency and selectivity of the compounds (e.g., chlorhexidine, benzamidine, etc.) used in the methods of the invention.

An Rgp inhibitor of the invention can be administered in the same composition as an additional therapeutically active agent. Alternatively, the additional therapeutically active agent can be administered separately before, concurrently with, or after administration of the Rgp inhibitor.

VI. Examples

Example 1. Preparation of N-(1-aminoisoquinolin-7-yl)-N-methylcyanamide (1)

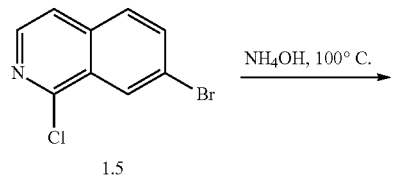

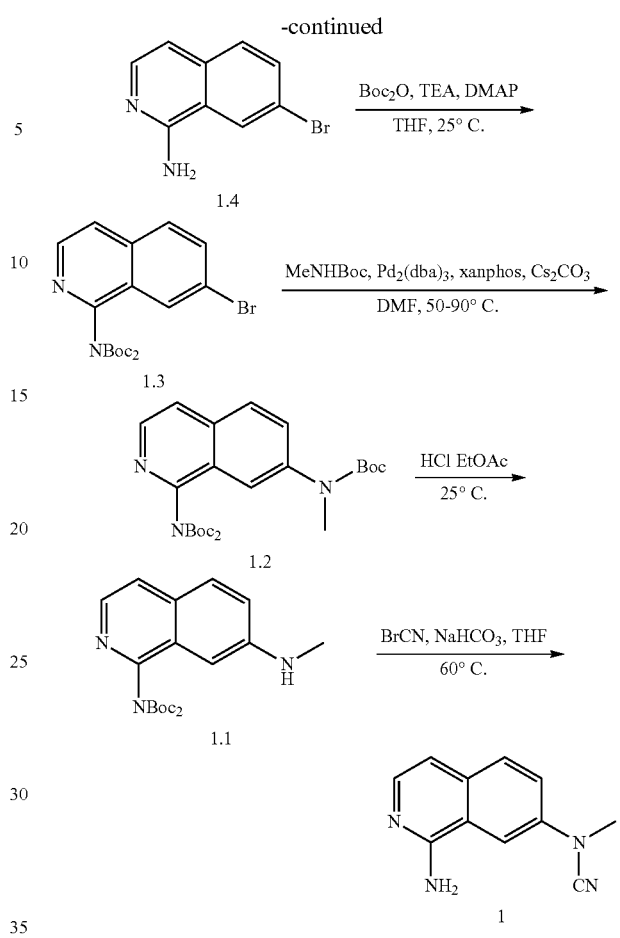

To a solution of compound 1.5 (3 g, 12.4 mmol, 1 eq) in NMP (30 mL) was added NH$_3$.H$_2$O (30 mL). The mixture was stirred 150° C. for 15 hours. The reaction mixture was quenched by addition H$_2$O 100 mL at 25° C., and then extracted with EtOAC (100 mL×3). The combined organic layers were washed with saturated brines (15 mL×1), dried over anhydrous sodium sulfate, filtered and concentrated under reduced pressure to give a crude product. The residue was purified by column chromatography (SiO$_2$, Petroleum ether/Ethyl acetate=1:1). Compound 1.4 (2.0 g, 9 mmol, 72.42% yield) was obtained as a brown oil. LCMS (ESI): m/z: [M+H] calcd for C$_9$H$_7$N$_2$Br: 223; found 223; RT=1.049 min.

To a solution of compound 1.4 (1.90 g, 8.52 mmol, 1 eq) in THF (40 mL) was added TEA (3.45 g, 34.08 mmol, 4.73 mL, 4 eq) and Boc$_2$O (4.65 g, 21.30 mmol, 4.89 mL, 2.50 eq) and DMAP (312.18 mg, 2.56 mmol, 0.30 eq). The mixture was stirred at 25° C. for 15 hours. The reaction mixture was quenched by addition H$_2$O 50 mL at 25° C. and extracted with EtOAc (50 mL×3). The combined organic layers were washed with saturated brines (20 mL×1), dried over anhydrous sodium sulfate, filtered and concentrated under reduced pressure to give a crude product. The residue was purified by column chromatography (SiO$_2$, Petroleum ether/Ethyl acetate=2: 1). Compound 1.3 (2.50 g, 5.91 mmol, 69.32% yield) was obtained as a yellow oil. $^1$H NMR (400 MHz, methanol-d$_4$) δ ppm 1.16-1.49 (m, 21H) 7.89 (d, J=5.77 Hz, 1H) 7.92-8.03 (m, 2H) 8.10 (s, 1H) 8.42 (d, J=5.77 Hz, 1H). LCMS (ESI): m/z: [M+H] calcd for C$_{19}$H$_{23}$N$_2$BrO$_4$: 423; found 423; RT=0.957 min.

To a solution of compound 1.3 (1.50 g, 3.54 mmol, 1 eq) in DMF (30 mL) was added tert-butyl N-methylcarbamate (557.21 mg, 4.25 mmol, 1.20 eq), Cs$_2$CO$_3$ (3.46 g, 10.62 mmol, 3 eq), 4, 5-BIS (DIPHENYLPHOSPHINO)-9, 9-DIMETHYLXANTHENE (819.33 mg, 1.42 mmol, 0.40 eq) and Pd$_2$(dba)$_3$ (972.49 mg, 1.06 mmol, 0.30 eq). The mixture was stirred at 80° C. for 2 hours. The reaction mixture was quenched by addition H$_2$O 50 mL at 25° C. and extracted with ethyl acetate (50 mL×3). The combined organic layers were washed with saturated brines (15 mL×1), dried over anhydrous sodium sulfate, filtered and concentrated under reduced pressure to give a crude product. The residue was purified by column chromatography (SiO$_2$, DCM:MeOH=10:1). Compound 1.2 (1.20 g, 2.53 mmol, 71.58% yield) was obtained as a yellow oil. LCMS (ESI): m/z: [M+H] calcd for C25H35N3O6:474; found 474; RT=0.936 min.

A mixture of compound 1.2 (1.20 g, 2.53 mmol, 1 eq) in HCl/EtOAc (10 mL) was stirred at 25° C. for 15 hours. The mixture was concentrated under reduced pressure to give compound 1.1 (600 mg, 2.12 mmol, 83.92% yield, 3HCl) was obtained as a yellow solid. $^1$H NMR (400 MHz, DEUTERIUM OXIDE) δ ppm 7.08 (d, J=7.06 Hz, 1H) 7.38 (d, J=6.84 Hz, 1H) 7.59-7.69 (m, 2H) 7.78 (d, J=8.60 Hz, 1H). LCMS (ESI): m/z: [M+H] calcd for C$_{10}$H$_{11}$N$_3$O$_6$: 174; found 174; RT=0.236 min.

To a solution of compound 1.1 (100 mg, 406.27 μmol, 1 eq, 2HCl) in DMSO (3 mL) was added NaHCO$_3$ (170.65 mg, 2.03 mmol, 79.01 μL, 5 eq) and BrCN (43.03 mg, 406.27 μmol, 29.88 μL, 1 eq). The mixture was stirred at 60° C. for 0.5 hour. The residue was purified by prep-HPLC (neutral condition). Product 1 (2 mg, 8.07 μmol, 1.99% yield, 80% purity) was obtained as a yellow solid. $^1$H NMR (400 MHz, DMSO-d$_6$) δ ppm 3.43-3.48 (m, 3H) 6.78-6.84 (m, 2H) 6.88-6.96 (m, 1H) 6.89-6.92 (m, 1H) 7.51-7.55 (m, 1H) 7.71 (d, J=2.43 Hz, 1H) 7.75 (d, J=5.73 Hz, 1H) 7.79 (d, J=8.82 Hz, 1H). LCMS (ESI): m/z: [M+H] calcd for C11H10ON4: 199; found 199; RT=2.246 min.

Example 2. Preparation of 3-((2-aminopyridin-4-yl)oxy)pyrrolidine-1-carbonitrile (2)

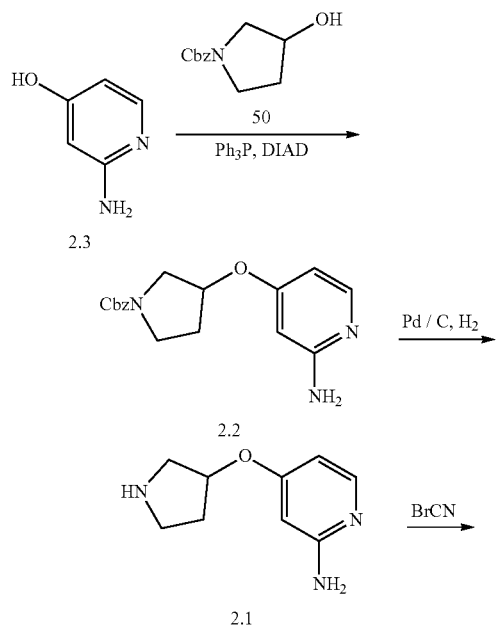

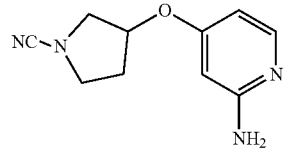

To a solution of compound 2.3 (800 mg, 7.27 mmol, 1 eq) in DCM (30 mL) was added compound 50 (1.61 g, 7.27 mmol, 1 eq), PPh$_3$ (2.86 g, 10.91 mmol, 1.50 eq) and DIAD (2.21 g, 10.91 mmol, 2.12 mL, 1.50 eq) in turn at 0° C. under N$_2$. The resulting mixture was stirred at 25° C. for 16 hours. The reaction mixture was added water 20 mL, extracted with EtOAc (20 mL×3). The combined organic layers were washed with brine (20 mL×1), dried over Na$_2$SO$_4$, filtered and concentrated under reduced pressure to give a residue. The residue was purified by column chromatography (SiO$_2$, Petroleum ether/Ethyl acetate=1:1). Compound 2.2 (750 mg, 2.39 mmol, 32.92% yield) was obtained as a white solid. $^1$H NMR (400 MHz, chloroform-d) ppm 2.09-2.20 (m, 2H) 3.51-3.74 (m, 4H) 4.45 (s, 2H) 4.90 (s, 1H) 5.93 (s, 1H) 6.21 (d, J=6.0 Hz, 1H) 7.33-7.37 (m, 5H) 7.91 (d, J=6.4 Hz, 1H).

H$_2$ was bubbled into a solution of compound 2.2 (400 mg, 1.28 mmol, 1 eq) and Pd/C (40 mg) in MeOH (40 mL) at 25° C. under 50 psi for 16 hours. The reaction mixture was filtered, the filter was concentrated under reduced pressure to remove solvent. Compound 2.1 (200 mg, 1.12 mmol, 87.18% yield) was obtained as a yellow oil. $^1$H NMR (400 MHz, methanol-d4) ppm 1.93-1.97 (m, 2H) 2.09-2.12 (m, 2H) 2.88-3.09 (m, 4H) 4.90-4.93 (m, 1H) 6.06 (d, J=2.0 Hz, 1H) 6.20 (dd, J=6.0 Hz, 2.0 Hz, 1H) 7.69 (d, J=6.4 Hz, 1H). LCMS (ESI): m/z: [M+H] calcd for C8H11N3O.2 (C2HF3O2): 166; found 166; RT=0.214 min.

To a solution of compound 2.1 (100 mg, 557.97 μmol, 1 eq) in THF (5 mL) was added DIEA (144.22 mg, 1.12 mmol, 194.89 μL, 2 eq) and BrCN (59.10 mg, 557.97 μmol, 41.04 μL, 1 eq) in turn at 0° C. under N$_2$. The resulting mixture was stirred at 0° C. for 2 hours. The reaction mixture was added water 10 mL, extracted with EtOAc (10 mL×3). The combined organic layers were washed with brine (20 mL×1), dried over Na$_2$SO$_4$, filtered and concentrated under reduced pressure to give a residue. The residue was purified by p-TLC (SiO$_2$, Ethyl acetate=0:1). Product 2 (9 mg, 44.07 μmol, 7.90% yield) was obtained as a white solid. LCMS (ESI): m/z: [M+H] calcd for C$_{10}$H$_{12}$N$_4$O: 204; found 205; RT=1.672 min. $^1$H NMR (400 MHz, chloroform-d) ppm 2.12-2.26 (m, 2H) 3.59-3.69 (m, 4H) 4.44 (s, 2H) 4.92 (s, 1H) 5.92 (d, J=2.0 Hz, 1H) 6.20 (dd, J=6.4 Hz, 2.0 Hz, 1H) 7.93 (d, J=6.0 Hz, 1H)

Example 3. Preparation of 2-(((2-aminopyridin-4-yl)oxy)methyl)pyrrolidine-1-carbonitrile (3)

To a mixture of compound 3.5 (700 mg, 3.48 mmol, 1 eq) and 4-methylbenzenesulfonyl chloride (796.15 mg, 4.18 mmol, 1.20 eq) in DCM (15 mL) was added DMAP (68.02 mg, 556.80 μmol, 0.16 eq) and TEA (528.21 mg, 5.22 mmol, 723.58 L, 1.50 eq) in one portion at 0° C. under N$_2$. The mixture was then heated to 25° C. and stirred for 10 hours. The reaction mixture was diluted with H$_2$O 20 mL and extracted with EtOAc 45 mL (15 mL×3). The combined organic layers were washed with brine 20 mL (20 mL×1), dried over Na$_2$SO$_4$, filtered and concentrated under reduced pressure to give compound 3.4

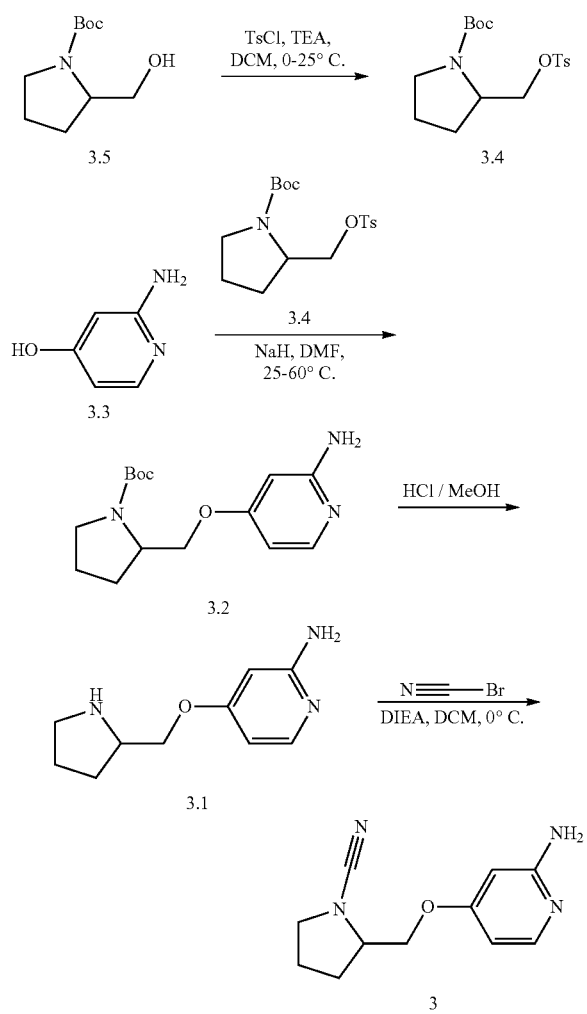

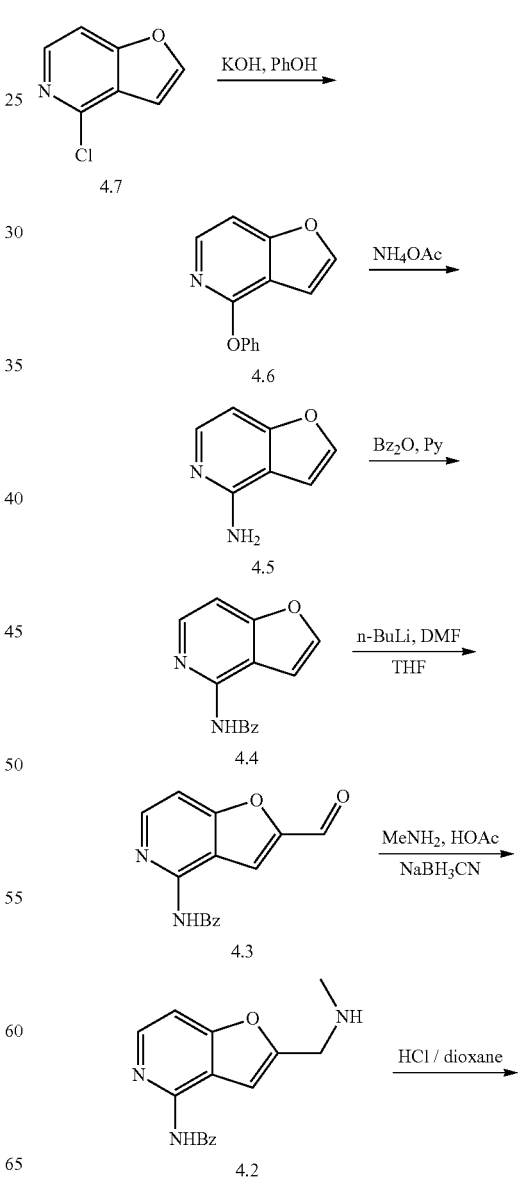

(1.30 g, crude) as a colorless oil. LCMS (ESI): m/z: [M+H] calcd for $C_{17}H_{25}NSO_5$: 355; found 300; RT=0.866 min.

To a solution of compound 3.3 (443.30 mg, 4.03 mmol, 1.10 eq) in DMF (20 mL) was added NaH (131.76 mg, 5.49 mmol, 1.50 eq) portionwise at 25° C. under $N_2$. The mixture was stirred at 25° C. for 30 mins, then was added compound 3.4 (1.30 g, 3.66 mmol, 1 eq). The mixture was heated to 60° C. and stirred for 9.5 hours. The reaction mixture was diluted with $H_2O$ 20 mL and extracted with EtOAc 45 mL (15 mL×3). The combined organic layers were washed with brine 20 mL (20 mL×1), dried over $Na_2SO_4$, filtered and concentrated under reduced pressure to give a residue. The residue was purified by column chromatography (SiO2, DCM:MeOH=20:1) to give compound 3.2 (200 mg, 681.76 μmol, 18.63% yield) as a colorless oil. LCMS (ESI): m/z: [M+H] calcd for $C_{15}H_{23}N_3O_3$: 293; found 294; RT=0.663 min.

Compound 3.2 (200 mg, 681.76 μmol, 1 eq) was added into a solution of HCl/MeOH (5 mL). The mixture was stirred at 25° C. for 15 hours. The reaction mixture was concentrated under reduced pressure to give compound 3.1 (220 mg, crude) as a yellow solid. LCMS (ESI): m/z: [M+H] calcd for $C_{10}H_{15}N_3O$: 193; found 194; RT=0.161 min.

To a mixture of compound 3.1 (100 mg, 517.46 μmol, 1 eq) and DIEA (267.51 mg, 2.07 mmol, 361.50 μL, 4 eq) in DCM (2 mL) was added carbononitridic bromide (54.81 mg, 517.46 μmol, 38.06 μL, 1 eq) in one portion at 0° C. under $N_2$. The mixture was stirred at 0° C. for 30 mins. The reaction mixture diluted with $H_2O$ 3 mL and extracted with DCM 9 mL (3 mL×3). The combined organic layers were washed with brine 4 mL (4 mL×1), dried over $Na_2SO_4$, filtered and concentrated under reduced pressure to give a residue. The residue was purified by prep-HPLC (neutral condition) to give product 3 (40 mg, 183.28 μmol, 35.42% yield) as a yellow solid. LCMS (ESI): m/z: [M+H] calcd for $C_{11}H_{14}N_4O$: 218; found 219; RT=1.884 min. $^1$H NMR (400 MHz, chloroform-d) δ ppm 1.83-1.93 (m, 1H) 1.93-2.05 (m, 2H) 2.07-2.18 (m, 1H) 3.38-3.58 (m, 2H) 3.89-4.06 (m, 3H) 4.46 (br s, 2H) 6 (d, J=2.01 Hz, 1H) 6.25 (dd, J=6.02, 2.01 Hz, 1H) 7.90 (d, J=5.52 Hz, 1H).

Example 4. Preparation of N-((4-aminofuro[3,2-c]pyridin-2-yl)methyl)-N-methylcyanamide (4)

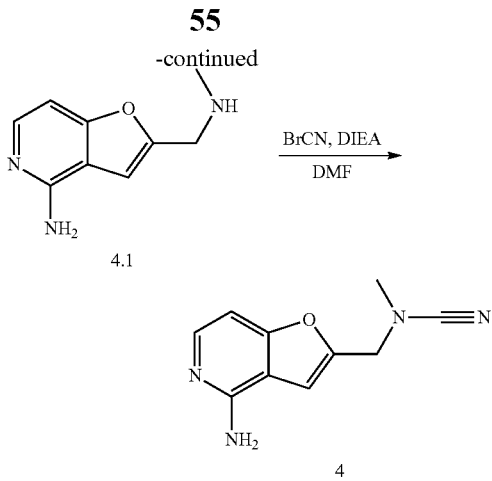

To a solution of compound 4.7 (500 mg, 3.26 mmol, 1 eq) in PhOH (2.45 g, 26.05 mmol, 2.29 mL, 8 eq) was added KOH (365.37 mg, 6.51 mmol, 2 eq) at 25° C. under $N_2$. The resulting mixture was stirred at 140° C. for 16 hrs. TLC (PE:EtOAc=5:1, Rf=0.49) showed the reaction was successful. The reaction mixture was added water (10 mL), extracted with EtOAc (15 mL×3). The organic phase was separated, washed with saturated NaCl (15 mL) and dried over $Na_2SO_4$, filtered and concentrated under reduced pressure to give a residue of compound 4.6 (0.5 g, crude) as a yellow oil which was combined with a second batch for a total of 1.5 g.

To a mixture of compound 4.6 (1.5 g, 7.10 mmol, 1 eq) in $NH_4OAc$ (12.50 g, 162.20 mmol, 22.84 eq) in one portion under $N_2$. The mixture was stirred at 140° C. for 12 hours, then heated to 180° C. and stirred for 12 hours. The mixture was allowed to cool to ambient temperature, after which 3 N sodium hydroxide (20 ml) was added with stirring. The thus obtained solution was extracted with ethyl acetate (2×10 ml) and the combined organic layers were extracted with 2 N hydrochloric acid (20 ml). Subsequently, the pH of the aqueous layer was adjusted to 12 with 2 N sodium hydroxide. Extraction with ethyl acetate (20 ml) then afforded an organic layer, which was washed with brine (10 ml), dried and concentrated under reduced pressure to give compound 4.5 (900 mg, 6.71 mmol, 94.48% yield) was obtained as light yellow solid. LCMS (ESI): m/z: [M+H] calcd for $C_7H_6N_2O$: 135; found 135; RT=0.199 min.

To a mixture of compound 4.5 (900 mg, 6.71 mmol, 1 eq) and benzoyl benzoate (3.04 g, 13.42 mmol, 2.53 mL, 2 eq) in Py (10 mL) in one portion under $N_2$. The mixture was stirred at 150° C. for 8 hours. The mixture was poured into 500 mL of water. The resulting precipated was filtered off, washed with water, and dried to afford crude product of compound 4.4 (1.5 g, 6.30 mmol, 93.84% yield) was obtained as white solid. LCMS (ESI): m/z: [M+H] calcd for $C_{14}H_{10}N_2O_2$: 239; found 239; RT=1.582 min.

To a mixture of compound 4.4 (500 mg, 2.10 mmol, 1 eq) in THF (3 mL) was added n-BuLi (2.5 M, 2.10 mL, 2.5 eq) in one portion at −78° C. under N2. The mixture was stirred at −78° C. for 1 h, then was added DMF (613.58 mg, 8.39 mmol, 645.87 μL, 4 eq) dropwise and stirred at −78° C. for 1 h. TLC (PE:EtOAc=3:1, Rf=0.4) showed the reaction was successful. The reaction mixture was quenched by addition $H_2O$ (20 mL), and extracted with EtOAc (10 mL×3). The combined organic layers were washed with saturated brines (10 mL×2), dried over anhydrous sodium sulfate, filtered and concentrated under reduced pressure to give a crude product of compound 4.3 (0.24 g, crude) as white solid.

To a mixture of compound 4.3 (200 mg, 751.17 μmol, 1 eq) in MeNH2 (116.65 mg, 3.76 mmol, 5 eq) stirred at 25° C. for 1 h, was added NaBH3CN (188.82 mg, 3 mmol, 4 eq) then was added AcOH (67.66 mg, 1.13 mmol, 64.44 μL, 1.5 eq) until pH=0.3. The mixture was stirred at 25° C. for 11 hr. TLC (PE:EtOAc=1:1, Rf=0.3) showed the reaction was successful. The reaction residue was diluted with H2O (20 mL) and extracted with EtOAc (20 mL×3). The aqueous layer added 5N aq.NaOH until PH=11 and extracted with EtOAc (20 mL×4). The combined organic layers were washed with brine 20 mL (10 mL×2), dried over $Na_2SO_4$, filtered and concentrated under reduced pressure to give a residue of compound 4.2 (100 mg, crude) was obtained as white solid.

To a mixture of compound 4.2 (100 mg, 355.48 μmol, 1 eq) in dioxane (0.5 mL) was added HCl (0.5 mL) in one portion at 80° C. under $N_2$. The mixture was stirred at 80° C. for 2 hours. The reaction solution was concentrated in vacuum to obtain compound 4.1 (100 mg, crude) as black brown solid. LCMS (ESI): m/z: [M+H] calcd for $C_9H_{11}N_3O$: 178; found: 178; RT=0.162 min.

To a mixture of compound 4.1 (100 mg, 399.80 μmol, 1 eq, 2HCl) in DMF (2 mL) was added DIPEA (206.69 mg, 1.60 mmol, 278.55 μL, 4 eq) in one portion at 25° C. under $N_2$. Then BrCN (46.58 mg, 439.78 μmol, 32.35 μL, 1.1 eq) added at 0° C. and stirred at 0° C. for 20 min. The residue was purified by prep-HPLC (neutral condition) to give product 4 (1.95 mg, 9.64 μmol, 2.41% yield) was obtained as light yellow oil. $^1$H NMR (400 MHz, methanol-$d_4$) δ ppm 7.76 (d, J=6.11 Hz, 1H) 6.97 (s, 1H) 6.83 (dd, J=6.11, 0.85 Hz, 1H) 4.36 (s, 2H) 2.92 (s, 3H). LCMS (ESI): m/z: [M+H] calcd for $C_{10}H_{10}N_4O$: 203; found 203; RT=1.683 min.

Example 5. Preparation of N-(2-(2-aminopyridin-4-yl)ethyl)-N-isopropylcyanamide (5)

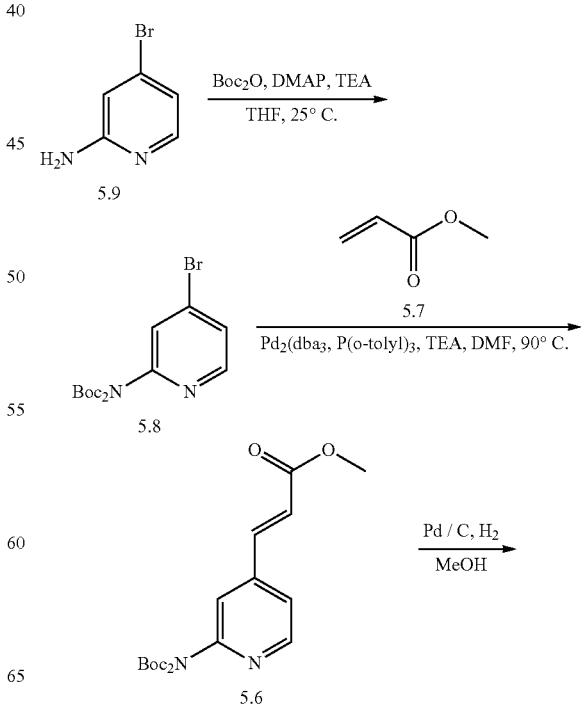

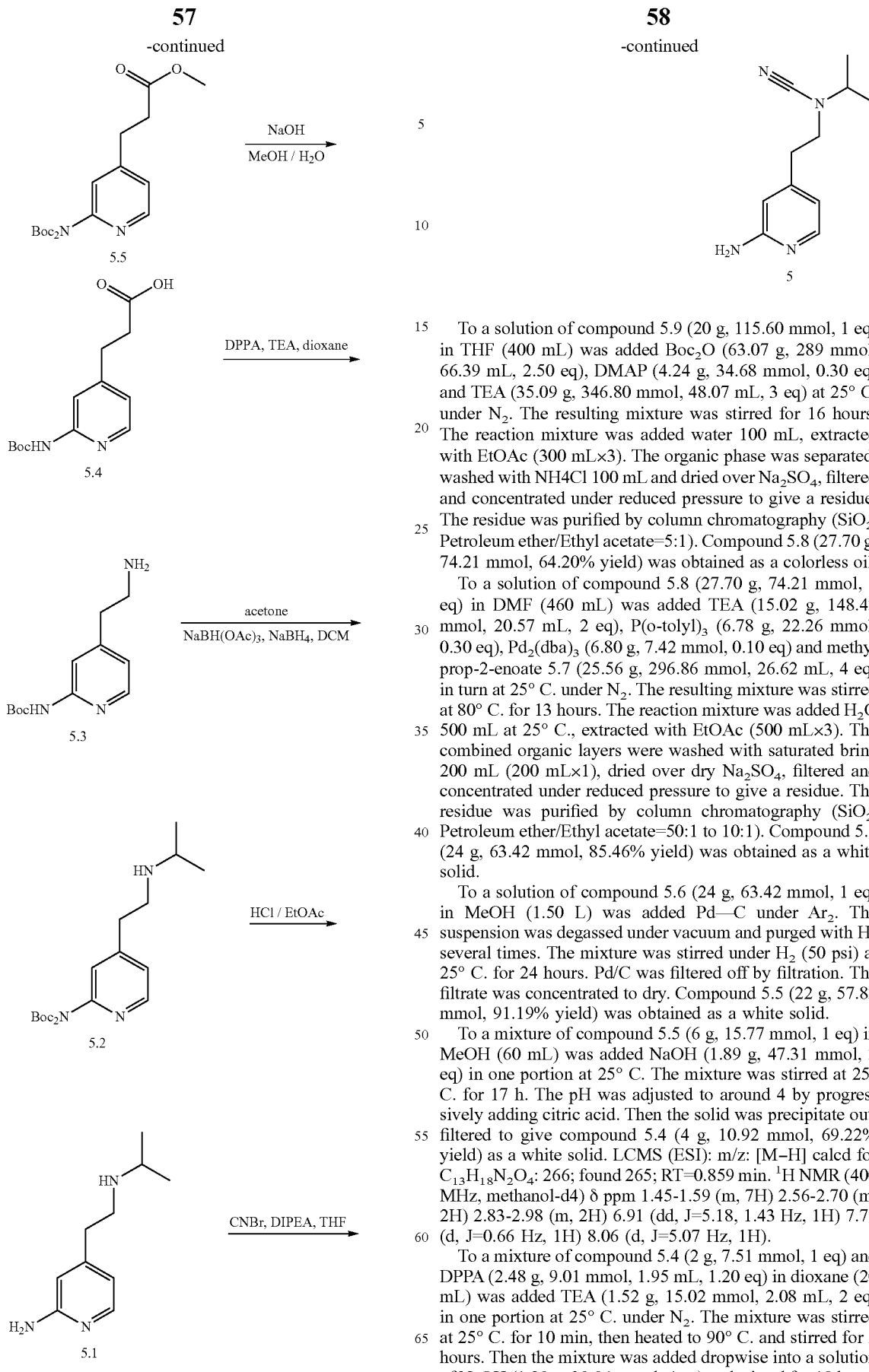

To a solution of compound 5.9 (20 g, 115.60 mmol, 1 eq) in THF (400 mL) was added Boc$_2$O (63.07 g, 289 mmol, 66.39 mL, 2.50 eq), DMAP (4.24 g, 34.68 mmol, 0.30 eq) and TEA (35.09 g, 346.80 mmol, 48.07 mL, 3 eq) at 25° C. under N$_2$. The resulting mixture was stirred for 16 hours. The reaction mixture was added water 100 mL, extracted with EtOAc (300 mL×3). The organic phase was separated, washed with NH4Cl 100 mL and dried over Na$_2$SO$_4$, filtered and concentrated under reduced pressure to give a residue. The residue was purified by column chromatography (SiO$_2$, Petroleum ether/Ethyl acetate=5:1). Compound 5.8 (27.70 g, 74.21 mmol, 64.20% yield) was obtained as a colorless oil.

To a solution of compound 5.8 (27.70 g, 74.21 mmol, 1 eq) in DMF (460 mL) was added TEA (15.02 g, 148.43 mmol, 20.57 mL, 2 eq), P(o-tolyl)$_3$ (6.78 g, 22.26 mmol, 0.30 eq), Pd$_2$(dba)$_3$ (6.80 g, 7.42 mmol, 0.10 eq) and methyl prop-2-enoate 5.7 (25.56 g, 296.86 mmol, 26.62 mL, 4 eq) in turn at 25° C. under N$_2$. The resulting mixture was stirred at 80° C. for 13 hours. The reaction mixture was added H$_2$O 500 mL at 25° C., extracted with EtOAc (500 mL×3). The combined organic layers were washed with saturated brine 200 mL (200 mL×1), dried over dry Na$_2$SO$_4$, filtered and concentrated under reduced pressure to give a residue. The residue was purified by column chromatography (SiO$_2$, Petroleum ether/Ethyl acetate=50:1 to 10:1). Compound 5.6 (24 g, 63.42 mmol, 85.46% yield) was obtained as a white solid.

To a solution of compound 5.6 (24 g, 63.42 mmol, 1 eq) in MeOH (1.50 L) was added Pd—C under Ar$_2$. The suspension was degassed under vacuum and purged with H$_2$ several times. The mixture was stirred under H$_2$ (50 psi) at 25° C. for 24 hours. Pd/C was filtered off by filtration. The filtrate was concentrated to dry. Compound 5.5 (22 g, 57.83 mmol, 91.19% yield) was obtained as a white solid.

To a mixture of compound 5.5 (6 g, 15.77 mmol, 1 eq) in MeOH (60 mL) was added NaOH (1.89 g, 47.31 mmol, 3 eq) in one portion at 25° C. The mixture was stirred at 25° C. for 17 h. The pH was adjusted to around 4 by progressively adding citric acid. Then the solid was precipitate out, filtered to give compound 5.4 (4 g, 10.92 mmol, 69.22% yield) as a white solid. LCMS (ESI): m/z: [M–H] calcd for C$_{13}$H$_{18}$N$_2$O$_4$: 266; found 265; RT=0.859 min. $^1$H NMR (400 MHz, methanol-d4) δ ppm 1.45-1.59 (m, 7H) 2.56-2.70 (m, 2H) 2.83-2.98 (m, 2H) 6.91 (dd, J=5.18, 1.43 Hz, 1H) 7.71 (d, J=0.66 Hz, 1H) 8.06 (d, J=5.07 Hz, 1H).

To a mixture of compound 5.4 (2 g, 7.51 mmol, 1 eq) and DPPA (2.48 g, 9.01 mmol, 1.95 mL, 1.20 eq) in dioxane (20 mL) was added TEA (1.52 g, 15.02 mmol, 2.08 mL, 2 eq) in one portion at 25° C. under N$_2$. The mixture was stirred at 25° C. for 10 min, then heated to 90° C. and stirred for 2 hours. Then the mixture was added dropwise into a solution of NaOH (1.20 g, 30.04 mmol, 4 eq) and stirred for 18 hours at 25° C. The pH was adjusted to around 6 by progessively adding 1M HCl, then the mixture was partitioned between EtOAc (30) and water (30). The combined organic layers were washed with brine 30 mL (30 mL×2), dried over Na$_2$SO$_4$, filtered and concentrated under reduced pressure to give compound 5.3 (800 mg, 3.37 mmol, 44.89% yield) as a white solid. LCMS (ESI): m/z: [M+H] calcd for C$_{12}$H$_{19}$N$_3$O$_2$: 237; found 294; RT=1.547 min.

To a solution of compound 5.3 (800 mg, 3.37 mmol, 1 eq) in DCM (15 mL) was added acetone (195.80 mg, 3.37 mmol, 247.85 µL, 1 eq) in one portion at 25° C. under N$_2$. Then the pH was adjusted to around 5 by progessively adding glacial acetic acid. The mixture was stirred at 25° C. for 2 hour. Then the mixture was added NaBH(OAc)$_3$ (1.81 g, 8.56 mmol, 2.54 eq) in one portion at 0° C. under N$_2$, then heated to 25° C. and stirred for 16 hours. The reaction was quenched by addition of 10 mL of H$_2$O, a clear yellow-brown solution was obtained which was extracted by DCM (3×15 mL). The residue was purified by prep-HPLC (TFA condition) to give compound 5.2 (400 mg, 1.43 mmol, 42.43% yield) as a white solid. LCMS (ESI): m/z: [M+H] calcd for C$_{15}$H$_{25}$N$_3$O$_2$: 279; found 280; RT=1.473 min. $^1$H NMR (400 MHz, methanol-d$_4$) δ ppm 1.33 (dd, J=6.50, 1.21 Hz, 13H) 1.55 (s, 9H) 2.97-3.12 (m, 5H) 3.35-3.45 (m, 3H) 6.83 (dd, J=6.73, 1.65 Hz, 1H) 6.90 (dd, J=1.54, 0.66 Hz, 1H) 7.20 (dd, J=5.73, 1.54 Hz, 1H) 7.55 (d, J=0.66 Hz, 1H) 7.78 (d, J=6.84 Hz, 1H) 8.19 (d, J=5.95 Hz, 1H).

Compound 5.2 (200 mg, 715.87 µmol, 1 eq) was added into a solution of HCl/EtOAc (5 mL). The mixture was stirred at 25° C. for 14 hours. The reaction mixture was concentrated under reduced pressure to give compound 5.1 (180 mg, crude) as a yellow solid. LCMS (ESI): m/z: [M+H] calcd for C$_{10}$H$_{17}$N$_3$: 179; found 180; RT=0.250 min.

To a mixture of compound 5.1 (110 mg, 613.63 µmol, 1 eq) and DIEA (317.22 mg, 2.45 mmol, 428.68 µL, 4 eq) in THF (2 mL) was added dropwise a solution of BrCN (65 mg, 613.63 µmol, 45.14 µL, 1 eq) in THF (2 mL), and stirring at 0° C. for 10 mins. The reaction mixture was partitioned between EtOAc 2 mL and water 2 mL. The organic phase was separated, washed with brine 2 mL (2 mL×1), dried over Na$_2$SO$_4$, filtered and concentrated under reduced pressure to give a residue. The residue was purified by by prep-TLC (SiO2, CH3CN:EtOAc=3:1) to give product 5 (11 mg, 53.85 µmol, 8.78% yield) as a light yellow oil. LCMS (ESI): m/z: [M+H] calcd for C$_{11}$H$_{16}$N$_4$: 204; found 205; RT=1.164 min. $^1$H NMR (400 MHz, chloroform-d) δ ppm 1.22 (d, J=6.62 Hz, 5H) 2.80-2.89 (m, 1H) 2.84 (t, J=7.28 Hz, 1H) 3.03-3.13 (m, 1H) 3.20 (t, J=7.28 Hz, 2H) 6.44 (s, 1H) 6.53 (dd, J=5.51, 1.32 Hz, 1H) 7.98 (d, J=5.51 Hz, 1H).

Example 6. Preparation of N-(3-(2-aminopyridin-4-yl)propyl)-N-isopropylcyanamide (6)

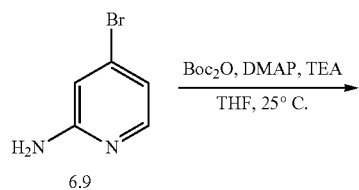

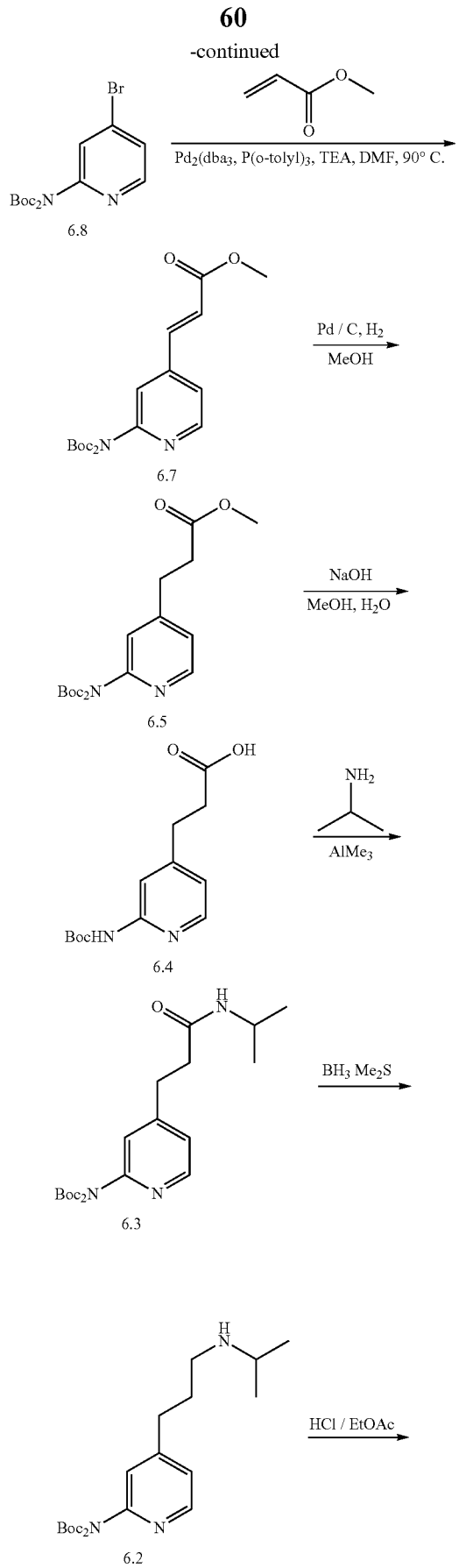

-continued

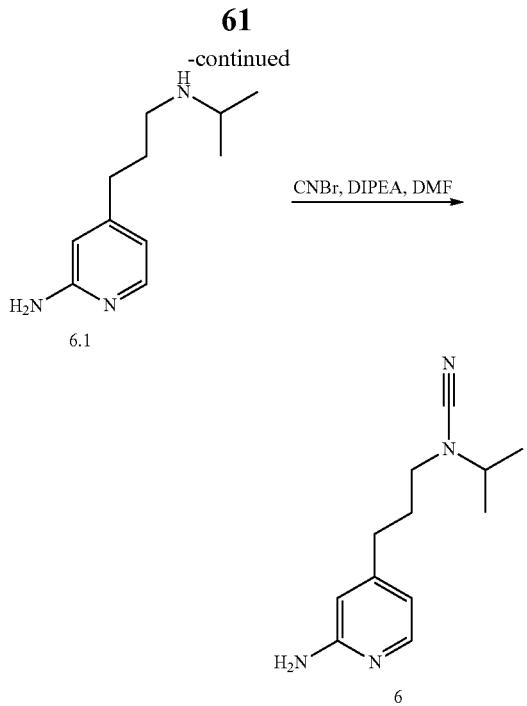

To a solution of compound 6.9 (20 g, 115.60 mmol, 1 eq) in THF (400 mL) was added Boc$_2$O (63.07 g, 289 mmol, 66.39 mL, 2.50 eq), DMAP (4.24 g, 34.68 mmol, 0.30 eq) and TEA (35.09 g, 346.80 mmol, 48.07 mL, 3 eq) at 25° C. under N$_2$. The resulting mixture was stirred for 16 hours. The reaction mixture was added water 100 mL, extracted with EtOAc (300 mL×3). The organic phase was separated, washed with NH4Cl 100 mL and dried over Na$_2$SO$_4$, filtered and concentrated under reduced pressure to give a residue. The residue was purified by column chromatography (SiO$_2$, Petroleum ether/Ethyl acetate=5:1). Compound 6.8 (27.70 g, 74.21 mmol, 64.20% yield) was obtained as a colorless oil.

To a solution of compound 6.8 (27.70 g, 74.21 mmol, 1 eq) in DMF (460 mL) was added TEA (15.02 g, 148.43 mmol, 20.57 mL, 2 eq), P(o-tolyl)$_3$ (6.78 g, 22.26 mmol, 0.30 eq), Pd$_2$(dba)$_3$ (6.80 g, 7.42 mmol, 0.10 eq) and methyl prop-2-enoate (25.56 g, 296.86 mmol, 26.62 mL, 4 eq) in turn at 25° C. under N$_2$. The resulting mixture was stirred at 80° C. for 13 hours. The reaction mixture was added H$_2$O 500 mL at 25° C., extracted with EtOAc (500 mL×3). The combined organic layers were washed with saturated brine 200 mL (200 mL×1), dried over dry Na$_2$SO$_4$, filtered and concentrated under reduced pressure to give a residue. The residue was purified by column chromatography (SiO$_2$, Petroleum ether/Ethyl acetate=50:1 to 10:1). Compound 6.7 (24 g, 63.42 mmol, 85.46% yield) was obtained as a white solid.

To a solution of compound 6.7 (24 g, 63.42 mmol, 1 eq) in MeOH (1.50 L) was added Pd—C under Ar$_2$. The suspension was degassed under vacuum and purged with H$_2$ several times. The mixture was stirred under H$_2$ (50 psi) at 25° C. for 24 hours. Pd/C was filtered off by filtration. The filtrate was concentrated to dry. Compound 6.6 (22 g, 57.83 mmol, 91.19% yield) was obtained as a white solid.

To a mixture of compound 6.5 (6 g, 15.77 mmol, 1 eq) in MeOH (60 mL) was added NaOH (1.89 g, 47.31 mmol, 3 eq) in one portion at 25° C. The mixture was stirred at 25° C. for 17 h. The pH was adjusted to around 4 by progressively adding citric acid. Then the solid was precipitate out, filtered to give compound 6.4 (4 g, 10.92 mmol, 69.22% yield) as a white solid. LCMS (ESI): m/z: [M−H] calcd for C$_{13}$H$_{18}$N$_2$O$_4$: 265; found 265; RT=0.859 min. $^1$H NMR (400 MHz, methanol-d$_4$) δ ppm 1.45-1.59 (m, 7H) 2.56-2.70 (m, 2H) 2.83-2.98 (m, 2H) 6.91 (dd, J=5.18, 1.43 Hz, 1H) 7.71 (d, J=0.66 Hz, 1H) 8.06 (d, J=5.07 Hz, 1H).

A solution of compound 6.4 (1 g, 2.63 mmol, 1 eq) was added in i-PrNH2 (6.90 g, 116.73 mmol, 10 mL, 44.38 eq) at 25° C. The mixture was added AlMe$_3$ (568.79 mg, 7.89 mmol, 3 mL, 3 eq) dropwised at 25° C. The resulting mixture was stirred at 25° C. for 23 hours. The reaction mixture was filtered and concentrated under reduced pressure to give compound 6.3 (677 mg, 1.66 mmol, 63.17% yield).

To a solution of compound 6.3 (670 mg, 2.18 mmol, 1 eq) in THF (10 mL) was added a solution of BH$_3$-Me$_2$S (10 M, 872 µL, 4 eq) dropwise with at 0° C. over a period of 1 mins under N$_2$. Then stirring at 25° C. 4 hours. The reaction was quenched by addition of 6 ml methanol, then the reaction mixture was concentrated under reduced pressure to remove solvent. The mixture was further purification by pre-HPLC to give compound 6.2 (70 mg, 238.58 µmol, 10.94% yield) (70 mg, 238.58 µmol, 10.94% yield) as a white solid. LCMS (ESI): m/z: [M+H] calcd for C$_{16}$H$_{27}$N$_3$O$_2$: 294; found 294; RT=0.735 min.

To a mixture of compound 6.2 (70 mg, 177.88 µmol, 1 eq) in HCl/EtOAc (2 mL) at 25° C. for 13 hours. The reaction mixture was concentrated under reduced pressure to give compound 6.1 (65 mg, crude) as light yellow oil.

To a mixture of compound 6.1 (63 mg, 236.66 µmol, 1 eq) and BrCN (25.07 mg, 236.66 µmol, 17.41 µL, 1 eq) in THF (3 mL) was added DIEA (122.34 mg, 946.64 µmol, 165.32 µL, 4 eq) in one portion at 0° C. under N$_2$. The mixture was stirred at 25° C. for 10 mins. The aqueous phase was extracted with ethyl acetate (10 mL×3). The combined organic phase was washed with brine (3 mL×3), dried with anhydrous Na$_2$SO$_4$, filtered and concentrated in vacuum. The residue was purified by prep-HPLC (neutral condition) to give 6 (10 mg, 45.81 µmol, 19.36% yield) as a yellow oil. LCMS (ESI): m/z: [M+H] calcd for C$_{12}$H$_{18}$N$_4$: 219; found 219; RT=2.279 min. $^1$H NMR (400 MHz, chloroform-d) δ ppm 1.25-1.28 (d, J=6.0 6 H) 1.90-2.10 (m, 2H) 2.50-2.62 (m, 2H) 2.96-2.99 (m, 2H) 3.08-3.13 (m, 1H) 4.37 (s, 2H) 6.35 (s, 1H) 6.4-6.50 (d, J=5.2 6 H) 7.98-7.99 (d, J=5.2 1 H).

Example 7. Preparation of 3-((2-aminopyridin-4-yl)oxy)azetidine-1-carbonitrile (7)

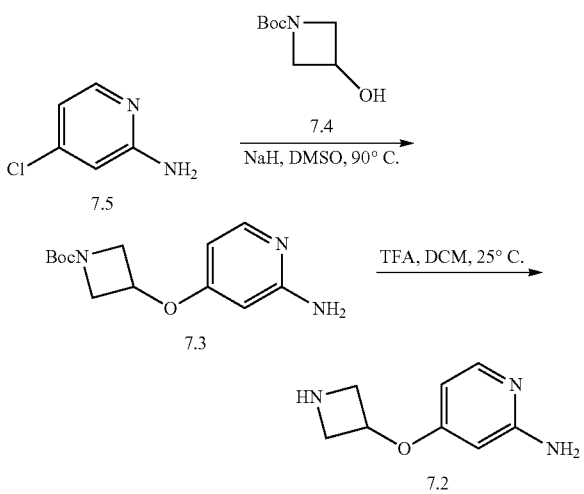

-continued

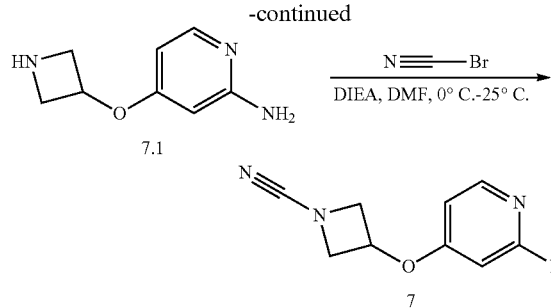

Example 8. Preparation of 4-((2-aminopyridin-4-yl)oxy)piperidine-1-carbonitrile (8)

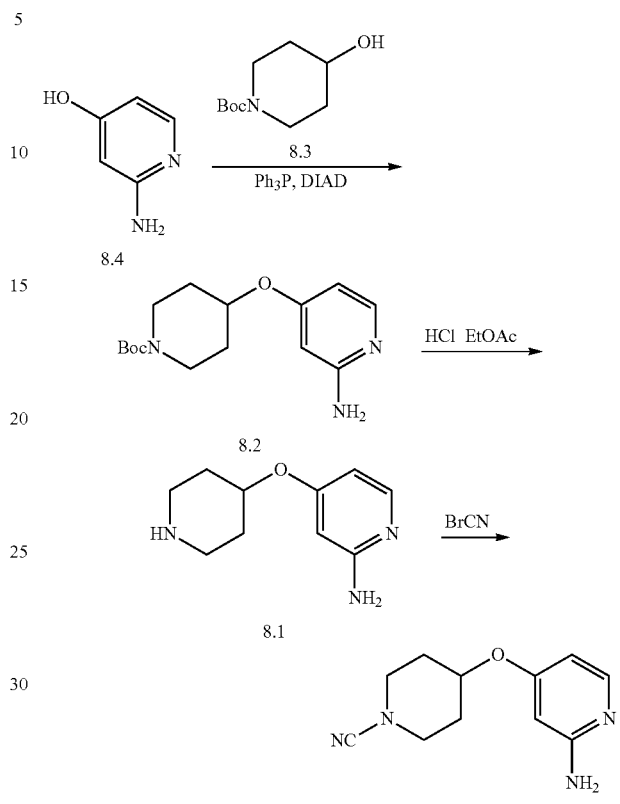

To a mixture of compound 7.4 (2 g, 11.55 mmol, 1 eq) in DMSO (40 mL) was added NaH (554.24 mg, 23.09 mmol, 2 eq) in one portion at 25° C. under $N_2$. The mixture was stirred at 25° C. for 2 hours, then added compound 7.5 (2.97 g, 23.09 mmol, 2 eq) to mixture and heated to 90° C. and stirred for 15 hours. The mixture was cooled to 25° C. and poured into ice-water (50 mL). The aqueous phase was extracted with ethyl acetate (40 mL×3). The combined organic phase was washed with brine (30 mL×1), dried with anhydrous $Na_2SO_4$ concentrated in vacuum to give a crude product as a brown solid. Then the crude product was purified by silica gel chromatography eluted with EtOAc:DCM=1:1 to give compound 7.2 (230 mg, 90%) as a brown oil. $^1$H NMR (400 MHz, chloroform-d) ppm 1.46 (s, 9H) 4 (dd, J=9.79, 3.76 Hz, 2H) 4.33 (dd, J=9.54, 6.53 Hz, 2H) 4.91 (t, J=3.76 Hz, 1H) 5.91-6.01 (m, 1H) 6.18 (dd, J=6.02, 1.51 Hz, 1H) 7.84 (d, J=6.02 Hz, 1H). LCMS (ESI): m/z: [M+H] calcd for $C_{13}H_{19}N_3O_3$: 266; found 266; RT=1.547 min.

Compound 7.2 (230 mg, 866.91 μmol, 1 eq) was dissolved DCM (5 mL) and TFA (1 mL) at 25° C. under $N_2$. The mixture was stirred at 25° C. for 15 hours. The mixture was added small amount of water and acetonitrile, then work up it by lyophilization to give compound 7.1 (300 mg, 724.75 μmol, 83.60% yield, 95% purity, 2 TFA) as brown oil. The crude product was used for next step directly without purification. $^1$H NMR (400 MHz, methanol-d4) ppm 4.27 (dd, J=12.55, 4.52 Hz, 2H) 4.63 (dd, J=12.80, 6.78 Hz, 2H) 5.25-5.42 (m, 1H) 6.27 (d, J=2.51 Hz, 1H) 6.58 (dd, J=7.28, 2.26 Hz, 1H) 7.81 (d, J=7.53 Hz, 1H). LCMS (ESI): m/z: [M+H] calcd for C8H11N3O.2(C2HF3O2): 166; found 166; RT=0.214 min.

The mixture of compound 7.1 (50 mg, 302.68 μmol, 1 eq), TEA (30.63 mg, 302.68 mol, 41.96 μL, 1 eq) and DIEA (117.36 mg, 908.04 μmol, 158.59 μL, 3 eq) in DCM (5 mL) was added dropwise solution of BrCN (32.06 mg, 302.68 μmol, 22.26 μL, 1 eq). The mixture was stirred at 25° C. for 10 min. The reaction mixture was quenched by addition $H_2O$ 5 mL at 25° C., and then extracted with DCM (5 mL×3). The combined organic layers were washed with saturated brines (3 mL×1), dried over anhydrous sodium sulfate, filtered and concentrated under reduced pressure to give a crude product. The crude product was purified by prep-HPLC (TFA condition) to give the product 7 (13 mg, 68.35 μmol, 22.58% yield) as a white solid. $^1$H NMR (400 MHz, chloroform-d) ppm 4.27 (dd, J=8.82, 4.41 Hz, 2H) 4.44 (br. s., 2H) 4.48-4.59 (m, 2H) 4.98 (br. s., 1H) 5.77 (s, 1H) 6.02-6.15 (m, 1H) 7.94 (d, J=5.73 Hz, 1H). LCMS (ESI): m/z: [M+H] calcd for $C_9H_{10}N_4O$: 191; found 191; RT=1.014 min.

To a solution of compound 8.4 (500 mg, 4.54 mmol, 1 eq) in DCM (15 mL) was added compound 8.3 (913.90 mg, 4.54 mmol, 1 eq) $PPh_3$ (1.79 g, 6.81 mmol, 1.50 eq) and DIAD (1.38 g, 6.81 mmol, 1.32 mL, 1.50 eq) in turn at 0° C. under $N_2$. The resulting mixture was stirred at 25° C. for 3 hours. The reaction mixture was added water 20 mL, extracted with EtOAc (20 mL×3). The combined organic layers were washed with brine (20 mL×1), dried over $Na_2SO_4$, filtered and concentrated under reduced pressure to give a residue. The residue was purified by column chromatography ($SiO_2$, Petroleum ether/Ethyl acetate=1:1). Compound 8.2 (300 mg, 1.02 mmol, 22.52% yield) was obtained as a white solid. $^1$H NMR (400 MHz, chloroform-d) ppm 1.47 (s, 9H) 1.72-1.77 (m, 2H) 1.88-1.93 (m, 2H) 3.33-3.37 (m, 2H) 3.64-3.68 (m, 2H) 4.37 (s, 2H) 4.47-4.51 (m, 1H) 5.98 (d, J=2.0 Hz, 1H) 6.25 (dd, J=6.0 Hz, 2.0 Hz, 1H) 7.90 (d, J=6.0 Hz, 1H).

A mixture of compound 8.2 (200 mg, 681.76 μmol, 1 eq) in EtOAc HCl (10 mL) was stirred at 25° C. for 16 hours. The reaction mixture was filtered, the cake was washed with EtOAc (10 mL). The solid was removed solvent under reduced pressure. Compound 8.1 (100 mg, 435.33 μmol, 63.85% yield) was obtained as a white solid. $^1$H NMR (400 MHz, $D_2O$-d4) ppm 2.02-2.13 (m, 4H) 3.18-3.36 (m, 4H) 4.84-4.85 (m, 1H) 6.33 (d, J=2.0 Hz, 1H) 6.49 (dd, J=7.2 Hz, 2.0 Hz, 1H) 7.69 (m, 1H).

To a solution of compound 8.1 (50 mg, 217.67 μmol, 1 eq) in THF (5 mL) was added DIEA (28.13 mg, 217.67 μmol, 38.02 μL, 1 eq) and BrCN (23.06 mg, 217.67 μmol, 16.01 μL, 1 eq) in turn at 0° C. under $N_2$. The resulting mixture was stirred at 0° C. for 2.5 hours. The reaction mixture was added water 5 mL, extracted with EtOAc (10 mL×3). The combined organic layers were washed with brine (5 mL×1), dried over $Na_2SO_4$, filtered and concentrated under reduced pressure to give a residue. The residue was purified by prep-HPLC (basic condition). Product 8 (6.50 mg, 29.78 µmol, 13.68% yield) was obtained as a white solid. LCMS (ESI): m/z: [M+H] calcd for $C_{11}H_{14}N_4O$: 218; found 219; RT=1.934 min. $^1$H NMR (400 MHz, chloroform-d) ppm 1.95-2.03 (m, 4H) 3.23-3.48 (m, 4H) 4.38 (s, 2H) 4.56 (m, 1H) 5.96 (s, 1H) 6.24 (s, 1H) 7.93 (d, J=5.2 Hz, 1H).

Example 9. Preparation of 3-((2-aminopyridin-4-yl)oxy)piperidine-1-carbonitrile (9)

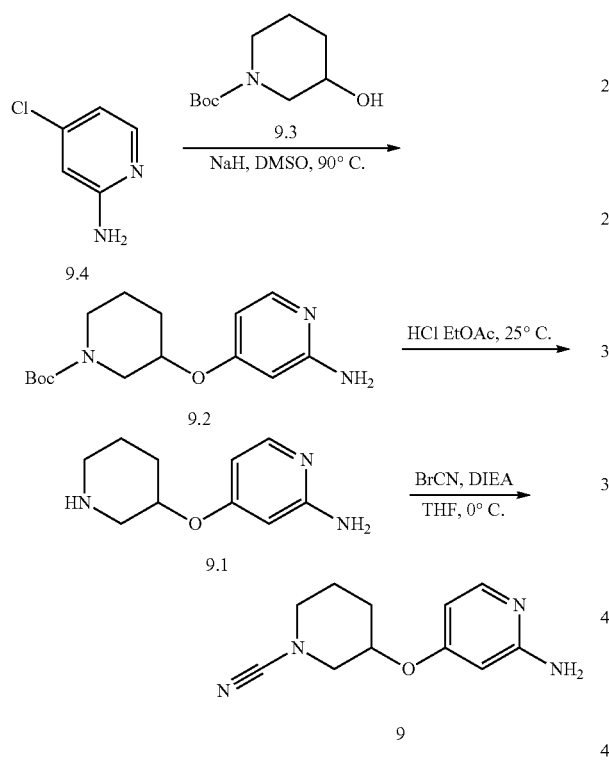

To a mixture of compound 9.3 (2 g, 9.94 mmol, 1 eq) in DMSO (40 mL) was added NaH (476.99 mg, 19.88 mmol, 2 eq) in one portion. The mixture was stirred under $N_2$ at 25° C. for 2 hours, then added compound 9.4 (2.56 g, 19.88 mmol, 2 eq) to the mixture and heated to 90° C. and stirred for 15 hours. The mixture was cooled to 25° C. and poured into ice-water (50 mL). The aqueous phase was extracted with ethyl acetate (40 mL×3). The combined organic phase was washed with brine (30 mL×1), dried with anhydrous $Na_2SO_4$ concentrated in vacuum to give a crude product as a brown solid. Then the crude product was purified by silica gel chromatography eluted with (EtOAc:DCM=1:1) to give compound 9.2 (130 mg, 420.98 µmol, 4.24% yield, 95% purity) as a brown oil. $^1$H NMR (400 MHz, methanol-d$_4$) δ ppm 1.17-1.49 (m, 9H) 1.49-1.62 (m, 1H) 1.74-2.06 (m, 3H) 2.94-3.15 (m, 1H) 3.32-4.14 (m, 3H) 4.58 (br. s., 1H) 6.32 (br. s., 1H) 6.46 (d, J=5.29 Hz, 1H) 7.59-7.81 (m, 1H). LCMS (ESI): m/z: [M+H] calcd for $C_{15}H_{23}N_3O_3$: 294; found 294; RT=1.046 min.

Compound 9.2 (130 mg, 443.14 µmol, 1 eq) was dissolved HCl/EtOAc (10 mL) and MeOH (5 mL) at 25° C. under $N_2$. The mixture was stirred at 25° C. for 5 h. The mixture was concentrated in vacuum to give compound 9.1 (80 mg, 393.27 µmol, 88.75% yield, 95% purity) as yellow oil. The crude product was used for next step directly without purification. $^1$H NMR (400 MHz, methanol-d4) δ ppm 1.79-1.91 (m, 1H) 1.94-2.15 (m, 3H) 3.17 (br. s., 1H) 3.33 (br. s., 1H) 3.39-3.63 (m, 3H) 5.03 (br. s., 1H) 6.49 (d, J=2.21 Hz, 1H) 6.62 (dd, J=7.28, 2.43 Hz, 1H) 7.77 (d, J=7.06 Hz, 1H).

To a solution of compound 9.1 (80 mg, 413.97 µmol, 1 eq) in THF (3 mL) and TEA (125.67 mg, 1.24 mmol, 172.15 µL, 3 eq) was added a solution of BrCN (43.85 mg, 413.97 mol, 30.45 µL, 1 eq) in THF (3 mL) drop-wise at 0° C. under $N_2$. The reaction mixture was stirred at 0° C. for 4 h. To the reaction mixture was added 4 mL water at 0° C. The aqueous phase was extracted with ethyl acetate (15 mL×3). The combined organic phase was washed with brine (5 mL×1), dried with anhydrous $Na_2SO_4$, filtered and concentrated in vacuum. The crude product was purified by prep-TLC (neutral condition) to give product 9 (12 mg, 50.58 µmol, 12.22% yield, 92% purity) as brown oil. $^1$H NMR (400 MHz, methanol-d4) ppm 1.59-1.72 (m, 1H) 1.88-1.97 (m, 3H) 3.34-3.41 (m, 1H) 3.42-3.51 (m, 1H) 4.62-4.72 (m, 1H) 5.09-5.20 (m, 1H) 6.22-6.32 (m, 1H) 6.38-6.56 (m, 1H) 7.65-7.80 (m, 1H). LCMS (ESI): m/z: [M+H] calcd for $C_{11}H_{14}N_4O$: 219; found 219; RT=1.148 min.

Example 10. Preparation of 3-(((2-aminopyridin-4-yl)oxy)methyl)azetidine-1-carbonitrile (10)

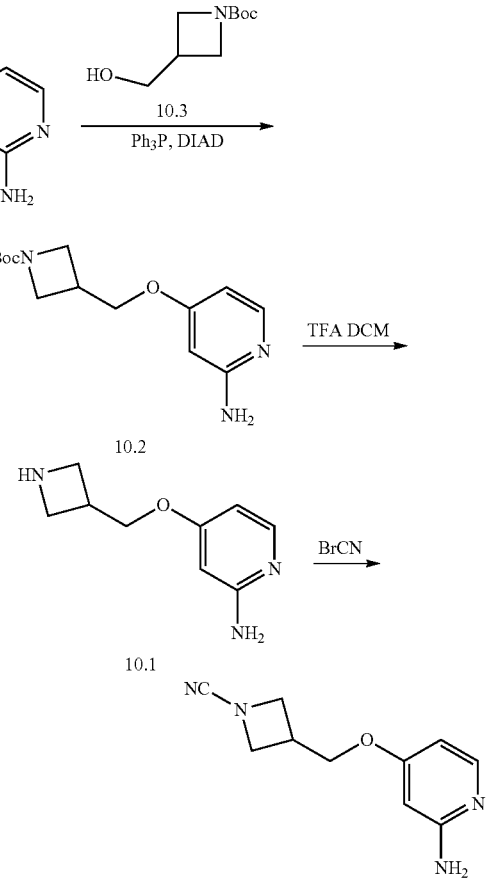

To a solution of compound 10.4 (1.50 g, 13.62 mmol, 1 eq) in DCM (15 mL) was added compound 10.3 (2.55 g, 13.62 mmol, 1 eq), PPh$_3$ (5.36 g, 20.43 mmol, 1.50 eq) and DIAD (4.13 g, 20.43 mmol, 3.97 mL, 1.50 eq) in turn at 0° C. under N$_2$. The resulting mixture was stirred at 25° C. for 10 hours. The reaction mixture was added water 5 mL, extracted with EtOAc (10 mL×3). The combined organic layers were washed with brine (5 mL×1), dried over Na$_2$SO$_4$, filtered and concentrated under reduced pressure to give a residue. The residue was purified by column chromatography (SiO$_2$, Petroleum ether/Ethyl acetate=1:1). Compound 10.2 (800 mg, 2.86 mmol, 21.03% yield) was obtained as a white solid. $^1$H NMR (400 MHz, chloroform-d) ppm 1.46 (s, 9H) 2.92-3 (m, 1H) 3.75-3.79 (m, 2H) 4.06-4.09 (m, 4H) 4.39 (s, 2H) 5.98 (d, J=2.0 Hz, 1H) 6.26 (dd, J=6.0 Hz, 2.0 Hz, 1H) 7.90 (d, J=5.6 Hz, 1H)

To a solution of compound 10.2 (300 mg, 1.07 mmol, 1 eq) in DCM (5 mL) was added TFA (1.54 g, 13.50 mmol, 1 mL, 12.62 eq) at 25° C. under N$_2$. The resulting mixture was stirred at 25° C. for 16 hours. The reaction mixture was concentrated under reduced pressure to give a residue and freezing dry. Compound 10.1 (500 mg, crude) was obtained as a white solid. $^1$H NMR (400 MHz, D$_2$O-d4) ppm 3.36-3.43 (m, 1H) 4.40-4.12 (m, 2H) 4.22-4.31 (m, 4H) 6.42 (d, J=2.8 Hz, 1H) 6.62 (dd, J=7.6 Hz, 2.4 Hz, 1H) 7.69 (d, J=6.8 Hz, 1H)

To a solution of compound 10.1 (300 mg, 736.61 μmol, 1 eq) in THF (5 mL) was added DIEA (285.60 mg, 2.21 mmol, 385.94 μL, 3 eq) and BrCN (78.02 mg, 736.61 μmol, 54.18 μL, 1 eq) in turn at 0° C. under N$_2$. The resulting mixture was stirred at 0° C. for 1 hour. The reaction mixture was added water 10 mL, extracted with EtOAc (10 mL×3). The combined organic layers were washed with brine (20 mL×1), dried over Na$_2$SO$_4$, filtered and concentrated under reduced pressure to give a residue. The residue was purified by p-TLC (SiO$_2$, Ethyl acetate=0:1). Product 10 (14 mg, 68.55 μmol, 9.31% yield) was obtained as a white solid. LCMS (ESI): m/z: [M+H] calcd for C$_{10}$H$_{12}$N$_4$O: 204; found 205; RT=1.750 min. $^1$H NMR (400 MHz, chloroform-d) ppm 3.13-3.19 (m, 1H) 4.08-4.11 (m, 4H) 4.31-4.35 (m, 2H) 4.96 (s, 2H) 6.05 (d, J=2.0 Hz, 1H) 6.30 (dd, J=6.0 Hz, 2.0 Hz, 1H) 7.88 (d, J=6.0 Hz, 1H).

Example 11. Preparation of 2-(((2-aminopyridin-4-yl)oxy)methyl)azetidine-1-carbonitrile (11)

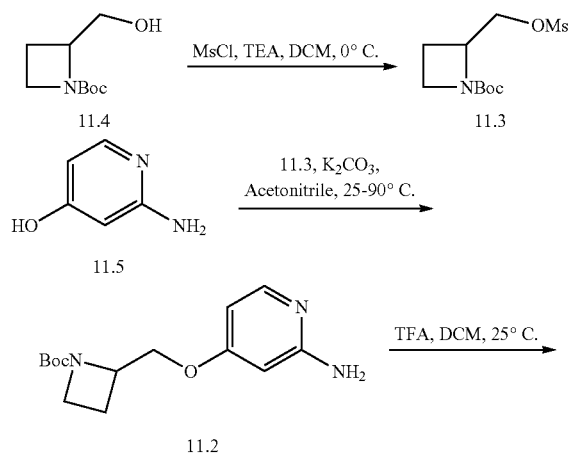

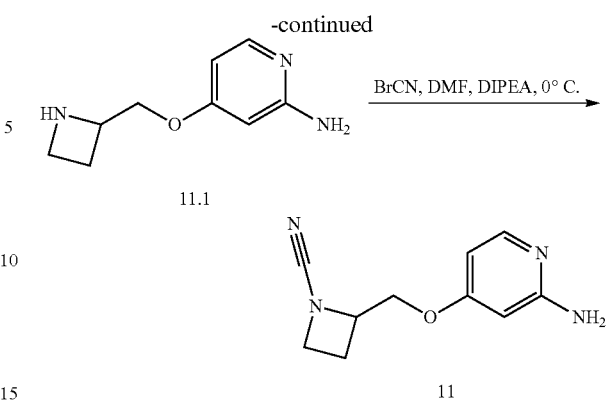

To a mixture of compound 11.4 (500 mg, 2.67 mmol, 1 eq) and TEA (540.35 mg, 5.34 mmol, 740.21 μL, 2 eq) in DCM (10 mL) was added MsCl (367.02 mg, 3.20 mmol, 247.99 μL, 1.20 eq) dropwise at 0° C. under N$_2$. The reaction mixture was diluted with H$_2$O 10 mL and extracted with DCM 10 mL (10 mL×3). The combined organic layers were washed with brine 20 mL (20 mL×1), dried over Na$_2$SO$_4$, filtered and concentrated under reduced pressure to give compound 11.3 (850 mg, crude) as a yellow oil. (Combined with a second batch to afford a total of 1.3 g). LCMS (ESI): m/z: [M+H] calcd for C$_{10}$H$_{19}$NSO$_5$: 265; found 166,210; RT=0.657, 0.693 min.

To a mixture of compound 11.3 (1 g, 3.77 mmol, 1 eq) and compound 11.5 (414.99 mg, 3.77 mmol, 1 eq) in acetonitrile (15 mL) was added K$_2$CO$_3$ (1.04 g, 7.54 mmol, 2 eq) in one portion at 25° C. under N$_2$. Then heated to 90° C. and stirred for 10 hours. The reaction mixture was diluted with H$_2$O 15 mL and extracted with EA 10 mL (10 mL×3). The combined organic layers were washed with brine 20 mL (20 mL×1), dried over Na$_2$SO$_4$, filtered and concentrated under reduced pressure to give a residue. Then the residue was purified by column (SiO2, DCM/MeOH=10:1) to give compound 11.2 (200 mg, 716 μmol, 18.99% yield) as a white solid. $^1$H NMR (400 MHz, chloroform-d) ppm 1.42 (s, 9H) 1.45 (s, 18H) 1.78 (br. s., 3H) 2.17-2.41 (m, 6H) 2.98-3.12 (m, 6H) 3.73-3.93 (m, 6H) 4.21-4.33 (m, 3H) 4.35-4.63 (m, 6H) 6.03 (d, J=1.51 Hz, 1H) 6.30 (dd, J=6.02, 2.01 Hz, 1H) 7.89 (d, J=6.02 Hz, 1H). LCMS (ESI): m/z: [M+H] calcd for C$_{14}$H$_{21}$N$_3$O$_3$: 279; found 187; RT=0.576, 0.630 min.

To a solution of compound 11.2 (200 mg, 716 μmol, 1 eq) in DCM (5 mL) was added TFA (1.54 g, 13.51 mmol, 1 mL, 18.86 eq) in one portion at 25° C. under N$_2$. The mixture was stirred at 25° C. for 10 hours. The reaction mixture was concentrated under reduced pressure to give compound 11.1 (240 mg, crude) as a light yellow solid. LCMS (ESI): m/z: [M+H] calcd for C$_9$H$_{13}$N$_3$O: 179; found 180; RT=0.175, 0.240 min.

To a mixture of compound 11.1 (50 mg, 278.99 μmol, 1 eq) and DIPEA (144.23 mg, 1.12 mmol, 194.91 μL, 4 eq) in DCM (2 mL) was added a solution of carbononitridic bromide (29.55 mg, 278.99 μmol, 20.52 μL, 1 eq) in 0.5 ml DCM dropwise at 0° C. under N$_2$. The mixture was stirred at 0° C. for 30 mins. The reaction mixture was diluted with H$_2$O 2 mL and extracted with DCM 2 mL (2 mL×3). The combined organic layers were washed with brine 3 mL (3 mL×1), dried over Na$_2$SO$_4$, filtered and concentrated under reduced pressure to give a residue. Then, the residue was purified by prep-HPLC (TFA condition) to give product 11 (10 mg, 48.96 μmol, 17.55% yield) as a yellow solid. $^1$H NMR (400 MHz, chloroform-d) ppm 2.32-2.43 (m, 1H)

2.43-2.54 (m, 1H) 4.06-4.25 (m, 3H) 4.43 (br. s., 1H) 4.64-4.77 (m, 1H) 6.03 (d, J=2.01 Hz, 1H) 6.30 (dd, J=5.52, 2.01 Hz, 1H) 7.94 (d, J=6.02 Hz, 1H). LCMS (ESI): m/z: [M+H] calcd for $C_{10}H_{12}N_4O$: 204; found 205; RT=1.754 min.

Example 12. Preparation of 2-(((2-aminopyridin-4-yl)oxy)methyl)piperidine-1-carbonitrile (12)

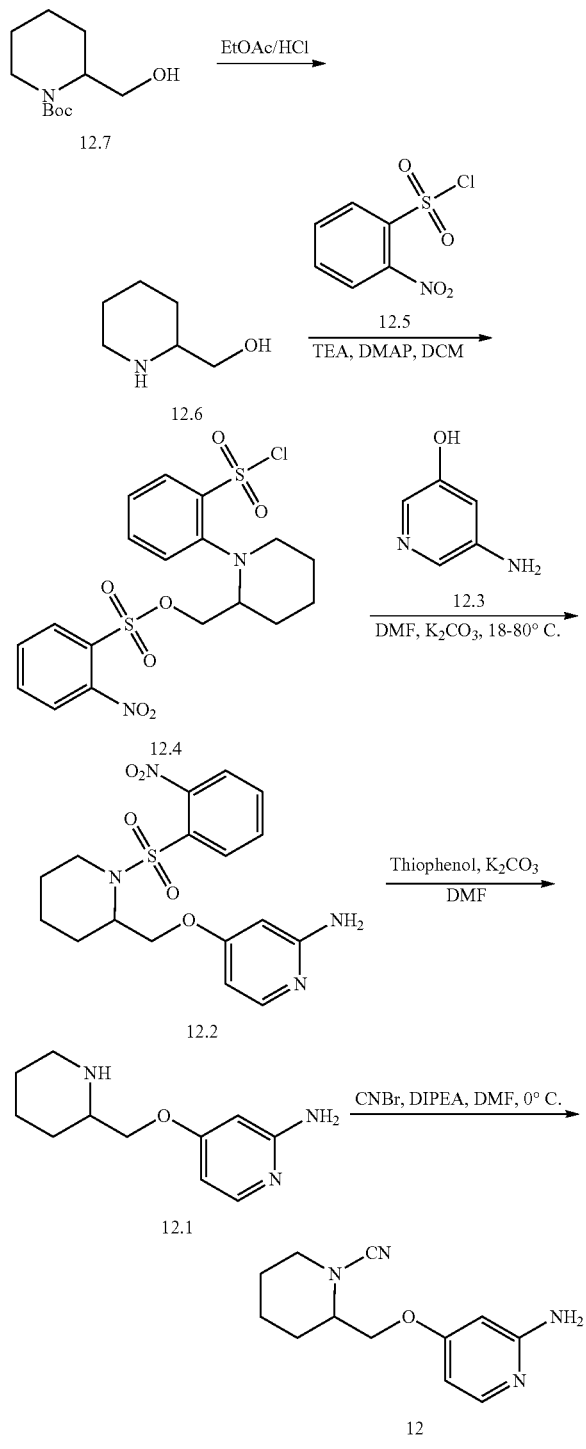

Compound 12.7 (2 g, 9.29 mmol, 1 eq) was added into HCl/EtOAc (20 mL), the reaction was stirred for 15 hours at 18° C. The reaction mixture was concentrated under reduced pressure to give compound 12.6 (2.10 g, crude) as a white solid.

To a mixture of compound 12.6 (2.10 g, 11.16 mmol, 1 eq, 2HCl) and TEA (3.39 g, 33.48 mmol, 4.64 mL, 3 eq) in DCM (25 mL) was added compound 12.5 (5.19 g, 23.44 mmol, 2.10 eq) in one portion at 0° C. The mixture was then heated to 18° C. and stirred for 15 hours. The reaction mixture was quenched by addition $H_2O$ 20 mL and then diluted with DCM 10 mL and extracted with DCM 20 mL (20 mL×3). The combined organic layers were washed with brine 40 mL (40 mL×1), dried over $Na_2SO_4$, filtered and concentrated under reduced pressure to give compound 12.4 (4.50 g, crude) as a yellow solid. LCMS (ESI): m/z: [M−H] calcd for $C_{18}H_{19}N_3O_9S_2$: 485; found 486; RT=0.869 min.

To a mixture of compound 12.4 (4.50 g, 9.27 mmol, 1 eq) and compound 12.3 (1.22 g, 11.12 mmol, 1.20 eq) in DMF (50 mL) was added $K_2CO_3$ (2.56 g, 18.54 mmol, 2 eq) in one portion at 18° C. under $N_2$. Then heated to 80° C. and stirred for 15 hours. The reaction mixture was diluted with $H_2O$ 50 mL and extracted with EtOAc 120 mL (40 mL×3). The combined organic layers were washed with brine 80 mL (80 mL×1), dried over $Na_2SO_4$, filtered and concentrated under reduced pressure to give a residue. The residue was purified by prep-TLC ($SiO_2$, DCM:MeOH=10:1) to give compound 12.2 (260 mg, 662.54 μmol, 7.15% yield) as a yellow solid. LCMS (ESI): m/z: [M−H] calcd for $C_{17}H_{20}N_4O_5S$: 392; found 393; RT=0.714 min.

To a mixture of compound 12.2 (260 mg, 662.54 μmol, 1 eq) and $K_2CO_3$ (366.28 mg, 2.65 mmol, 4 eq) in DMF (2 mL) was added THIOPHENOL (146 mg, 1.33 mmol, 135.18 μL, 2 eq) dropwise at 18° C. under $N_2$. The mixture was stirred at 18° C. for 4 hours. The residue was purified by prep-HPLC (TFA condition) to give compound 12.1 (80 mg, 385.97 μmol, 58.26% yield) as a white solid. LCMS (ESI): m/z: [M−H] calcd for $C_{11}H_{17}N_3O$: 207; found 208; RT=1.039 min. $^1H$ NMR (400 MHz, methanol-$d_4$) δ ppm 1.60-1.83 (m, 2H) 1.91-2.10 (m, 2H) 3.04-3.18 (m, 1H) 3.49 (br d, J=12.80 Hz, 1H) 3.65 (td, J=7.37, 3.45 Hz, 1H) 4.27 (dd, J=10.79, 7.28 Hz, 1H) 4.41 (dd, J=10.79, 3.39 Hz, 1H) 6.45 (d, J=2.51 Hz, 1H) 6.62 (dd, J=7.28, 2.51 Hz, 1H) 7.79 (d, J=7.28 Hz, 1H)

To a mixture of compound 12.1 (70 mg, 337.72 μmol, 1 eq) and DIEA (174.59 mg, 1.35 mmol, 235.93 μL, 4 eq) in DMF (3 mL) was added carbononitridic bromide (35.77 mg, 337.72 μmol, 24.84 μL, 1 eq) in one portion at 0° C. under $N_2$. The mixture was stirred at 0° C. for 30 mins. The reaction mixture diluted with $H_2O$ 3 mL and extracted with DCM 9 mL (3 mL×3). The combined organic layers were washed with brine 4 mL (4 mL×1), dried over $Na_2SO_4$, filtered and concentrated under reduced pressure to give a residue. The residue was purified by prep-HPLC (neutral condition) to give product 12 (15 mg, 64.58 μmol, 19.12% yield) as a yellow solid. LCMS (ESI): m/z: [M−H] calcd for $C_{12}H_{16}N_4O$: 232; found 233; RT=1.970 min. $^1H$ NMR (400 MHz, DMSO-$d_6$) δ ppm 1.48 (br d, J=8.03 Hz, 2H) 1.60 (br s, 1H) 1.74 (br d, J=6.65 Hz, 2H) 3.10-3.19 (m, 1H) 3.43 (br s, 1H) 3.54 (br s, 1H) 4.29 (d, J=4.89 Hz, 2H) 6.38 (d, J=2.38 Hz, 1H) 6.57 (dd, J=7.28, 2.51 Hz, 1H) 7.83 (br s, 2H) 7.87 (d, J=7.28 Hz, 1H)

Example 13. Preparation of N-(2-((2-aminopyridin-4-yl)oxy)ethyl)-N-methylcyanamide (13)

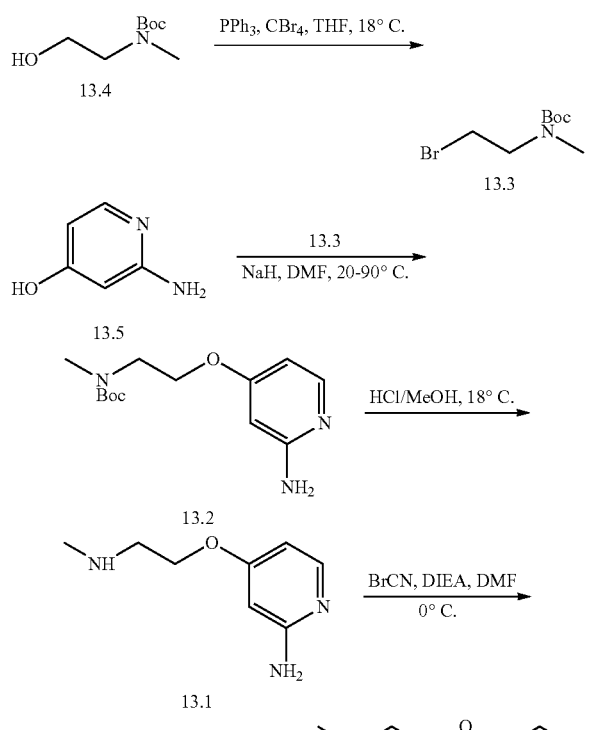

To a mixture of compound 13.4 (2 g, 11.41 mmol, 1 eq) and CBr$_4$ (5.68 g, 17.11 mmol, 1.50 eq) in THF (20 mL) was added PPh$_3$ (4.49 g, 17.11 mmol, 1.50 eq) in one portion at 18° C. under N$_2$. The mixture was stirred at 18° C. for 1 hour. The reaction mixture was filtered and concentrated under reduced pressure to give a residue. The residue was purified by column chromatography (SiO2, DCM) to give compound 13.3 (1.80 g, 7.56 mmol, 66.25% yield) as a colorless oil. $^1$H NMR (400 MHz, chloroform-d) ppm 1.31-1.47 (m, 9H) 2.80-2.91 (m, 3H) 3.37 (br. s., 2H) 3.46-3.59 (m, 2H).

To a solution of compound 13.5 (832.35 mg, 7.56 mmol, 1 eq) in DMF (2 mL) was added NaH (362.84 mg, 15.12 mmol, 2 eq) portionwise at 20° C. under N2. The mixture was stirred at 20° C. for 0.5 hour. Then the mixture was added compound 13.3 (1.80 g, 7.56 mmol, 1 eq) in one portion and heated to 90° C. stirred for 14.5 hours. The reaction mixture was diluted with H$_2$O 3 mL and extracted with EA 2 mL (2 mL×3). The combined organic layers were washed with brine 5 mL (5 mL×1), dried over Na$_2$SO$_4$, filtered and concentrated under reduced pressure to give compound 13.2 (1 g, crude) as a yellow oil. $^1$H NMR (400 MHz, methanol-d4) δ ppm 1.37-1.56 (m, 9H) 2.86 (s, 4H) 2.94 (br. s., 2H) 2.99 (s, 5H) 3.54-3.68 (m, 1H) 4.01-4.16 (m, 2H) 6.10 (d, J=2.21 Hz, 1H) 6.18-6.32 (m, 1H) 7.70 (d, J=5.73 Hz, 1H) 7.98 (s, 1H). LCMS (ESI): m/z: [M+H] calcd for C$_{13}$H$_{21}$N$_3$O$_3$: 267; found 268; RT=0.631, 0.833 min.

Compound 13.2 (500 mg, 1.87 mmol, 1 eq) was added into a solution of HCl/MeOH (8 mL). The mixture was stirred at 18° C. for 15 hours. The reaction mixture was concentrated under reduced pressure to give compound 13.1 (300 mg, 1.79 mmol, 95.94% yield) as a yellow solid. LCMS (ESI): m/z: [M+H] calcd for C$_5$H$_{13}$N$_3$O: 167; found 168; RT=0.166, 0.258 min.

To a mixture of compound 13.1 (150 mg, 897.08 μmol, 1 eq) and DIEA (463.75 mg, 3.59 mmol, 626.69 μL, 4 eq) in DCM (3 mL) was added carbononitridic bromide (95.02 mg, 897.08 μmol, 65.98 μL, 1 eq) in one portion at 0° C. under N$_2$. The mixture was stirred at 0° C. for 30 mins. The reaction mixture diluted with H$_2$O 3 mL and extracted with DCM 3 mL (3 mL×3). The combined organic layers were washed with brine 4 mL (4 mL×1), dried over Na$_2$SO$_4$, filtered and concentrated under reduced pressure to give a residue. The residue was purified by prep-HPLC (neutral condition) to give product 13 (10 mg, 52.02 μmol, 5.80% yield) as a yellow solid. $^1$H NMR (400 MHz, DMSO-d6) δ ppm 2.83-2.93 (m, 3H) 3.37 (t, J=4.85 Hz, 2H) 4.06-4.15 (m, 2H) 5.90 (br. s., 2H) 5.99 (d, J=2.21 Hz, 1H) 6.11-6.21 (m, 1H) 7.74 (d, J=6.17 Hz, 1H). LCMS (ESI): m/z: [M+H] calcd for C$_9$H$_{14}$N$_4$O: 192; found 193; RT=0.508 min.

Example 14. Preparation of N-(1-((2-aminopyridin-4-yl)oxy)propan-2-yl)-N-methylcyanamide (14)

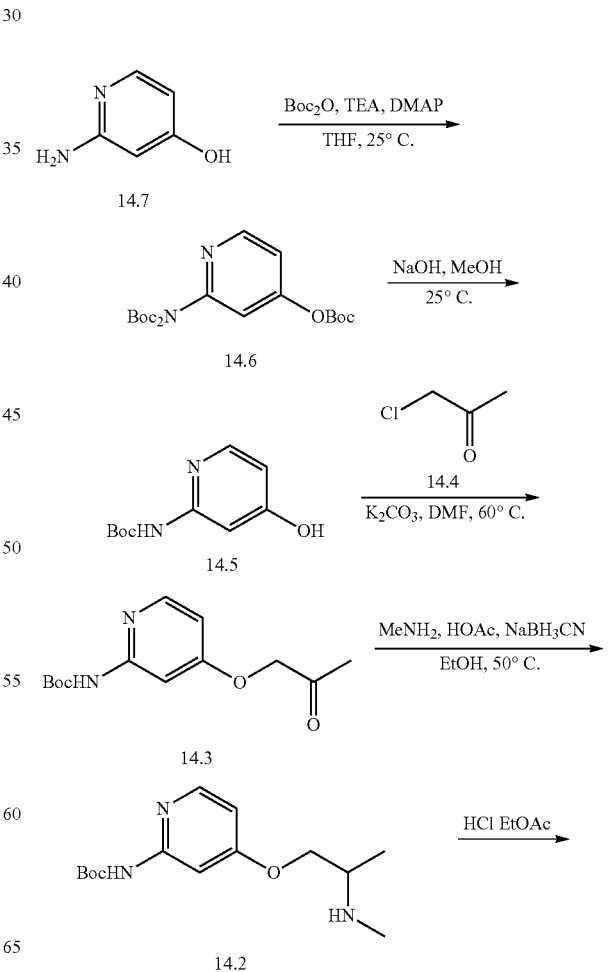

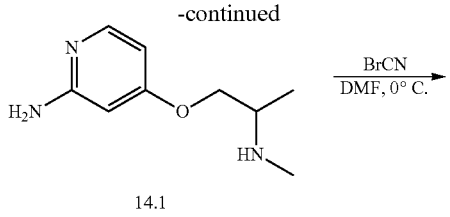

14.1

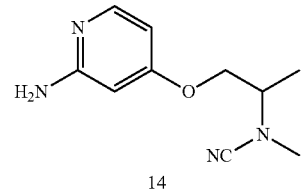

14

To a solution of compound 14.7 (1 g, 9.08 mmol, 1 eq) in THF (20 mL) was added Boc₂O (5.95 g, 27.24 mmol, 6.26 mL, 3 eq), TEA (3.68 g, 36.32 mmol, 5.03 mL, 4 eq) and DMAP (332.79 mg, 2.72 mmol, 0.30 eq) at 25° C. under N₂. The resulting mixture was stirred at 25° C. for 16 hours. The reaction mixture was added water (30 mL), extracted with EtOAc (50 mL×3). The organic phase was separated, washed with saturated NaCl (30 mL) and dried over Na₂SO₄, filtered and concentrated under reduced pressure to give a residue. The residue was purified by column chromatography (SiO₂, Petroleum ether/Ethyl acetate=20:1 to 3:1). Compound 14.6 (1.50 g, 3.65 mmol, 40.25% yield) was obtained as a yellow solid.

To a solution of compound 14.6 (1.50 g, 3.65 mmol, 1 eq) in MeOH (20 mL) was added NaOH (438 mg, 10.95 mmol, 3 eq) at 25° C. under N₂. The resulting mixture was stirred at 25° C. for 16 hours. The reaction mixture was added water (30 mL), extracted with EtOAc (50 mL×3). The organic phase was separated, washed with saturated NaCl (30 mL) and dried over Na₂SO₄, filtered and concentrated under reduced pressure to give a residue. The residue was purified by column chromatography (SiO₂, Petroleum ether/Ethyl acetate=20:1 to 3:1). Compound 14.5 (550 mg, 2.62 mmol, 71.68% yield) was obtained as a white solid.

To a mixture of compound 14.5 (500 mg, 2.38 mmol, 1 eq) and compound 14.4 (330.30 mg, 3.57 mmol, 1.50 eq) in DMSO (20 mL) was added K₂CO₃ (657.88 mg, 4.76 mmol, 2 eq) in one portion at 20° C. under N₂. The mixture was stirred at 20° C. for 15 hours. The aqueous phase was extracted with EtOAc (20 mL×3). The combined organic phase was washed with brine (5 mL), dried with anhydrous Na₂SO₄, filtered and concentrated in vacuum. Compound 14.3 (900 mg, crude) was obtained as a colorless oil. ¹H NMR (400 MHz, chloroform-d) ppm 1.54 (s, 9H), 2.29 (s, 3H), 4.63 (s, 2H), 6.52 (dd, J=5.6 Hz, 2.0 Hz, 1H), 7.58 (d, J=2.0 Hz, 1H), 8.13 (d, J=6.0 Hz, 1H), 9.12 (s, 1H).

To a mixture of compound 14.3 (360 mg, 1.35 mmol, 1 eq) and methanamine (2 M, 1.35 mL, 2 eq) in EtOH (2 mL) was added CH₃COOH (40.59 mg, 675.95 μmol, 38.66 μL, 0.50 eq) and NaBH₃CN (212.38 mg, 3.38 mmol, 2.50 eq) in one portion at 20° C. under N₂. The mixture was stirred at 20° C. for 20 hours. The mixture was diluted with water (5 mL), neutralized with solid NaHCO₃ until no CO₂ was evolved. The residue was purified by column chromatography (SiO₂, Petroleum ether/Ethyl acetate=10:1 to 0:1). Compound 14.2 (110 mg, 390.97 μmol, 28.96% yield) was obtained as a colorless oil. ¹H NMR (400 MHz, chloroform-d) ppm 1.18 (d, J=6.4 Hz, 3H), 1.53 (s, 9H), 2.49 (s, 3H), 3.03-3.06 (m, 1H), 3.89-4.02 (m, 2H), 6.53 (dd, J=5.6 Hz, 2.4 Hz, 1H), 7.54 (d, J=2.4 Hz, 1H), 8.04 (d, J=6.0 Hz, 1H).

To a solution of compound 14.2 (110 mg, 390.97 μmol, 1 eq) in HCl/EtOAc (20 mL) at 20° C. under N₂. The mixture was stirred at 20° C. for 15 hours. Filtered and concentrated in vacuum. Filtered and concentrated in vacuum. Compound 14.1 (110 mg, 378.50 μmol, 96.81% yield, 3HCl) was obtained as a black brown solid. ¹H NMR (400 MHz, methanol-d4) ppm 1.46 (d, J=6.8 Hz, 3H), 2.78 (s, 3H), 2.73-2.75 (m, 1H), 2.49 (s, 3H), 4.29-4.49 (m, 2H), 6.46 (d, J=2.4 Hz, 1H), 6.63 (dd, J=2.4 Hz, J=7.2 Hz, 1H), 7.78 (d, J=7.2 Hz, 1H).

To a mixture of compound 14.1 (80 mg, 441.43 μmol, 1 eq) and carbononitridic bromide (46.76 mg, 441.43 μmol, 32.47 μL, 1 eq) in DMF (1 mL) was added DIEA (228.20 mg, 1.77 mmol, 308.38 μL, 4 eq) in one portion at 0° C. under N₂. The mixture was stirred at 0° C. for 10 mins. The residue was purified by prep-HPLC (basic condition). Product 14 (10 mg, 48.49 μmol, 10.98% yield) was obtained as a black brown solid. ¹H NMR (400 MHz, DMSO-d6) ppm 1.22 (d, J=6.8 Hz, 3H), 2.87 (s, 3H), 3.43-3.45 (m, 1H), 3.89-4.02 (m, 2H), 5.83 (s, 2H), 5.97 (d, J=2.4 Hz, 1H), 6.16 (dd, J=2.0 Hz, J=5.6 Hz, 1H), 7.73 (d, J=6.0 Hz, 1H). LCMS (ESI): m/z: [M+H] calcd for C₁₀H₁₄N₄O: 207; found 207; RT=1.842 min.

Example 15. Preparation of N-(2-((2-aminopyridin-4-yl)oxy)propyl)-N-methylcyanamide (15)

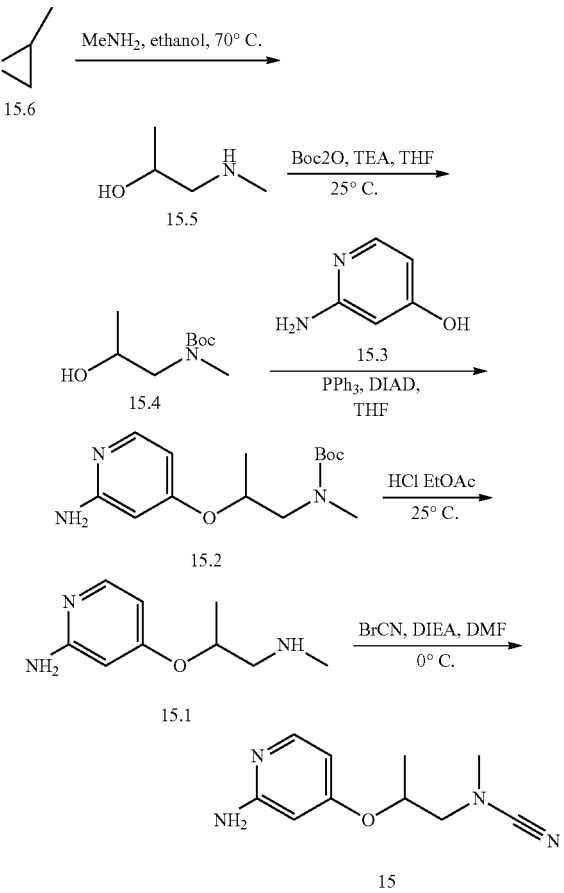

The solution of compound 15.6 (1 g, 17.22 mmol, 1.20 mL, 1 eq) in MeNH$_2$ (ethanol solution) (534.80 mg, 17.22 mmol, 3 mL, 1 eq) was stirred at 70° C. for 15 hour. The mixture was concentrated under reduced pressure to give a residue. The crude product compound 15.5 (1 g, 11.22 mmol, 65.15% yield) was used into the next step without further purification. $^1$H NMR (400 MHz, chloroform-d) ppm 1.05-1.16 (m, 3H) 2.27-2.46 (m, 4H) 2.57 (dd, J=12.13, 2.87 Hz, 1H) 3.79 (d, J=6.17 Hz, 1H).

To a solution of compound 15.5 (1 g, 11.22 mmol, 1 eq) in THF (10 mL) was added TEA (2.27 g, 22.44 mmol, 3.11 mL, 2 eq) and Boc$_2$O (3.67 g, 16.83 mmol, 3.87 mL, 1.50 eq). The mixture was stirred at 25° C. for 15 hours. The reaction mixture was quenched by addition H$_2$O 15 mL at 25° C., and extracted with DCM (20 mL×3). The combined organic layers were washed with saturated brines (15 mL×1), dried over anhydrous sodium sulfate, filtered and concentrated under reduced pressure to give a crude product. The crude product was purified by column chromatography (SiO$_2$, Petroleum:ether/Ethyl acetate=2:1) to give compound 15.4 (1.30 g, 6.87 mmol, 61.22% yield) as a yellow oil. $^1$H NMR (400 MHz, chloroform-d) ppm 1.15 (d, J=6.17 Hz, 3H) 1.36-1.54 (m, 9H) 2.91 (s, 3H) 3.03-3.43 (m, 2H) 3.88-4.13 (m, 1H).

To a solution of compound 15.4 (1.20 g, 6.34 mmol, 1 eq) and compound 15.3 (698.19 mg, 6.34 mmol, 1 eq) in DCM (20 mL) was added PPh$_3$ (2.49 g, 9.51 mmol, 1.50 eq) and DIAD (1.92 g, 9.51 mmol, 1.85 mL, 1.50 eq). The mixture was stirred at 25° C. for 15 hours. The reaction mixture was quenched by addition H$_2$O 25 mL at 25° C., and extracted with DCM (20 mL×3). The combined organic layers were washed with saturated brines (15 mL×1), dried over anhydrous sodium sulfate, filtered and concentrated under reduced pressure to give a crude product. The crude product was purified by column chromatography (SiO$_2$, Petroleum: ether/Ethyl acetate=1:1) to give compound 15.2 (200 mg, crude) as a white solid. $^1$H NMR (400 MHz, chloroform-d) δ ppm 1.21-1.31 (m, 4H) 1.34 (d, J=6.02 Hz, 6H) 1.46 (br. s., 10H) 2.05 (s, 1H) 2.75-3.05 (m, 3H) 4.13 (d, J=7.53 Hz, 1H) 4.35 (br. s., 3H) 4.50-4.77 (m, 2H) 5.90-6.11 (m, 2H) 6.24 (dd, J=6.02, 2.01 Hz, 2H) 7.89 (d, J=6.02 Hz, 2H). LCMS (ESI): m/z: [M+H] calcd for C$_{14}$H$_{23}$N$_3$O$_3$: 282; found 282; RT=0.705 min.

A mixture of compound 15.2 (200 mg, 710.86 μmol, 1 eq) in HCl/EtOAc (5 mL) was stirred at 25° C. for 1 hour. The reaction mixture concentrated under reduced pressure to give a crude product compound 15.1 (120 mg, crude, 2 HCl) as a white solid. $^1$H NMR (400 MHz, methanol-d4) ppm 1.24 (s, 2H) 1.39 (d, J=6.02 Hz, 4H) 1.45 (d, J=6.02 Hz, 3H) 2.78 (s, 3H) 3.35-3.45 (m, 2H) 4.72-4.83 (m, 1H) 4.99-5.11 (m, 1H) 6.36 (s, 1H) 6.49 (s, 1H) 6.52 (d, J=2.51 Hz, 1H) 6.63 (s, 1H) 7.65-7.73 (m, 1H) 7.78 (d, J=7.53 Hz, 1H). LCMS (ESI): m/z: [M+H] calcd for C$_9$H$_{15}$N$_3$O: 182; found 182; RT=0.092 min.

To a solution of compound 15.1 (120 mg, 472.14 μmol, 1 eq, 2HCl) in DMF (1.50 mL) was added DIEA (244.08 mg, 1.89 mmol, 329.84 μL, 4 eq) and BrCN (50.01 mg, 472.14 μmol, 34.73 μL, 1 eq). The mixture was stirred at 0° C. for 10 mins. The residue was purified by prep-HPLC (neutral condition) to give the product product 15 (3 mg, 14.55 μmol, 3.08% yield) as a white solid. $^1$H NMR (400 MHz, methanol-d$_4$) δ ppm 1.35 (d, J=6.02 Hz, 3H) 2.96 (s, 3H) 3.23-3.32 (m, 2H) 4.72-4.82 (m, 1H) 6.16 (d, J=2.01 Hz, 1H) 6.30 (dd, J=6.02, 2.51 Hz, 1H) 7.69-7.81 (m, 1H). LCMS (ESI): m/z: [M+H] calcd for C$_{14}$H$_{23}$N$_3$O$_3$: 207; found 207; RT=1.083 min.

Example 16. Preparation of 2-(2-((2-aminopyridin-4-yl)oxy)ethyl)pyrrolidine-1-carbonitrile (16)

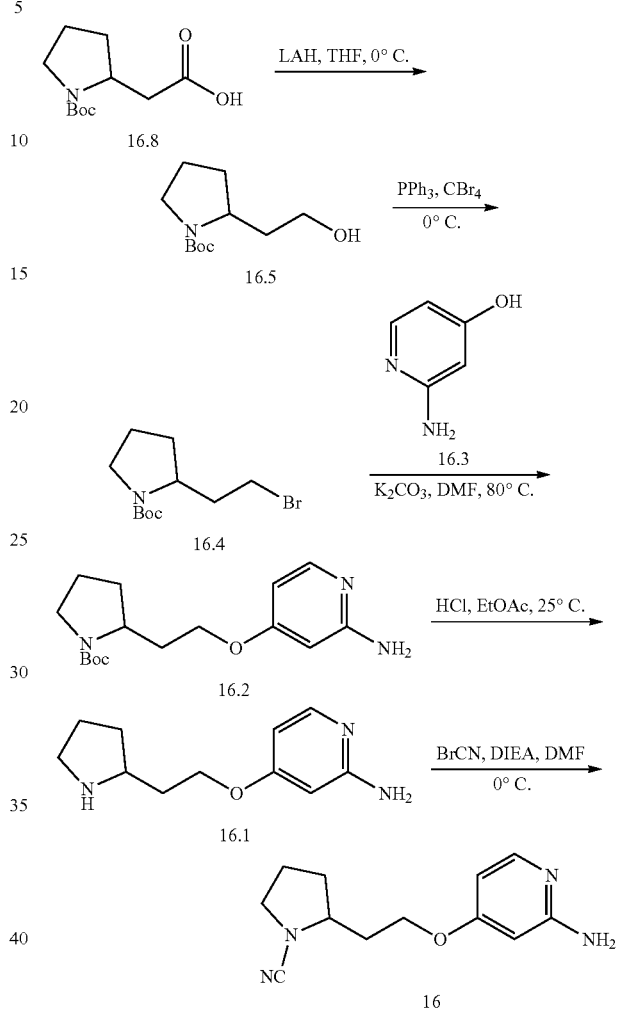

To a mixture of compound 16.6 (2 g, 8.72 mmol, 1 eq) in THF (20 mL) was added LAH (661.85 mg, 17.44 mmol, 2 eq) in one portion at 0° C. under N$_2$. The mixture was stirred at 0° C. for 2 hours. After the reaction mixture was cooled to 0° C., the reaction mixture was quenched by addition of 5 mL of H$_2$O, followed by 2 mL of 15% aqueous NaOH. After being stirred at room temperature for 10 mins, the solid was removed by filtration. The filtrate was concentrated to dryness to give crude product. The residue was purified by column chromatography (SiO$_2$, Petroleum ether/Ethyl acetate=10/1 to 2:1). Compound 16.5 (1.38 g, 6.41 mmol, 73.51% yield) was obtained as a colorless oil.

To a mixture of compound 16.5 (800 mg, 3.72 mmol, 1 eq) and carbon tetrabromide (1.85 g, 5.58 mmol, 1.50 eq) in THF (15 mL) was added PPh$_3$ (1.46 g, 5.58 mmol, 1.50 eq) in one portion at 0° C. under N$_2$. The mixture was stirred at 0° C. for 2 hours. The aqueous phase was extracted with ethyl acetate (10 mL×3). The combined organic phase was washed with brine (5 mL), dried with anhydrous Na$_2$SO$_4$, filtered and concentrated in vacuum. The residue was purified by column chromatography (SiO$_2$, Petroleum ether/ ethyl acetate=20/1 to 5:1). Compound 16.4 (640 mg, 2.30 mmol, 61.84% yield) was obtained as a colorless oil. LCMS (ESI): m/z: [M+H−56] called for $C_{12}H_{20}BrNO_2$: 222; found 222; RT=0.103 min.

To a mixture of compound 16.4 (300 mg, 1.08 mmol, 1 eq) and compound 16.3 (118.92 mg, 1.08 mmol, 1 eq) in DMF (10 mL) was added $K_2CO_3$ (298.53 mg, 2.16 mmol, 2 eq) in one portion at 15° C. under $N_2$. The mixture was stirred at 80° C. for 2 hours. The aqueous phase was extracted with ethyl acetate (10 mL×3). The combined organic phase was washed with brine (5 mL), dried with anhydrous $Na_2SO_4$, filtered and concentrated in vacuum. Compound 16.2 (70 mg, crude) was obtained as black brown oil. It was combined with a second batch for a total of 140 mg, crude. LCMS (ESI): m/z: [M+H] called for $C_{16}H_{25}N_3O_3$: 308; found 308; RT=0.689 min.

A mixture of compound 16.2 (140 mg, 455.45 µmol, 1 eq) in HCl/EtOAc (10 mL) was stirred at 15° C. for 15 hours. The mixture was concentrated in vacuum to give crude product. Compound 16.1 (75 mg, 361.85 µmol, 79.45% yield) was obtained as a colorless oil. LCMS (ESI): m/z: [M+H] called for $C_{11}H_{17}N_3O$: 208; found 208; RT=0.102 min.

To a mixture of compound 16.1 (75 mg, 361.85 µmol, 1 eq) and DIEA (93.53 mg, 723.69 µmol, 126.39 µL, 2 eq) in DMF (2 mL) was added carbononitridic bromide (38.33 mg, 361.85 µmol, 26.62 µL, 1 eq) in one portion at 0° C. under $N_2$. The mixture was stirred at 15° C. for 15 hours. The residue was purified by prep-HPLC (basic conditions). Product 16 (2 mg, 8.61 µmol, 2.38% yield) was obtained as a white solid. $^1$H NMR (400 MHz, methanol-$d_4$) δ ppm 1.57-1.79 (m, 1H) 1.84-2.29 (m, 5H) 2.92 (br d, J=13.23 Hz, 1H) 3.38-3.58 (m, 2H) 3.83 (quin, J=6.73 Hz, 1H) 4.02-4.26 (m, 2H) 6.10 (d, J=2.21 Hz, 1H) 6.25 (dd, J=6.06, 2.32 Hz, 1H) 7.70 (d, J=6.17 Hz, 1H). LCMS (ESI): m/z: [M+H] called for $C_{12}H_{16}N_4O$: 233; found 233; RT=0.983 min.

Example 17. Preparation of 3-(2-((2-aminopyridin-4-yl)oxy)ethyl)pyrrolidine-1-carbonitrile (17)

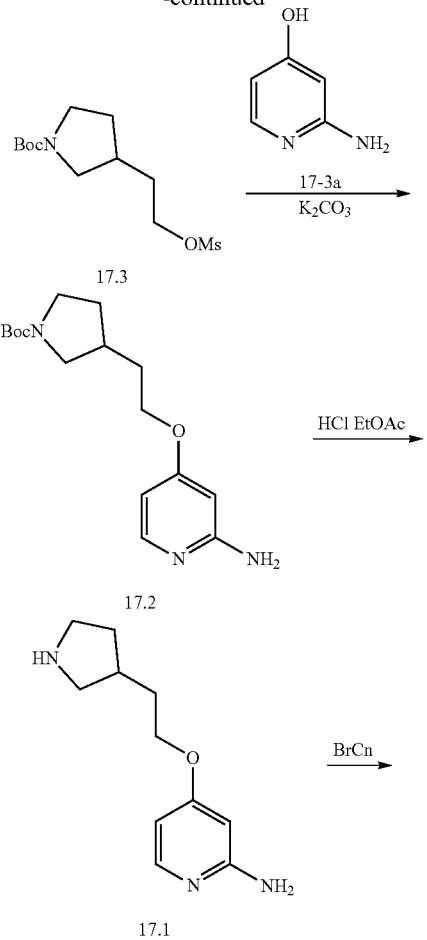

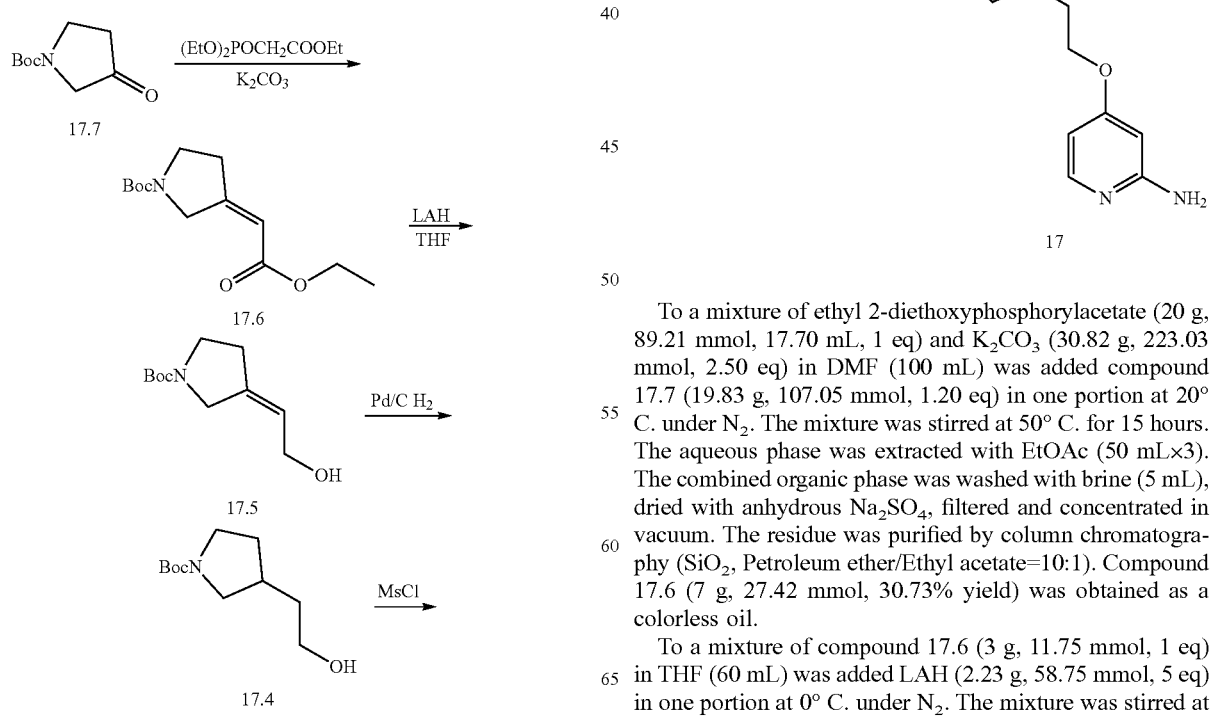

To a mixture of ethyl 2-diethoxyphosphorylacetate (20 g, 89.21 mmol, 17.70 mL, 1 eq) and $K_2CO_3$ (30.82 g, 223.03 mmol, 2.50 eq) in DMF (100 mL) was added compound 17.7 (19.83 g, 107.05 mmol, 1.20 eq) in one portion at 20° C. under $N_2$. The mixture was stirred at 50° C. for 15 hours. The aqueous phase was extracted with EtOAc (50 mL×3). The combined organic phase was washed with brine (5 mL), dried with anhydrous $Na_2SO_4$, filtered and concentrated in vacuum. The residue was purified by column chromatography ($SiO_2$, Petroleum ether/Ethyl acetate=10:1). Compound 17.6 (7 g, 27.42 mmol, 30.73% yield) was obtained as a colorless oil.

To a mixture of compound 17.6 (3 g, 11.75 mmol, 1 eq) in THF (60 mL) was added LAH (2.23 g, 58.75 mmol, 5 eq) in one portion at 0° C. under $N_2$. The mixture was stirred at 0° C. for 2 hours. After the reaction mixture was cooled to 0° C., the reaction mixture was quenched by addition of 50 mL of H₂O, followed by 10 mL of 15% aqueous NaOH. After being stirred at room temperature for 10 mins, the solid was removed by filtration. The filtrate was concentrated to dryness to give crude product. The residue was purified by column chromatography (SiO₂, Petroleum ether/Ethyl acetate=10:1 to 4:1). Compound 17.5 (1.07 g, 5.02 mmol, 42.70% yield) was obtained as a colorless oil.

To a solution of compound 17.5 (670 mg, 3.14 mmol, 1 eq) in MeOH (10 mL) was added Pd/C (200 mg, 10% purity) under N₂. The suspension was degassed under vacuum and purged with H₂ several times. The mixture was stirred under H₂ (15 psi) at 15° C. for 3 hours. The reaction mixture was filtered and the filter was concentrated. Compound 17.4 (500 mg, 2.32 mmol, 73.96% yield) was obtained as a colorless oil.

To a mixture of compound 17.4 (400 mg, 1.86 mmol, 1 eq) and methanesulfonyl chloride (319.24 mg, 2.79 mmol, 215.71 μL, 1.50 eq) in DCM (2 mL) was added TEA (376.01 mg, 3.72 mmol, 515.09 μL, 2 eq) in one portion at 0° C. under N₂. The mixture was stirred at 0° C. for 2 hours. The aqueous phase was extracted with EtOAc (20 mL×3). The combined organic phase was washed with brine (5 mL), dried with anhydrous Na₂SO₄, filtered and concentrated in vacuum. Compound 17.3 (400 mg, crude) was obtained as a colorless oil.

To a solution of compound 17.3a (149.75 mg, 1.36 mmol, 1 eq) in ACN (7 mL) was added K₂CO₃ (375.93 mg, 2.72 mmol, 2 eq) and compound 17.3 (400 mg, 1.36 mmol, 1 eq) at 25° C. under N₂. The resulting mixture was stirred at 80° C. for 16 hours. The reaction mixture was added water (5 mL), extracted with EtOAc (10 mL×3). The combined organic layers were washed with brine (10 mL×1), dried over Na₂SO₄, filtered and concentrated under reduced pressure to give a residue. The residue was purified by column chromatography (SiO₂, DCM:MeOH=100:1 to 5:1). Compound 17.2 (200 mg, 650.64 mol, 47.84% yield) was obtained as a yellow oil. ¹H NMR (400 MHz, chloroform-d) ppm 1.47-1.58 (m, 11H) 1.84-1.89 (m, 2H) 2.04-2.06 (m, 1H) 2.34 (m, 1H) 2.93-2.98 (m, 1H) 3.27-3.66 (m, 3H) 3.97-4 (m, 2H) 4.40 (s, 2H) 5.97 (s, 1H) 6.25 (d, J=5.6 Hz, 1H) 7.90 (d, J=5.6 Hz, 1H)

A solution of compound 17.2 (200 mg, 650.64 μmol, 1 eq) in HCl/EtOAc (5 mL) was stirred at 25° C. for 1 h. The reaction mixture was concentrated under reduced pressure to give a residue. Compound 17.1 (90 mg, 321.21 μmol, 49.37% yield) was obtained as a yellow solid. ¹H NMR (400 MHz, methanol-d4) ppm 1.73-1.77 (m, 1H) 2.02-2.03 (m, 2H) 2.26-2.65 (m, 1H) 2.52-2.54 (m, 1H) 2.94-2.97 (m, 1H) 3.42-3.61 (m, 4H) 4.22-4.26 (m, 2H) 6.41 (d, J=2.4 Hz, 1H) 6.54 (dd, J=7.2 Hz, 2.0 Hz, 1H) 7.90 (d, J=7.6 Hz, 1H).

To a solution of compound 17.1 (90 mg, 321.21 μmol, 1 eq) in DMF (3 mL) was added DIEA (166.05 mg, 1.28 mmol, 224.39 μL, 4 eq) and BrCN (34.02 mg, 321.21 μmol, 23.63 μL, 1 eq) in turn at 0° C. under N₂. The resulting mixture was stirred at 0° C. for 1 hour. The reaction mixture was added water 10 mL, extracted with EtOAc (10 mL×3). The combined organic layers were washed with brine (20 mL×1), dried over Na₂SO₄, filtered and concentrated under reduced pressure to give a residue. The residue was purified by prep-HPLC (basic condition). Product 17 (10 mg, 43.05 μmol, 13.40% yield) was obtained as a white solid. LCMS (ESI): m/z: [M+H] calcd for C₁₂H₁₆N₄O: 232; found 233; RT=1.506 min. ¹H NMR (400 MHz, chloroform-d) ppm 1.47-1.67 (m, 1H) 1.86-1.90 (m, 2H) 2.11-2.13 (m, 1H) 2.35-2.46 (m, 1H) 3.10-3.12 (m, 1H) 3.40-3.61 (m, 3H) 3.97-4.01 (m, 2H) 4.40 (s, 2H) 5.95 (d, J=2.0 Hz, 1H) 6.23 (dd, J=6.0 Hz, 2.0 Hz, 1H) 7.91 (d, J=5.6 Hz, 1H).

Example 18. Preparation of 2-(3-((2-aminopyridin-4-yl)oxy)propyl)pyrrolidine-1-carbonitrile (18)

To a mixture of compound 18.12 (20 g, 92.92 mmol, 1 eq), EDCI (17.81 g, 92.92 mmol, 1 eq) and HOBt (12.55 g, 92.92 mmol, 1 eq) in DMF (200 mL) was added DIEA (48 g, 92.92 mmol, 1 eq) and compound 18.11 (9.06 g, 92.92 mmol, 1 eq) in one portion at 0° C. under N₂. The mixture was stirred at 0° C. for 2 hours. The aqueous phase was extracted with EtOAc (50 mL×3). The combined organic phase was washed with brine (5 mL), dried with anhydrous Na₂SO₄, filtered and concentrated in vacuum. The residue was purified by column chromatography (SiO₂, Petroleum ether/Ethyl acetate=3:1). Compound 18.10 (19.60 g, 75.88 mmol, 81.66% yield) was obtained as a black brown oil.

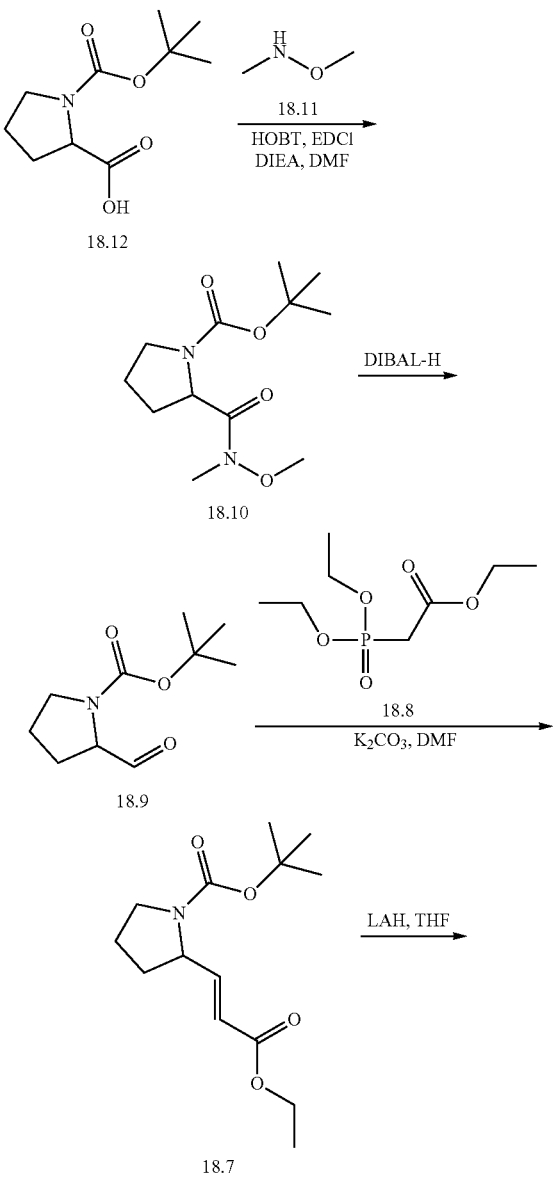

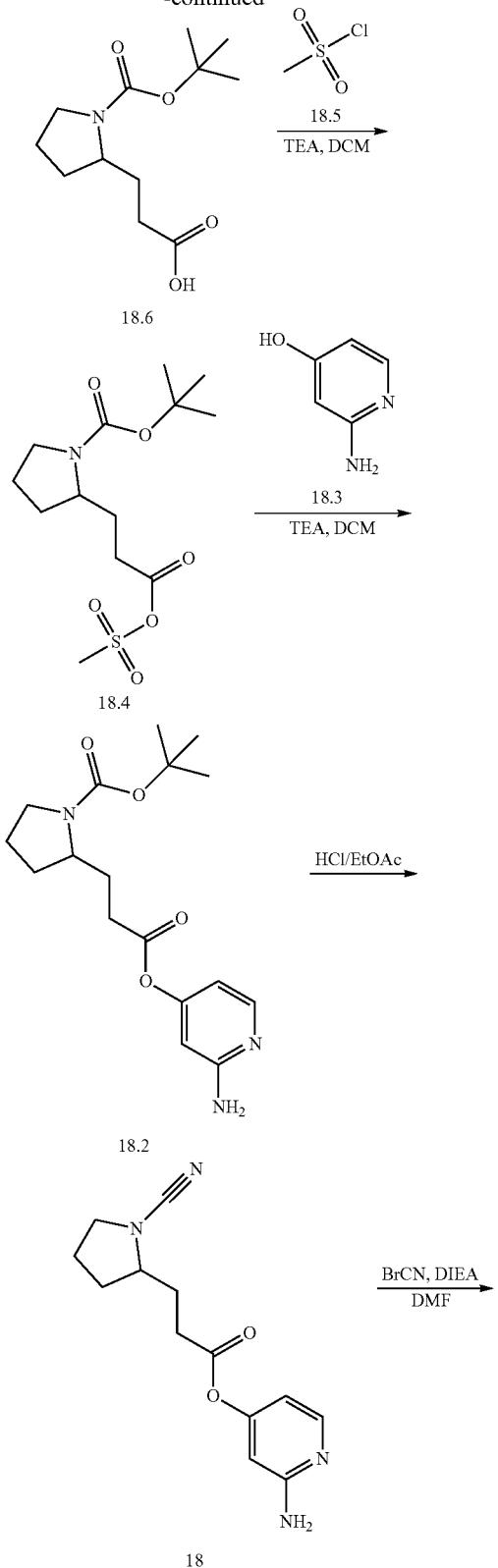

cooled to 0° C., the reaction mixture was quenched by addition of 100 mL of H₂O, followed by 15 mL of 15% aqueous NaOH. After being stirred at room temperature for 10 min, the solid was removed by filtration. The filtrate was concentrated to dryness to give crude product. Compound 18.9 (6.70 g, crude) was obtained as colorless oil.

To a mixture of compound 18.8 (4.69 g, 20.91 mmol, 4.15 mL, 1 eq) and $K_2CO_3$ (7.23 g, 52.27 mmol, 2.50 eq) in DMF (100 mL) was added compound 18.9 (5 g, 25.09 mmol, 1.20 eq) in one portion at 20° C. under $N_2$. The mixture was stirred at 50° C. for 15 hours. The aqueous phase was extracted with ethyl acetate (50 mL×3). The combined organic phase was washed with brine (5 mL), dried with anhydrous $Na_2SO_4$, filtered and concentrated in vacuum. The residue was purified by column chromatography ($SiO_2$, Petroleum ether/Ethyl acetate=10:1). Compound 18.7 (3.20 g, 11.88 mmol, 56.82% yield) was obtained as a colorless oil.

To a solution of compound 18.7 (2 g, 7.43 mmol, 1 eq) in THF (30 mL) was added LAH (1.41 g, 37.15 mmol, 5 eq) in one portion at 0° C. under $N_2$. The mixture was stirred at 0° C. for 15 min. After the reaction mixture was cooled to 0° C., the reaction mixture was quenched by addition of 5 mL of H₂O, followed by 2 mL of 15% aqueous NaOH. After being stirred at room temperature for 10 min, the solid was removed by filtration. The filtrate was concentrated to dryness to give crude product. The residue was purified by prep-TLC ($SiO_2$, PE:ethyl acetate=2:1). Compound 18.6 (1.08 g, 4.71 mmol, 63.39% yield) was obtained as rless oil. LCMS (ESI): m/z: [M+H] called for $C_{12}H_{23}NO_3$: 230; found 230; RT=0.741 min.

To a mixture of compound 18.6 (300 mg, 1.31 mmol, 1 eq) and TEA (198.84 mg, 1.96 mmol, 272.38 μL, 1.50 eq) in DCM (10 mL) was added compound 18.5 (180.07 mg, 1.57 mmol, 121.67 μL, 1.20 eq) in one portion at 0° C. under $N_2$. The mixture was stirred at 0° C. for 15 min. The aqueous phase was extracted with ethyl acetate (30 mL×3). The combined organic phase was washed with brine (5 mL), dried with anhydrous $Na_2SO_4$, filtered and concentrated in vacuum. Compound 18.4 (600 mg, crude) was obtained as light yellow oil.

To a mixture of compound 18.4 (600 mg, 1.95 mmol, 1 eq) and compound 18.3 (214.91 mg, 1.95 mmol, 1 eq) in DMF (5 mL) was added $K_2CO_3$ (539.51 mg, 3.90 mmol, 2 eq) in one portion at 15° C. under $N_2$. The mixture was stirred at 65° C. for 15 hours. The aqueous phase was extracted with ethyl acetate (30 mL×3). The combined organic phase was washed with brine (5 mL), dried with anhydrous $Na_2SO_4$, filtered and concentrated in vacuum. Compound 18.2 (50 mg, 155.56 μmol, 7.98% yield) was obtained as colorless oil.

A mixture of compound 18.2 (50 mg, 155.56 μmol, 1 eq) in HCl/EtOAc (4 M, 10 mL, 257.14 eq), the mixture was stirred at 15° C. for 15 hours. Then the mixture was concentrated in vacuum. Compound 18.1 (50 mg, crude) was obtained as a white solid. LCMS (ESI): m/z: [M+H] called for $C_{12}H_{19}N_3O$: 220; found 220; RT=0.114 min.

To a mixture of compound 18.1 (50 mg, 225.94 μmol, 1 eq) and DIEA (58.40 mg, 451.88 μmol, 78.92 μL, 2 eq) in DMF (2 mL) was added carbononitridic bromide (23.93 mg, 225.94 μmol, 16.62 μL, 1 eq) in one portion at 0° C. under $N_2$. The mixture was stirred at 15° C. for 15 hours. The aqueous phase was extracted with ethyl acetate (30 mL×3). The combined organic phase was washed with brine (5 mL), dried with anhydrous $Na_2SO_4$, filtered and concentrated in vacuum. The residue was purified by prep-HPLC (basic condition). Product 18 (1.20 mg, 4.87 μmol, 2.16% yield)

To a solution of compound 18.10 (10 g, 38.71 mmol, 1 eq) in THF (200 mL) was added DIBAL-H (6.01 g, 42.58 mmol, 1.10 eq) in one portion at −78° C. under $N_2$. The mixture was stirred at −78° C. for 2 hours. After the reaction mixture was was obtained as a white solid. $^1$H NMR (400 MHz, chloroform-d) δ ppm 1.35-1.75 (m, 5H) 1.77-2.01 (m, 6H) 2.02-2.21 (m, 2H) 3.33-3.54 (m, 2H) 3.62 (br d, J=6.15 Hz, 2H) 3.88-4.10 (m, 2H) 4.41 (br s, 2H) 5.98 (s, 1H) 6.14-6.37 (m, 1H) 7.76-8.02 (m, 1H). LCMS (ESI): m/z: [M+H] calcd for $C_{13}H_{18}N_4O$: 247; found 247; RT=1.044 min.

Example 19. Preparation of (S)-2-(((2-aminopyridin-4-yl)oxy)methyl)pyrrolidine-1-carbonitrile (19)

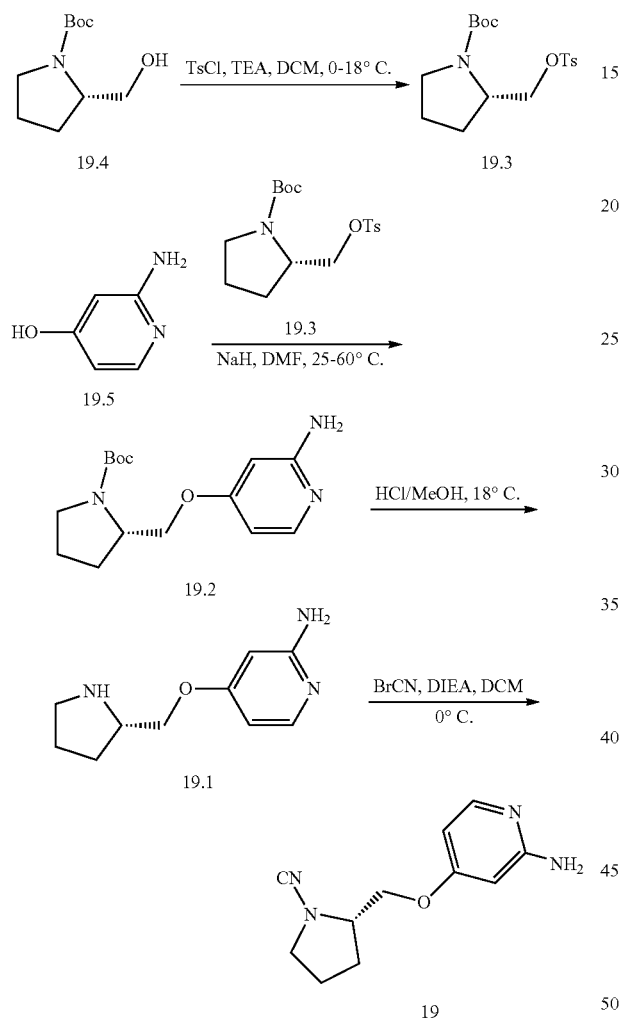

To a mixture of compound 19.4 (1 g, 4.97 mmol, 1 eq) and 4-methylbenzenesulfonyl chloride (1.14 g, 5.96 mmol, 1.20 eq) in DCM (15 mL) was added DMAP (97.12 mg, 794.99 μmol, 0.16 eq) and TEA (754.17 mg, 7.45 mmol, 1.03 mL, 1.50 eq) in one portion at 0° C. under $N_2$. The mixture was then heated to 18° C. and stirred for 10 hours. The reaction mixture was diluted with $H_2O$ 20 mL and extracted with EtOAc 45 mL (15 mL×3). The combined organic layers were washed with brine 20 mL (20 mL×1), dried over $Na_2SO_4$, filtered and concentrated under reduced pressure to give compound 19.3 (1.70 g, crude) as a colorless oil. LCMS (ESI): m/z: [M+H] calcd for $C_{17}H_{25}NSO_5$: 355; found 300; RT=0.890 min.

To a solution of compound 19.5 (579.28 mg, 5.26 mmol, 1.10 eq) in DMF (20 mL) was added NaH (172.18 mg, 7.17 mmol, 1.50 eq) portionwise at 25° C. under $N_2$. The mixture was stirred at 25° C. for 30 mins, then was added compound 19.3 (1.70 g, 4.78 mmol, 1 eq). The mixture was heated to 60° C. and stirred for 9.5 hours. The reaction mixture was diluted with $H_2O$ 20 mL and extracted with EtOAc 45 mL (15 mL×3). The combined organic layers were washed with brine 20 mL (20 mL×1), dried over $Na_2SO_4$, filtered and concentrated under reduced pressure to give a residue. The residue was purified by column chromatography ($SiO_2$, DCM:MeOH=20:1) to give compound 19.2 (700 mg, 2.39 mmol, 49.92% yield) as a colorless oil. LCMS (ESI): m/z: [M+H] calcd for $C_{15}H_{23}N_3O_3$: 293; found 294; RT=0.667 min.

Compound 19.2 (700 mg, 2.39 mmol, 1 eq) was added into a solution of HCl/MeOH (10 mL). The mixture was stirred at 18° C. for 15 hours. The reaction mixture was concentrated under reduced pressure to give compound 19.1 (550 mg, crude) as a yellow solid. $^1$H NMR (400 MHz, DMSO-$d_6$) δ ppm 1.74 (dq, J=12.66, 8.20 Hz, 1H) 1.83-2.05 (m, 2H) 2.06-2.18 (m, 1H) 3.14-3.28 (m, 2H) 3.67 (br s, 1H) 3.87-3.99 (m, 1H) 4.40 (d, J=5.90 Hz, 2H) 6.43 (d, J=2.51 Hz, 1H) 6.54 (dd, J=7.28, 2.51 Hz, 1H) 7.92 (d, J=7.28 Hz, 1H) 8.04 (br s, 2H).

To a mixture of compound 19.1 (200 mg, 1.03 mmol, 1 eq) and DIEA (532.47 mg, 4.12 mmol, 719.55 μL, 4 eq) in DCM (3 mL) was added carbononitridic bromide (109.10 mg, 1.03 mmol, 75.76 μL, 1 eq) in one portion at 0° C. under N2. The mixture was stirred at 0° C. for 30 mins. The reaction mixture diluted with H2O 3 mL and extracted with DCM 9 mL (3 mL×3). The combined organic layers were washed with brine 4 mL (4 mL×1), dried over $Na_2SO_4$, filtered and concentrated under reduced pressure to give a residue. The residue was purified by prep-HPLC (neutral condition) to give product 19 (30 mg, 137.46 μmol, 13.35% yield) as a yellow solid. LCMS (ESI): m/z: [M+H] calcd for $C_{11}H_{14}N_4O$: 218; found 219; RT=1.953 min. $^1$H NMR (400 MHz, DMSO-$d_6$) δ ppm 1.72 (dq, J=12.27, 6.16 Hz, 1H) 1.82-1.96 (m, 2H) 1.99-2.09 (m, 1H) 3.36-3.49 (m, 2H) 3.89-4 (m, 2H) 4-4.07 (m, 1H) 5.81 (s, 2H) 5.97 (d, J=2.13 Hz, 1H) 6.14 (dd, J=5.77, 2.26 Hz, 1H) 7.74 (d, J=5.77 Hz, 1H).

Example 20. Preparation of (R)-2-(((2-aminopyridin-4-yl)oxy)methyl)pyrrolidine-1-carbonitrile (20)

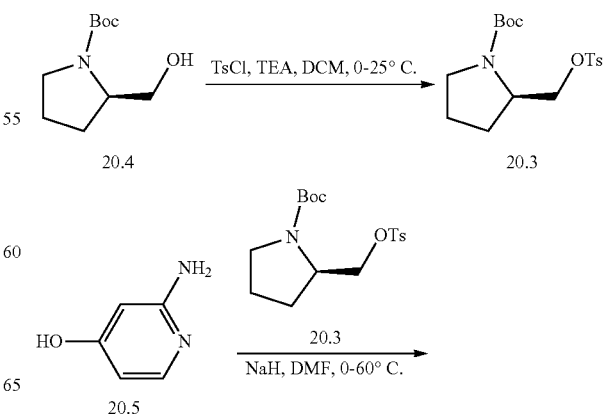

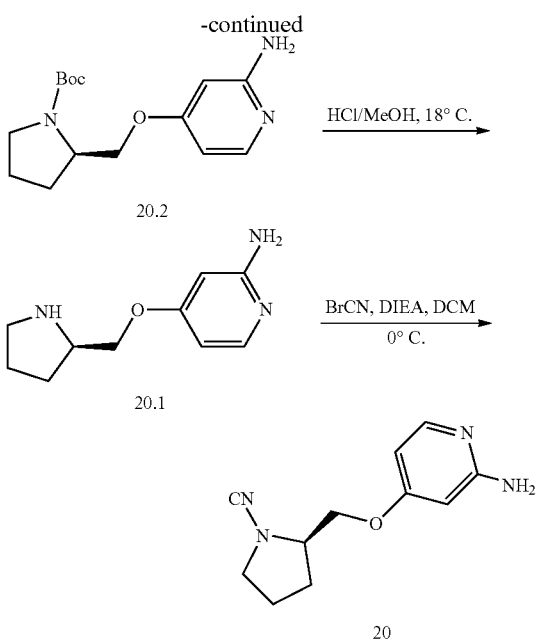

To a mixture of compound 20.4 (1 g, 4.97 mmol, 1 eq) and 4-methylbenzenesulfonyl chloride (1.14 g, 5.96 mmol, 1.20 eq) in DCM (15 mL) was added DMAP (97.12 mg, 794.99 μmol, 0.16 eq) and TEA (754.17 mg, 7.45 mmol, 1.03 mL, 1.50 eq) in one portion at 0° C. under N₂. The mixture was then heated to 25° C. and stirred for 10 hours. The reaction mixture was diluted with H₂O 20 mL and extracted with EtOAc 15 mL (15 mL×3). The combined organic layers were washed with brine 20 mL (20 mL×1), dried over Na₂SO₄, filtered and concentrated under reduced pressure to give compound 20.3 (1.90 g, crude) as a yellow oil. ¹H NMR (400 MHz, chloroform-d) ppm 1.30-1.48 (m, 9H) 1.71-2.02 (m, 4H) 2.39-2.51 (m, 3H) 3.21-3.42 (m, 2H) 3.80-4.03 (m, 1H) 4.09 (d, J=6.15 Hz, 1H) 7.35 (d, J=4.77 Hz, 2H) 7.78 (d, J=8.16 Hz, 2H). LCMS (ESI): m/z: [M+H] calcd for C₁₇H₂₅NSO₅: 355; found 256,300; RT=1.119 min.

To a solution of compound 20.5 (647.43 mg, 5.88 mmol, 1.10 eq) in DMF (20 mL) was added NaH (192.43 mg, 8.02 mmol, 1.50 eq) portionwise at 0° C. under N2. The mixture was stirred at 0° C. for 30 mins, then was added compound 20.3 (1.90 g, 5.35 mmol, 1 eq). The mixture was heated to 60° C. and stirred for 9.5 hours. The reaction mixture was diluted with H₂O 20 mL and extracted with EtOAc 15 mL (15 mL×3). The combined organic layers were washed with brine 20 mL (20 mL×1), dried over Na₂SO₄, filtered and concentrated under reduced pressure to give a residue. Then the residue was purified by column (SiO2, DCM/MeOH=10:1) to give compound 20.2 (900 mg, 3.07 mmol, 57.34% yield) as a yellow oil. ¹H NMR (400 MHz, methanol-d4) ppm 1.82-1.93 (m, 1H) 1.95-2.08 (m, 3H) 3.36-3.41 (m, 2H) 3.90-4.02 (m, 1H) 4.04-4.20 (m, 2H) 6.12 (d, J=15.94 Hz, 1H) 6.26 (dd, J=6.09, 2.32 Hz, 1H) 7.64-7.76 (m, 1H). LCMS (ESI): m/z: [M+H] calcd for C₁₅H₂₃N₃O₃: 293; found 294; RT=0.671 min.

Compound 20.2 (900 mg, 3.07 mmol, 1 eq) was added into a solution of HCl/MeOH (10 mL). The mixture was stirred at 18° C. for 15 hours. The reaction mixture was concentrated under reduced pressure to give compound 20.1 (900 mg, crude) as a yellow solid. ¹H NMR (400 MHz, methanol-d4) ppm 1.84-1.96 (m, 1H) 1.98-2.20 (m, 2H) 2.21-2.35 (m, 1H) 3.27 (dt, J=3.20, 1.71 Hz, 1H) 3.33-3.41 (m, 2H) 4.28-4.41 (m, 1H) 4.49 (dd, J=11.03, 3.53 Hz, 1H) 6.46 (d, J=2.21 Hz, 1H) 6.58 (dd, J=7.28, 2.43 Hz, 1H) 7.70-7.82 (m, 1H). LCMS (ESI): m/z: [M+H] calcd for C₁₀H₁₅N₃O: 193; found 194; RT=0.086 min.

To a mixture of compound 20.1 (200 mg, 1.03 mmol, 1 eq) and DIEA (532.47 mg, 4.12 mmol, 719.55 μL, 4 eq) in DCM (3 mL) was added carbononitridic bromide (109.10 mg, 1.03 mmol, 75.76 μL, 1 eq) in one portion at 0° C. under N₂. The mixture was stirred at 0° C. for 30 mins. The reaction mixture diluted with H₂O 3 mL and extracted with DCM 3 mL (3 mL×3). The combined organic layers were washed with brine 4 mL (4 mL×1), dried over Na₂SO₄, filtered and concentrated under reduced pressure to give a residue. The residue was purified by prep-HPLC (neutral condition) to give product 20 (100 mg, 458.19 μmol, 44.48% yield) as a yellow solid. ¹H NMR (400 MHz, DMSO-d6) δ ppm 1.71 (dq, J=12.23, 6.17 Hz, 1H) 1.79-1.96 (m, 2H) 1.97-2.11 (m, 1H) 3.35-3.49 (m, 2H) 3.89-4 (m, 2H) 4-4.08 (m, 1H) 5.93 (s, 1H) 5.99 (d, J=2.26 Hz, 1H) 6.11-6.20 (m, 1H) 7.74 (d, J=6.02 Hz, 1H). LCMS (ESI): m/z: [M+H] calcd for C₁₁H₁₄N₄O: 218; found 219; RT=1.981 min.

Example 21. Preparation of 2-(2-(2-aminopyridin-4-yl)ethyl)pyrrolidine-1-carbonitrile (21)

To a solution of compound 21.12 (58 g, 419.92 mmol, 1 eq) in MeOH (600 mL) was added SOCl₂ (99.92 g, 839.84 mmol, 60.93 mL, 2 eq) dropwise at 0° C. under N₂. The mixture was stirred at 0° C. for 30 mins, then was heated to 18° C. and stirred at 18° C. for 14.5 hours. The reaction mixture was concentrated under reduced pressure to give compound 21.11 (65 g, crude) as a white solid. LCMS (ESI): m/z: [M+H] calcd for C₁H₈N₂O₂: 152; found 153; RT=0.100 min.

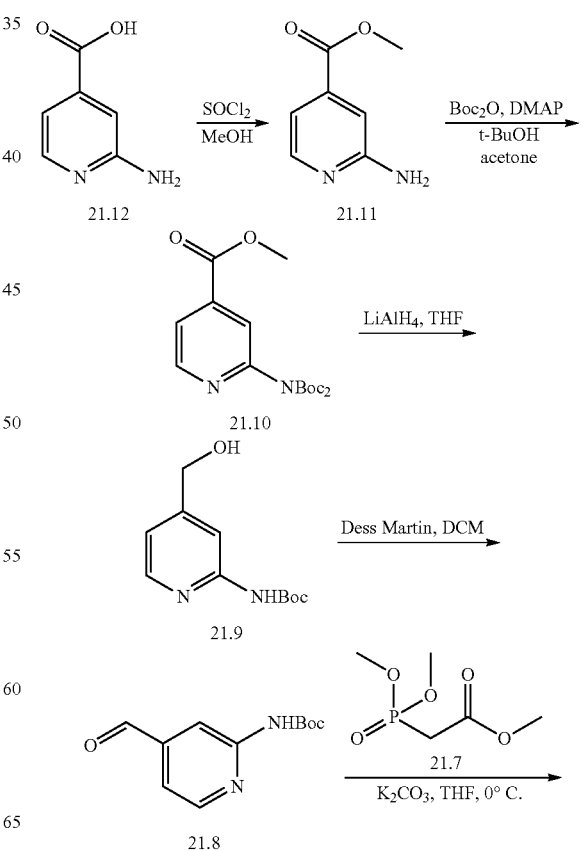

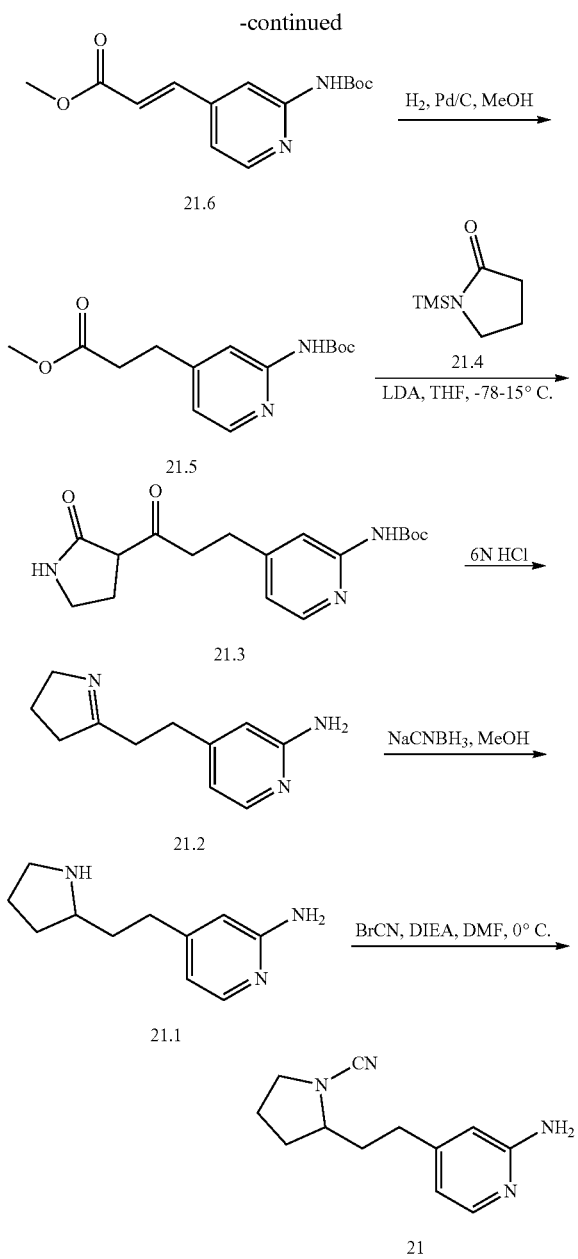

To a mixture of compound 21.11 (65 g, 427.21 mmol, 1 eq) and DMAP (2.61 g, 21.36 mmol, 0.05 eq) in t-BuOH (500 mL) and acetone (150 mL) was added Boc₂O (279.72 g, 1.28 mol, 294.44 mL, 3 eq) dropwies at 18° C. under N₂. The mixture was stirred at 18° C. for 15 hours. The solution was diluted with pentane (200 ml), cooled in the refrigerator for 3 hours and filtered to obtain compound 21.10 (110 g, 312.16 mmol, 73.07% yield) as a white solid. LCMS (ESI): m/z: [M+H] calcd for $C_{17}H_{24}N_2O_6$: 352; found 353; RT=0.877 min. ¹H NMR (400 MHz, chloroform-d) δ ppm 1.39-1.50 (m, 19H) 3.97 (s, 3H) 7.77 (dd, J=5.02, 1.38 Hz, 1H) 7.82 (s, 1H) 8.62 (d, J=5.02 Hz, 1H)

To a solution of compound 21.10 (60 g, 170.27 mmol, 1 eq) in THF (1 L) was added LiAlH₄ (12.92 g, 340.54 mmol, 2 eq) portionwise at 0° C. under N2. The mixture was stirred at 0° C. for 1 hours, then heated to 18° C. and stirred at 18° C. for 14 hours. The reaction mixture was quenched by addition 8% NaOH (15 ml), filtered and then diluted with H₂O 1000 mL and extracted with EtOAc 1500 mL (500 mL×3). The combined organic layers were washed with brine 1000 mL (1000 mL×1), dried over Na₂SO₄, filtered and concentrated under reduced pressure to give a residue. The residue was purified by column chromatography (SiO₂, Petroleum ether/Ethyl acetate=2:1) to give compound 21.9 (15 g, 66.89 mmol, 39.28% yield) as a white solid. LCMS (ESI): m/z: [M+H] calcd for $C_{11}H_{16}N_2O_3$: 293; found 294; RT=0.313 min.

To a solution of compound 21.9 (8 g, 35.67 mmol, 1 eq) in DCM (60 mL) was added Dess-Martin periodinane (18.16 g, 42.81 mmol, 13.25 mL, 1.20 eq) portionwise at 18° C. under N2. The mixture was stirred at 18° C. for 2 hours. The reaction mixture was diluted with H₂O 60 mL and extracted with DCM 150 mL (50 mL×3). The combined organic layers were washed with brine 100 mL (100 mL×1), dried over Na₂SO₄, filtered and concentrated under reduced pressure to give a residue. The residue was purified by column chromatography (SiO2, Petroleum ether/Ethyl acetate=5:1) to give compound 21.8 (5.10 g, 22.95 mmol, 64.33% yield) as a white solid. LCMS (ESI): m/z: [M+H] calcd for $C_{11}H_{14}N_2O_3$: 222; found 223; RT=0.313 min. ¹H NMR (400 MHz, chloroform-d) δ ppm 1.59 (s, 9H) 7.41 (dd, J=5.08, 1.32 Hz, 1H) 8.48 (s, 1H) 8.52 (d, J=5.15 Hz, 1H) 8.83 (br s, 1H).

To a mixture of compound 21.8 (2.50 g, 11.25 mmol, 1 eq) and methyl 2-dimethoxyphosphorylacetate 21.7 (2.05 g, 11.25 mmol, 1.63 mL, 1 eq) in THF (30 mL) was added K₂CO₃ (3.11 g, 22.50 mmol, 2 eq) in one portion at 50° C. under N₂. The mixture was stirred at 50° C. for 15 hours. The reaction mixture was diluted with H₂O 30 mL and extracted with EtOAc 90 mL (30 mL×3). The combined organic layers were washed with brine 50 mL (50 mL×1), dried over Na₂SO₄, filtered and concentrated under reduced pressure to give a residue. The residue was purified by column chromatography (SiO₂, Petroleum ether/Ethyl acetate=5:1) to give compound 21.6 (2.40 g, 8.62 mmol, 76.62% yield) as a white solid.

LCMS (ESI): m/z: [M+H] calcd for $C_{14}H_{18}N_2O_4$: 278; found 279; RT=0.739 min.

To a solution of compound 21.6 (1.40 g, 5.03 mmol, 1 eq) in MeOH (100 mL) was added Pd—C (10%, 0.2 g) under N₂. The suspension was degassed under vacuum and purged with H₂ several times. The mixture was stirred under H₂ (50 psi) at 20° C. for 15 hours. The reaction mixture was filtered and concentrated under reduced pressure to give a residue. The residue was purified by column chromatography (SiO2, Petroleum ether/Ethyl acetate=3:1) to give compound 21.5 (1.30 g, 4.64 mmol, 92.20% yield) as a white solid. LCMS (ESI): m/z: [M+H] calcd for $C_{14}H_{20}N_2O_4$: 280; found 281; RT=0.617 min. ¹H NMR (400 MHz, chloroform-d) δ ppm 1.47 (s, 9H) 2.59 (t, J=7.78 Hz, 2H) 2.78-2.98 (m, 2H) 3.50-3.71 (m, 3H) 6.66-6.82 (m, 1H) 7.79 (s, 1H) 8.13 (d, J=5.15 Hz, 1H) 8.83 (s, 1H)

To a solution of DIPA (505.95 mg, 5 mmol, 702.71 μL, 2 eq) in THF (10 mL) was added n-BuLi (2.5 M, 1.50 mL, 1.50 eq) dropwise at −78° C. under N₂. The mixture was then added compound 21.4 (589.84 mg, 3.75 mmol, 601.88 μL, 1.50 eq) in one portion at −78° C., the mixture was stirred at −78° C. for 30 mins, then was added compound 21.5 (700 mg, 2.50 mmol, 1 eq) in one portion at −78° C., the mixture was heated to 18° C. and stirred for 14.5 hours. The reaction mixture was quenched by addition H₂O 10 mL and then diluted with EtOAc 5 mL and extracted with EtOAc 15 mL (5 mL×3). The combined organic layers were washed with brine 10 mL (10 mL×1), dried over Na₂SO₄, filtered and concentrated under reduced pressure to give a residue. The residue was purified by prep-TLC (SiO2, PE:EA=2:1) to give compound 21.3 (180 mg, 539.92 μmol, 21.60% yield) as a white solid. LCMS (ESI): m/z: [M+H] calcd for $C_{17}H_{23}N_3O_4$: 333; found 334; RT=0.597 min.

Compound 21.3 (180 mg, 539.92 μmol, 1 eq) was mixed with 6 N HCl (5 mL), heated at 100° C. for 15 hours. The mixture was concentrated at reduced pressure to a syrup and then basified with 10% KOH (10 ml), the resulting two phase mixture was extracted with EtOAc 15 ml (5 ml×3) and the extract dry $Na_2SO_4$ and concentrated to give compound 21.2 (90 mg, crude) as a white solid. LCMS (ESI): m/z: [M+H] calcd for $C_{16}H_{23}N_3O_2$: 189; found 190; RT=0.097 min.

To a mixture of compound 21.2 (90 mg, 475.54 μmol, 1 eq) and NaBH3CN (44.82 mg, 713.30 μmol, 1.50 eq) in MeOH (1 mL) was added HCl/MeOH (500 μL) in one portion at 18° C. under $N_2$. The mixture was stirred at 18° C. for 4 hours. The reaction mixture was concentrated under reduced pressure to give a residue, then was diluted with $H_2O$ 2 mL and extracted with EtOAc 6 mL (2 mL×3). The combined organic layers were washed with brine 5 mL (5 mL×1), dried over $Na_2SO_4$, filtered and concentrated under reduced pressure to give compound 21.1 (90 mg, 470.54 μmol, 98.95% yield) as a white solid. LCMS (ESI): m/z: [M+H] calcd for $C_{11}H_{17}N_3$: 191; found 192; RT=0.095 min. $^1$H NMR (400 MHz, DMSO-$d_6$) δ ppm 1.27-1.39 (m, 2H) 1.64-1.85 (m, 4H) 1.88-1.99 (m, 1H) 2.43-2.59 (m, 2H) 2.78-2.88 (m, 1H) 2.93-3.04 (m, 2H) 5.86 (s, 2H) 6.38 (s, 1H) 6.46 (dd, J=5.29, 1.32 Hz, 1H) 7.89 (d, J=5.07 Hz, 1H).

To a mixture of compound 21.1 (40 mg, 209.13 μmol, 1 eq) and DIEA (108.11 mg, 836.51 μmol, 146.10 μL, 4 eq) in DMF (1 mL) was added carbononitridic bromide (22.15 mg, 209.13 μmol, 15.38 μL, 1 eq) in one portion at 0° C. under N2. The mixture was stirred at 0° C. for 30 mins. The residue was purified by prep-HPLC (neutral condition) to give product 21 (5 mg, 23.12 μmol, 11.05% yield) as a white solid. LCMS (ESI): m/z: [M+H] calcd for $C_{12}H_{16}N_4$: 216; found 217; RT=2.153 min. $^1$H NMR (400 MHz, DMSO-$d_6$) δ ppm 1.48-1.60 (m, 1H) 1.60-1.70 (m, 1H) 1.76-1.93 (m, 3H) 1.94-2.04 (m, 1H) 2.42-2.47 (m, 2H) 3.35-3.44 (m, 2H) 3.48-3.57 (m, 1H) 5.77 (s, 2H) 6.28 (s, 1H) 6.33-6.40 (m, 1H) 7.78 (d, J=5.15 Hz, 1H).

Example 22. Preparation of 2-(((2-(methylamino)pyridin-4-yl)oxy)methyl)pyrrolidine-1-carbonitrile (22)

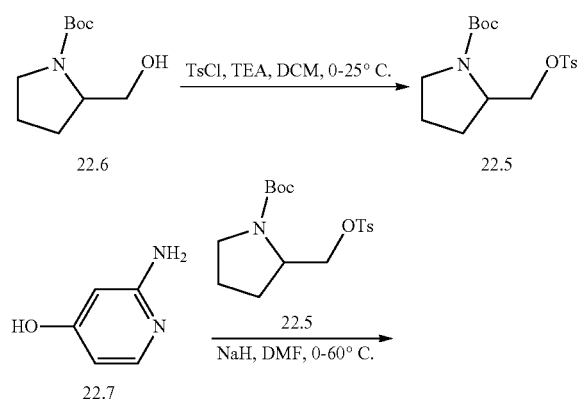

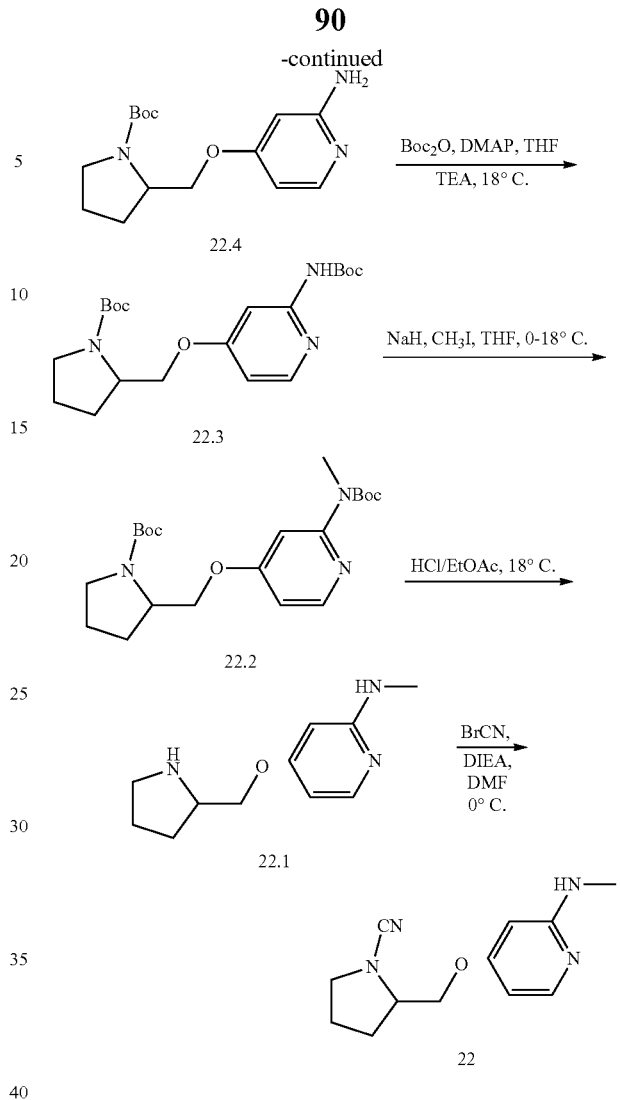

To a mixture of compound 22.6 (4.50 g, 22.36 mmol, 1 eq) and 4-methylbenzenesulfonyl chloride (5.12 g, 26.83 mmol, 1.20 eq) in DCM (15 mL) was added DMAP (437.06 mg, 3.58 mmol, 0.16 eq) and TEA (3.39 g, 33.54 mmol, 4.65 mL, 1.50 eq) in one portion at 0° C. under $N_2$. The mixture was then heated to 25° C. and stirred for 10 hours. The reaction mixture was diluted with $H_2O$ 20 mL and extracted with EtOAc 15 mL (15 mL×3). The combined organic layers were washed with brine 20 mL (20 mL×1), dried over $Na_2SO_4$, filtered and concentrated under reduced pressure to give compound 22.5 (8 g, crude) as a colorless oil. $^1$H NMR (400 MHz, chloroform-d) δ ppm 1.20-1.52 (m, 9H) 1.81 (br. s., 1H) 1.93 (br. s., 2H) 2.39-2.54 (m, 3H) 3.17-3.44 (m, 2H) 3.80-4.04 (m, 1H) 4.10 (d, J=6.02 Hz, 1H) 7.30-7.42 (m, 2H) 7.67-7.86 (m, 2H).

To a solution of compound 22.7 (2.73 g, 24.76 mmol, 1.10 eq) in DMF (20 mL) was added NaH (810.24 mg, 33.76 mmol, 1.50 eq) portionwise at 0° C. under $N_2$. The mixture was stirred at 0° C. for 30 mins, then was added compound 22.5 (8 g, 22.51 mmol, 1 eq). The mixture was heated to 60° C. and stirred for 9.5 hours. The reaction mixture was diluted with $H_2O$ 20 mL and extracted with EA 15 mL (15 mL×3). The combined organic layers were washed with brine 20 mL (20 mL×1), dried over $Na_2SO_4$, filtered and concentrated under reduced pressure to give a residue. The residue was purified by column chromatography (SiO$_2$, DCM:

MeOH=20:1) to give compound 22.4 (4 g, 13.64 mmol, 60.57% yield) as a yellow oil. $^1$H NMR (400 MHz, chloroform-d) δ ppm 1.40-1.57 (m, 9H) 1.78-2.05 (m, 4H) 3.37 (d, J=19.07 Hz, 2H) 3.66-4 (m, 1H) 4.12 (dd, J=14.05, 7.03 Hz, 2H) 4.38 (br. s., 2H) 5.89-6.15 (m, 1H) 6.28 (d, J=4.02 Hz, 1H) 7.88 (br. s., 1H). LCMS (ESI): m/z: [M+H] calcd for $C_{15}H_{23}N_3O_3$: 293; found 294; RT=0.681 min.

To a mixture of compound 22.4 (800 mg, 2.73 mmol, 1 eq) and TEA (828.75 mg, 8.19 mmol, 1.14 mL, 3 eq) in THF (10 mL) was added $Boc_2O$ (714.99 mg, 3.28 mmol, 752.62 μL, 1.20 eq) in one portion at 18° C. under N2. The mixture was stirred at 18° C. for 10 hours. The reaction mixture was diluted with $H_2O$ 10 mL and extracted with EtOAc 10 mL (10 mL×3). The combined organic layers were washed with brine 20 mL (20 mL×1), dried over $Na_2SO_4$, filtered and concentrated under reduced pressure to give a residue. The residue was purified by prep-TLC (SiO2, DCM:MeOH=10:1) to give compound 22.3 (400 mg, 1.02 mmol, 37.24% yield) as a white solid. $^1$H NMR (400 MHz, chloroform-d) δ ppm 1.47 (s, 9H) 1.53 (s, 9H) 1.86 (br. s., 1H) 2 (br. s., 3H) 3.21-3.55 (m, 2H) 3.83-4.05 (m, 1H) 4.13 (q, J=7.03 Hz, 4H) 6.55 (br. s., 1H) 7.52 (br. s., 1H) 7.72-7.92 (m, 1H) 8.05 (d, J=6.02 Hz, 1H). LCMS (ESI): m/z: [M+H] calcd for $C_{20}H_{31}N_3O_5$: 393; found 394; RT=0.764 min.

To a solution of compound 22.3 (210 mg, 533.70 μmol, 1 eq) in THF (5 mL) was added NaH (21.35 mg, 533.70 μmol, 60% purity, 1 eq) portionwise at 0° C. under $N_2$. The mixture was stirred at 0° C. for 30 mins, then the mixture was added $CH_3I$ (75.75 mg, 533.70 mol, 33.22 μL, 1 eq) dropwise at 0° C., the mixture was heated to 18° C. and stirred for 1.5 hours. The reaction mixture was diluted with $H_2O$ 2 mL and extracted with EtOAc 2 mL (2 mL×3). The combined organic layers were washed with brine 5 mL (5 mL×1), dried over $Na_2SO_4$, filtered and concentrated under reduced pressure to give a residue. The residue was purified by prep-TLC (SiO2, DCM:MeOH=10:1) to give compound 22.2 (160 mg, 392.64 mol, 73.57% yield) as a colorless oil, Combined ET6889-326 and ET6889-329 to afford compound 10 (210 mg). LCMS (ESI): m/z: [M+H] calcd for $C_{21}H_{33}N_3O_5$: 407; found 408; RT=0.777, 0.813 min.

Compound 22.2 (210 mg, 515.34 μmol, 1 eq) was added into a solution of HCl/EtOAc (5 mL). The mixture was stirred at 18° C. for 15 hours. The reaction mixture was concentrated under reduced pressure to give compound 22.1 (200 mg, crude) as a yellow solid. LCMS (ESI): m/z: [M+H] calcd for $C_{11}H_{17}N_3O$: 207; found 208; RT=0.093, 0.191 min.

To a mixture of compound 22.1 (100 mg, 356.90 μmol, 1 eq, 2HCl) and DIEA (184.50 mg, 1.43 mmol, 249.32 μL, 4 eq) in DMF (2 mL) was added carbononitridic bromide (30.24 mg, 285.52 μmol, 21 μL, 0.80 eq) in one portion at 0° C. under $N_2$. The mixture was stirred at 0° C. for 30 mins. The reaction mixture diluted with $H_2O$ 3 mL and extracted with DCM 3 mL (3 mL×3). The combined organic layers were washed with brine 4 mL (4 mL×1), dried over $Na_2SO_4$, filtered and concentrated under reduced pressure to give a residue. The residue was purified by prep-HPLC (neutral condition) to give product 22 (5 mg, 21.53 mol, 6.03% yield) as a yellow solid. $^1$H NMR (400 MHz, chloroform-d) δ ppm 1.85-2.07 (m, 3H) 2.08-2.20 (m, 1H) 2.90 (d, J=5.27 Hz, 3H) 3.40-3.51 (m, 1H) 3.51-3.60 (m, 1H) 3.93-4.02 (m, 1H) 4.02-4.09 (m, 2H) 5.78-5.93 (m, 1H) 6.20 (dd, J=5.84, 2.07 Hz, 1H) 7.87-8 (m, 1H). LCMS (ESI): m/z: [M+H] calcd for $C_{12}H_{16}N_4O$: 232; found 233; RT=0.976 min.

Example 23. Preparation of 2-(((2-(dimethylamino)pyridin-4-yl)oxy)methyl)pyrrolidine-1-carbonitrile (23)

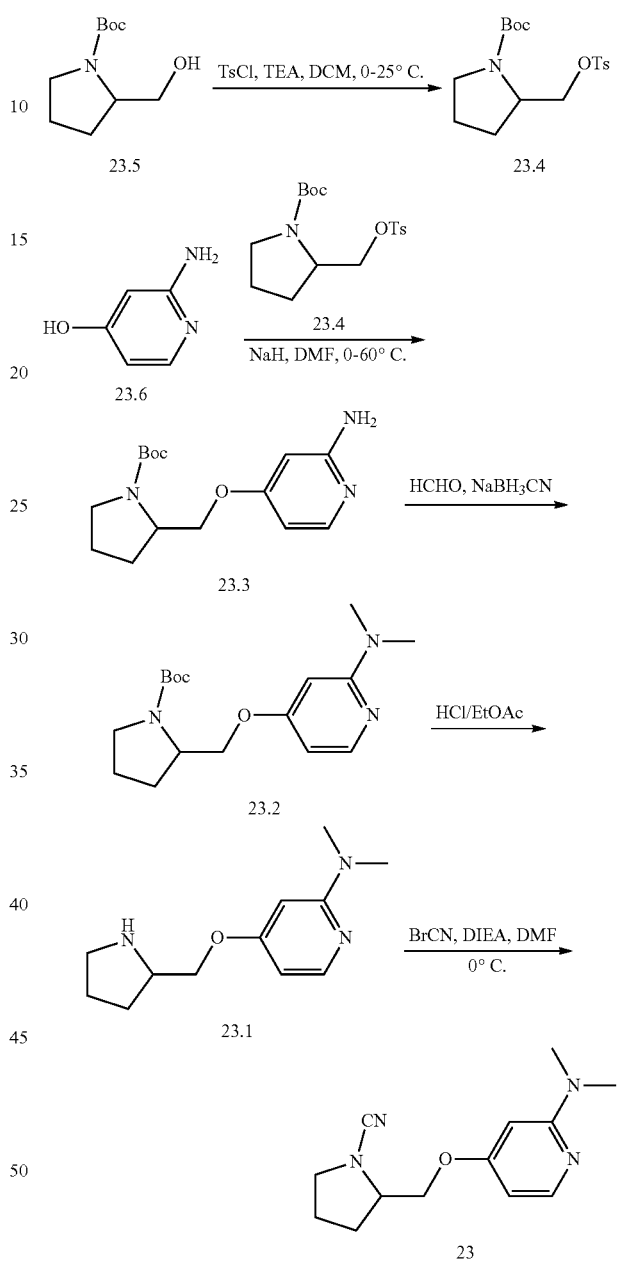

To a mixture of compound 23.5 (4.50 g, 22.36 mmol, 1 eq) and 4-methylbenzenesulfonyl chloride (5.12 g, 26.83 mmol, 1.20 eq) in DCM (15 mL) was added DMAP (437.06 mg, 3.58 mmol, 0.16 eq) and TEA (3.39 g, 33.54 mmol, 4.65 mL, 1.50 eq) in one portion at 0° C. under $N_2$. The mixture was then heated to 25° C. and stirred for 10 hours. The reaction mixture was diluted with $H_2O$ 20 mL and extracted with EtOAc 45 mL (15 mL×3). The combined organic layers were washed with brine 20 mL (20 mL×1), dried over $Na_2SO_4$, filtered and concentrated under reduced pressure to give compound 23.4 (8 g, crude) as a colorless oil. $^1$H NMR (400 MHz, chloroform-d) δ ppm 1.20-1.52 (m, 9H) 1.81 (br.

s., 1H) 1.93 (br. s., 2H) 2.39-2.54 (m, 3H) 3.17-3.44 (m, 2H) 3.80-4.04 (m, 1H) 4.10 (d, J=6.02 Hz, 1H) 7.30-7.42 (m, 2H) 7.67-7.86 (m, 2H).

To a solution of compound 23.4 (2.73 g, 24.76 mmol, 1.10 eq) in DMF (20 mL) was added NaH (810.24 mg, 33.76 mmol, 1.50 eq) portionwise at 0° C. under $N_2$. The mixture was stirred at 0° C. for 30 mins, then was added compound 23.6 (8 g, 22.51 mmol, 1 eq). The mixture was heated to 60° C. and stirred for 9.5 hours. The reaction mixture was diluted with $H_2O$ 20 mL and extracted with EtOAc 45 mL (15 mL×3). The combined organic layers were washed with brine 20 mL (20 mL×1), dried over $Na_2SO_4$, filtered and concentrated under reduced pressure to give a residue. The residue was purified by column chromatography ($SiO_2$, DCM:MeOH=20:1) to give compound 23.3 (4 g, 13.64 mmol, 60.57% yield) as a yellow oil. $^1$H NMR (400 MHz, chloroform-d) δ ppm 1.40-1.57 (m, 9H) 1.78-2.05 (m, 4H) 3.37 (d, J=19.07 Hz, 2H) 3.66-4 (m, 1H) 4.12 (dd, J=14.05, 7.03 Hz, 2H) 4.38 (br. s., 2H) 5.89-6.15 (m, 1H) 6.28 (d, J=4.02 Hz, 1H) 7.88 (br. s., 1H). LCMS (ESI): m/z: [M+H] calcd for $C_{15}H_{23}N_3O_3$: 293; found 294; RT=0.681 min.

To a solution of compound 23.3 (100 mg, 340.88 μmol, 1 eq) in H2O (250 μL) and ACETONITRILE (1 mL) was added HCHO (327 mg, 4.03 mmol, 300 μL, 37% purity, 11.82 eq) and NaBH3CN (64.26 mg, 1.02 mmol, 3 eq) in one portion at 0° C. under $N_2$. The mixture was stirred at 0° C. for 30 mins, then was added $CH_3COOH$ (21 mg, 349.71 μmol, 20 μL, 1.03 eq) dropwise at 0° C., then heated to 18° C. and stirred for 1.5 hours. The reaction mixture was quenched by addition $H_2O$ 5 mL then diluted with DCM 3 mL and extracted with DCM 3 mL (3 mL×3). The combined organic layers were washed with brine 5 mL (5 mL×1), dried over $Na_2SO_4$, filtered and concentrated under reduced pressure to give a residue. The residue was purified by prep-TLC (SiO2, DCM:MeOH=10:1) to give compound 23.2 (60 mg, 186.68 μmol, 54.76% yield) as a colorless oil. LCMS (ESI): m/z: [M+H] calcd for $C_{17}H_{27}N_3O_3$: 321; found 322; RT=0.712 min.

Compound 23.2 (60 mg, 186.67 μmol, 1 eq) was added into a solution of HCl/EtOAc (3 mL). The mixture was stirred at 18° C. for 1.5 hours. The reaction mixture was concentrated under reduced pressure to give compound 23.1 (60 mg, crude) as a yellow solid. LCMS (ESI): m/z: [M+H] calcd for $C_{12}H_{19}N_3O$: 221; found 222; RT=0.096 min.

To a mixture of compound 23.1 (60 mg, 232.77 μmol, 1 eq, HCl) and DIEA (120.34 mg, 931.08 μmol, 162.62 μL, 4 eq) in DMF (2 mL) was added carbononitridic bromide (24.65 mg, 232.77 μmol, 17.12 μL, 1 eq) in one portion at 0° C. under $N_2$. The mixture was stirred at 0° C. for 30 mins. The residue was purified by prep-HPLC (neutral condition) to give product 23 (10 mg, 40.60 μmol, 17.44% yield) as a white solid. LCMS (ESI): m/z: [M+H] calcd for $C_{13}H_{18}N_4O$: 246; found 247; RT=2.441 min. $^1$H NMR (400 MHz, chloroform-d) δ ppm 1.91-2.08 (m, 3H) 2.10-2.21 (m, 1H) 3.10 (s, 6H) 3.45-3.52 (m, 1H) 3.54-3.61 (m, 1H) 3.97-4.04 (m, 1H) 4.04-4.11 (m, 2H) 5.99 (d, J=2.01 Hz, 1H) 6.19 (dd, J=5.77, 2.01 Hz, 1H) 8.04 (d, J=5.90 Hz, 1H)

Example 24. Preparation of 2-(((2-aminopyridin-4-yl)oxy)methyl)indoline-1-carbonitrile (24)

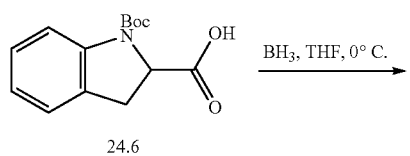

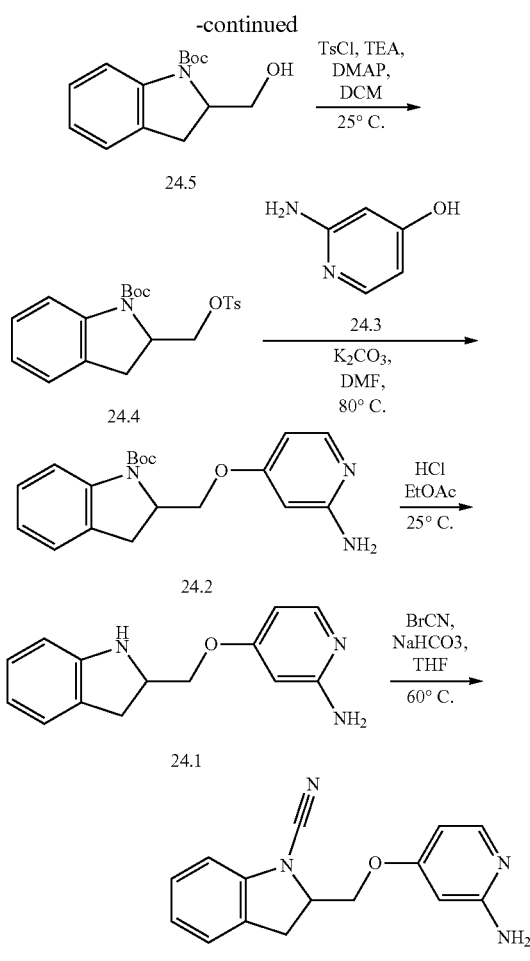

To a solution of compound 24.6 (950 mg, 3.61 mmol, 1 eq) in THF (15 mL) was added $BH_3$-$Me_2S$ (10 M, 721.64 μL, 2 eq) at 0° C. The mixture was stirred at 25° C. for 15 hours. The reaction mixture was quenched by addition $H_2O$ 30 mL at 25° C. and extracted with ethyl acetate (15 mL×3). The combined organic layers were washed with saturated brines (5 mL×1), dried over anhydrous sodium sulfate, filtered and concentrated under reduced pressure to give a crude product. Compound 24.5 (750 mg, 3.01 mmol, 83.34% yield) was obtained as a yellow oil. LCMS (ESI): m/z: [M+H] called for $C_{14}H_{19}NO_3$: 250; found 250; RT=0.800 min.

To a solution of compound 24.5 (750 mg, 3.01 mmol, 1 eq) in DCM (20 mL) was added TEA (1.52 g, 15.04 mmol, 2.09 mL, 5 eq) and TosCl (1.72 g, 9.03 mmol, 3 eq) and DMAP (183.77 mg, 1.50 mmol, 0.50 eq). The mixture was stirred at 25° C. for 15 hours. The reaction mixture was quenched by addition $H_2O$ 50 mL at 25° C. and extracted with DCM (50 mL×3). The combined organic layers were washed with saturated brines (15 mL×1), dried over anhydrous sodium sulfate, filtered and concentrated under reduced pressure to give a crude product. Compound 24.4 (1.40 g, crude) was obtained as a yellow oil. LCMS (ESI): m/z: [M+H] called for $C_{21}H_{25}NO_5S$: 404; found 404; RT=0.925 min.

To a solution of compound 24.4 (1.40 g, 3.47 mmol, 1 eq) in DMF (30 mL) was added $K_2CO_3$ (959.10 mg, 6.94 mmol, 2 eq) and compound 24.3 (458.46 mg, 4.16 mmol, 1.20 eq).

The mixture was stirred at 80° C. for 15 hours. The reaction mixture was quenched by addition H₂O 50 mL at 25° C. and extracted with ethyl acetate (50 mL×3). The combined organic layers were washed with saturated brines (15 mL×1), dried over anhydrous sodium sulfate, filtered and concentrated under reduced pressure to give a crude product. Compound 24.2 (200 mg, 585.82 µmol, 16.88% yield) was obtained as a yellow oil. ¹H NMR (400 MHz, chloroform-d) δ ppm 1.59 (s, 9H) 2.46 (s, 1H) 3.01-3.13 (m, 1H) 3.35 (dd, J=16.25, 9.72 Hz, 1H) 3.90 (br s, 1H) 4.22 (br s, 1H) 4.38-4.61 (m, 2H) 4.79 (br s, 1H) 6 (br s, 1H) 6.22-6.31 (m, 1H) 6.93-7.03 (m, 1H) 7.14-7.23 (m, 2H) 7.87 (d, J=5.77 Hz, 1H). LCMS (ESI): m/z: [M+H] called for $C_{19}H_{23}N_3O_3$: 342; found 342; RT=0.759 min.

A mixture of compound 24.2 (50 mg, 146.46 µmol, 1 eq) in HCl/EtOAc (5 mL) was stirred at 25° C. for 15 hours. The mixture was concentrated under reduced pressure to give a residue. Compound 24.1 (45 mg, 143.22 µmol, 97.79% yield, 2HCl) was obtained as a yellow oil. LCMS (ESI): m/z: [M+H] called for $C_{14}H_{15}N_3O$: 242; found 242; RT=0.129 min.

To a solution of compound 24.1 (40 mg, 127.30 µmol, 1 eq, 2HCl) in DMSO (2 mL) was added NaHCO₃ (53.47 mg, 636.52 µmol, 24.76 µL, 5 eq) and BrCN (13.48 mg, 127.30 µmol, 9.36 µL, 1 eq). The mixture was stirred at 60° C. for 2 hours. The residue was purified by prep-HPLC (TFA condition). Product 24 (1 mg, 3.76 µmol, 2.95% yield) was obtained as a yellow solid. ¹H NMR (400 MHz, methanol-d₄) δ ppm 3.10 (dd, J=16.44, 5.90 Hz, 1H) 3.51 (dd, J=16.44, 10.04 Hz, 1H) 4.32-4.43 (m, 1H) 4.45-4.54 (m, 1H) 4.78-4.84 (m, 1H) 6.39 (d, J=2.51 Hz, 1H) 6.53 (dd, J=7.28, 2.38 Hz, 1H) 6.93 (d, J=8.03 Hz, 1H) 7.02-7.10 (m, 1H) 7.26 (br d, J=7.15 Hz, 2H) 7.73 (d, J=7.28 Hz, 1H). LCMS (ESI): m/z: [M+H] called for $C_{15}H_{14}N_4O$: 267; found 267; RT=1.955 min.

Example 25. Preparation of 1-(((2-aminopyridin-4-yl)oxy)methyl)isoindoline-2-carbonitrile (25)

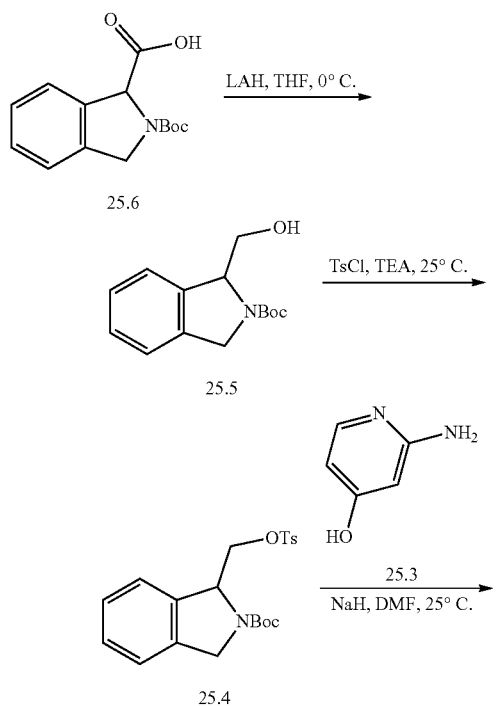

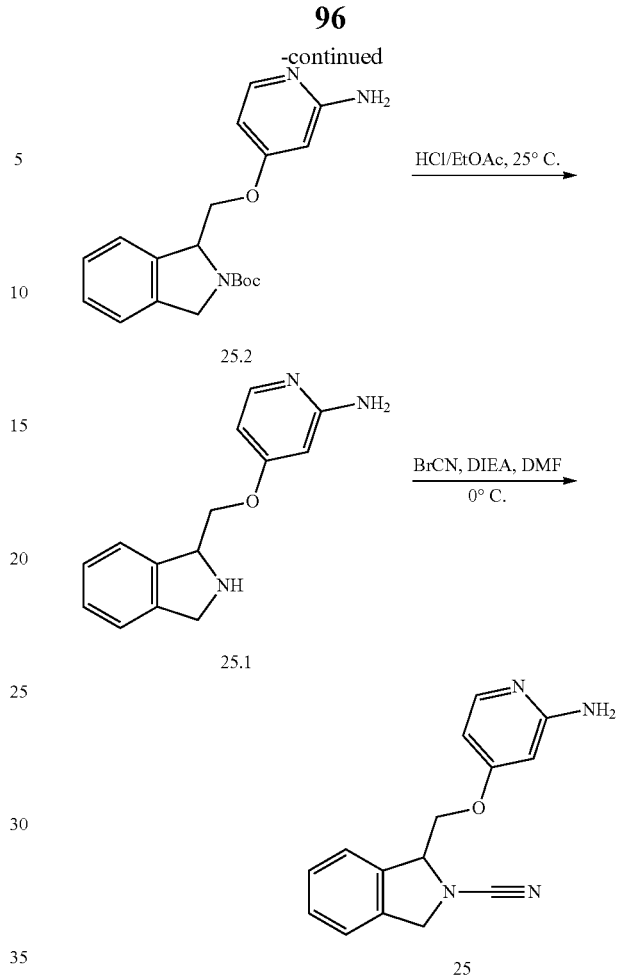

To a solution of compound 25.6 (800 mg, 3.04 mmol, 1 eq) in THF (8 mL) was added BH₃-Me₂S (10 M, 608 µL, 2 eq) at 0° C. The mixture was stirred at 25° C. for 15 hours. The reaction mixture was quenched by addition H₂O 20 mL at 25° C. and extracted with ethyl acetate (15 mL×3). The combined organic layers were washed with saturated brines (10 mL×1), dried over anhydrous sodium sulfate, filtered and concentrated under reduced pressure to give a crude product. Compound 25.5 (600 mg, 2.41 mmol, 79.17% yield) was obtained as a yellow oil. LCMS (ESI): m/z: [M+H] called for $C_{14}H_{19}NO_3$: 250; found 250; RT=0.752 min.

To a solution of compound 25.5 (100 mg, 401.11 µmol, 1 eq) in DCM (2 mL) was added TosCl (229.41 mg, 1.20 mmol, 3 eq) and TEA (202.94 mg, 2.01 mmol, 278 µL, 5 eq) and DMAP (14.70 mg, 120.33 µmol, 0.30 eq). The mixture was stirred at 25° C. for 15 hours. The reaction mixture was quenched by addition H₂O 10 mL at 25° C. and extracted with DCM (15 mL×3). The combined organic layers were washed with saturated brines (5 mL×1), dried over anhydrous sodium sulfate, filtered and concentrated under reduced pressure to give a crude product. Compound 25.4 (230 mg, crude) was obtained as a yellow oil. ¹H NMR (400 MHz, chloroform-d) δ ppm 1.07-1.21 (m, 1H) 1.32-1.42 (m, 2H) 1.32-1.42 (m, 1H) 1.44-1.55 (m, 8H) 2.26-2.50 (m, 5H) 3.02-3.36 (m, 1H) 3.02-3.36 (m, 5H) 4.15-4.81 (m, 4H) 6.64 (d, J=7.03 Hz, 1H) 7.11-7.41 (m, 8H) 7.56-7.72 (m, 2H) 7.83 (d, J=8.16 Hz, 1H) 8.24 (d, J=7.15 Hz, 1H). LCMS (ESI): m/z: [M+H] called for $C_{21}H_{25}NO_5S$: 404; found 404; RT=0.925 min.

To a solution of compound 25.4 (230 mg, 570.03 μmol, 1 eq) in DMF (3 mL) was added K$_2$CO$_3$ (157.57 mg, 1.14 mmol, 2 eq) and compound 25.3 (75.32 mg, 684.04 μmol, 1.20 eq). The mixture was stirred at 80° C. for 15 hours. The reaction mixture was quenched by addition H$_2$O 10 mL at 25° C. and extracted with ethyl acetate (15 mL×3). The combined organic layers were washed with saturated brines (5 mL×1), dried over anhydrous sodium sulfate, filtered and concentrated under reduced pressure to give a crude product. The residue was purified by column chromatography (SiO2, DCM:MeOH=10:1). Compound 25.2 (50 mg, 146.46 μmol, 25.69% yield) was obtained as a black brown oil. LCMS (ESI): m/z: [M+H] called for C$_{19}$H$_{23}$N$_3$O$_3$: 342; found 342; RT=0.742 min.

A mixture of compound 25.2 (50 mg, 146.46 μmol, 1 eq) in HCl/EtOAc (5 mL) was stirred at 25° C. for 15 hours. The mixture was concentrated under reduced pressure to give a residue. Compound 25.1 (30 mg, 95.48 μmol, 65.19% yield, 2HCl) was obtained as a black brown oil. LCMS (ESI): m/z: [M+H] called for C$_{14}$H$_{15}$N$_3$O: 242; found 242; RT=0.099 min.

To a solution of compound 25.1 (30 mg, 95.48 μmol, 1 eq, 2HCl) in DMF (1 mL) was added DIEA (49.36 mg, 381.91 μmol, 66.70 μL, 4 eq) and BrCN (10.11 mg, 95.48 μmol, 7.02 μL, 1 eq). The mixture was stirred at 0° C. for 5 min. The residue was purified by prep-HPLC (basic condition). Product 25 (5 mg, 18.78 μmol, 19.66% yield) was obtained as a white solid. $^1$H NMR (400 MHz, methanol-d$_4$) δ ppm 4.25 (dd, J=10.36, 5.95 Hz, 1H) 4.47 (dd, J=10.36, 3.53 Hz, 1H) 4.79-4.88 (m, 2H) 5.29-5.41 (m, 1H) 6.12 (d, J=2.20 Hz, 1H) 6.25 (dd, J=6.06, 2.32 Hz, 1H) 7.30-7.49 (m, 4H) 7.71 (d, J=6.17 Hz, 1H). LCMS (ESI): m/z: [M+H] called for C$_{15}$H$_{14}$N$_4$O: 267; found 267; RT=2.440 min.

Example 26. Preparation of N-((1-aminoisoquinolin-6-yl)methyl)-N-methylcyanamide (26)

To a solution of compound 26.7 (2 g, 8.25 mmol, 1 eq) in NMP (20 mL) was added NH$_3$.H$_2$O (18.20 g, 519.26 mmol, 20 mL, 62.94 eq). The mixture was stirred at 150° C. for 15 hours. The reaction mixture was quenched by addition H$_2$O 50 mL at 25° C. and extracted with ethyl acetate (50 mL×3). The combined organic layers were washed with saturated brines (10 mL×1), dried over anhydrous sodium sulfate, filtered and concentrated under reduced

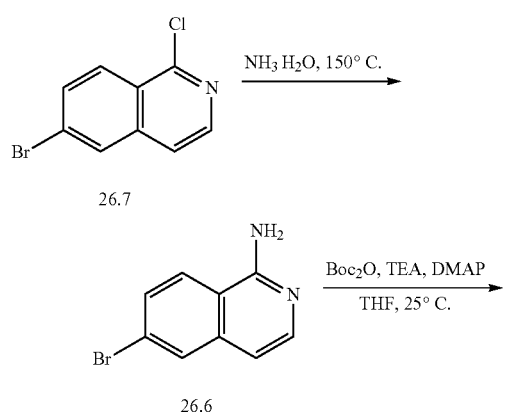

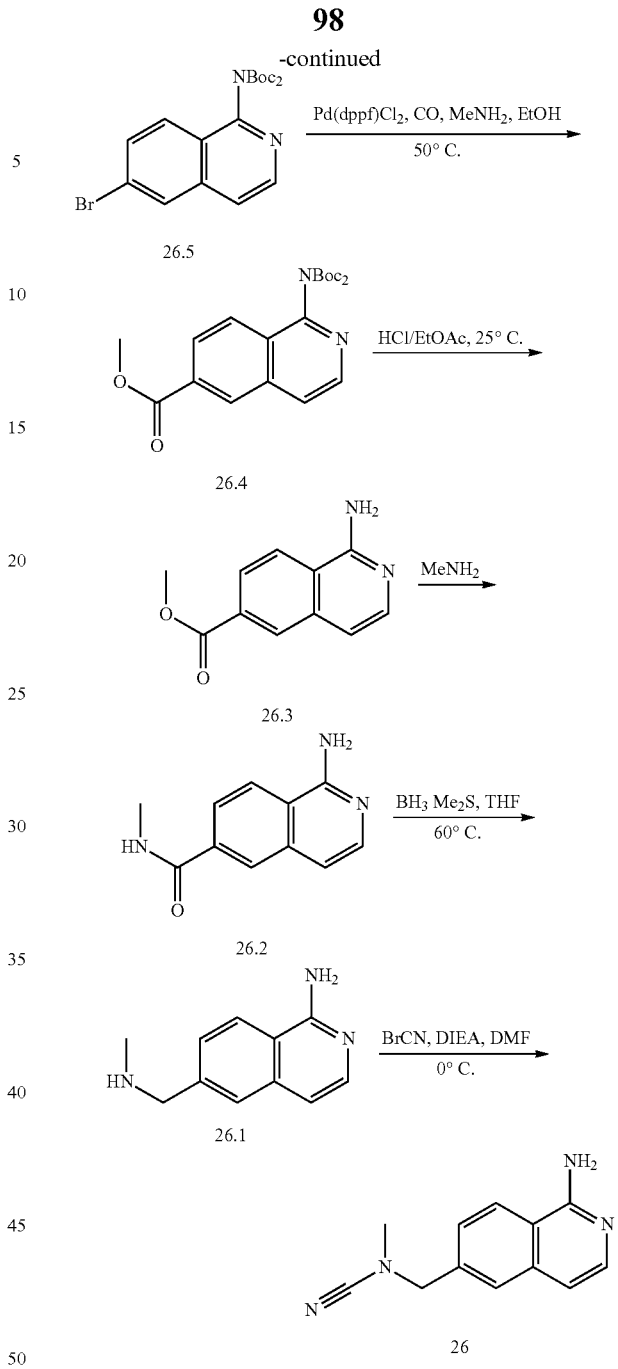

pressure to give a crude product. Compound 26.6 (5 g, crude) was obtained as a yellow oil. LCMS (ESI): m/z: [M+H] called for C$_9$H$_7$N$_2$Br: 224; found 224; RT=0.589 min.

To a solution of compound 26.6 (2.50 g, 11.21 mmol, 1 eq) in THF (40 mL) was added TEA (4.54 g, 44.83 mmol, 6.21 mL, 4 eq) and Boc$_2$O (6.11 g, 28.02 mmol, 6.44 mL, 2.50 eq) and DMAP (410.76 mg, 3.36 mmol, 0.30 eq). The mixture was stirred at 25° C. for 15 hours. The reaction mixture was quenched by addition H$_2$O 50 mL at 25° C. and extracted with ethyl acetate (50 mL×3). The combined organic layers were washed with saturated brines (20 mL×1), dried over anhydrous sodium sulfate, filtered and concentrated under reduced pressure to give a crude product. The residue was purified by re-crystallization from ethyl acetate (5 mL) to give compound 26.5 (3 g, 7.09 mmol, 63.22% yield) as yellow solid. $^1$H NMR (400 MHz, chloroform-d) δ ppm 1.19-1.45 (m, 19H) 7.57 (d, J=5.77 Hz, 1H) 7.71 (dd, J=8.97, 1.82 Hz, 1H) 7.84 (d, J=8.91 Hz, 1H) 8.06 (d, J=1.76 Hz, 1H) 8.46 (d, J=5.77 Hz, 1H). LCMS (ESI): m/z: [M+H] called for $C_{19}H_{23}BrN_2O_4$: 424; found 424; RT=0.896 min.

To a solution of compound 26.5 (1.65 g, 3.90 mmol, 1 eq) in toluene (120 mL) and MeOH (60 mL) was added TEA (1.58 g, 15.60 mmol, 2.16 mL, 4 eq) and Pd(dppf)$C_{12}.CH_2Cl_2$ (318.32 mg, 390 μmol, 0.10 eq) under $N_2$. The suspension was degassed under vacuum and purged with CO several times. The mixture was stirred under CO (50 psi) at 50° C. for 15 hours. The mixture was filtered and concentrated under reduced pressure to give a residue. The residue was purified by column chromatography (SiO$_2$, Petroleum ether/Ethyl acetate=1:1). Compound 26.4 (1.20 g, 2.98 mmol, 76.46% yield) was obtained as a white solid. $^1$H NMR (400 MHz, methanol-d4) δ ppm 1.07-1.58 (m, 20H) 4.01 (s, 3H) 7.99-8.04 (m, 1H) 8.05-8.10 (m, 1H) 8.29 (dd, J=8.82, 1.54 Hz, 1H) 8.47 (d, J=5.73 Hz, 1H) 8.74 (d, J=1.32 Hz, 1H). LCMS (ESI): m/z: [M+H] called for $C_{21}H_{26}N_2O_6$: 403; found 403; RT=1.360 min.

A mixture of compound 26.4 (100 mg, 248.48 μmol, 1 eq) in HCl/EtOAc (20 mL) was stirred at 25° C. for 15 hours. The mixture was filtered and concentrated under reduced pressure to give a residue. Compound 26.3 (50 mg, 209.49 μmol, 84.31% yield, HCl) was obtained as a yellow solid. LCMS (ESI): m/z: [M+H] called for $C_{11}H_{10}N_2O_2$: 203; found 203; RT=0.119 min. A mixture of compound 26.3 (50 mg, 247.27 μmol, 1 eq) in MeNH2 (10 mL) was stirred at 80° C. for 15 hours. The mixture was filtered and concentrated under reduced pressure to give compound 26.2 (65 mg, crude) as a brown oil. LCMS (ESI): m/z: [M+H] called for $C_{11}H_{11}N_3O$: 202; found 202; RT=1.093 min.

To a solution of compound 26.2 (65 mg, 323.01 μmol, 1 eq) in THF (5 mL) was added $BH_3$-$Me_2S$ (10 M, 323.01 μL, 10 eq) at 0° C. The mixture was stirred at 70° C. for 4 hours. The reaction mixture was quenched by addition MeOH 20 mL at 25° C., then concentrated under reduced pressure to give a crude product, to the crude product was added HCl (15 mL), the mixture was stirred at 25° C. for 2 hours and extracted with DCM (25 mL×5). The combined organic layers were washed with saturated brines (5 mL×1), dried over anhydrous sodium sulfate, filtered and concentrated under reduced pressure to give a crude product. The residue was purified by prep-HPLC (neutral condition). Compound 26.1 (40 mg, 213.63 μmol, 66.14% yield) was obtained as a yellow oil. LCMS (ESI): m/z: [M+H] called for $C_{11}H_{13}N_3$: 188; found 188; RT=0.506 min.

To a solution of compound 26.1 (10 mg, 53.41 μmol, 1 eq) in DMF (1 mL) was added DIEA (20.71 mg, 160.23 μmol, 27.98 μL, 3 eq) and BrCN (5.66 mg, 53.41 μmol, 3.93 μL, 1 eq). The mixture was stirred at 0° C. for 10 min. The residue was purified by prep-HPLC (neutral condition). Product 26 (1 mg, 4.71 μmol, 8.82% yield) was obtained as a yellow oil. $^1$H NMR (400 MHz, chloroform-d) δ ppm 2.85 (s, 3H) 4.33 (s, 2H) 7.06 (d, J=5.90 Hz, 1H) 7.52 (d, J=8.41 Hz, 1H) 7.65 (s, 1H) 7.88 (d, J=8.41 Hz, 1H) 7.97 (d, J=6.02 Hz, 1H). LCMS (ESI): m/z: [M+H] called for $C_{12}H_{12}N_4$: 213; found 213; RT=2.098 min.

Example 27. Preparation of N-(2-((2-aminopyridin-4-yl)oxy)phenyl)-N-methylcyanamide (27)

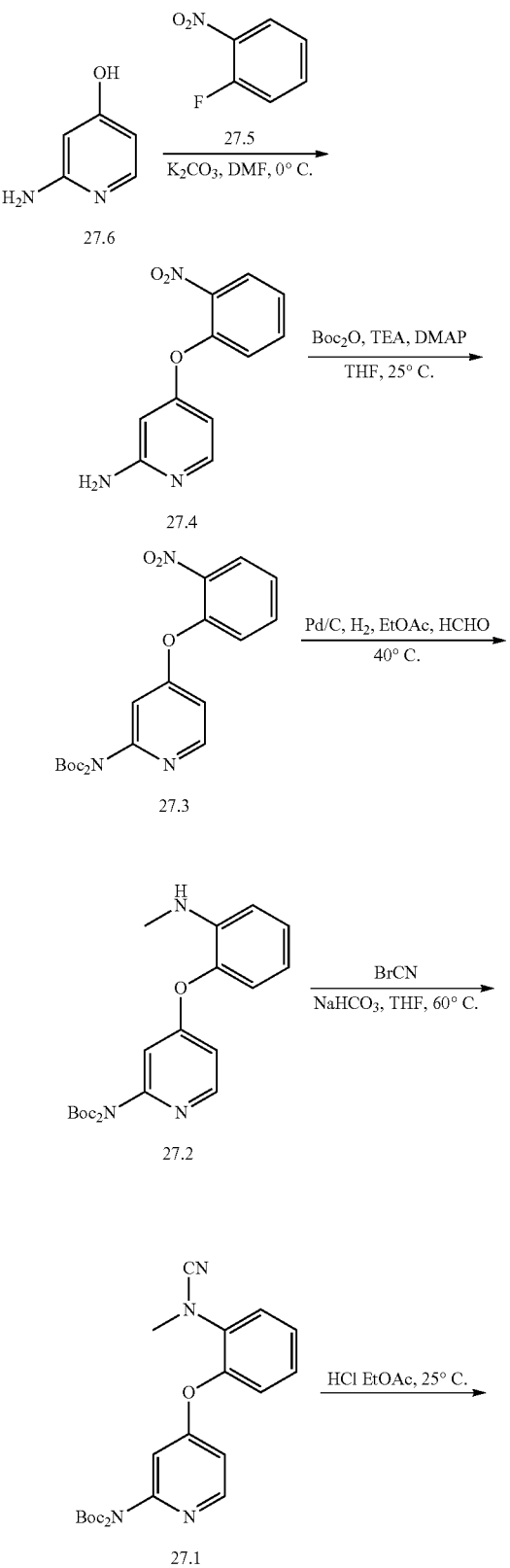

-continued

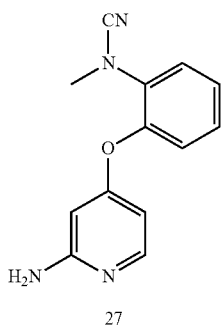

27

To a solution of compound 27.6 (3 g, 27.25 mmol, 1 eq) in DMF (100 mL) was added K$_2$CO$_3$ (7.53 g, 54.50 mmol, 2 eq) and compound 27.5 (4.61 g, 32.70 mmol, 3.44 mL, 1.20 eq). The mixture was stirred at 50° C. for 15 hours. The reaction mixture was quenched by addition H$_2$O 100 mL at 25° C. and extracted with ethyl acetate (100 mL×3). The combined organic layers were washed with saturated brines (20 mL×1), dried over anhydrous sodium sulfate, filtered and concentrated under reduced pressure to give a crude product. The residue was purified by column chromatography (SiO$_2$, Petroleum ether/Ethyl acetate=1:1). Compound 27.4 (3.30 g, 14.27 mmol, 52.38% yield) was obtained as a brown solid. $^1$H NMR (400 MHz, chloroform-d) δ ppm 6.06 (d, J=1.98 Hz, 1H) 6.32 (dd, J=5.84, 2.09 Hz, 1H) 7.22-7.35 (m, 1H) 7.42 (td, J=7.83, 1.10 Hz, 1H) 7.69 (ddd, J=8.21, 7.44, 1.76 Hz, 1H) 7.99-8.16 (m, 2H). LCMS (ESI): m/z: [M+H] called for C$_{11}$H$_9$N$_3$O$_3$: 232; found 232; RT=0.522 min.

To a solution of compound 27.4 (3.30 g, 14.27 mmol, 1 eq) in THF (50 mL) was added TEA (5.78 g, 57.08 mmol, 7.92 mL, 4 eq) and Boc$_2$O (7.79 g, 35.67 mmol, 8.20 mL, 2.50 eq) and DMAP (523.11 mg, 4.28 mmol, 0.30 eq). The mixture was stirred at 25° C. for 15 hours. The reaction mixture was quenched by addition H$_2$O 100 mL at 25° C. and extracted with ethyl acetate (50 mL×3). The combined organic layers were washed with saturated brines (10 mL×1), dried over anhydrous sodium sulfate, filtered and concentrated under reduced pressure to give a crude product. The residue was purified by column chromatography (SiO$_2$, Petroleum ether/Ethyl acetate=2:1). Compound 27.3 (3.20 g, 7.42 mmol, 51.98% yield) was obtained as a yellow oil. LCMS (ESI): m/z: [M+H] called for C$_{21}$H$_{25}$N$_3$O$_7$: 432; found 432; RT=0.904 min.

To a solution of compound 27.3 (1.50 g, 3.48 mmol, 1 eq) in MeOH (150 mL) was added Pd—C (10%, 150 mg) and formaldehyde (12 M, 261 μL, 0.90 eq) under N$_2$. The suspension was degassed under vacuum and purged with H$_2$ several times. The mixture was stirred under H$_2$ (40 psi) at 40° C. for 3 hours. The reaction mixture was filtered and the filter was concentrated. The residue was purified by column chromatography (SiO2, Petroleum ether/Ethyl acetate=2:1). Compound 27.2 (900 mg, 2.17 mmol, 62.25% yield) was obtained as a yellow oil. LCMS (ESI): m/z: [M+H] called for C$_{22}$H$_{29}$N$_3$O$_5$: 416; found 416; RT=0.926 min.

To a solution of compound 27.2 (100 mg, 240.69 μmol, 1 eq) in THF (2 mL) was added BrCN (43.34 mg, 409.17 μmol, 30.10 μL, 1.70 eq) and NaHCO$_3$ (60.66 mg, 722.07 mol, 28.08 μL, 3 eq). The mixture was stirred at 60° C. for 3 hours. The residue was purified by prep-TLC (SiO$_2$, Petroleum ether/Ethyl acetate=2:1). Compound 27.1 (35 mg, 79.46 mol, 33.01% yield) was obtained as a yellow oil. It was combined with a second batch for a total of 55 mg.

$^1$H NMR (400 MHz, chloroform-d) δ ppm 1.46 (s, 18H) 3.29 (s, 3H) 6.75 (dd, J=5.71, 2.32 Hz, 1H) 6.86 (d, J=2.26 Hz, 1H) 7.12 (dd, J=7.59, 1.95 Hz, 1H) 7.30 (td, J=5.21, 2.51 Hz, 2H) 7.37-7.41 (m, 1H) 8.36 (d, J=5.65 Hz, 1H). LCMS (ESI): m/z: [M+H] called for C$_{23}$H$_{28}$N$_4$O$_5$: 441; found 441; RT=0.878 min.

A mixture of compound 27.1 (55 mg, 124.86 μmol, 1 eq) in DCM (1 mL) and TFA (200 μL) was stirred at 25° C. for 15 hours. The reaction mixture was concentrated under reduced pressure to give a residue. The residue was purified by prep-HPLC (neutral condition). Product 27 (2 mg, 8.32 μmol, 6.67% yield) was obtained as a white solid. $^1$H NMR (400 MHz, DMSO-d$_6$) δ ppm 3.23-3.25 (m, 3H) 5.82 (d, J=2.21 Hz, 1H) 5.97 (s, 2H) 6.10 (dd, J=5.73, 2.43 Hz, 1H) 7.17-7.23 (m, 1H) 7.28-7.37 (m, 2H) 7.41-7.46 (m, 1H) 7.80 (d, J=5.73 Hz, 1H). LCMS (ESI): m/z: [M+H] called for C$_{13}$H$_{12}$N$_4$O: 241; found 241; RT=2.348 min.

Example 28. Preparation of (S)-2-(((2-aminopyridin-4-yl)thio)methyl)pyrrolidine-1-carbonitrile (28)

To a mixture of compound 28.7 (1 g, 4.97 mmol, 1 eq) and TEA (1.51 g, 14.91 mmol, 2.07 mL, 3 eq) in DCM (20 mL) was added methanesulfonyl chloride (683.18 mg, 5.96 mmol, 461.61 μL, 1.20 eq) in one portion at 0° C. under N$_2$. The mixture was stirred at 0° C. for 0.5 hr. The reaction was monitored by TLC (PE:EtOAc=2:1). The aqueous phase was

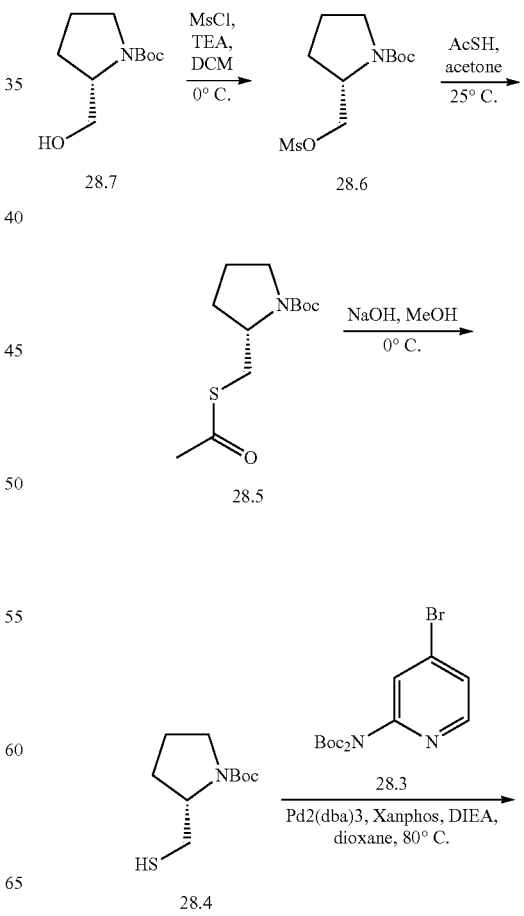

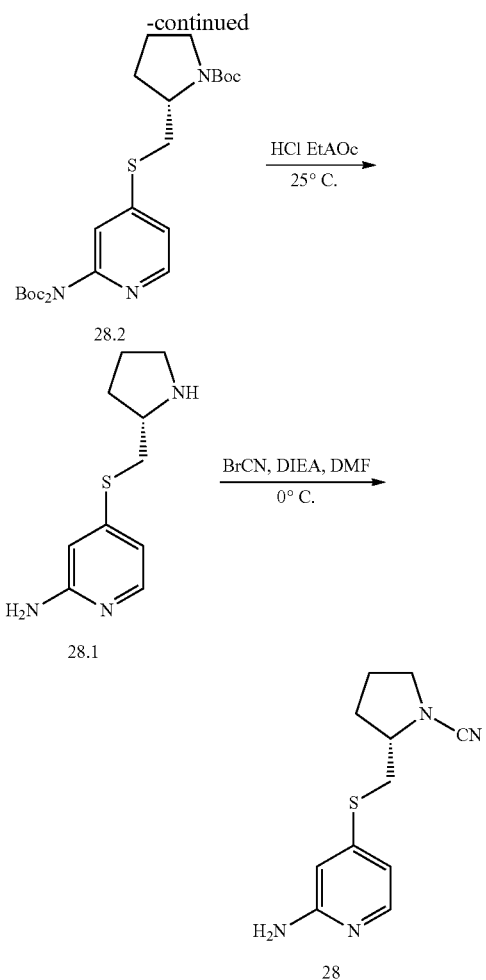

extracted with DCM (20 mL×3). The combined organic phase was washed with brine (5 mL), dried over anhydrous Na$_2$SO$_4$, filtered and concentrated in vacuum to afford compound 28.6 (1.80 g, crude) was obtained as a black brown oil. The crude was used for next step directly. But it didn't work. The crude was purified by by column chromatography (SiO$_2$, Petroleum ether/Ethyl acetate=10:1 to 2:1) to afford pure compound 28.6 (1.67 g, yield 59.87%).

To a mixture of compound 28.6 (800 mg, 2.86 mmol, 1 eq) in acetone (20 mL) was added acetylsulfanylpotassium (327.07 mg, 2.86 mmol, 1 eq) at 20° C. under N$_2$. The mixture was stirred at 50° C. for 15 hours. Filtered and concentrated in vacuum. The aqueous phase was extracted with EtOAc (20 mL×3). The combined organic phase was washed with brine (5 mL), dried with anhydrous Na$_2$SO$_4$, filtered and concentrated in vacuum. The residue was purified by column chromatography (SiO$_2$, Petroleum ether/Ethyl acetate=10:1 to 2:1) to afford compound 28.5 (420 mg, 1.62 mmol, 56.62% yield) as a colorless oil. $^1$H NMR (400 MHz, methanol-d4) ppm 1.49 (s, 9H), 1.76-2.23 (m, 4H), 2.34 (s, 3H), 2.96-3.42 (m, 4H), 3.88-3.94 (m, 1H). LCMS (ESI): m/z: [M+H−56] calcd for C12H22NO3S: 204; found 204; RT=0.859 min.

To a solution of compound 28.5 (200 mg, 771.13 µmol, 1 eq) in MeOH (5 mL) was added NaOH (1 M, 925.36 µL, 1.20 eq) in one portion at 20° C. under N$_2$. The mixture was stirred at 20° C. for 3 hours. The aqueous phase was extracted with EtOAc (20 mL×3). The combined organic phase was washed with brine (5 mL), dried with anhydrous Na$_2$SO$_4$, filtered and concentrated in vacuum to give compound 28.4 (100 mg, 460.13 µmol, 59.67% yield) as black brown oil. $^1$H NMR (400 MHz, DMSO-d6) ppm 1.26-1.46 (m, 1H), 1.47 (s, 9H), 1.79-2 (m, 4H), 2.55-2.84 (m, 2H), 3.35-3.50 (m, 2H) 3.82-3.88 (m, 1H).

To a mixture of compound 28.4 (100 mg, 460.13 µmol, 1 eq) and compound 28.3 (257.61 mg, 690.20 µmol, 1.50 eq), Xanphos (106.50 mg, 184.05 µmol, 0.40 eq), DIEA (237.87 mg, 1.84 mmol, 321.45 µL, 4 eq) in 1,4-dioxane (2 mL) was added Pd$_2$(dba)$_3$ (126.41 mg, 138.04 µmol, 0.30 eq) in one portion at 20° C. under N$_2$. The mixture was stirred at 80° C. for 15 hours. The reaction was monitored by LCMS. The aqueous phase was extracted with EtOAc (20 mL×3). The combined organic phase was washed with brine (5 mL), dried with anhydrous Na$_2$SO$_4$, filtered and concentrated in vacuum to give compound 28.2 (140 mg, crude) was obtained as light yellow oil. $^1$H NMR (400 MHz, DMSO-d6) ppm 1.45-1.53 (m, 27H), 1.84-2.04 (m, 4H), 2.74-2.79 (m, 1H), 3.37-3.63 (m, 3H), 4.05 (m, 1H), 7.15 (s, 1H), 7.35 (m, 1H), 8.30 (m, 1H).

A solution of compound 28.2 (140 mg crude) in HCl/EtOAc (5 mL) was stirred at 20° C. for 15 hours under N$_2$. The reaction was monitored by TLC (SiO$_2$, PE:EtOAc=1:1). After the reaction was completed, the solution was concentrated in vacuum to give compound 28.1 (50 mg, 156.89 µmol, 79.96% yield, 3HCl) was obtained as a light yellow solid.

To a mixture of compound 28.1 (50 mg, 238.88 µmol, 1 eq) and BrCN (25.30 mg, 238.88 µmol, 17.57 µL, 1 eq) in DMF (1 mL) was added DIEA (123.49 mg, 955.52 µmol, 166.88 µL, 4 eq) in one portion at 0° C. under N$_2$. The mixture was stirred at 0° C. for 10 min. The reaction was monitored by LC-MS promptly until the reaction was completed. The crude was purified by prep-HPLC (basic condition) to afford product 28 (10 mg, 42.68 µmol, 17.87% yield) as light yellow oil. $^1$H NMR (400 MHz, DMSO-d6) ppm 1.79-1.94 (m, 1H), 1.94-1.98 (m, 2H), 2.11-2.15 (m, 1H), 2.88-2.94 (m, 1H), 3.35-3.54 (m, 3H), 3.84-3.85 (m, 1H), 4.48 (s, 2H), 6.40 (s, 1H), 6.54 (dd, J=1.6 Hz, J=5.6 Hz, 1H), 7.91 (d, J=5.6 Hz, 1H). LCMS (ESI): m/z: [M+H] calcd for C$_{11}$H$_{14}$N$_4$S: 235; found 235; RT=2.209 min.

Example 29. Preparation of (S)-2-(((2-amino-5-methylpyridin-4-yl)oxy)methyl)pyrrolidine-1-carbonitrile (29)

To a mixture of compound 29.8 (5 g, 24.84 mmol, 1 eq) and 4-methylbenzenesulfonyl chloride (5.68 g, 29.81 mmol, 1.20 eq) in DCM (50 mL) was added TEA (3.77 g, 37.26 mmol, 5.16 mL, 1.50 eq) and DMAP (485.62 mg, 3.97 mmol, 0.16 eq) in one portion at 0° C. under N2. The mixture was then heated to 25° C. and stirred for 10 hours. The reaction mixture was diluted with H$_2$O 50 mL and extracted with DCM 30 mL (30 mL×

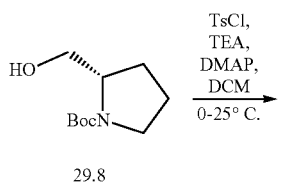

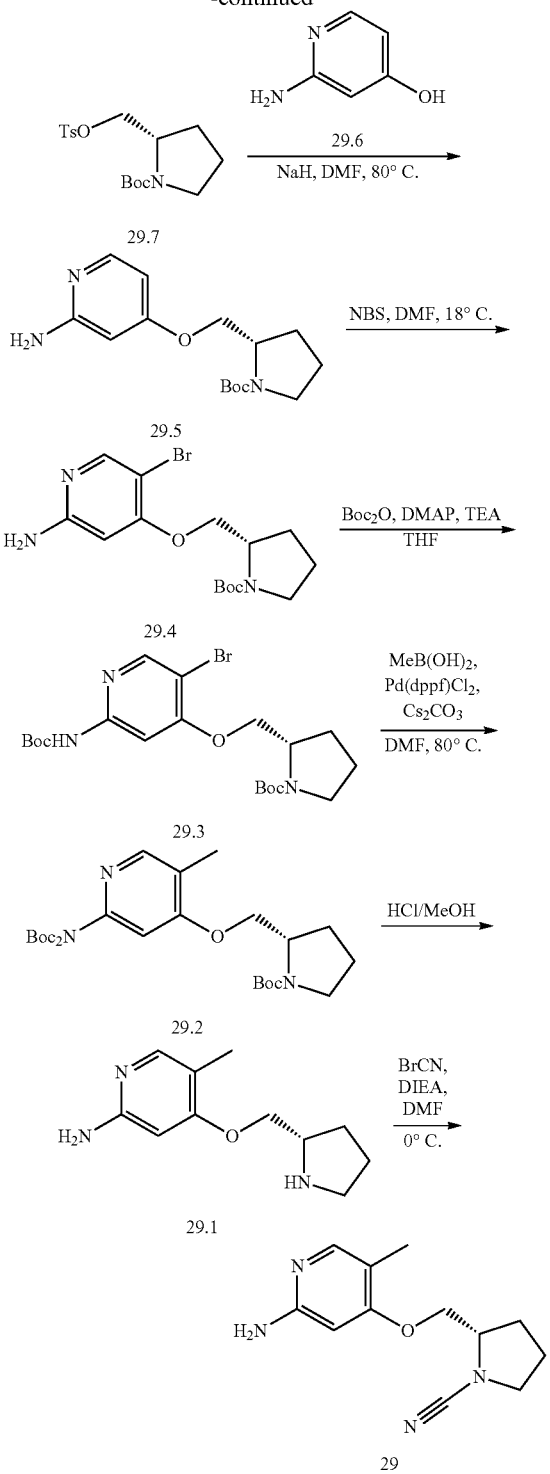

3). The combined organic layers were washed with brine 60 mL (60 mL×1), dried over Na₂SO₄, filtered and concentrated under reduced pressure to give compound 29.7 (8.90 g, crude) as a yellow oil. LCMS (ESI): m/z: [M+H] calcd for C₁₇H₂₅NO₅S: 355; found 300,256; RT=0.890 min.

To a mixture of compound 29.7 (8.84 g, 24.87 mmol, 1 eq) and compound 29.6 (3.01 g, 27.36 mmol, 1.10 eq) in DMF (100 mL) was added NaH (895.44 mg, 37.31 mmol, 1.50 eq) portionwise at 80° C. under N₂. The mixture was stirred at 80° C. for 10 hours. The reaction mixture was quenched by addition H₂O 100 mL, and then extracted with EtOAc 80 mL (80 mL×3). The combined organic layers were washed with brine 150 mL (150 mL×1), dried over Na₂SO₄, filtered and concentrated under reduced pressure to give compound 29.5 (4.50 g, 15.34 mmol, 61.68% yield) as a white solid. ¹H NMR (400 MHz, chloroform-d) δ ppm 1.40 (s, 9H) 1.71-1.95 (m, 4H) 3.28 (br s, 2H) 3.63-3.91 (m, 1H) 3.97-4.15 (m, 1H) 4.05 (br dd, J=14.18, 7.03 Hz, 1H) 5.85-6.05 (m, 1H) 6.22 (br d, J=4.39 Hz, 1H) 7.81 (br d, J=5.14 Hz, 1H). LCMS (ESI): m/z: [M+H] calcd for C₁₅H₂₃N₃O₂: 293; found 294; RT=0.692 min.

To a mixture of compound 29.5 (1 g, 3.41 mmol, 1 eq) in DMF (15 mL) was added NBS (606.69 mg, 3.41 mmol, 1 eq) in one portion at 18° C. under N₂. The mixture was stirred at 18° C. for 3 hours. The reaction mixture was quenched by addition H₂O 15 mL and extracted with EtOAc 10 mL (10 mL×3). The combined organic layers were washed with brine 10 mL (10 mL×1), dried over Na₂SO₄, filtered and concentrated under reduced pressure to give compound 29.4 (1 g, 2.69 mmol, 78.78% yield) as a colorless oil. ¹H NMR (400 MHz, DMSO-d₆) δ ppm 1.38 (br d, J=4.19 Hz, 9H) 1.72-1.83 (m, 1H) 1.93 (br s, 1H) 1.98-2.17 (m, 2H) 3.24-3.31 (m, 2H) 3.94-4.10 (m, 4H) 6.02 (s, 2H) 6.10 (s, 1H) 7.72-7.92 (m, 1H). LCMS (ESI): m/z: [M+H] calcd for C₁₅H₂₂N₃BrO₃: 372; found 372,374; RT=0.763 min.

To a mixture of compound 29.4 (800 mg, 2.15 mmol, 1 eq) and DMAP (42.01 mg, 344 μmol, 0.16 eq), TEA (869.84 mg, 8.60 mmol, 1.19 mL, 4 eq) in THF (15 mL) was added Boc₂O (1.17 g, 5.38 mmol, 1.23 mL, 2.50 eq) in one portion at 18° C. under N2. The mixture was stirred at 18° C. for 10 hours. The reaction mixture was diluted with H₂O 20 mL and extracted with EtOAc 30 mL (10 mL×3). The combined organic layers were washed with brine 20 mL (20 mL×1), dried over Na₂SO₄, filtered and concentrated under reduced pressure to give a residue. The residue was purified by column chromatography (SiO2, Petroleum ether/Ethyl acetate=5:1) to give compound 29.3 (900 mg, 1.57 mmol, 73.02% yield) as a yellow oil. ¹H NMR (400 MHz, chloroform-d) δ ppm 1.40 (s, 27H) 1.81 (br s, 1H) 1.95-2.17 (m, 3H) 3.28-3.48 (m, 2H) 4.13 (br s, 3H) 6.70-6.95 (m, 1H) 8.33 (br s, 1H). LCMS (ESI): m/z: [M+H] calcd for C₂₅H₃₈N₃BrO₇: 572; found 574,572; RT=18 min.

To a mixture of compound 29.3 (750 mg, 1.59 mmol, 1 eq), Cs2CO3 (2.07 g, 6.36 mmol, 4 eq) and methylboronic acid (142.77 mg, 2.38 mmol, 1.50 eq) in DMF (15 mL) was added Pd(dppf)Cl₂ (349.03 mg, 477 μmol, 0.30 eq) in one portion at 80° C. under N₂. The mixture was stirred at 80° C. for 10 hours. The reaction mixture was diluted with H₂O 20 mL and extracted with EA 30 mL (10 mL×3). The combined organic layers were washed with brine 30 mL (30 mL×1), dried over Na₂SO₄, filtered and concentrated under reduced pressure to give compound 29.2 (800 mg, crude) as a yellow solid. LCMS (ESI): m/z: [M+H] calcd for C₂₁H₃₃N₃O₅: 407; found 208; RT=0.150 min.

Compound 29.2 (800 mg, 1.58 mmol, 1 eq) was added into a solution of HCl/MeOH (15 mL). The mixture was stirred at 18° C. for 10 hours. The reaction mixture was concentrated under reduced pressure to give a residue. The residue was purified by prep-HPLC (TFA condition) to give compound 29.1 (200 mg, 964.92 μmol, 61.07% yield) as a white solid. LCMS (ESI): m/z: [M+H] calcd for C₁₁H₁₇N₃O: 207; found 208; RT=0.173 min.

To a mixture of compound 29.1 (100 mg, 482.46 μmol, 1 eq) and DIPEA (249.41 mg, 1.93 mmol, 337.05 μL, 4 eq) in DMF (3 mL) was added CNBr (56.21 mg, 530.71 μmol, 39.04 µL, 1.10 eq) in one portion at 0° C. under $N_2$. The mixture was stirred at 0° C. for 10 min. The residue was purified by prep-HPLC (neutral condition) to give product 29 (10 mg, 43.05 mol, 8.92% yield) as a yellow solid. $^1$H NMR (400 MHz, chloroform-d) δ ppm 1.87-2.04 (m, 4H) 2.07 (s, 2H) 2.10-2.21 (m, 1H) 3.41-3.65 (m, 2H) 3.91-4.12 (m, 2H) 5.95 (s, 1H) 7.72 (s, 1H). LCMS (ESI): m/z: [M+H] calcd for $C_{12}H_{16}N_4O$: 232; found 233; RT=2.181 min.

Example 30. Preparation of (S)-2-(((2-amino-5-bromopyridin-4-yl)oxy)methyl)pyrrolidine-1-carbonitrile (30)

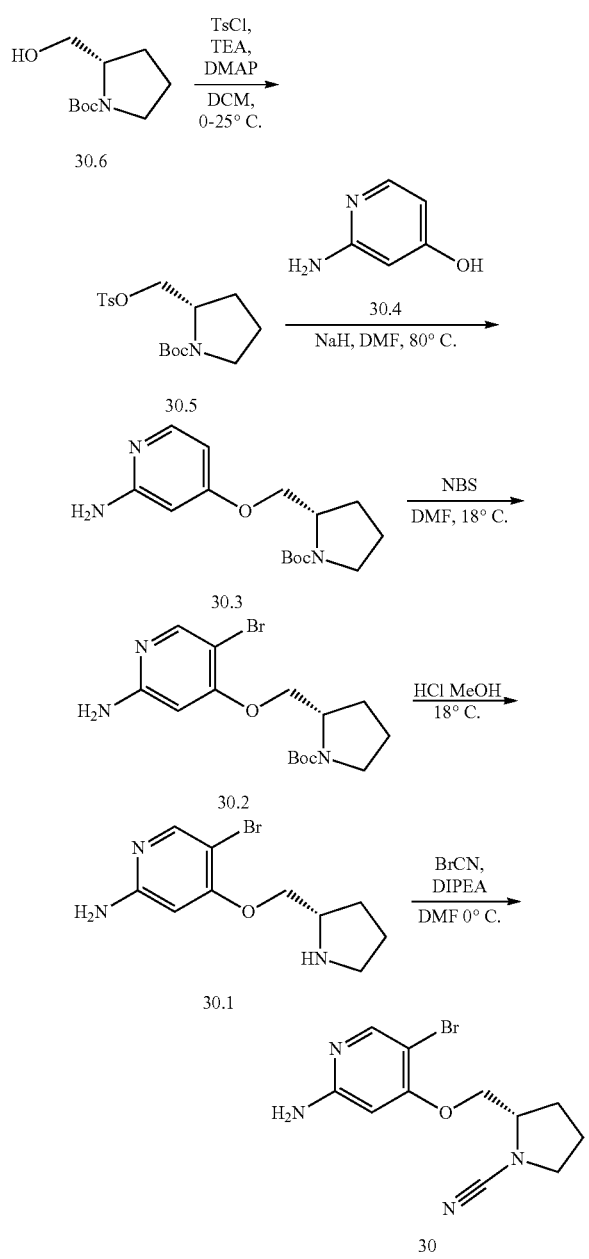

To a mixture of compound 30.6 (5 g, 24.84 mmol, 1 eq) and 4-methylbenzenesulfonyl chloride (5.68 g, 29.81 mmol, 1.20 eq) in DCM (50 mL) was added TEA (3.77 g, 37.26 mmol, 5.16 mL, 1.50 eq) and DMAP (485.62 mg, 3.97 mmol, 0.16 eq) in one portion at 0° C. under $N_2$. The mixture was then heated to 25° C. and stirred for 10 hours. The reaction mixture was diluted with $H_2O$ 50 mL and extracted with DCM 90 mL (30 mL×3). The combined organic layers were washed with brine 60 mL (60 mL×1), dried over $Na_2SO_4$, filtered and concentrated under reduced pressure to give compound 30.5 (8.90 g, crude) as a yellow oil. LCMS (ESI): m/z: [M+H] calcd for $C_{17}H_{25}NO_5S$: 356; found 300; RT=0.890 min.

To a mixture of compound 30.5 (8.84 g, 24.87 mmol, 1 eq) and compound 30.4 (3.01 g, 27.36 mmol, 1.10 eq) in DMF (100 mL) was added NaH (895.44 mg, 37.31 mmol, 1.50 eq) portionwise at 80° C. under $N_2$. The mixture was stirred at 80° C. for 10 hours. The reaction mixture was quenched by addition $H_2O$ 1000 mL, and then extracted with EtOAc 240 mL (80 mL×3). The combined organic layers were washed with brine 150 mL (150 mL×1), dried over $Na_2SO_4$, filtered and concentrated under reduced pressure to give a residue. The residue was purified by column chromatography (SiO₂, DCM/MeOH=10:1) to give compound 30.3 (4.50 g, 15.34 mmol, 61.68% yield) as a white solid. LCMS (ESI): m/z: [M+H] calcd for $C_{15}H_{23}N_3O_3$: 294; found 294; RT=0.692 min.

To a mixture of compound 30.3 (1 g, 3.41 mmol, 1 eq) in DMF (15 mL) was added NBS (606.69 mg, 3.41 mmol, 1 eq) in one portion at 18° C. under $N_2$. The mixture was stirred at 18° C. for 3 hours. The reaction mixture was quenched by addition $H_2O$ 15 mL and extracted with EtOAc 30 mL (10 mL×3). The combined organic layers were washed with brine 10 mL (10 mL×1), dried over $Na_2SO_4$, filtered and concentrated under reduced pressure to give a residue. The residue was purified by column chromatography (SiO₂, Ethyl acetate) to give compound 30.2 (1 g, 2.69 mmol, 78.78% yield) as a colorless oil. LCMS (ESI): m/z: [M+H] calcd for $C_{15}H_{22}BrN_3O_3$: 372; found 372, 374; RT=0.763 min.

Compound 30.2 (100 mg, 268.63 µmol, 1 eq) was added into a solution of HCl/MeOH (5 mL). The mixture was stirred at 18° C. for 10 hours. The reaction mixture was concentrated under reduced pressure to give compound 30.1 (120 mg, 440.95 µmol, 164.15% yield) as a white solid. LCMS (ESI): m/z: [M+H] calcd for $C_{10}H_{14}N_3OBr$: 272; found 272,274; RT=0.096 min.

To a mixture of compound 30.1 (100 mg, 367.46 µmol, 1 eq) and DIPEA (189.96 mg, 1.47 mmol, 256.70 µL, 4 eq) in DMF (3 mL) was added CNBr (42.81 mg, 404.20 µmol, 29.73 µL, 1.10 eq) in one portion at 0° C. under $N_2$. The mixture was stirred at 0° C. for 10 min. The residue was purified by prep-HPLC (TFA condition) to give product 30 (20 mg, 67.31 mol, 18.32% yield) as a yellow solid. LCMS (ESI): m/z: [M+H] calcd for $C_{11}H_{13}N_4O$: 297; found 297, 299; RT=2.364 min.

Example 31. Preparation of (2S)-2-(2-(2-aminopyridin-4-yl)-1-hydroxyethyl)pyrrolidine-1-carbonitrile (31)

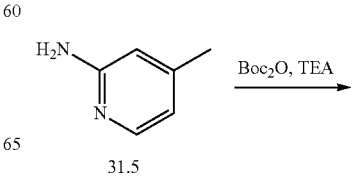

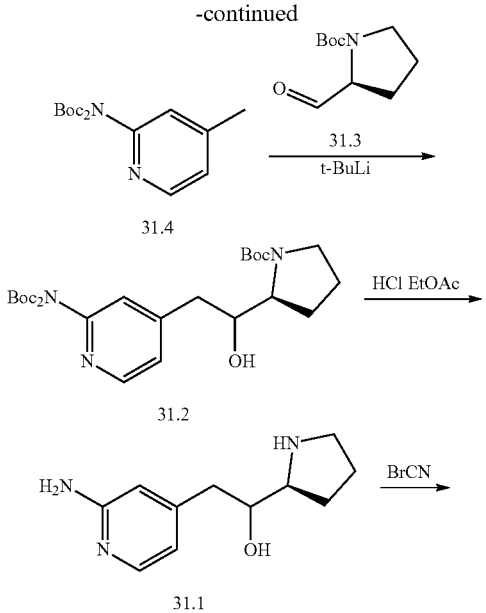

To a solution of compound 31.5 (1 g, 9.25 mmol, 1 eq) in THF (50 mL) was added Boc$_2$O (6.06 g, 27.75 mmol, 6.38 mL, 3 eq), TEA (3.74 g, 37 mmol, 5.13 mL, 4 eq) and DMAP (339.02 mg, 2.77 mmol, 0.30 eq) at 25° C. under N$_2$. The resulting mixture was stirred at 25° C. for 16 hours. The reaction mixture was added water (30 mL), extracted with EtOAc (50 mL×3). The organic phase was separated, washed with saturated NaCl (20 mL) and dried over Na$_2$SO$_4$, filtered and concentrated under reduced pressure to give a residue. The residue was purified by column chromatography (SiO$_2$, Petroleum ether/Ethyl acetate=10:1 to 1:1). Compound 31.4 (1.50 g, 4.86 mmol, 52.59% yield) was obtained as a yellow solid.

To a solution of compound 31.4 (1.50 g, 4.86 mmol, 1 eq) in THF (20 mL) was added t-BuLi (1.3 M, 7.48 mL, 2 eq) drop-wise at −78° C. under N$_2$. During which the temperature was maintained below −78° C. The reaction mixture was stirred at −78° C. for 1 h. Then compound 31.3 (969.21 mg, 4.86 mmol, 1 eq) was added to above mixture. The resulting mixture was stirred at 25° C. for 16 hours. The reaction mixture was added water (10 mL), extracted with EtOAc (20 mL×3). The organic phase was separated, washed with saturated NaCl (10 mL) and dried over Na$_2$SO$_4$, filtered and concentrated under reduced pressure to give a residue. The residue was purified by column chromatography (SiO$_2$, Petroleum ether/Ethyl acetate=10:1 to 1:1). Compound 31.2 (500 mg, 984.99 μmol, 20.27% yield) was obtained as a yellow oil.

To a solution of compound 31.2 (500 mg, 984.99 μmol, 1 eq) in HCl/EtOAc (10 mL) was stirred at 25° C. for 16 hours. The reaction mixture was concentrated under reduced pressure to give a residue. Compound 31.1 (400 mg, crude) was obtained as a yellow oil.

To a solution of compound 31.1 (400 mg, 1.43 mmol, 1 eq, 2HCl) in DMF (5 mL) was added DIEA (553.51 mg, 4.28 mmol, 747.99 μL, 3 eq) and BrCN (151.21 mg, 1.43 mmol, 105.01 μL, 1 eq) at 25° C. under N$_2$. The resulting mixture was stirred at 25° C. for 2 hours. The reaction mixture was added water (10 mL), extracted with EtOAc (10 mL×3). The organic phase was separated, washed with saturated NaCl (10 mL) and dried over Na$_2$SO$_4$, filtered and concentrated under reduced pressure to give a residue. The residue was purified by prep-HPLC (neutral condition). Product 30 (15 mg, 64.58 μmol, 4.52% yield) was obtained as a white solid. LCMS (ESI): m/z: [M+H] calcd for C$_{12}$H$_{16}$N$_4$O$_2$:232; found 233; RT=2.141, 2.394 min. $^1$H NMR (400 MHz, methanol-d4) δ ppm 1.70-2.12 (m, 4H) 2.58-2.60 (m, 1H) 2.91-2.98 (m, 1H) 3.46-3.99 (m, 2H) 4.13-4.16 (m, 1H) 5.12-5.14 (m, 1H) 6.48-6.58 (m, 2H) 7.78-7.82 (m, 1H)

Example 32. Preparation of (S,E)-2-(2-(2-amino-pyridin-4-yl)vinyl)pyrrolidine-1-carbonitrile (32)

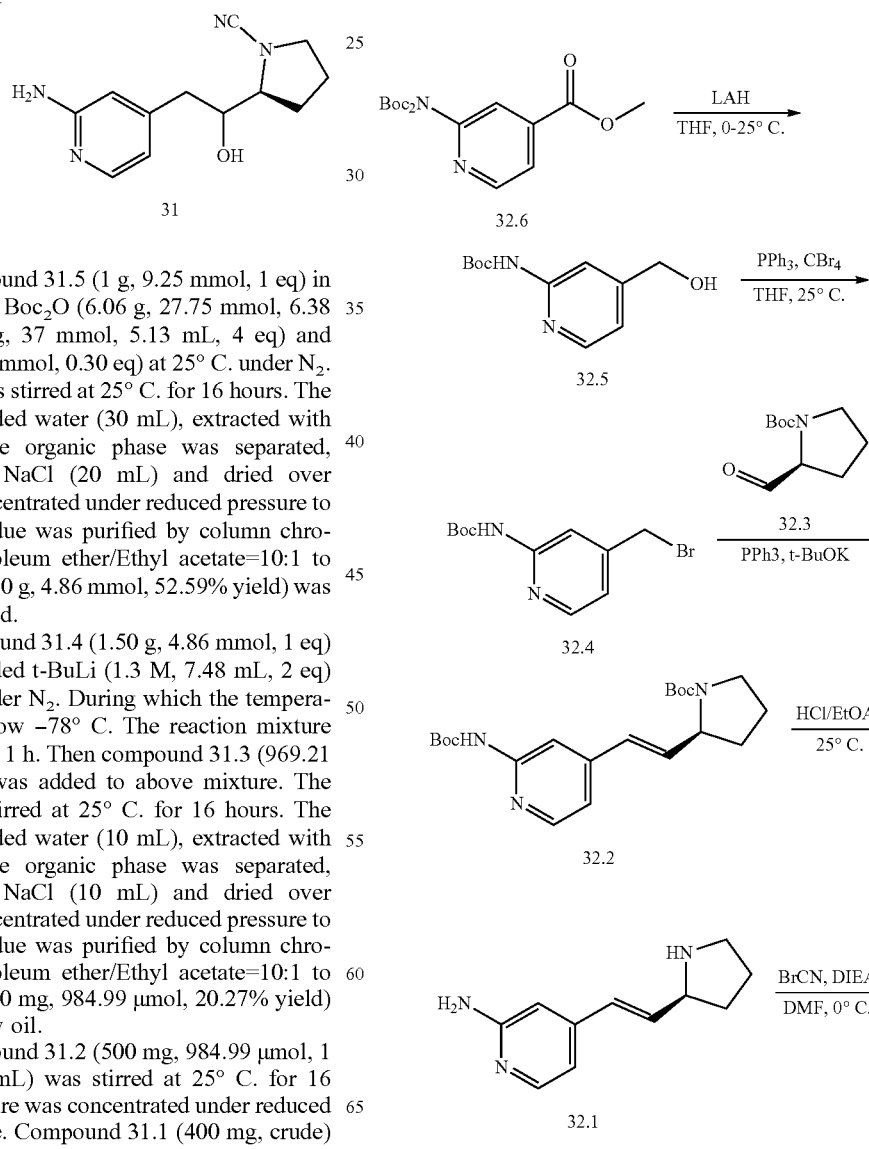

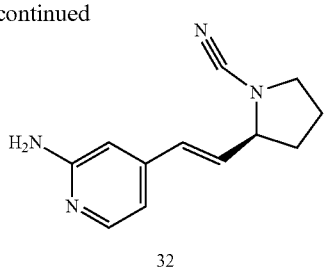

32

To a solution of compound 32.6 (5 g, 14.19 mmol, 1 eq) in THF (50 mL) was added LAH (1.35 g, 35.48 mmol, 2.50 eq) at 0° C. and stirred for 1 hour. The mixture was warmed to 25° C. gradually and stirred for 11 hr. The reaction mixture was quenched by addition 8% NaOH solution 2 mL at 25° C., and then diluted with H$_2$O 20 mL and extracted with EtOAc 60 mL (20 mL×3). The combined organic layers were washed with brines 20 mL (20 mL×1), dried over Na$_2$SO$_4$, filtered and concentrated under reduced pressure to give a residue. The residue was purified by column chromatography (SiO$_2$, Petroleum ether/Ethyl acetate=1:1) to give compound 32.5 (1.50 g, 6.69 mmol, 47.14% yield) as a white solid. LCMS (ESI): m/z: [M+H] calcd for C$_{11}$H$_{16}$N$_2$O$_3$: 224; found 225; RT=0.404 min.

To a solution of compound 32.5 (1.50 g, 6.69 mmol, 1 eq) in THF (15 mL) was added CBr$_4$ (3.33 g, 10.03 mmol, 1.50 eq) and PPh$_3$ (2.63 g, 10.03 mmol, 1.50 eq). The mixture was stirred at 25° C. for 2 hours. The reaction mixture was diluted with H$_2$O 20 mL and extracted with EtOAc 45 mL (15 mL×3). The combined organic layers were washed with brine 20 mL (20 mL×1), dried over Na$_2$SO$_4$, filtered and concentrated under reduced pressure to give a residue. The residue was purified by column chromatography (SiO$_2$, Petroleum ether/Ethyl acetate=3:1) to give compound 32.4 (1.10 g, 3.83 mmol, 57.26% yield) as a white solid. 1H NMR (400 MHz, chloroform-d) δ ppm 1.54 (s, 9H) 4.36 (s, 2H) 6.97 (dd, J=5.29, 1.54 Hz, 1H) 7.94-8.08 (m, 1H) 8.29 (d, J=5.29 Hz, 1H) 9.23 (s, 1H)

To a solution of compound 32.4 (400 mg, 1.39 mmol, 1 eq) in toluene (7 mL) was added PPh$_3$ (401.04 mg, 1.53 mmol, 1.10 eq) under nitrogen and reflux 120° C. for 3 hours. After cooling to 25° C., the white solid was filtered off, washed with EtOAc and dried under vacuum. Then the mixture was stirred in THF (4 mL) under nitrogen and t-BuOK (171.57 mg, 1.53 mmol, 1.10 eq) was added. The mixture was stirred at 70° C. for 1 hr. After cooling to 25° C., compound 32.3 (415.44 mg, 2.09 mmol, 1.50 eq) in THF (1 mL) was added to the reaction flask and reflux for 30 min. The reaction mixture was diluted with H$_2$O 15 mL and extracted with EtOAc 45 mL (15 mL×3). The combined organic layers were washed with brine 15 mL (15 mL×1), dried over Na$_2$SO$_4$, filtered and concentrated under reduced pressure to give a residue. The residue was purified by prep-TLC (SiO$_2$, Petroleum ether/Ethyl acetate=1:1) to give compound 32.2 (200 mg, 513.49 μmol, 36.94% yield) as a brown oil. LCMS (ESI): m/z: [M+H] calcd for C$_{21}$H$_{31}$N$_3$O$_4$: 389; found 390; RT=1.508 min.

To a solution of compound 32.2 (180 mg, 462.14 μmol, 1 eq) in HCl/EtOAc (5 mL) was stirred at 25° C. for 12 hours. The reaction mixture was concentrated under reduced pressure to remove solvent to give compound 32.1 (150 mg, crude) as a brown oil. LCMS (ESI): m/z: [M+H] calcd for C$_{11}$H$_{15}$N$_3$: 189; found 190; RT=0.382 min.

To a solution of compound 32.1 (150 mg, 792.56 μmol, 1 eq) in DMF (2 mL) was added DIEA (409.72 mg, 3.17 mmol, 553.68 μL, 4 eq) at 0° C. When the pH>9, the mixture was added BrCN (83.95 mg, 792.56 μmol, 58.30 μL, 1 eq) and stirred at 0° C. for 10 min. The residue was purified by prep-HPLC (column: YMC-Actus Triart C18 150×30 5u; mobile phase: [water (10 mM NH4HCO3)-ACN]; B %: 10%-30%, 12 min) to give product 32 (5 mg, 23.34 μmol, 2.94% yield) as a brown oil. LCMS (ESI): m/z: [M+H] calcd for C$_{12}$H$_{14}$N$_4$: 214; found 215; RT=2.160 min. 1H NMR (400 MHz, methanol-d4) δ ppm 1.63-1.74 (m, 1H) 1.78-2 (m, 3H) 2.03-2.15 (m, 1H) 3.33-3.54 (m, 2H) 4.16 (q, J=7.01 Hz, 1H) 6.22-6.30 (m, 1H) 6.42 (s, 1H) 6.45-6.49 (m, 1H) 6.62 (d, J=4.52 Hz, 1H) 7.65-7.82 (m, 1H).

Example 33. Preparation of 4-(2-aminopyridin-4-yl)piperazine-1-carbonitrile (33)

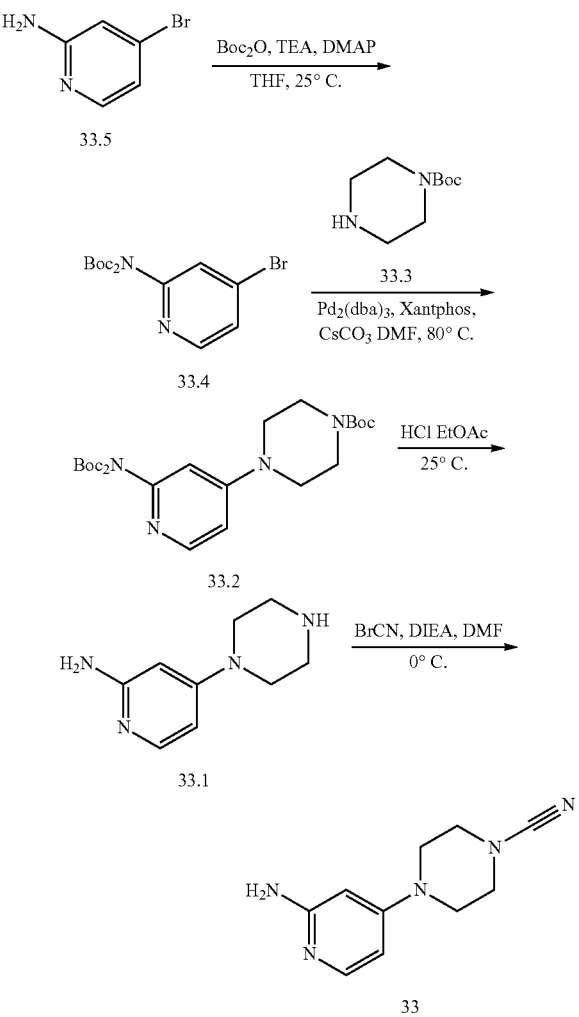

To a solution of compound 33.5 (1 g, 5.78 mmol, 1 eq) in THF (20 mL) was added Boc$_2$O (3.15 g, 14.45 mmol, 3.32 mL, 2.50 eq), TEA (2.34 g, 23.12 mmol, 3.21 mL, 4 eq) and DMAP (211.84 mg, 1.73 mmol, 0.30 eq) at 25° C. under N$_2$. The result mixture was stirred at 25° C. for 16 hours. The reaction mixture was added water (20 mL), extracted with EtOAc (20 mL×3). The organic phase was separated, washed with saturated NaCl (10 mL) and dried over Na₂SO₄, filtered and concentrated under reduced pressure to give a residue. The residue was purified by column chromatography (SiO2, Petroleum ether/Ethyl acetate=10:1 to 1:1). Compound 33.4 (1 g, 2.68 mmol, 46.35% yield) was obtained as a yellow solid.

To a solution of compound 33.4 (1 g, 2.68 mmol, 1 eq) in DMF (10 mL) was added compound 33.3 (499.01 mg, 2.68 mmol, 1 eq) Pd₂(dba)₃ (245.34 mg, 267.92 μmol, 0.10 eq) and Cs2CO3 (2.62 g, 8.04 mmol, 3 eq) at 25° C. under N₂. The result mixture was stirred at 80° C. for 16 hours. The reaction mixture was added water (10 mL), extracted with EtOAc (10 mL×3). The organic phase was separated, washed with saturated NaCl (10 mL) and dried over Na₂SO₄, filtered and concentrated under reduced pressure to give a residue. Compound 33.2 (500 mg, 1.04 mmol, 38.98% yield) was obtained as a white solid. LCMS (ESI): m/z: [M+H] called for C₂₄H₃₈N₄O₆: 479; found 479; RT=0.771 min.

To a solution of compound 33.2 (500 mg, 1.04 mmol, 1 eq) in HCl/EtOAc (5 mL) was stirred at 25° C. for 16 hours. The reaction mixture was concentrated under reduced pressure to give a residue. Compound 33.1 (100 mg, 561.07 μmol, 53.95% yield) was obtained as a white solid.

To a solution of compound 33.1 (100 mg, 398.15 μmol, 1 eq, 2HCl) in DMF (3 mL) was added DIEA (205.83 mg, 1.59 mmol, 278.15 μL, 4 eq) and BrCN (42.17 mg, 398.15 mol, 29.28 μL, 1 eq). The mixture was stirred at 0° C. for 10 min. The residue was purified by prep-HPLC (neutral condition). Product 33 (2 mg, 9.84 μmol, 2.47% yield) was obtained as a yellow solid. ¹H NMR (400 MHz, methanol-d4) δ ppm 3.33-3.38 (m, 4H) 3.40-3.46 (m, 4H) 6 (s, 1H) 6.22-6.32 (m, 1H) 7.62 (d, J=6.39 Hz, 1H). LCMS (ESI): m/z: [M+H] called for C₁₀H₁₃N₅: 204; found 204; RT=1.133 min.

Example 34. Preparation of N-(1-((2-aminopyridin-4-yl)oxy)-3-methylbutan-2-yl)-N-methylcyanamide (34)

To a solution of compound 34.8 (1 g, 9.69 mmol, 1.06 mL, 1 eq) in THF (15 mL) was added IMIDAZOLE (2.64 g, 38.76 mmol, 4 eq) and TBDPSCl (5.33 g, 19.38 mmol, 4.98 mL, 2 eq). The mixture was stirred at 25° C. for 14 hours. The reaction mixture was quenched by addition H₂O 50 mL at 25° C., and extracted with EtOAc (50 mL×3). The combined

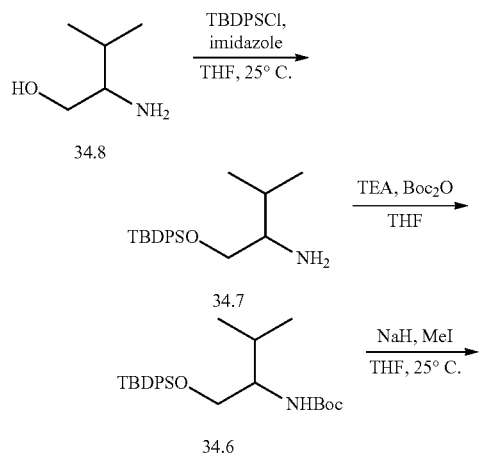

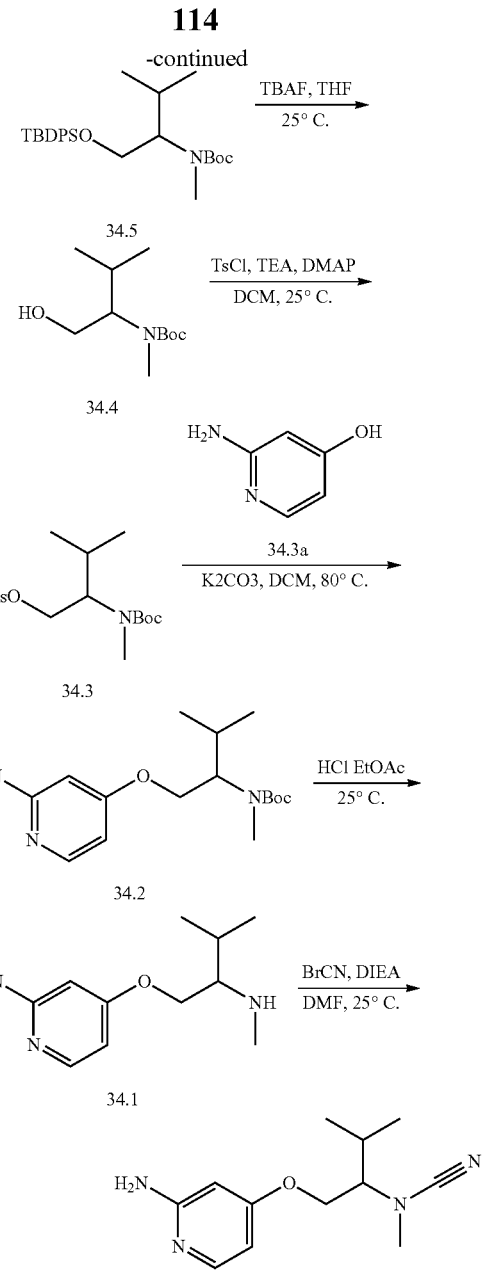

organic layers were washed with saturated brine (25 mL×1), dried over anhydrous sodium sulfate, filtered and concentrated under reduced pressure to give a residue. Compound 34.7 (4 g, crude) was obtained as a yellow oil, and the crude product was used into the next step without further purification.

To a solution of compound 34.7 (4 g, 11.71 mmol, 1 eq) in THF (30 mL) was added TEA (4.74 g, 46.84 mmol, 6.49 mL, 4 eq) and Boc₂O (3.83 g, 17.57 mmol, 4.04 mL, 1.50 eq). The mixture was stirred at 25° C. for 14 hours. The reaction mixture was quenched by addition H₂O 50 mL at 25° C., and extracted with ethyl acetate (50 mL×3). The combined organic layers were washed with saturated brine (25 mL×1), dried over anhydrous sodium sulfate, filtered and concentrated under reduced pressure to give a residue. The residue was purified by column chromatography (SiO2, Petroleum ether/Ethyl acetate=5/1). Compound 34.6 (3 g, 6.79 mmol, 93.69% yield) was obtained as a colorless oil.

To a solution of compound 34.6 (1 g, 2.26 mmol, 1 eq) in THF (20 mL) was added NaH (108.48 mg, 4.52 mmol, 2 eq) the mixture was stirred at 25° C. for 1 hr. Then to the mixture was added MeI (384.94 mg, 2.71 mmol, 168.83 μL, 1.20 eq). The mixture was stirred at 0° C. for 12 hours. The reaction mixture was quenched by addition H₂O 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography (SiO₂, Petroleum ether/Ethyl acetate=2:1). Compound 34.5 (600 mg, 1.32 mmol, 58.41% yield) was obtained as a yellow oil.

To a solution of compound 34.5 (600 mg, 1.32 mmol, 1 eq) in THF (15 mL) was added TBAF (345.13 mg, 1.32 mmol, 1 eq) the mixture was stirred at 25° C. for 2 hours. The reaction mixture was quenched by addition H₂O 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography (SiO₂, Petroleum ether/Ethyl acetate=2:1). Compound 34.4 (250 mg, 1.15 mmol, 87.16% yield) was obtained as a yellow oil.

To a solution of compound 34.4 (250 mg, 1.15 mmol, 1 eq) in DCM (5 mL) was added TEA (349.11 mg, 3.45 mmol, 478.23 μL, 3 eq) and DMAP (28.10 mg, 230 μmol, 0.20 eq) and TosCl (263.10 mg, 1.38 mmol, 1.20 eq). The mixture was stirred at 25° C. for 2 hours. The reaction mixture was quenched by addition H₂O 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. Compound 34.3 (500 mg, crude) was obtained as a yellow oil.

To a solution of compound 34.3 (400 mg, 1.08 mmol, 1 eq) and compound 34.3a (118.56 mg, 1.08 mmol, 1 eq) in DMF (10 mL) was added K₂CO₃ (595.27 mg, 4.31 mmol, 4 eq). The mixture was stirred at 80° C. for 13 hours. The reaction mixture was quenched by addition H₂O 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography (SiO₂, DCM:MeOH=10:1). Compound 34.2 (200 mg, 646.41 μmol, 60.03% yield) was obtained as a yellow oil. LCMS (ESI): m/z: [M+H] called for $C_{16}H_{27}N_3O_3$: 310; found 310; RT=0.591 min.

A mixture of compound 34.2 (200 mg, 646.41 μmol, 1 eq) in HCl/EtOAc (15 mL) was stirred at 25° C. for 13 hours. The mixture was concentrated under reduced pressure to give a residue. Compound 34.1 (170 mg, 602.39 μmol, 93.19% yield, 2HCl) was obtained as a yellow solid. LCMS (ESI): m/z: [M+H] called for $C_{11}H_{19}N_3O$: 210; found 210; RT=0.098 min.

To a solution of compound 34.1 (170 mg, 602.39 μmol, 1 eq, 2HCl) in DMF (2 mL) was added DIEA (311.41 mg, 2.41 mmol, 420.83 μL, 4 eq) and BrCN (63.80 mg, 602.39 mol, 44.31 μL, 1 eq). The mixture was stirred at 0° C. for 10 min. The residue was purified by prep-HPLC (neutral condition). Product 34 (40 mg, 170.72 μmol, 28.34% yield) was obtained as a yellow oil. ¹H NMR (400 MHz, methanol-d₄) δ ppm 0.96-1.17 (m, 6H) 1.87-2.19 (m, 1H) 2.88-3.07 (m, 4H) 4.02-4.35 (m, 2H) 6.14 (d, J=1.76 Hz, 1H) 6.30 (dd, J=6.06, 1.87 Hz, 1H) 7.73 (d, J=5.95 Hz, 1H). LCMS (ESI): m/z: [M+H] called for $C_{12}H_{18}N_4O$: 235; found 235; RT=2.295 min.

Example 35. Preparation of N-(1-((2-aminopyridin-4-yl)oxy)butan-2-yl)-N-methylcyanamide (35)

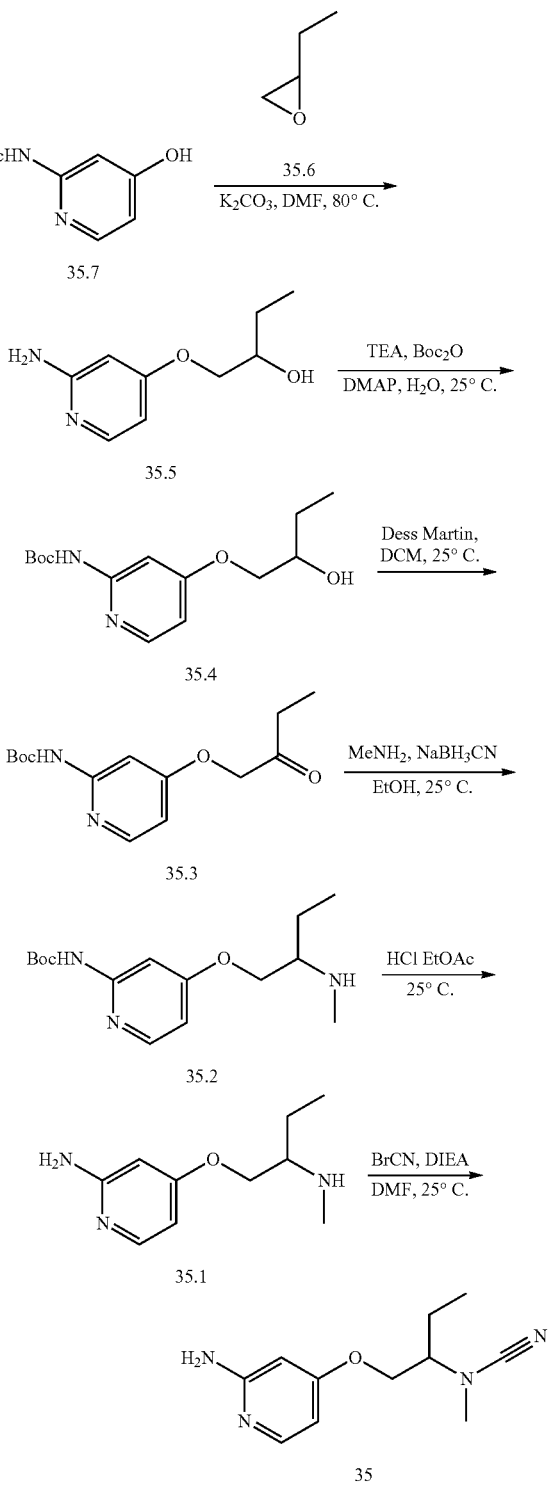

To a solution of compound 35.7 (1 g, 4.76 mmol, 1 eq) and compound 35.6 (342.98 mg, 4.76 mmol, 413.23 µL, 1 eq) in DMF (25 mL) was added $K_2CO_3$ (1.97 g, 14.27 mmol, 3 eq). The mixture was stirred at 80° C. for 14 hours. The reaction mixture was quenched by addition $H_2O$ 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. Compound 35.5 (2.5 g, crude) was obtained as a yellow oil. It was used into the next step without further purification.

To a solution of compound 35.5 (2 g, 3.29 mmol, 1 eq) in THF (20 mL) and $H_2O$ (30 mL) was added TEA (1.67 g, 16.46 mmol, 2.28 mL, 5 eq) and $Boc_2O$ (2.16 g, 9.88 mmol, 2.27 mL, 3 eq) and DMAP (120.68 mg, 987.82 µmol, 0.30 eq). The mixture was stirred at 25° C. for 15 hours. The reaction mixture was quenched by addition $H_2O$ 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography ($SiO_2$, Petroleum ether/Ethyl acetate=1:1). Compound 35.4 (230 mg, 814.65 mol, 24.74% yield) was obtained as a yellow oil. LCMS (ESI): m/z: [M+H] called for $C_{14}H_{22}N_4O_2$: 283; found 283; RT=0.654 min.

To a solution of compound 35.4 (230 mg, 814.65 µmol, 1 eq) in DCM (5 mL) was added Dess-Martin periodinane (691.05 mg, 1.63 mmol, 504.42 µL, 2 eq) mixture was stirred at 25° C. for 14 hours. The reaction mixture was quenched by addition $H_2O$ 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography ($SiO_2$, Petroleum ether/Ethyl acetate=2:1). Compound 35.3 (225 mg, 802.65 µmol, 98.53% yield) was obtained as a yellow oil. $^1$H NMR (400 MHz, chloroform-d) δ ppm 1.13 (t, J=7.28 Hz, 3H) 1.48-1.59 (m, 1H) 1.48-1.59 (m, 10H) 2.63 (q, J=7.28 Hz, 2H) 4.65 (s, 2H) 6.53 (dd, J=5.73, 2.43 Hz, 1H) 7.58 (d, J=1.98 Hz, 1H) 8.07-8.22 (m, 1H). LCMS (ESI): m/z: [M+H] called for $C_{14}H_{20}N_4O_2$: 281; found 281; RT=0.615 min.

A mixture of compound 35.3 (100 mg, 356.74 µmol, 1 eq) in $MeNH_2$ (2 mL) was stirred at 0° C. for 1 hr. To the mixture was added HOAc (32.13 mg, 535.10 µmol, 30.60 µL, 1.50 eq) make the mixture to pH=4 and then added $NaBH_3CN$ (89.67 mg, 1.43 mmol, 4 eq). The mixture was stirred at 25° C. for 12 hours. The reaction mixture was quenched by addition saturated $NaHCO_3$ 20 mL at 25° C. make the pH>7 and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography ($SiO_2$, DCM:MeOH=10:1). Compound 35.2 (80 mg, 270.84 µmol, 75.92% yield) was obtained as a yellow oil. It was combined with a second batch for a total of 160 mg. LCMS (ESI): m/z: [M+H] called for $C_{15}H_{25}N_3O_3$: 296; found 296; RT=0.520 min.

A mixture of compound 35.2 (160 mg, 541.68 µmol, 1 eq) in HCl/EtOAc (5 mL) was stirred at 25° C. for 13 hours. The mixture was concentrated under reduced pressure to give a residue. Compound 35.1 (140 mg, 522.04 µmol, 96.38% yield, 2HCl) was obtained as a yellow oil.

To a solution of compound 35.1 (140 mg, 522.04 µmol, 1 eq, 2HCl) in DMF (2 mL) was added DIEA (269.87 mg, 2.09 mmol, 364.69 µL, 4 eq) and BrCN (55.29 mg, 522.04 mol, 38.40 µL, 1 eq). The mixture was stirred at 0° C. for 10 min. The residue was purified by prep-HPLC (neutral condition). Product 35 (40 mg, 181.60 µmol, 34.79% yield) was obtained as a yellow oil. $^1$H NMR (400 MHz, methanol-$d_4$) δ ppm 1.07 (t, J=7.39 Hz, 3H) 1.60-1.82 (m, 2H) 2.98 (s, 3H) 3.15-3.30 (m, 1H) 3.97-4.19 (m, 2H) 6.13 (d, J=2.21 Hz, 1H) 6.28 (dd, J=6.17, 2.20 Hz, 1H) 7.73 (d, J=6.17 Hz, 1H). LCMS (ESI): m/z: [M+H] called for $C_{11}H_{16}N_4O$: 221; found 221; RT=2.115 min.

Example 36. Preparation of N-(2-((2-aminopyridin-4-yl)oxy)-1-phenylethyl)-N-methylcyanamide (36)

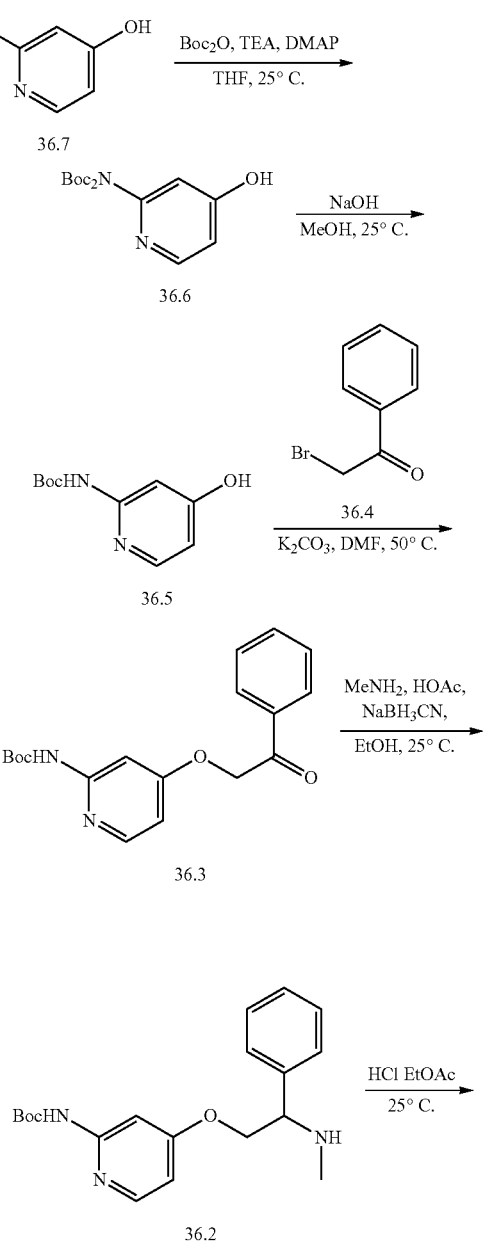

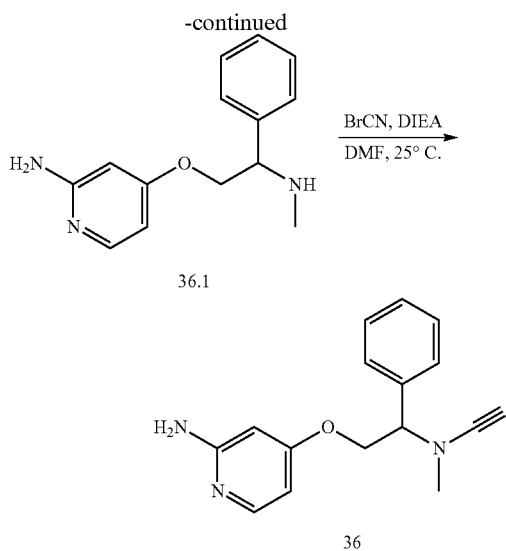

The solution of 36.7 (5 g, 45.41 mmol, 1 eq) in THF (50 mL) was added triethyl amine (18.38 g, 181.64 mmol, 25.18 mL, 4 eq) and Boc₂O (29.73 g, 136.23 mmol, 31.29 mL, 3 eq) and DMAP (1.66 g, 13.62 mmol, 0.30 eq). The mixture was stirred at 25° C. for 16 hours. The rethyl acetatection mixture was quenched by addition H$_2$O 50 mL at 25° C., and extracted with ethyl acetate (50 mL×3). The combined organic layers were washed with saturated brine (25 mL×1), dried over anhydrous sodium sulfate, filtered and concentrated under reduced pressure to give a residue. The crude product compound 36.6 (4 g, 9.75 mmol,) was used into the next step without further purification. LCMS (ESI): m/z: [M+H] calcd for C$_{20}$H$_{30}$N$_2$O$_7$: 311; found 411; RT=0.941 min.

To a solution of compound 36.6 (3 g, 9.67 mmol, 1 eq) in MeOH (40 mL) and H$_2$O (4 mL) was added NaOH (966.65 mg, 24.17 mmol, 2.50 eq). The mixture was stirred at 25° C. for 16 hours. The rethyl acetatection mixture was quenched by addition H$_2$O 25 mL at 25° C., and extracted with ethyl acetate (25 mL×3). The combined organic layers were washed with saturated brine (25 mL×1), dried over anhydrous sodium sulfate, filtered and concentrated under reduced pressure to give a residue. The residue was purified by column chromatography (SiO$_2$, Petroleum ether/Ethyl acetate=4/1) to give a compound 36.5 (1.50 g, 7.14 mmol, 73.79% yield) as a white solid. LCMS (ESI): m/z: [M+H] calcd for C$_{10}$H$_{14}$O$_3$N$_2$: 211; found 211; RT=0.352 min.

To a solution of compound 36.5 (500 mg, 2.38 mmol, 1 eq) in DMF (30 mL) was added K$_2$CO$_3$ (986.82 mg, 7.14 mmol, 3 eq) and compound 36.4 (570 mg, 2.86 mmol, 1.2 eq). The mixture was stirred at 25° C. for 14 hours. The reaction mixture was quenched by addition H$_2$O 20 mL at 25° C., and extracted with ethyl acetate (20 mL×3). The combined organic layers were washed with saturated brine (20 mL×1), dried over anhydrous sodium sulfate, filtered and concentrated under reduced pressure to give a compound 36.3 (260 mg, 791.81 μmol, crude) as a white solid, and the crude product was without further purification. LCMS (ESI): m/z: [M+H] calcd for C$_{18}$H$_{20}$O$_4$N$_2$: 329; found 329; RT=0.701 min.

To a solution of compound 36.3 (200 mg, 609.09 μmol, 1 eq) in NH$_2$CH$_3$ (2 mL) was added HOAc (54.86 mg, 913.63 μmol, 52.25 μL, 1.50 eq) and NaBH$_3$CN (153.10 mg, 2.44 mmol, 4 eq). The mixture was stirred at 25° C. for 14 hours. The rethyl acetatection mixture was quenched by addition H$_2$O 50 mL at 25° C., and extracted with ethyl acetate (50 mL×3). The combined organic layers were washed with saturated brine (25 mL×1), dried over anhydrous sodium sulfate, filtered and concentrated under reduced pressure to give a residue. The residue was purified by column chromatography (SiO$_2$, Petroleum ether/Ethyl acetate=2/1) to give a compound 36.2 (80 mg, 232.95 μmol, 38.25% yield) as a white solid. $^1$H NMR (400 MHz, chloroform-d) δ ppm 1.50 (s, 9H) 2.35 (s, 3H) 3.95-4.06 (m, 2H) 4.07-4.14 (m, 1H) 6.49 (dd, J=5.70, 2.19 Hz, 1H) 7.28-7.33 (m, 1H) 7.34-7.44 (m, 4H) 7.50 (d, J=1.75 Hz, 1H) 8.03 (d, J=5.70 Hz, 1H). LCMS (ESI): m/z: [M+H] calcd for C$_{19}$H$_{25}$O$_3$N$_3$: 343; found 343; RT=0.587 min.

To a solution of compound 36.2 (80 mg, 232.95 μmol, 1 eq) in HCl/EtOAc (15 mL). The mixture was stirred at 25° C. for 14 hours. The rethyl acetatection mixture was filtered and concentrated under to give the compound 36.1 (50 mg, 205.51 μmol, 88.22% yield) as a white solid. LCMS (ESI): m/z: [M+H] calcd for C$_{14}$H$_{17}$N$_3$O: 244; found 244; RT=0.104 min.

To a solution of compound 36.1 (50 mg, 308.26 μmol, 1 eq) in DMF (5 mL) was added BrCN (32.65 mg, 308.26 μmol, 22.67 μL, 1 eq) and DIETHYL ACETATE (159.36 mg, 1.23 mmol, 215.35 μL, 4 eq). The mixture was stirred at 0° C. for 0.5 hour. The residue was purified by prep-HPLC (neutral condition) to give product 36 (25 mg, 93.18 μmol, 45.34% yield) as a white solid. $^1$H NMR (400 MHz, chloroform-d) δ ppm 1.57 (s, 9H) 2.87 (s, 3H) 4.14-4.33 (m, 2H) 4.33-4.55 (m, 3H) 5.99 (d, J=1.98 Hz, 2H) 6.27 (dd, J=5.95, 2.20 Hz, 1H) 7.36-7.53 (m, 5H) 7.90 (d, J=5.95 Hz, 2H). LCMS (ESI): m/z: [M+H] calcd for C$_{15}$H$_{16}$N$_4$O: 269; found 269; RT=2.835 min.

Example 37. Preparation of 2-(1-aminoisoquinolin-6-yl)piperidine-1-carbonitrile (37)

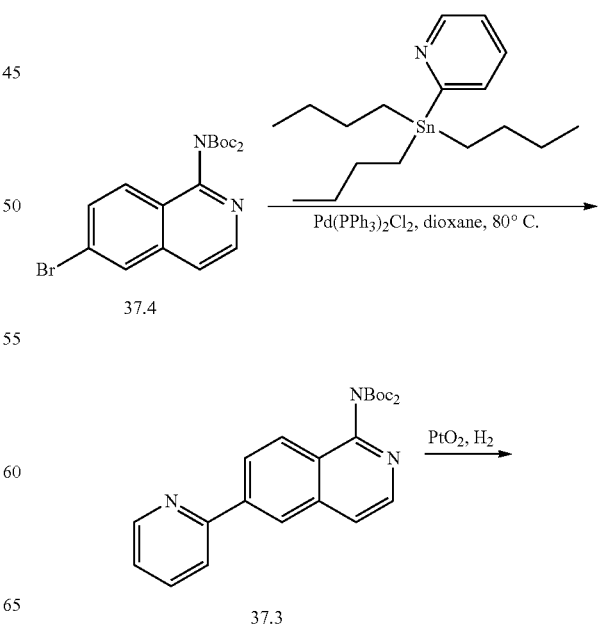

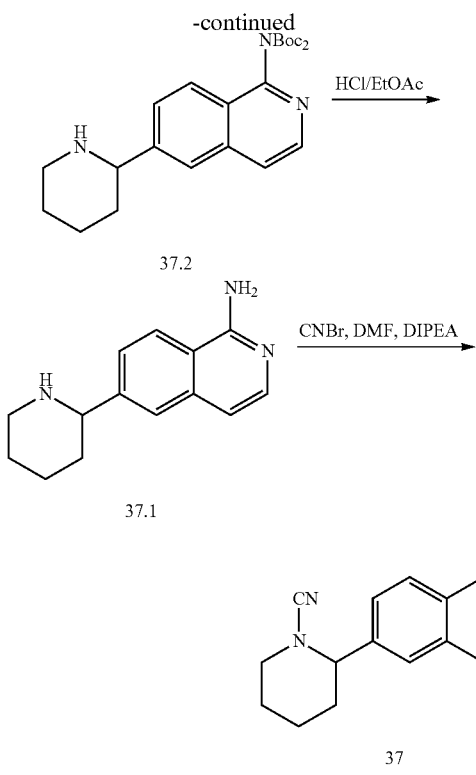

A mixture of compound 37.4 (250 mg, 590.60 µmol, 1 eq), tributyl(2-pyridyl)stannane (434.86 mg, 1.18 mmol, 2 eq), Pd(PPh$_3$)$_2$Cl$_2$ (41.45 mg, 59.06 µmol, 0.10 eq) in dioxane (2 mL) was degassed and purged with N$_2$ for 3 times, and then the mixture was stirred at 80° C. for 10 hour under N$_2$ atmosphere. TLC (PE:EtOAc=2:1, Rf=0.45) showed the reaction was completed. The reaction mixture was quenched by addition H$_2$O 50 mL at 25° C., and extracted with ethyl acetate (50 mL×3). The combined organic layers were washed with saturated brines (10 mL×1), dried over anhydrous sodium sulfate, filtered and concentrated under reduced pressure to give a crude product. The residue was purified by column chromatography (SiO$_2$, Petroleum ether/Ethyl acetate=30/1 to 1:1) to give compound 37.3 (200 mg, 474.51 µmol, 80.34% yield) as a white solid. $^1$H NMR (400 MHz, chloroform-d) δ ppm 1.28-1.40 (m, 19H) 7.31-7.38 (m, 1H) 7.70-7.98 (m, 3H) 8.08 (d, J=8.80 Hz, 1H) 8.29 (dd, J=8.86, 1.16 Hz, 1H) 8.43-8.57 (m, 2H) 8.79 (d, J=4.77 Hz, 1H).

To a solution of compound 37.3 (200 mg, 474.51 µmol, 1 eq) in MeOH (5 mL) was added PtO$_2$ (21.55 mg, 94.90 µmol, 0.20 eq). The mixture was stirred under H$_2$ (50 Psi) at 50° C. for 12 hour. The reaction mixture was concentrated under reduced pressure to give a residue. The residue was purified by column chromatography (SiO$_2$, Petroleum ether/Ethyl acetate=30/1 to 1:1) to give compound 37.2 (150 mg, 350.84 µmol, 73.94% yield) as a white solid. $^1$H NMR (400 MHz, methanol-d$_4$) δ ppm 1.28 (s, 14H) 1.61-1.78 (m, 4H) 1.94-2.04 (m, 2H) 2.87 (br t, J=12.13 Hz, 1H) 3.23 (br d, J=12.79 Hz, 1H) 3.91 (br d, J=10.14 Hz, 1H) 7.79 (br d, J=8.60 Hz, 1H) 7.87 (d, J=5.73 Hz, 1H) 7.94 (d, J=8.60 Hz, 1H) 8 (s, 1H) 8.35 (d, J=5.95 Hz, 1H). LCMS (ESI): m/z: [M+H] calcd for C$_{24}$H$_{33}$N$_3$O$_4$: 428; found 428; RT=0.971 min.

To a solution of compound 37.2 (150 mg, 350.84 µmol, 1 eq) was added HCl/EtOAc (12.81 mg, 350.84 µmol, 2 mL, 1 eq). The mixture was stirred at 25° C. for 3 hours. The reaction mixture was concentrated under reduced pressure to give compound 37.1 (35 mg, 153.98 µmol, 43.89% yield) as a white solid. LCMS (ESI): m/z: [M+H] calcd for C$_{14}$H$_{17}$N$_3$: 228; found 228; RT=0.131 min.

To a solution of compound 37.1 (35 mg, 153.98 µmol, 1 eq) in DMF (1 mL) was added CNBr (16.31 mg, 153.98 µmol, 11.33 µL, 1 eq) and DIPEA (59.70 mg, 461.94 µmol, 80.68 µL, 3 eq). The mixture was stirred at 25° C. for 5 min. The residue was purified by prep-HPLC (TFA condition) to give Product 37 (10 mg, 39.63 µmol, 25.74% yield) as a white solid. $^1$H NMR (400 MHz, DMSO-d$_6$) δ ppm 1.50-1.93 (m, 6H) 3.28 (td, J=11.84, 3.51 Hz, 1H) 3.49-3.57 (m, 1H) 4.27 (dd, J=10.52, 3.07 Hz, 1H) 6.50 (br s, 2H) 6.93 (d, J=5.70 Hz, 1H) 7.48 (dd, J=8.55, 1.53 Hz, 1H) 7.70 (s, 1H) 7.82 (d, J=5.70 Hz, 1H) 8.19 (d, J=8.77 Hz, 1H). LCMS (ESI): m/z: [M+H] calcd for C$_{15}$H$_{16}$N$_4$: 253; found 253; RT=2.505 min.

Example 38. Preparation of 3-((2-aminopyridin-4-yl)thio)pyrrolidine-1-carbonitrile (38)

To a solution of compound 38.2 (90 mg, 181.59 µmol, 1 eq) in HCl/EtOAc (5 mL) at 20° C. under N$_2$. The mixture was stirred at 20° C. for 4 hours. Filtered and concentrated in vacuum to give compound 38.1 (50 mg, 164.11 µmol, 90.37% yield, 3HCl) as a light yellow solid.

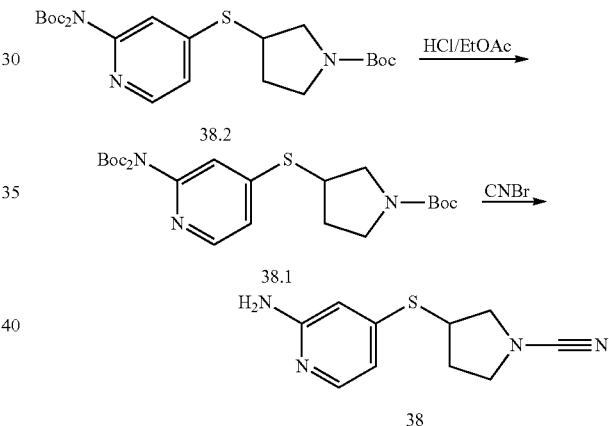

To a mixture of compound 38.1 (50 mg, 256.04 µmol, 1 eq) and carbononitridic bromide (27.12 mg, 256.04 µmol, 18.83 µL, 1 eq) in DMF (1 mL) was added DIEA (132.36 mg, 1.02 mmol, 178.87 µL, 4 eq) in one portion at 0° C. under N$_2$. The mixture was stirred at 0° C. for 10 min. The residue was purified by prep-HPLC (basic condition) to give Product 38 (4.40 mg, 19.97 µmol, 7.80% yield) as a light yellow oil. LCMS (ESI): m/z: [M+H] calcd for C$_{10}$H$_{12}$N$_4$S: 221; found 221; RT=0.943 min. 1H NMR (400 MHz, chloroform-d) δ ppm 1.46 (br s, 5H) 1.90-2 (m, 1H) 2.24-2.36 (m, 1H) 3.32 (dd, J=10.23, 4.71 Hz, 1H) 3.46 (td, J=8.63, 5.33 Hz, 1H) 3.53-3.62 (m, 1H) 3.77 (dd, J=10.29, 6.53 Hz, 1H) 3.86 (quin, J=5.62 Hz, 1H) 4.38 (br s, 2H) 6.28 (d, J=1.13 Hz, 1H) 6.44 (dd, J=5.52, 1.51 Hz, 1H) 7.87 (d, J=5.52 Hz, 1H).

Examples 39 and 40. Preparation of N-(2-((2-aminopyridin-4-yl)oxy)ethyl)-N-isopropylcyanamide (39) and N-(2-((2-aminopyridin-4-yl)oxy)ethyl)-N-cyclohexylcyanamide (40)

To a mixture of compound 39.5 (5 g, 45.41 mmol, 1 eq) and compound 39.4 (10.18 g, 45.41 mmol, 1 eq) in DMF (20 mL) was added NaH (2.18 g, 54.49 mmol, 60% purity, 1.20 eq) in portions at 0° C. under N₂. The mixture was stirred at 15° C. for 15 hours. The reaction was monitored by LCMS. After the reaction was completed, water (120 mL) was added dropwise at 0° C. The aqueous phase was extracted with EtOAc (30 mL×3). The combined organic phase was washed with brine (5 mL), dried with anhydrous Na₂SO₄, filtered and concentrated in vacuum. The residue was purified by column chromatography (SiO₂, Petroleum ether/Ethyl acetate=10:1 to 2:1) to give compound 39.3 (2.80 g, 11.05 mmol, 24.34% yield) was obtained as a white solid. $^1$H NMR (400 MHz, methanol-d4) ppm 1.45 (s, 9H), 3.52 (d, J=5.2 Hz, 2H), 4 (t, J=5.2 Hz, 2H), 4.43 (br, 2H), 5.05 (br, 1H), 5.96 (d, J=1.6 Hz, 1H), 6.25 (dd, J=1.6 Hz, J=6.0 Hz, 1H), 7.90 (d, J=6.0 Hz, 1H). LCMS (ESI): m/z: [M+H] calcd for $C_{12}H_{20}N_3O_3$: 254; found 254; RT=0.585 min.

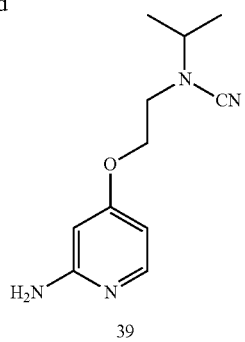

39

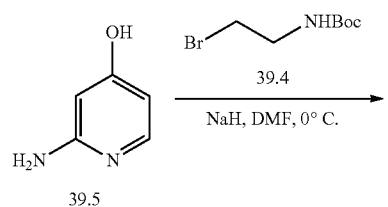

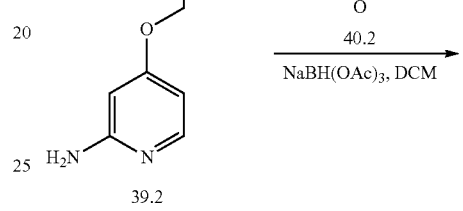

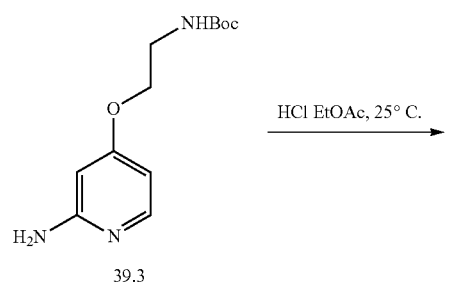

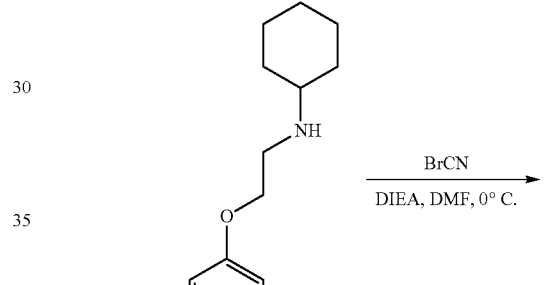

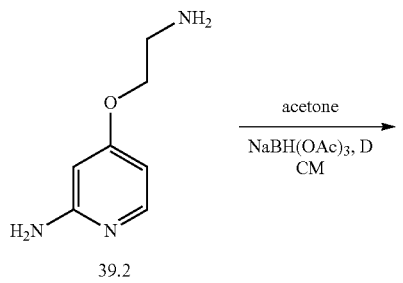

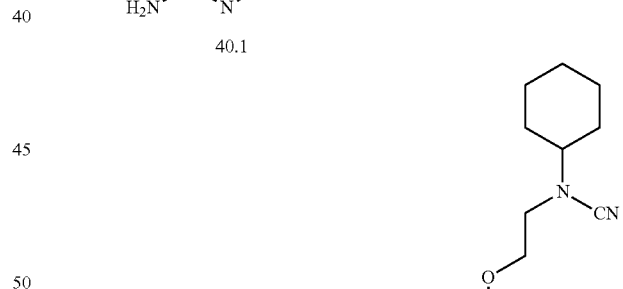

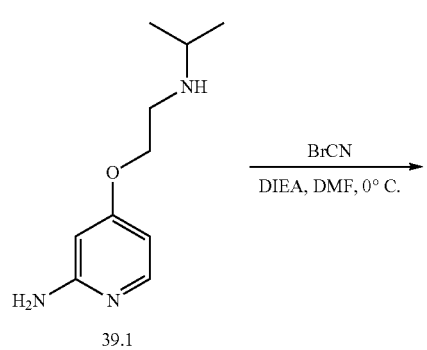

A solution of compound 39.3 (2.80 g, 11.05 mmol, 1 eq) in HCl/MeOH (40 mL) was stirred at 15° C. for 2 hrs under N₂. The mixture was concentrated in vacuum to give compound 39.2 (2.40 g, crude, HCl salt) was obtained as a white solid.

To a mixture of compound 39.2 (400 mg, 2.61 mmol, 1 eq) and acetone (379.16 mg, 6.53 mmol, 479.95 μL, 2.50 eq) in CH₃CN (10 mL) was added NaBH(OAc)₃ (1.38 g, 6.53 mmol, 2.50 eq) at 0° C. under N₂. The mixture was stirred at 0° C. for 30 mins, then added CH₃COOH (31.36 mg, 522 µmol, 29.87 µL, 0.20 eq) at 0° C. and stirred for 1 hr. The reaction was monitored by LCMS. Filtered and concentrated in vacuum. Compound 39.1 (1.40 g, crude) was obtained as black brown oil. LCMS (ESI): m/z: [M+H] calcd for C$_{10}$H$_{19}$N$_3$O: 196; found 196; RT=0.528 min.

To a mixture of compound 39.1 (400 mg, crude) and BrCN (216.98 mg, 2.05 mmol, 150.68 µL, 1 eq) in DMF (1 mL) was added DIEA (1.06 g, 8.19 mmol, 1.43 mL, 4 eq) in one portion at 0° C. under N$_2$. The mixture was stirred at 0° C. for 5 mins. The reaction was monitored by LCMS promptly until the reaction was completed. Water (50 mL) was added. The aqueous phase was extracted with EtOAc (30 mL×3). The combined organic phase was washed with brine (5 mL), dried with anhydrous Na$_2$SO$_4$, filtered and concentrated in vacuum. The residue was purified by prep-HPLC (basic condition) to give Product 39 (20 mg, 45.40 µmol, 2.21% yield, 50% purity) was obtained as a colorless oil. $^1$H NMR (400 MHz, DMSO-d6) ppm 1.30 (d, J=6.4, 6H), 3.28 (m, 1H), 3.42 (t, J=5.2 Hz, 2H), 4.16 (t, J=5.2 Hz, 2H), 4.68 (br, 2H) 6.01 (d, J=2.4, 1H), 6.27 (dd, J=2.4 Hz, J=6.0 Hz, 1H), 7.89 (d, J=6.0 Hz, 1H). LCMS (ESI): m/z: [M+H] calcd for C11H17N4O: 221; found 221; RT=2.091 min.

To a mixture of compound 39.2 (188 mg, 831.49 µmol, 1 eq, 2HCl) and cyclohexanone 40.2 (244.81 mg, 2.49 mmol, 257.69 µL, 3 eq) in CH$_3$CN (5 mL) was added NaBH(OAc)$_3$ (528.68 mg, 2.49 mmol, 3 eq) in one portion at 0° C. under N$_2$. The mixture was stirred at 0° C. for 30 mins, then added AcOH (9.99 mg, 166.30 µmol, 9.51 µL, 0.20 eq) at 0° C. and stirred for 1 hours. The reaction was monitored by LCMS. Filtered and concentrated in vacuum to give compound 40.1 (1.40 g, crude) as black brown oil. LCMS (ESI): m/z: [M+H] calcd for C13H22N3O: 236; found 236; RT=1.159 min.

To a mixture of compound 40.1 (180 mg, 764.92 µmol, 1 eq) and BrCN (81.02 mg, 764.92 µmol, 56.26 µL, 1 eq) in DMF (1 mL) was added DIEA (395.43 mg, 3.06 mmol, 534.37 µL, 4 eq) in one portion at 0° C. under N$_2$. The mixture was stirred at 0° C. for 12 mins. The reaction was monitored by LC-MS promptly until the reaction was completed. The residue was purified by prep-HPLC (basic condition) to give product 40 (10 mg, 38.41 µmol, 5.02% yield) was obtained as a white solid. $^1$H NMR (400 MHz, DMSO-d6) δ ppm 1.18-1.30 (m, 3H), 1.41-1.47 (m, 2H), 1.64-1.67 (m, 1H), 1.84-1.87 (m, 2H), 1.99-2.02 (m, 2H), 2.82-2.88 (m, 1H), 3.44 (t, J=4.8 Hz, 2H), 4.14 (t, J=4.8 Hz, 2H), 4.42 (br. s, 2H), 5.99 (s, 1H), 6.26 (d, J=6.0 Hz, 1H), 7.92 (d, J=6.0 Hz, 1H). LCMS (ESI): m/z: [M+H] calcd for C14H21N4O: 261; found 261; RT=2.546 min.

Examples 41 and 42. Preparation of (S)-2-(((2-amino-5-chloropyridin-4-yl)oxy)methyl)pyrrolidine-1-carbonitrile (41) and (S)-2-(((2-amino-3-chloro-pyridin-4-yl)oxy)methyl)pyrrolidine-1-carbonitrile (42)

To a mixture of compound 41.6 (5 g, 24.84 mmol, 1 eq) and 4-methylbenzenesulfonyl chloride (5.68 g, 29.81 mmol, 1.20 eq) in DCM (50 mL) was added TEA (3.77 g, 37.26 mmol, 5.16 mL, 1.50 eq) and DMAP (485.62 mg, 3.97 mmol, 0.16 eq) in one portion at 0° C. under N$_2$. The mixture was then heated to 25° C. and stirred for 10 hours. The reaction mixture was diluted with H$_2$O 50 mL and extracted with DCM 90 mL (30 mL×

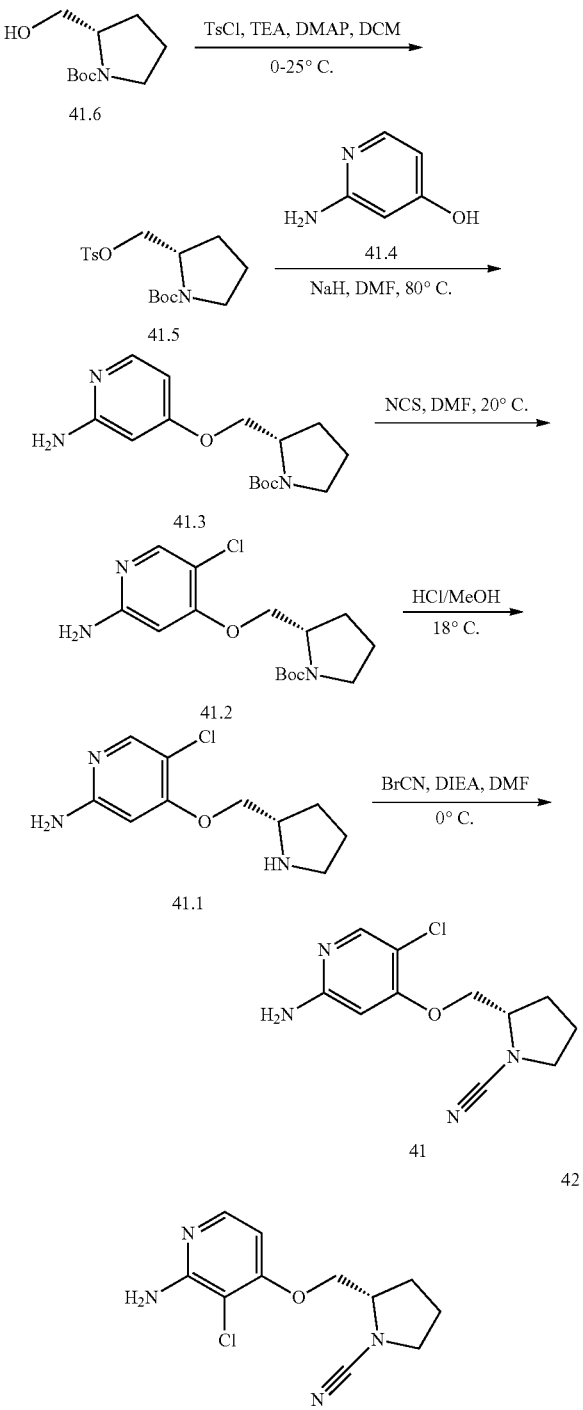

3). The combined organic layers were washed with brine 60 mL (60 mL×1), dried over Na$_2$SO$_4$, filtered and concentrated under reduced pressure to give compound 41.5 (8.90 g, crude) as a yellow oil. LCMS (ESI): m/z: [M+H] calcd for C$_{17}$H$_{25}$NO$_5$S: 356; found 300; RT=0.890 min.

To a mixture of compound 41.5 (8.84 g, 24.87 mmol, 1 eq) and compound 41.4 (3.01 g, 27.36 mmol, 1.10 eq) in DMF (100 mL) was added NaH (895.44 mg, 37.31 mmol, 1.50 eq) portionwise at 80° C. under N$_2$. The mixture was stirred at 80° C. for 10 hours. The reaction mixture was quenched by addition H$_2$O 1000 mL, and then extracted with EtOAc 240 mL (80 mL×3). The combined organic layers were washed with brine 150 mL (150 mL×1), dried over Na$_2$SO$_4$, filtered and concentrated under reduced pressure to give a residue. The residue was purified by column chromatography (SiO$_2$, DCM/MeOH=10:1) to give compound 41.3 (4.50 g, 15.34 mmol, 61.68% yield) as a white solid. LCMS (ESI): m/z: [M+H] calcd for C$_{15}$H$_{23}$N$_3$O$_3$: 294; found 294; RT=0.692 min.

To a mixture of compound 41.3 (300 mg, 1.02 mmol, 1 eq) in DMF (5 mL) was added NCS (136.20 mg, 1.02 mmol, 1 eq) in one portion at 20° C. under N$_2$. The mixture was stirred at 20° C. for 10 hours. The reaction mixture was diluted with H$_2$O 5 mL and extracted with EtOAc 15 mL (5 mL×3). The combined organic layers were washed with brine 10 mL (10 mL×1), dried over Na$_2$SO$_4$, filtered and concentrated under reduced pressure to give a residue. The residue was purified by column chromatography (SiO2, Ethyl acetate) to give compound 41.2 (100 mg, 305.05 μmol, 29.91% yield) as a colorless oil. LCMS (ESI): m/z: [M+H] calcd for C$_{15}$H$_{22}$ClN$_3$O$_3$: 327; found 321; RT=0.912 min. $^1$H NMR (400 MHz, methanol-d4) δ ppm 1.45 (s, 9H) 1.81-1.93 (m, 1H) 2.02-2.22 (m, 4H) 3.34-3.47 (m, 2H) 4.13-4.23 (m, 2H) 6.22 (br d, J=17.42 Hz, 1H) 6.49 (br dd, J=12.57, 5.51 Hz, 1H) 7.67-7.79 (m, 1H)

Compound 41.2 (100 mg, 305.05 μmol, 1 eq) was added into a solution of HCl/MeOH (5 mL). The mixture was stirred at 18° C. for 10 hours. The reaction mixture was concentrated under reduced pressure to give compound 41.1 (130 mg, crude) as a yellow solid. LCMS (ESI): m/z: [M+H] calcd for C$_{10}$H$_{14}$ClN$_3$O: 227; found 228; RT=0.096 min.

To a mixture of compound 41.1 (120 mg, 527.03 μmol, 1 eq) and DIPEA (272.45 mg, 2.11 mmol, 368.18 μL, 4 eq) in DMF (3 mL) was added CNBr (61.41 mg, 579.73 μmol, 42.65 μL, 1.10 eq) in one portion at 0° C. under N2. The mixture was stirred at 0° C. for 10 min. The residue was purified by prep-HPLC (neutral condition) to give product 41 (12 mg, 47.49 mol, 9.01% yield) and product 42 (12 mg, 47.49 μmol, 9.01% yield) as a yellow oil.

LCMS (ESI): m/z: [M+H] calcd for C$_{11}$H$_{13}$N$_4$OCl: 252; found 253; RT=2.314 min. $^1$H NMR (400 MHz, chloroform-d) δ ppm 1.90-2.09 (m, 2H) 2.10-2.23 (m, 2H) 3.43-3.52 (m, 1H) 3.60 (dt, J=8.75, 6.23 Hz, 1H) 3.98-4.08 (m, 2H) 4.09-4.16 (m, 1H) 4.49 (br s, 2H) 6.02 (s, 1H) 7.93 (s, 1H).

LCMS (ESI): m/z: [M+H] calcd for C$_{11}$H$_{13}$N$_4$OCl: 252; found 253; RT=2.226 min. $^1$H NMR (400 MHz, chloroform-d) δ ppm 1.90-2.09 (m, 2H) 2.10-2.24 (m, 2H) 3.42-3.54 (m, 1H) 3.61 (dt, J=9, 6.16 Hz, 1H) 3.99-4.06 (m, 1H) 4.07-4.12 (m, 1H) 4.13-4.20 (m, 1H) 4.86 (br s, 2H) 6.31 (d, J=5.77 Hz, 1H) 7.90 (d, J=5.77 Hz, 1H).

Examples 43 and 44. Preparation of (R)-2-(1-aminoisoquinolin-6-yl)pyrrolidine-1-carbonitrile (43) and (S)-2-(1-aminoisoquinolin-6-yl)pyrrolidine-1-carbonitrile (44)

To a mixture of compound 43.7 (2 g, 4.72 mmol, 1 eq), compound 43.6 (996.01 mg, 4.72 mmol, 1 eq), K$_2$CO$_3$ (3.91 g, 28.32 mmol, 6 eq) in dioxane (40 mL) and H$_2$O (10 mL) was added Pd(dppf)Cl$_2$ (1.04 g, 1.42 mmol, 0.30 eq) in one portion at 15° C. under N$_2$. The mixture was stirred at 80° C. for 8 hours. The reaction mixture was quenched by addition H$_2$O 100 mL at 25° C., and extracted with EtOAc (50 mL×3). The combined organic layers were washed with saturated brines (20 mL×2), dried over anhydrous sodium sulfate, filtered and concentrated under reduced pressure to give a crude product. The residue was purified by silica gel chromatography (Petroleum ether/Ethyl acetate=20/1, 3/1) to afford compound 43.4

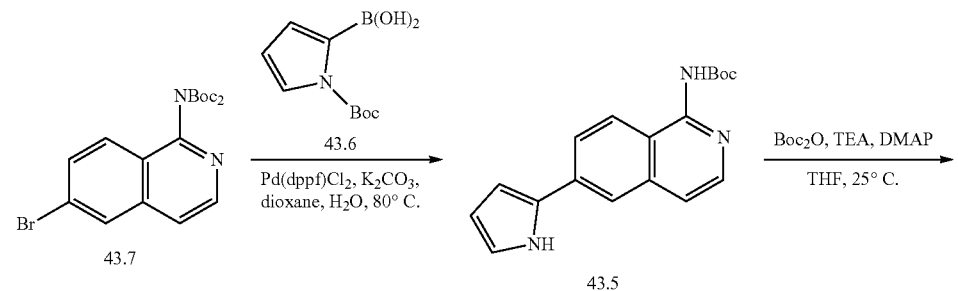

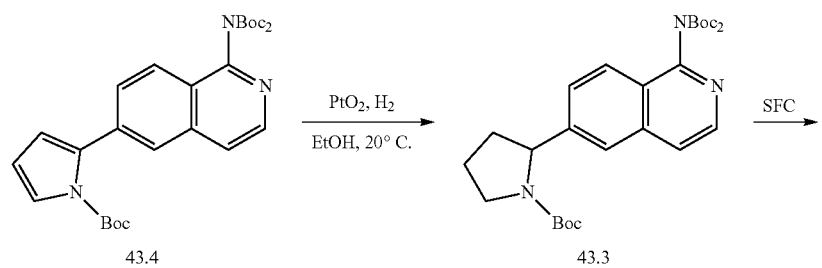

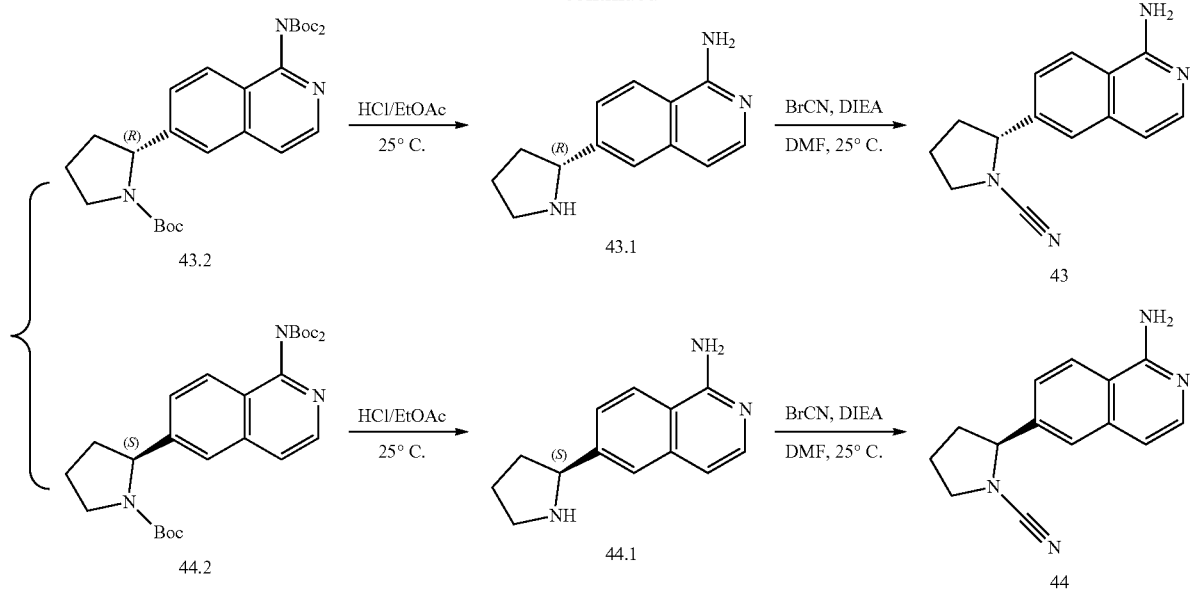

(660 mg, 1.30 mmol, 27.54% yield) and compound 43.5 (1 g, 3.23 mmol, 68.48% yield) as brown solid. LCMS (ESI): m/z: compound 43.5: [M+H] calcd for C18H19N3O$_2$:310; found 310; RT=1.775 min; compound 43.4: [M+H] calcd for C28H35N3O6:510; found 510; RT=3.724 min.

To a mixture of compound 43.5 (1 g, 3.23 mmol, 1 eq) in THF (10 mL) was added Boc$_2$O (3.53 g, 16.16 mmol, 3.71 mL, 5 eq), TEA (1.31 g, 12.93 mmol, 1.79 mL, 4 eq), DMAP (394.91 mg, 3.23 mmol, 1 eq) in one portion at 15° C. under N$_2$. The mixture was stirred at 15° C. for 12 hours. The reaction mixture was diluted with H$_2$O 50 mL and extracted with EtOAc 120 mL (40 mL×3). The combined organic layers were washed with brine 20 mL (10 mL×2), dried over Na$_2$SO$_4$, filtered and concentrated under reduced pressure to give a residue. The residue was purified by silica gel chromatography (Petroleum ether/Ethyl acetate=20/1, 3/1) to obtain compound 43.4 (440 mg, 863.44 μmol, 26.71% yield) as brown solid. LCMS (ESI): m/z: [M+H] calcd for C28H35N3O6:510; found 510; RT=1.616 min.

To a mixture of compound 43.4 (1.10 g, 2.16 mmol, 1 eq) in EtOH (30 mL) was added PtO$_2$ (490.17 mg, 2.16 mmol, 1 eq) in one portion at 15° C. under H$_2$. The mixture was stirred at 15° C., 50 Psi for 12 hours. The reaction mixture was filtered and concentrated in vacuum. The residue was purified by silica gel chromatography (Petroleum ether/Ethyl acetate=20/1, 3/1) and future purification by SFC to obtain compound 43.2 (300 mg, 584.08 mol, 27.04% yield) and compound 44.2 (300 mg, 584.08 μmol, 27.04% yield) as light yellow oil. LCMS (ESI): m/z: [M+H] calcd for C28H39N3O6:514; found 514; RT=1.494 min.

To a mixture of HCl/EtOAc (4 M, 5 mL) in compound 43.2 (300 mg, 584.08 μmol, 1 eq) in one portion at 15° C. The mixture was stirred at 15° C. for 12 hour. The reaction solution was concentrated in vacuum to obtain compound 43.1 (180 mg, crude, 2HCl) was obtained as light yellow solid. LCMS (ESI): m/z: [M+H] calcd for C13H15N3:214; found 214; RT=0.177 min.

To a mixture of compound 43.1 (140 mg, 489.17 μmol, 1 eq, 2HCl) and DIPEA (252.88 mg, 1.96 mmol, 341.73 μL, 4 eq) in DMF (2 mL) was added BrCN (56.99 mg, 538.09 μmol, 39.58 μL, 1.10 eq) at 0° C. under N2. The mixture was stirred at 0° C. for 10 min. The residue was purified by prep-HPLC (neutral condition) to give product 4.3 (50 mg, 209.83 μmol, 42.90% yield) was obtained as light yellow solid. $^1$H NMR (400 MHz, chloroform-d) δ ppm 7.97 (d, J=5.86 Hz, 1H) 7.82 (d, J=8.55 Hz, 1H) 7.63 (s, 1H) 7.41 (d, J=8.68 Hz, 1H) 7.05 (d, J=5.86 Hz, 1H) 5.11 (br s, 2H) 4.82 (t, J=7.03 Hz, 1H) 3.75-3.83 (m, 1H) 3.62-3.69 (m, 1H) 2.43 (dq, J=12.65, 6.45 Hz, 1H) 2.07 (dt, J=14.27, 6.98 Hz, 2H) 1.89-1.99 (m, 1H). LCMS (ESI): m/z: [M+H] calcd for C14H14N4:239; found 239; RT=2.035 min.

To a mixture of compound 44.2 (300 mg, 584.08 μmol, 1 eq) in HCl/EtOAc (4 M, 5 mL) in one portion at 15° C. under N$_2$. The mixture was stirred at 15° C. for 5 hours. The reaction solution was concentrated in vacuum to obtain compound 44.1 (180 mg, crude, 2HCl) was obtained as light yellow solid. LCMS (ESI): m/z: [M+H] calcd for C13H15N3:214; found 214; RT=10 min.

To a mixture of compound 44.1 (140 mg, 489.17 μmol, 1 eq, 2HCl), DIPEA (252.88 mg, 1.96 mmol, 341.73 μL, 4 eq) in DMF (2 mL) in one portion at 0° C. under N2. Then added BrCN (56.99 mg, 538.09 μmol, 39.58 μL, 1.10 eq) at 0° C. The mixture was stirred at 0° C. for 10 mins. The residue was purified by prep-HPLC (neutral condition) to give product 44 (40 mg, 167.86 μmol, 34.32% yield) was obtained as light yellow solid. $^1$H NMR (400 MHz, chloroform-d) δ ppm 7.98 (d, J=5.86 Hz, 1H) 7.82 (d, J=8.55 Hz, 1H) 7.63 (s, 1H) 7.41 (d, J=8.43 Hz, 1H) 7.05 (d, J=5.86 Hz, 1H) 5.11 (br s, 2H) 4.82 (t, J=7.03 Hz, 1H) 3.75-3.84 (m, 1H) 3.62-3.70 (m, 1H) 2.43 (dq, J=12.74, 6.42 Hz, 1H) 2.03-2.13 (m, 2H) 1.89-2 (m, 1H). LCMS (ESI): m/z: [M+H] calcd for C14H14N4:239; found 239; RT=2.050 min.

Examples 45 and 46. Preparation of 2-(1-aminoisoquinolin-6-yl)pyrrolidine-1-carbonitrile (45) and N-(1-(1-aminoisoquinolin-6-yl)ethyl)-N-methylcyanamide (46)

To a solution of compound 45.7 (2.50 g, 10.31 mmol, 1 eq) in NMP (20 mL) was added NH$_3$.H$_2$O (22.74 g, 648.87 mmol, 24.99 mL, 62.94 eq). The mixture was stirred at 150°

C. for 15 hours. The reaction mixture was quenched by addition H₂O 50 mL at 25° C. and extracted with ethyl acetate (50 mL×3). The combined organic layers were washed with saturated brines (10 mL×1), dried over anhydrous sodium sulfate, filtered and concentrated under reduced pressure to give a crude product. Compound 45.6 (4 g, crude) was obtained as a yellow oil. It was combined with obtained second batch to obtain 8 g crude which was purified by column chromatography (SiO₂, Petroleum ether/Ethyl acetate=0:1). The purified compound (2 g, 11.20 mmol, 35.72% yield) was obtained as a yellow oil. ¹H NMR (400 MHz, methanol-d₄) δ ppm 6.91 (d, J=6.14 Hz, 1H) 7.58 (dd, J=8.77, 2.19 Hz, 1H) 7.75 (d, J=5.70 Hz, 1H) 7.90 (d, J=1.75 Hz, 1H) 8.01 (d, J=9.21 Hz, 1H). LCMS (ESI): m/z: [M+H] called for C₉H₇N₂Cl: 179; found 179; RT=0.557 min.

To a solution of compound 45.6 (2 g, 8.97 mmol, 1 eq) in THF (40 mL) was added TEA (3.63 g, 35.86 mmol, 4.97 mL, 4 eq) and Boc₂O (4.89 g, 22.41 mmol, 5.15 mL, 2.50 eq) and DMAP (328.61 mg, 2.69 mmol, 0.30 eq). The mixture was stirred at 25° C. for 15 hours. The reaction mixture was quenched by addition H₂O 50 mL at 25° C. and extracted with ethyl acetate (50 mL×3). The combined organic layers were washed with saturated brines (20 mL×1), dried over anhydrous sodium sulfate, filtered and concentrated under reduced pressure to give a crude product. The residue was purified by re-crystallization from ethyl acetate (15 mL) to give the crude product compound 45.5 (2.90 g, 6.85 mmol, 76.38% yield) as yellow solid. ¹H NMR (400 MHz, chloroform-d) δ ppm 1.30-1.34 (m, 1H) 1.32 (s, 17H) 7.57 (d, J=5.70 Hz, 1H) 7.71 (dd, J=8.77, 1.75 Hz, 1H) 7.83 (d, J=8.77 Hz, 1H) 8.05 (d, J=1.75 Hz, 1H) 8.45 (d, J=5.70 Hz, 1H). LCMS (ESI): m/z: [M+H] called for C₁₉H₂₃BrN₂O₄: 424; found 424; RT=0.962 min.

To a solution of compound 45.5 (500 mg, 1.18 mmol, 1 eq) and (1-tert-butoxycarbonylpyrrol-2-yl) boronic acid (249 mg, 1.18 mmol, 1 eq) in dioxane (20 mL) and H₂O (5 mL) was added Pd(dppf)Cl₂ (259.03 mg, 354 μmol, 0.30 eq) and K₂CO₃ (489.26 mg, 3.54 mmol, 3 eq). The mixture was stirred at 80° C. for 14 hours. The reaction mixture was

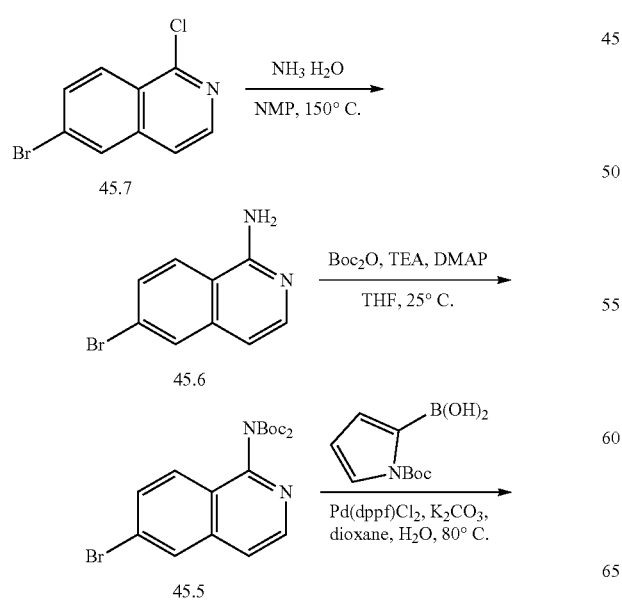

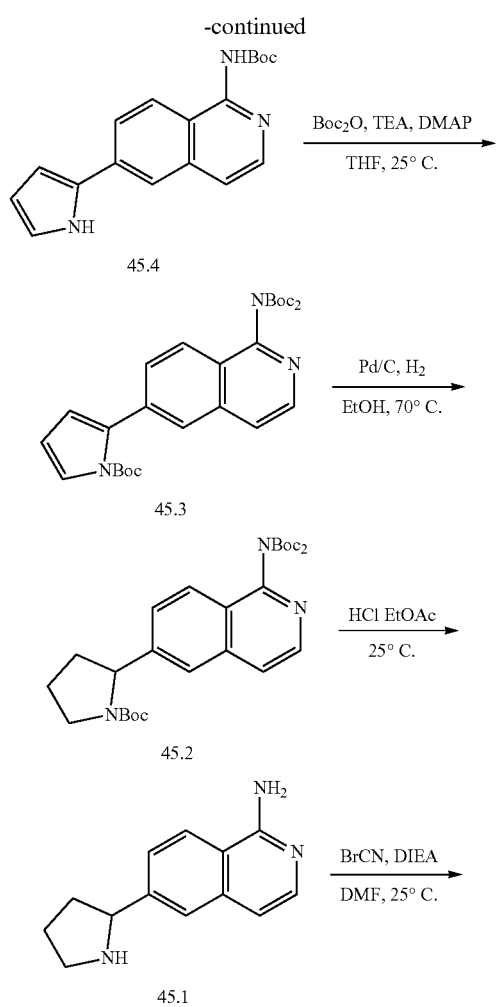

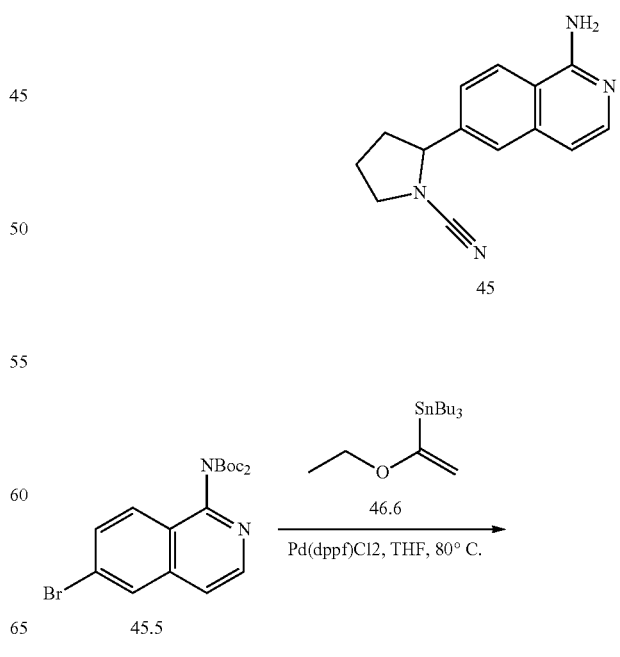

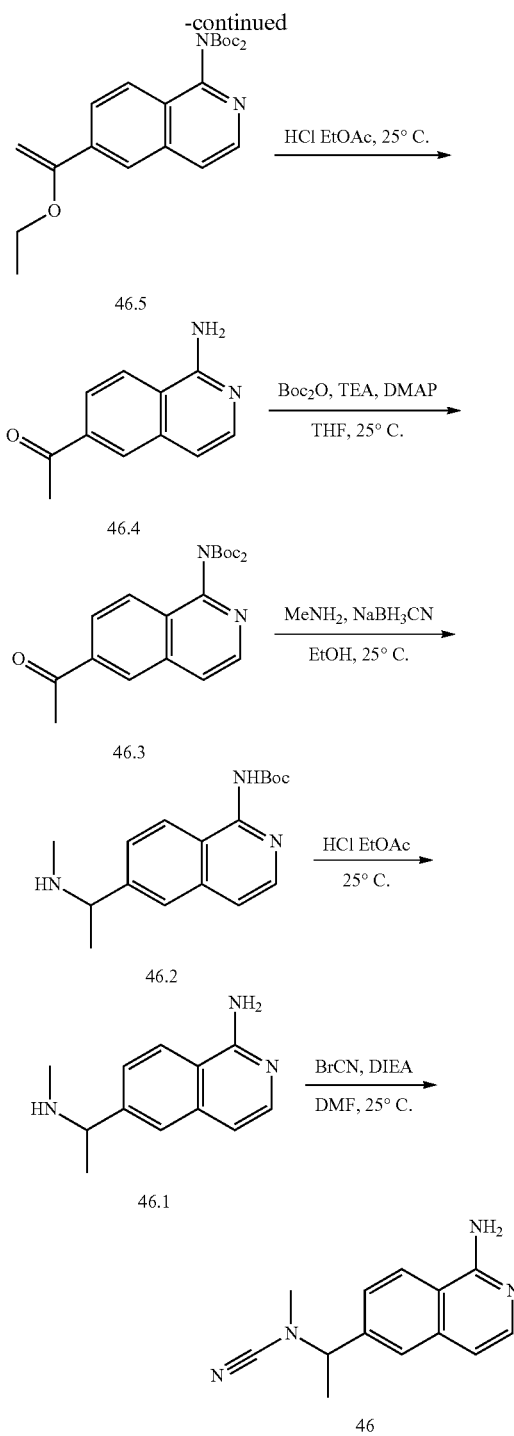

quenched by addition H₂O 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography (SiO2, Petroleum ether/Ethyl acetate=2:1). Compound 45.4 (100 mg, 196.24 µmol, 16.63% yield) was obtained as a yellow oil. LCMS (ESI): m/z: [M+H] called for $C_{18}H_{19}N_3O_2$: 310; found 310; RT=0.734 min.

To a solution of compound 45.4 (400 mg, 1.29 mmol, 1 eq) in THF (10 mL) was added TEA (522.14 mg, 5.16 mmol, 715.26 µL, 4 eq) and Boc₂O (703.86 mg, 3.23 mmol, 740.90 µL, 2.50 eq) and DMAP (47.28 mg, 387 µmol, 0.30 eq). The mixture was stirred at 25° C. for 14 hours. The reaction mixture was quenched by addition H2O 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography (SiO₂, Petroleum ether/Ethyl acetate=2:1). Compound 45.3 (160 mg, 313.98 mol, 24.34% yield) was obtained as a yellow oil. ¹H NMR (400 MHz, chloroform-d) δ ppm 1.34 (s, 19H) 6.28-6.33 (m, 1H) 6.37 (dd, J=3.20, 1.65 Hz, 1H) 7.45 (dd, J=3.20, 1.65 Hz, 1H) 7.58-7.68 (m, 2H) 7.83 (s, 1H) 7.92 (d, J=8.82 Hz, 1H) 8.43 (d, J=5.73 Hz, 1H).

To a solution of compound 45.3 (160 mg, 313.98 µmol, 1 eq) in EtOH (5 mL) was added PtO₂ (11 mg) under N₂. The suspension was degassed under vacuum and purged with H₂ several times. The mixture was stirred under H₂ (50 psi) at 25° C. for 12 hours. The mixture was filtered and concentrated under reduced pressure to give a residue. The residue was purified by column chromatography (SiO₂, Petroleum ether/Ethyl acetate=2:1). Compound 45.2 (150 mg, 292.04 µmol, 93.01% yield) was obtained as a yellow oil. LCMS (ESI): m/z: [M+H] called for $C_{28}H_{39}N_3O_6$: 514; found 514; RT=1.672 min.

A mixture of compound 45.2 (150 mg, 292.04 µmol, 1 eq) in HCl/EtOAc (20 mL) was stirred at 25° C. for 14 hours. The mixture was concentrated under reduced pressure to give a residue. Compound 45.1 (80 mg, 279.52 µmol, 95.71% yield, 2HCl) was obtained as a white solid. LCMS (ESI): m/z: [M+H] called for $C_{13}H_{15}N_3$: 214; found 214; RT=0.175 min.

To a solution of compound 45.1 (80 mg, 279.52 µmol, 1 eq, 2HCl) in DMF (2 mL) was added DIEA (144.50 mg, 1.12 mmol, 195.27 µL, 4 eq) and BrCN (32.57 mg, 307.47 mol, 22.62 µL, 1.10 eq). The mixture was stirred at 0° C. for 10 min. The residue was purified by prep-HPLC (neutral condition). Product 45 (20 mg, 83.93 µmol, 30.03% yield) was obtained as a yellow solid. ¹H NMR (400 MHz, methanol-d₄) δ ppm 1.84-2.02 (m, 1H) 2.03-2.14 (m, 2H) 2.44 (dq, J=12.47, 6.24 Hz, 1H) 3.57-3.70 (m, 1H) 3.80 (q, J=7.78 Hz, 1H) 7 (d, J=5.99 Hz, 1H) 7.49 (d, J=8.68 Hz, 1H) 7.68 (s, 1H) 7.75 (d, J=5.99 Hz, 1H) 8.14 (d, J=8.68 Hz, 1H). LCMS (ESI): m/z: [M+H] called for $C_{14}H_{14}N_4$: 239; found 239; RT=2.277 min.

To a solution of compound 45.5 (500 mg, 1.18 mmol, 1 eq) in dioxane (15 mL) was added Pd(PPh₃)₂Cl₂ (82.82 mg, 118 µmol, 0.10 eq) and compound 46.6 (852.31 mg, 2.36 mmol, 796.56 µL, 2 eq). The mixture was stirred at 80° C. for 14 hours. The reaction mixture was quenched by addition H₂O 20 mL at 25° C. and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography (SiO2, Petroleum ether/Ethyl acetate=2:1). Compound 46.5 (450 mg, 1.09 mmol, 92.01% yield) was obtained as a yellow oil. ¹H NMR (400 MHz, chloroform-d) δ ppm 1.21-1.37 (m, 20H) 1.50 (br t, J=7.02 Hz, 3H) 3.93-4.09 (m, 2H) 4.43 (br s, 1H) 4.89 (br s, 1H) 7.67 (br d, J=5.26 Hz, 1H) 7.88 (q, J=8.77 Hz, 2H) 8.14 (s, 1H) 8.41 (br d, J=5.70 Hz, 1H). LCMS (ESI): m/z: [M+H] called for $C_{23}H_{30}N_2O$: 415; found 415; RT=0.979 min.

A mixture of compound 46.5 (450 mg, 1.09 mmol, 1 eq) in HCl/EtOAc (10 mL) was degassed and purged with N₂ for 3 times and then the mixture was stirred at 25° C. for 15 hours. The mixture was concentrated under reduced pressure to give a residue. Compound 46.4 (230 mg, 1.03 mmol, 94.76% yield, HCl) was obtained as a yellow solid. ¹H NMR (400 MHz, methanol-d₄) δ ppm 2.75 (s, 3H) 7.37 (d, J=7.06 Hz, 1H) 7.65 (d, J=7.06 Hz, 1H) 8.25 (dd, J=8.82, 1.32 Hz, 1H) 8.53 (br d, J=6.17 Hz, 2H).

To a solution of compound 46.4 (230 mg, 1.24 mmol, 1 eq) in THF (5 mL) was added TEA (501.90 mg, 4.96 mmol, 687.54 µL, 4 eq) and Boc₂O (676.58 mg, 3.10 mmol, 712.18 µL, 2.50 eq) and DMAP (45.45 mg, 372 µmol, 0.30 eq). The mixture was stirred at 25° C. for 14 hours. The reaction mixture was quenched by addition H₂O 20 mL at 25° C. and extracted with ethyl acetate (20 mL×3). The combined organic layers were washed with saturated brines (10 mL×1), dried over anhydrous sodium sulfate, filtered and concentrated under reduced pressure to give a crude product. The residue was purified by column chromatography (SiO2, Petroleum ether/Ethyl acetate=2:1). Compound 46.3 (200 mg, 517.54 mol, 41.74% yield) was obtained as a yellow solid. LCMS (ESI): m/z: [M+H] called for C₂₁H₂₆N₂O₅: 387; found 287; RT=0.626 min.

A mixture of compound 46.3 (100 mg, 258.77 µmol, 1 eq) in MeNH₂ (2 mL) was stirred at 0° C. for 1 hour. To the mixture was added NaBH₃CN (65.04 mg, 1.04 mmol, 4 eq) and then added HOAc (23.31 mg, 388.16 µmol, 22.20 µL, 1.50 eq) make the mixture to pH=4. The mixture was stirred at 25° C. for 12 hours. The reaction mixture was quenched by addition saturated NaHCO₃ 20 mL at 25° C. make the pH>7 and extracted with ethyl acetate (20 mL×3). The combined organic layers were washed with saturated brines (20 mL×1), dried over anhydrous sodium sulfate, filtered and concentrated under reduced pressure to give a crude product. The residue was purified by column chromatography (SiO2, DCM:MeOH=10:1). Compound 46.2 (50 mg, 124.53 µmol, 48.12% yield) was obtained as a yellow oil. LCMS (ESI): m/z: [M+H] called for C₂₂H₃₁N₃O₄: 302; found 302; RT=0.565 min.

A mixture of compound 46.2 (50 mg, 165.90 µmol, 1 eq) in HCl/EtOAc (20 mL) was stirred at 25° C. for 13 hours. The mixture was concentrated under reduced pressure to give a residue. Compound 46.1 (45 mg, 164.12 µmol, 98.93% yield, 2HCl) was obtained as a yellow oil. LCMS (ESI): m/z: [M+H] called for C₁₂H₁₅N₃: 202; found 202; RT=0.116 min.

To a solution of compound 46.1 (45 mg, 164.12 µmol, 1 eq, 2HCl) in DMF (2 mL) was added DIEA (84.84 mg, 656.48 µmol, 114.65 µL, 4 eq) and BrCN (17.38 mg, 164.12 mol, 12.07 µL, 1 eq). The mixture was stirred at 0° C. for 10 mins. The residue was purified by prep-HPLC (neutral condition). Product 46 (5 mg, 22.10 µmol, 13.46% yield) was obtained as a yellow solid. ¹H NMR (400 MHz, methanol-d4) δ ppm 1.67 (d, J=7.06 Hz, 3H) 2.79 (s, 3H) 4.33 (q, J=6.98 Hz, 1H) 7 (d, J=5.95 Hz, 1H) 7.53 (d, J=8.60 Hz, 1H) 7.68 (s, 1H) 7.76 (d, J=5.95 Hz, 1H) 8.16 (d, J=8.60 Hz, 1H). LCMS (ESI): m/z: [M+H] called for C₁₃H₁₄N₄: 227; found 227; RT=2.247 min.

Example 47. Preparation of 3-(((2-aminopyridin-4-yl)oxy)methyl)pyrrolidine-1-carbonitrile (47)

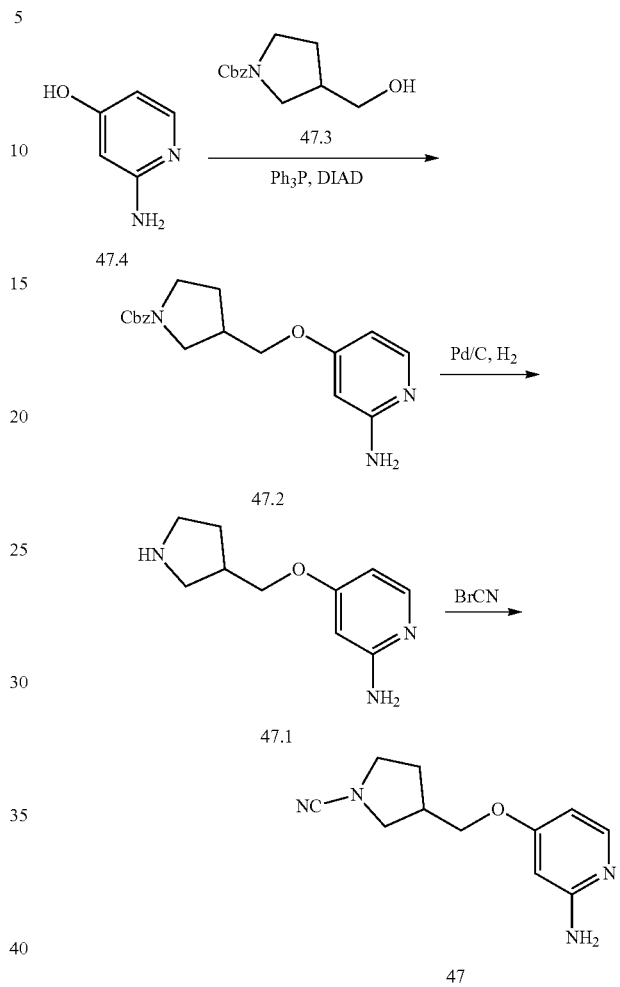

To a solution of compound 47.4 (800 mg, 7.27 mmol, 1 eq) in DCM (40 mL) was added compound 47.3 (1.71 g, 7.27 mmol, 1 eq), PPh₃ (2.86 g, 10.90 mmol, 1.50 eq) and DIAD (2.20 g, 10.90 mmol, 2.12 mL, 1.50 eq) in turn at 0° C. under N₂. The resulting mixture was stirred at 25° C. for 16 hours. The reaction mixture was added water 20 mL, extracted with EtOAc (20 mL×3). The combined organic layers were washed with brine (20 mL×1), dried over Na₂SO₄, filtered and concentrated under reduced pressure to give a residue. The residue was purified by column chromatography (SiO₂, Petroleum ether/Ethyl acetate=1:1). Compound 47.2 (700 mg, 2.14 mmol, 29.45% yield) was obtained as a white solid. ¹H NMR (400 MHz, chloroform-d) ppm 2.06-2.10 (m, 1H) 2.66-2.72 (m, 1H) 3.27-3.29 (m, 1H) 3.46-3.68 (m, 3H) 3.87-3.94 (m, 5H) 4.43 (s, 2H) 5.15 (s, 2H) 5.95 (d, J=2.0 Hz, 1H) 6.24 (dd, J=6.0 Hz, 2.0 Hz, 1H) 7.30-7.37 (m, 5H) 7.89 (d, J=6.0 Hz, 1H).

H₂ was bubbled into a solution of compound 47.2 (400 mg, 1.22 mmol, 1 eq) and H₂ in MeOH (40 mL) at 25° C. under 50 psi for 10 hours. The reaction mixture was filtered, the filter was concentrated under reduced pressure to remove solvent. Compound 47.1 (200 mg, 1.03 mmol, 84.83% yield) was obtained as a yellow oil. ¹H NMR (400 MHz, methanol-d4) ppm 1.58-1.63 (m, 1H) 2.02-2.04 (m, 1H)

2.60-2.79 (m, 2H) 2.94-3.14 (m, 3H) 3.91-3.98 (m, 2H) 6.09 (d, J=2.0 Hz, 1H) 6.23 (dd, J=6.0 Hz, 2.0 Hz, 1H) 7.69 (d, J=6.4 Hz, 1H).

To a solution of compound 47.1 (100 mg, 517.46 μmol, 1 eq) in THF (5 mL) was added DIEA (133.75 mg, 1.03 mmol, 180.75 μL, 2 eq) and BrCN (54.81 mg, 517.46 μmol, 38.06 μL, 1 eq) in turn at 0° C. under N₂. The resulting mixture was stirred at 0° C. for 1 hour. The reaction mixture was added water 10 mL, extracted with EtOAc (10 mL×3). The combined organic layers were washed with brine (20 Ml×1), dried over Na₂SO₄, filtered and concentrated under reduced pressure to give a residue. The residue was purified by p-TLC (SiO₂, Ethyl acetate=0:1). Product 47 (14 mg, 64.15 μmol, 12.40% yield) was obtained as a white solid. LCMS (ESI): m/z: [M+H] calcd for C₁₁H₁₄N₄O: 218; found 219; RT=2.522 min. ¹H NMR (400 MHz, chloroform-d) ppm 1.85-1.88 (m, 1H) 2.12-2.17 (m, 1H) 2.73-2.75 (m, 1H) 3.32-3.35 (m, 1H) 3.50-3.63 (m, 3H) 3.92-3.98 (m, 2H) 5 (s, 2H) 6.04 (s, 1H) 6.27 (dd, J=6.0 Hz, 2.0 Hz, 1H) 7.85 (d, J=6.0 Hz, 1H).

Example 48. Preparation of N-((7-aminofuro[2,3-c]pyridin-2-yl)methyl)-N-methylcyanamide (48)

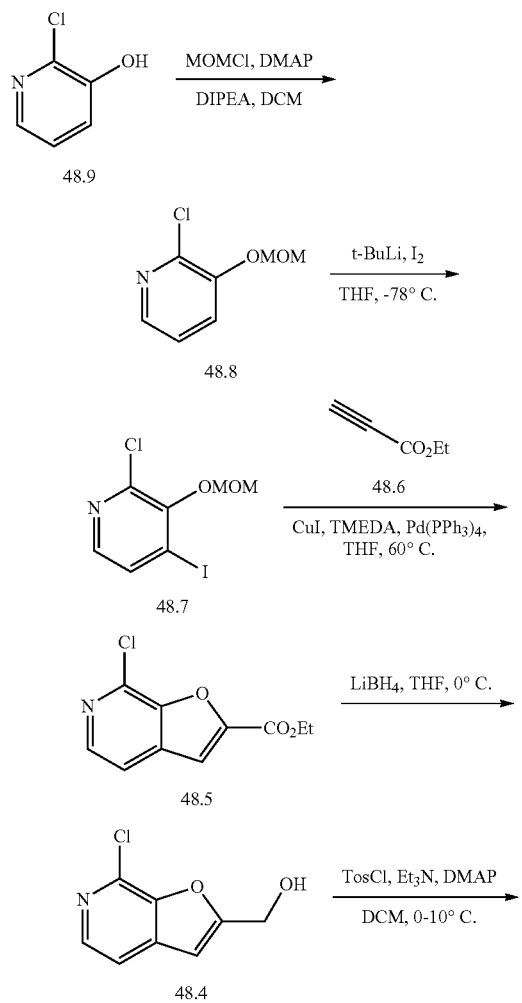

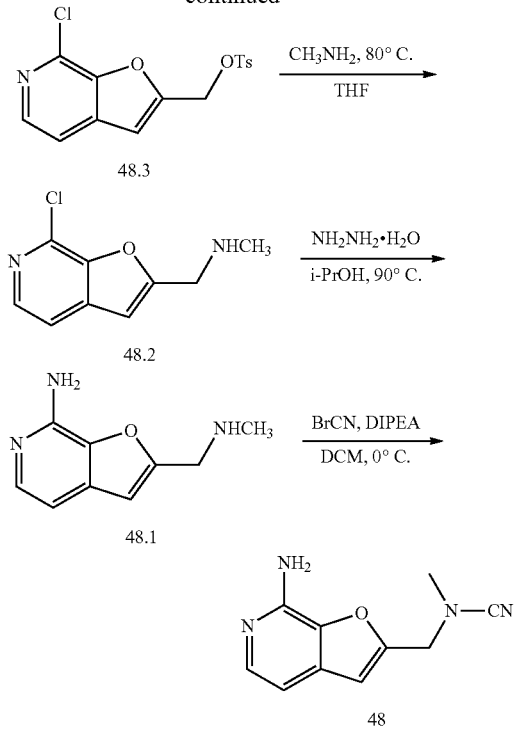

To a solution of compound 48.9 (10 g, 77.20 mmol, 1 eq) in DCM (100 mL) was added chloro(methoxy)methane (7.46 g, 92.64 mmol, 7.04 mL, 1.20 eq) and DMAP (1.51 g, 12.35 mmol, 0.16 eq) and DIPEA (19.95 g, 154.40 mmol, 26.96 mL, 2 eq) at 0° C. The mixture was stirred at 10° C. for 12 hours. The reaction mixture was diluted with H₂O 30 mL and extracted with DCM 90 mL (30 mL×3). The combined organic layers were washed with brine 30 mL (30 mL×1), dried over Na₂SO₄, filtered and concentrated under reduced pressure to give a residue. The residue was purified by column chromatography (SiO₂, Petroleum ether/Ethyl acetate=20/1 to 3:1) to give compound 48.8 (13.20 g, 76.04 mmol, 98.50% yield) as a colorless solid. LCMS (ESI): m/z: [M+H] calcd for C₇H₈ClNO₂: 173; found 174; RT=0.937 min. ¹H NMR (400 MHz, chloroform-d) δ ppm 3.51 (s, 3H) 5.23-5.30 (m, 2H) 7.18 (dd, J=8.11, 4.60 Hz, 1H) 7.47 (dd, J=8.11, 1.53 Hz, 1H) 8.04 (dd, J=4.82, 1.32 Hz, 1H).

To a solution of compound 48.8 (4.40 g, 25.35 mmol, 1 eq) in THF (130 mL) was added dropwise t-BuLi (1.3 M, 48.74 mL, 2.50 eq) at −78° C. The mixture was stirred at −78° C. for 1 hour. Then I₂ (11.58 g, 45.62 mmol, 9.19 mL, 1.80 eq) was added above mixture at −78° C. The mixture was stirred at 10° C. for 12 hours. The reaction mixture was quenched by addition H₂O 10 mL at 0° C., and then diluted with H₂O 50 mL and extracted with EtOAc 150 mL (50 mL×3). The combined organic layers were washed with brine 50 mL (50 mL×1), dried over Na₂SO₄, filtered and concentrated under reduced pressure to give a residue. The residue was purified by column chromatography (SiO₂, Petroleum ether/Ethyl acetate=20/1 to 3:1) to give compound 48.7 (12.80 g, 42.74 mmol, 56.21% yield) as a yellow solid. ¹H NMR (400 MHz, chloroform-d) δ ppm 3.68-3.82 (m, 3H) 5.18-5.27 (m, 2H) 7.70 (d, J=5.01 Hz, 1H) 7.80 (d, J=5.01 Hz, 1H).

To a solution of compound 48.7 (3.90 g, 13.02 mmol, 1 eq) in THF (100 mL) was added ethyl compound 48.6 (1.53 g, 15.63 mmol, 1.53 mL, 1.20 eq) and TMEDA (18.01 g, 154.96 mmol, 23.39 mL, 11.90 eq). The mixture was degassed with $N_2$ for 10 mins. Then the mixture was added CuI (496.01 mg, 2.60 mmol, 0.20 eq) and $Pd(PPh_3)_4$ (3.01 g, 2.60 mmol, 0.20 eq). Then the mixture was stirred at 60° C. for 15 hours. The reaction mixture was diluted with $H_2O$ 40 mL and extracted with EtOAc 180 mL (60 mL×3). The combined organic layers were washed with brine 60 mL (60 mL×1), dried over $Na_2SO_4$, filtered and concentrated under reduced pressure to give a residue. The residue was purified by column chromatography ($SiO_2$, Petroleum ether/Ethyl acetate=20/1 to 5:1) to give compound 48.5 (940 mg, 4.17 mmol, 16.01% yield) as a white solid.

To a solution of compound 48.5 (710 mg, 3.15 mmol, 1 eq) in THF (2 mL) was added $LiBH_4$ (102.80 mg, 4.72 mmol, 1.50 eq) and stirred at 0° C. for 12 hours. The reaction mixture was diluted with $H_2O$ 15 mL and extracted with EtOAc 45 mL (15 mL×3). The combined organic layers were washed with brine 15 mL (15 mL×1), dried over $Na_2SO_4$, filtered and concentrated under reduced pressure to give a residue. The residue was purified by column chromatography ($SiO_2$, Petroleum ether/Ethyl acetate=2/1 to 1:1) to give compound 48.4 (300 mg, 1.63 mmol, 51.88% yield) as a colorless solid. LCMS (ESI): m/z: [M+H] calcd for C8H6ClNO2:183; found 184; RT=0.593 min.

To a solution of compound 48.4 (150 mg, 817.04 µmol, 1 eq) in DCM (2 mL) was added TosCl (186.92 mg, 980.45 µmol, 1.20 eq), DMAP (19.96 mg, 163.41 µmol, 0.20 eq) and $Et_3N$ (248.03 mg, 2.45 mmol, 339.76 µL, 3 eq) at 0° C. The mixture was stirred at 10° C. for 2 hours. The reaction mixture was diluted with $H_2O$ 10 mL and extracted with DCM 30 mL (10 mL×3). The combined organic layers were washed with brine 10 mL (10 mL×1), dried over $Na_2SO_4$, filtered and concentrated under reduced pressure to give compound 48.3 (130 mg, crude) as a yellow solid. LCMS (ESI): m/z: [M+H] calcd for C15H12ClNO4S: 337; found 338; RT=0.842 min.

To a solution of compound 48.3 (130 mg, 384.87 µmol, 1 eq) in THF (2 mL) was added MeNH2 (11.95 mg, 384.87 µmol, 2 mL, 1 eq). The mixture was stirred at 80° C. for 12 hours. The reaction mixture was diluted with $H_2O$ 10 mL and extracted with EtOAc 30 mL (10 mL×3). The combined organic layers were washed with brine 10 mL (10 mL×1), dried over $Na_2SO_4$, filtered and concentrated under reduced pressure to give compound 48.2 (50 mg, crude) as a yellow oil. LCMS (ESI): m/z: [M+H] calcd for C9H9ClN2O: 196; found 197; RT=0.152 min.

To a solution of compound 48.2 (50 mg, 254.28 µmol, 1 eq) in i-PrOH (7 mL) was added $NH_2NH_2.H_2O$ (2.40 g, 48.01 mmol, 2.33 mL, 188.80 eq). The mixture was stirred at 90° C. for 72 hours. The reaction mixture was concentrated under reduced pressure to remove solvent to give compound 48.1 (60 mg, crude) as a yellow oil.

To a solution of compound 48.1 (60 mg, 338.60 µmol, 1 eq) in DMF (2 mL) was added BrCN (35.86 mg, 338.60 µmol, 24.91 µL, 1 eq) and DIPEA (131.28 mg, 1.02 mmol, 176.93 µL, 3 eq). The mixture was stirred at 0° C. for 0.2 hour. The residue was purified by prep-HPLC to give product 48 (2 mg, 9.89 µmol, 2.92% yield) as a colorless oil. LCMS (ESI): m/z: [M+H] calcd for C10H10N4O: 202; found 203; RT=2.484 min. $^1$H NMR (400 MHz, methanol-d4) δ ppm 2.95 (s, 3H) 4.43 (s, 2H) 6.75-6.98 (m, 2H) 7.69 (d, J=5.62 Hz, 1H).

Example 49. Preparation of (2R,4R)-2-(1-aminoisoquinolin-6-yl)-4-hydroxypyrrolidine-1-carbonitrile (49)

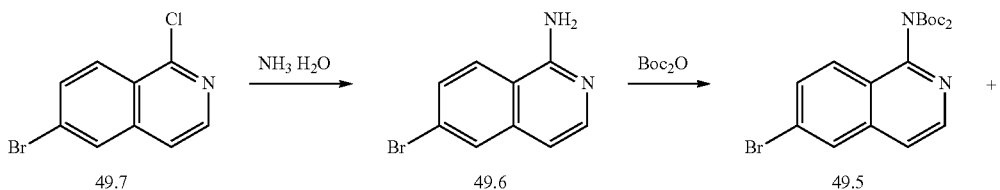

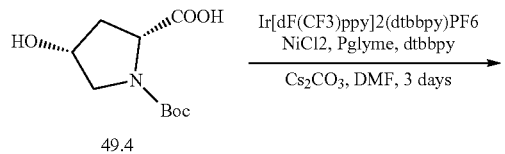

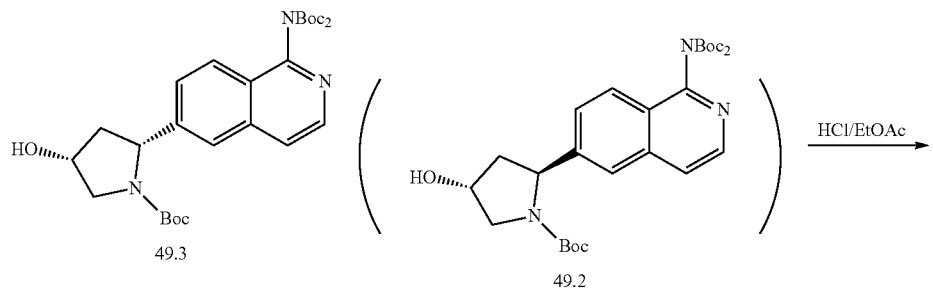

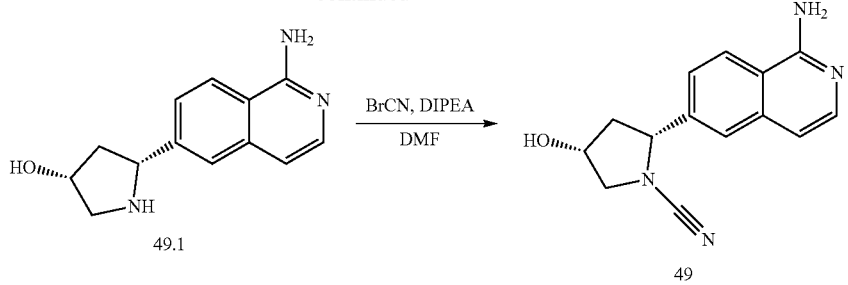

To a solution of compound 49.7 (1.5 g, 6.19 mmol, 1 eq) in NMP (15 mL) was added NH$_3$.H$_2$O (54.58 g, 389.32 mmol, 15 mL, 25% purity, 62.94 eq). The mixture was stirred at 150° C. for 15 hours. The reaction mixture was quenched by addition of H$_2$O (500 mL) at 25° C. and extracted with EtOAc (500 mL×3). The combined organic layers were washed with saturated brine 50 mL (50 mL), dried over anhydrous sodium sulfate, filtered and concentrated under reduced pressure to give a crude product. The residue was purified by column chromatography (SiO$_2$, DCM:MeOH=10:1) to give compound 49.6 (1.6 g, 7.17 mmol, 38.65% yield) as yellow oil.

To a solution of compound 49.6 (1.6 g, 7.17 mmol, 1 eq) in THF (20 mL) was added Boc$_2$O (6.26 g, 28.69 mmol, 6.59 mL, 4 eq) dropwise at 18° C. under N$_2$. Then to the mixture was added TEA (3.63 g, 35.86 mmol, 4.99 mL, 5 eq) and DMAP (140.20 mg, 1.15 mmol, 0.16 eq). This mixture was stirred at 18° C. for 10 hours. The reaction mixture was concentrated under reduced pressure to give a residue. The residue was purified by column chromatography (SiO$_2$, Petroleum ether/Ethyl acetate=1:1) to give compound 49.5 (1.1 g, 2.60 mmol, 36% yield) as a white solid. LCMS (ESI) m/z: [M+H] calcd for C$_7$H$_8$N$_2$O$_2$: 423; found 424; RT=1.501 min.

To a mixture of compound 49.5 (1.1 g, 2.60 mmol, 1 eq), compound 49.4 (901.38 mg, 3.90 mmol, 1.5 eq), Ir[dF(CF$_3$)ppy]$_2$(dtbbpy)PF$_6$ (2.81 mg, 26 µmol, 0.01 eq), NiCl$_2$.Pglyme (56.31 mg, 259.86 µmol, 0.1 eq), dtbbpy (104.08 mg, 389.79 µmol, 0.15 eq) in DMF (40 mL) was added Cs$_2$CO$_3$ (1.27 g, 3.90 mmol, 1.5 eq) in one portion in the glovebox. Then the mixture was irradiated with two 34 W fluorescent lamps for 72 hours at 25° C. The residue was purified by prep-HPLC (TFA conditions) to give compound 49.2 (60 mg, 113.3 µmol, 4.4% yield) and compound 49.3 (100 mg, 188.8 µmol, 7.3% yield) as yellow solid.

Compound 49.3 (100 mg, 188.81 µmol, 1 eq) was dissolved into HCl/EtOAc (10 mL), the mixture was stirred at 15° C. for 10 hours. The reaction mixture was concentrated under reduced pressure to give compound 49.1 (60 mg, crude) as a white solid.

To a mixture of compound 49.1 (60 mg, 261.7 µmol, 1 eq) and cyanogen bromide (27.7 mg, 261.7 µmol, 19.25 µL, 1 eq) in DMF (1 mL) was added DIPEA (101.5 mg, 785.5 µmol, 136.75 µL, 3 eq) in one portion at 0° C. under N$_2$. The mixture was stirred at 0° C. for 10 mins. The residue was purified by prep-HPLC (neutral conditions) to give 49, (4 mg, 15.7 µmol, 6% yield) as a white solid. LCMS (ESI) m/z: [M+H] calcd. for C$_{14}$H$_{14}$N$_4$O: 254; found 255; RT=1.77 min. $^1$H NMR (400 MHz, METHANOL-d4) δ: 1.88-1.99 (m, 1H), 2.47-2.58 (m, 1H), 3.57 (d, J=10.51 Hz, 1H), 4 (dd, J=10.51, 3.91 Hz, 1H), 4.52 (br s, 1H), 5.59 (dd, J=10.09, 6.42 Hz, 1H), 7.13 (d, J=6.24 Hz, 1H), 7.55-7.61 (m, 1H), 7.82 (d, J=6.36 Hz, 2H) and 8.12 (d, J=8.44 Hz, 1H) ppm.

Examples 50a and 50b. Preparation of (2S,4S)-2-(1-aminoisoquinolin-6-yl)-4-hydroxypyrrolidine-1-carbonitrile (50a) and (2R,4S)-2-(1-aminoisoquinolin-6-yl)-4-hydroxypyrrolidine-1-carbonitrile (50b)

To a solution of compound 50.5 (1.5 g, 6.19 mmol, 1 eq) in NMP (15 mL) was added NH$_3$.H$_2$O (54.58 g, 389.32 mmol, 15 mL, 63 eq). The mixture was stirred at 150° C. for 15 hours. The reaction mixture was quenched by addition H$_2$O (500 mL) at 25° C. and extracted with EtOAc (500 mL×3). The combined organic layers were washed with saturated brine (50 mL), dried over anhydrous sodium sulfate, filtered and concentrated under

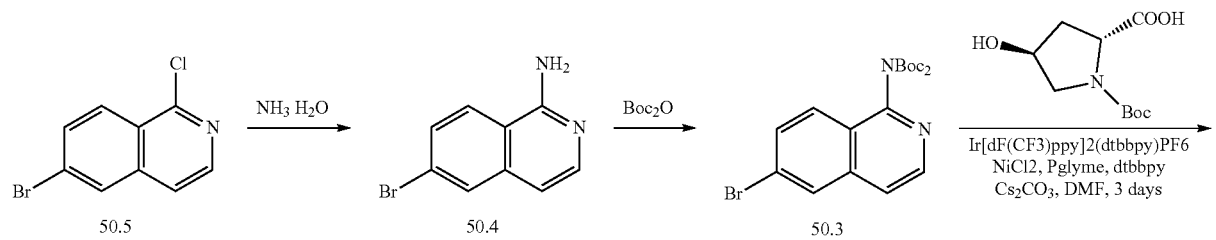

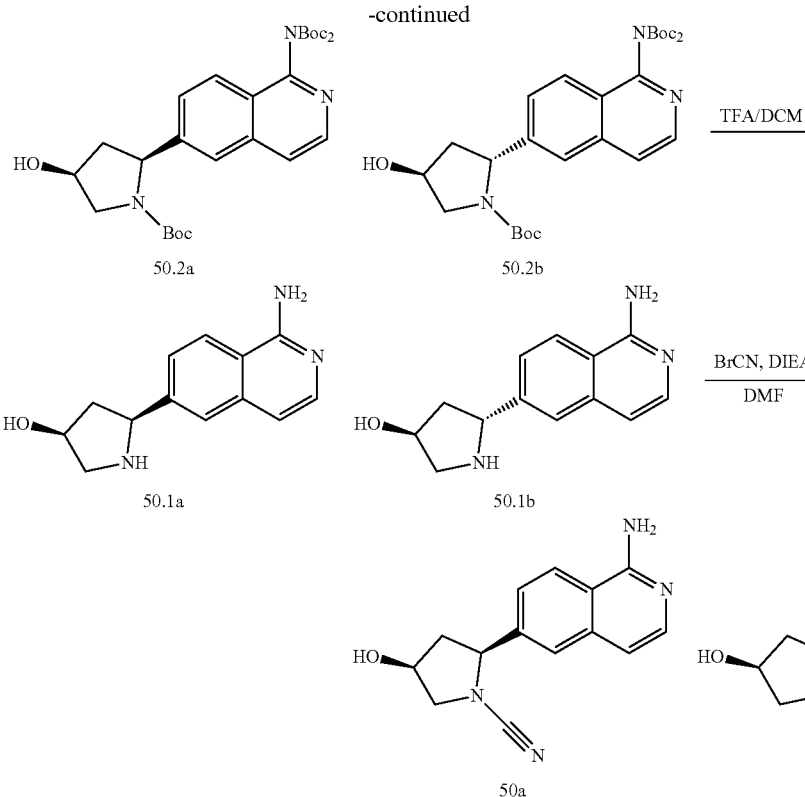

reduced pressure to give a crude product. The residue was purified by column chromatography (SiO$_2$, DCM: MeOH=10:1) to give compound 50.4 (1.6 g, 7.17 mmol, 39% yield) as yellow oil.

To a solution of compound 50.4 (1.6 g, 7.17 mmol, 1 eq) in THF (20 mL) was added Boc$_2$O (6.26 g, 28.69 mmol, 6.59 mL, 4 eq) dropwise at 18° C. under N$_2$. Then the mixture was added TEA (3.63 g, 35.86 mmol, 4.99 mL, 5 eq) and DMAP (140.2 mg, 1.15 mmol, 0.16 eq), and stirred at 18° C. for 10 hours. The reaction mixture was concentrated under reduced pressure to give a residue. The residue was purified by column chromatography (SiO$_2$, Petroleum ether/ Ethyl acetate=1:1) to give compound 50.3 (1.5 g) as a white solid. LCMS (ESI) m/z: [M+H] calcd for C$_7$H$_8$N$_2$O$_2$: 423; found 424; RT=1.501 min.

To a mixture of compound 50.3 (1.5 g, 3.54 mmol, 1 eq), (2R,4S)-1-tert-butoxycarbonyl-4-hydroxy-pyrrolidine-2-carboxylic acid (1.23 g, 5.32 mmol, 1.5 eq), Ir[dF(CF$_3$)ppy]$_2$(dtbbpy)PF$_6$ (3.83 mg, 35.44 μmol, 0.01 eq), NiCl$_2$.Pglyme (76.79 mg, 354.36 μmol, 0.1 eq), dtbbpy (141.92 mg, 531.54 μmol, 0.15 eq) in DMF (40 mL) was added Cs2CO3 (1.73 g, 5.32 mmol, 1.5 eq) in one portion in the glovebox. Then the mixture was irradiated with two 34 W fluorescent lamps for 72 hours at 25° C. The residue was purified by prep-HPLC (TFA condition) to give compound 50.2a (100 mg, 188.81 μmol, 5% yield) and compound 50.2b (100 mg, 188.81 μmol, 5% yield) as yellow solid.

To a solution of compound 50.2a (100 mg, 188.81 μmol, 1 eq) in DCM (5 mL) was added TFA (1 mL) in one portion at 18° C. under N$_2$. The mixture was stirred at 18° C. for 10 hours. The reaction mixture was concentrated under reduced pressure to give compound 50.1a (110 mg) as a white solid. $^1$H NMR (400 MHz, METHANOL-d4) δ: 2.41-2.62 (m, 2H), 3.38-3.46 (m, 1H), 3.67-3.77 (m, 2H), 4.76 (br t, J=3.75 Hz, 1H), 5.19 (br dd, J=11.91, 6.39 Hz, 1H), 7.25 (d, J=7.06 Hz, 1H), 7.63 (d, J=7.06 Hz, 1H), 7.88 (dd, J=8.71, 1.65 Hz, 1H), 8.02-8.10 (m, 1H) and 8.54 (d, J=8.82 Hz, 1H) ppm.

To a mixture of compound 50.1a (110 mg, 192.53 μmol, 1 eq) and cyanogen bromide (20.39 mg, 192.53 μmol, 14.16 μL, 1 eq) in DMF (1 mL) was added DIPEA (74.65 mg, 577.58 μmol, 100.6 μL, 3 eq) in one portion at 0° C. under N$_2$. The mixture was stirred at 0° C. for 10 mins. The residue was purified by prep-HPLC (neutral condition) to give 50a (5 mg, 19.66 μmol, 10% yield) as a white solid. LCMS (ESI) m/z: [M+H] calcd for C$_{14}$H$_{15}$N$_4$O: 255; found 255; RT=1.787 min. $^1$H NMR (400 MHz, METHANOL-d4) δ: 1.98-2.09 (m, 1H), 2.38 (dd, J=13.59, 6.14 Hz, 1H), 3.52 (d, J=10.52 Hz, 1H), 3.98 (dd, J=10.52, 3.51 Hz, 1H), 4.52 (br s, 1H), 5.06 (dd, J=10.52, 6.14 Hz, 1H), 7.01 (d, J=6.14 Hz, 1H), 7.54 (dd, J=8.77, 1.75 Hz, 1H), 7.74 (dd, J=3.73, 1.97 Hz, 2H) and 8.17 (d, J=8.77 Hz, 1H) ppm.

To a solution of compound 50.2b (100 mg, 188.81 μmol, 1 eq) in DCM (5 mL) was added TFA (1 mL) in one portion at 18° C. under N$_2$. The mixture was stirred at 18° C. for 10 hours. The reaction mixture was concentrated under reduced pressure to give compound 50.1b (110 mg, crude) as a white solid. $^1$H NMR (400 MHz, METHANOL-d4) δ: 2.46-2.55 (m, 1H), 2.58-2.68 (m, 1H), 3.40-3.49 (m, 1H), 3.68 (dd, J=12.24, 3.86 Hz, 1H), 4.79 (br t, J=3.64 Hz, 1H), 5.66 (br dd, J=11.69, 6.39 Hz, 1H), 7.46-7.54 (m, 1H), 7.69-7.76 (m, 1H), 7.84-7.93 (m, 1H), 8.19-8.27 (m, 1H) and 8.52-8.60 (m, 1H) ppm.

To a mixture of compound 50.1b (110 mg, 192.53 μmol, 1 eq, 3 TFA) and cyanogen bromide (20.39 mg, 192.53 μmol, 14.16 μL, 1 eq) in DMF (1 mL) was added DIPEA (74.65 mg, 577.58 μmol, 100.6 μL, 3 eq) in one portion at 18° C. under N$_2$. The mixture was stirred at 18° C. for 10 mins. The residue was purified by semi-preparative scale HPLC (TFA condition) to give 50b (5 mg, 19.7 μmol, 10% yield) as a white solid. LCMS (ESI) m/z: [M+H] calcd for $C_{14}H_{15}N_4O$: 255; found 255; RT=1.779 min. $^1$H NMR (400 MHz, METHANOL-d4) δ: 1.94 (ddd, J=13.48, 9.98, 4.17 Hz, 1H), 2.53 (dd, J=13.59, 6.58 Hz, 1H), 3.53-3.60 (m, 1H), 4 (dd, J=10.74, 3.73 Hz, 1H), 4.52 (br s, 1H), 5.60 (dd, J=10.09, 6.58 Hz, 1H), 7.14 (d, J=6.58 Hz, 1H), 7.58 (t, J=7.89 Hz, 1H), 7.80-7.87 (m, 2H) and 8.13 (d, J=8.33 Hz, 1H) ppm.

Examples 51a and 51b. Preparation of (S)-2-(1-(methylamino)isoquinolin-6-yl)pyrrolidine-1-carbonitrile (51a) and (R)-2-(1-(methylamino)isoquinolin-6-yl)pyrrolidine-1-carbonitrile (51b)

To a solution of compound 51.8 (2.5 g, 10.31 mmol, 1 eq) in NMP (30 mL) was added $NH_3.H_2O$ (30 mL, 33% aqueous solution) in one portion at 150° C. under $N_2$. The mixture was stirred at 150° C. for 10 hours. The reaction mixture was diluted with $H_2O$ (500 mL) and extracted with EtOAc (500 mL×3). The combined organic layers were washed with brine (500 mL), dried over $Na_2SO_4$, filtered and concentrated under reduced pressure to give a residue. The residue was purified by column chromatography ($SiO_2$, Petroleum ether/Ethyl acetate=1:2) to give compound 51.7 (35 g, 95% yield) as a white solid. LCMS (ESI) m/z: [M+H] calcd for $C_9H_8BrN_2$: 223; found 223; RT=0.761 min.

To a solution of compound 51.7 (7 g, 31.4 mmol, 1 eq) in DMF (70 mL) was added NaH (1.26 g, 31.4 mmol, 60% suspension in mineral oil, 1 eq) portion-wise at 0° C. under $N_2$. The mixture was stirred at 0° C. for 30 mins, then the mixture was added $CH_3I$ (6.68 g, 47.1 mmol, 2.93 mL, 1.5 eq) in one portion, and heated to 25° C. and stirred for 1.5 hours. The reaction mixture was quenched by addition of $H_2O$ (70 mL) and then was extracted with EtOAc (70 mL×3). The combined organic layers were washed with $H_2O$ (70 mL×3), and then with brine (70 mL), dried over $Na_2SO_4$, filtered and concentrated. This residue was purified by medium pressure liquid chromatography (MPLC) ($SiO_2$, petroleum ether/ethyl acetate=10/1 to 0:1) to give compound 51.5 (2.8 g, 11.81 mmol, 38% yield) as an orange solid and to give compound 51.6 (1.09 g, 4.34 mmol, 14% yield) as yellow oil. $^1$H NMR (400 MHz, chloroform-d) δ: 8.03 (d, J=5.70 Hz, 1H), 7.82 (d, J=1.75 Hz, 1H), 7.56-7.61 (m, 1H), 7.47-7.53 (m, 1H), 6.82 (d, J=5.70 Hz, 1H), 5.33 (br s, 1H), 3.58 (s, 1H) and 3.15 (d, J=4.82 Hz, 3H) ppm.

A mixture of compound 51.5 (2.7 g, 11.4 mmol, 1 eq), N-(t-butoxycarbonyl)pyrrole)-2-boronic acid (2.64 g, 12.53 mmol, 1.1 eq), $Pd(dppf)Cl_2.CH_2Cl_2$ (2.79 g, 3.42 mmol, 0.3 eq), $K_2CO_3$ (9.44 g, 68.33 mmol, 6 eq) in dioxane (28 mL) and $H_2O$ (7 mL) was degassed and purged with $N_2$ 3 times; then the mixture was stirred at 80° C. for 5 hour under $N_2$ atmosphere. The reaction mixture was quenched by addition $H_2O$ (15 mL) and then extracted with EtOAc (15 mL×3). The combined organic layers were washed with

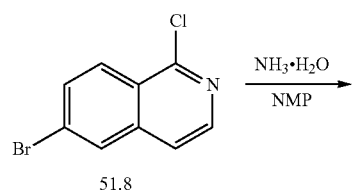

51.8

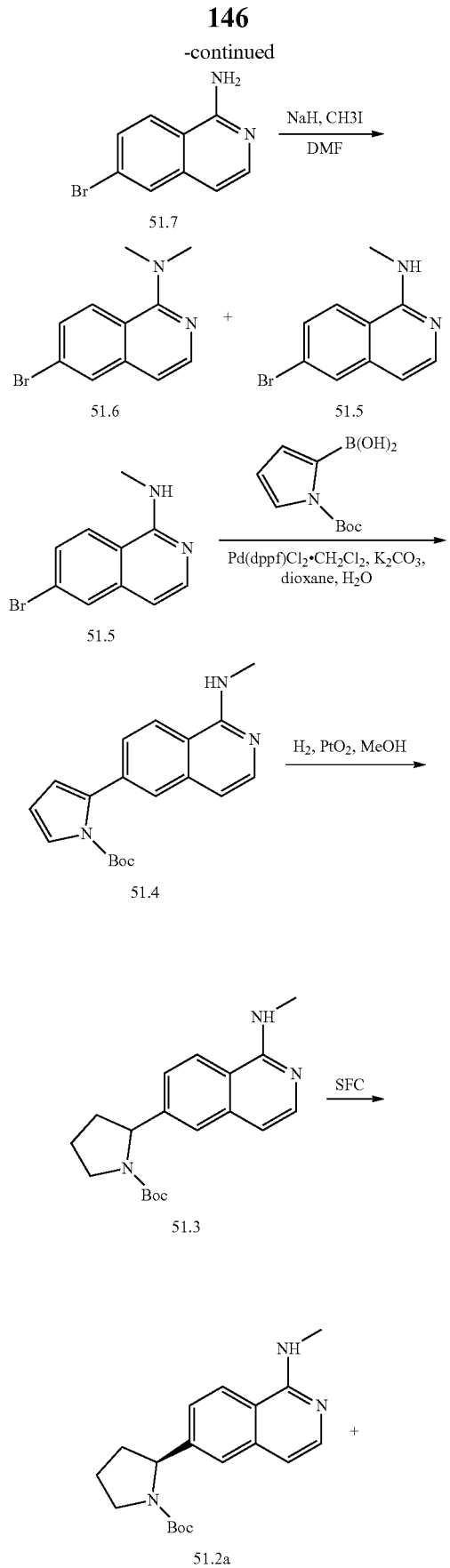

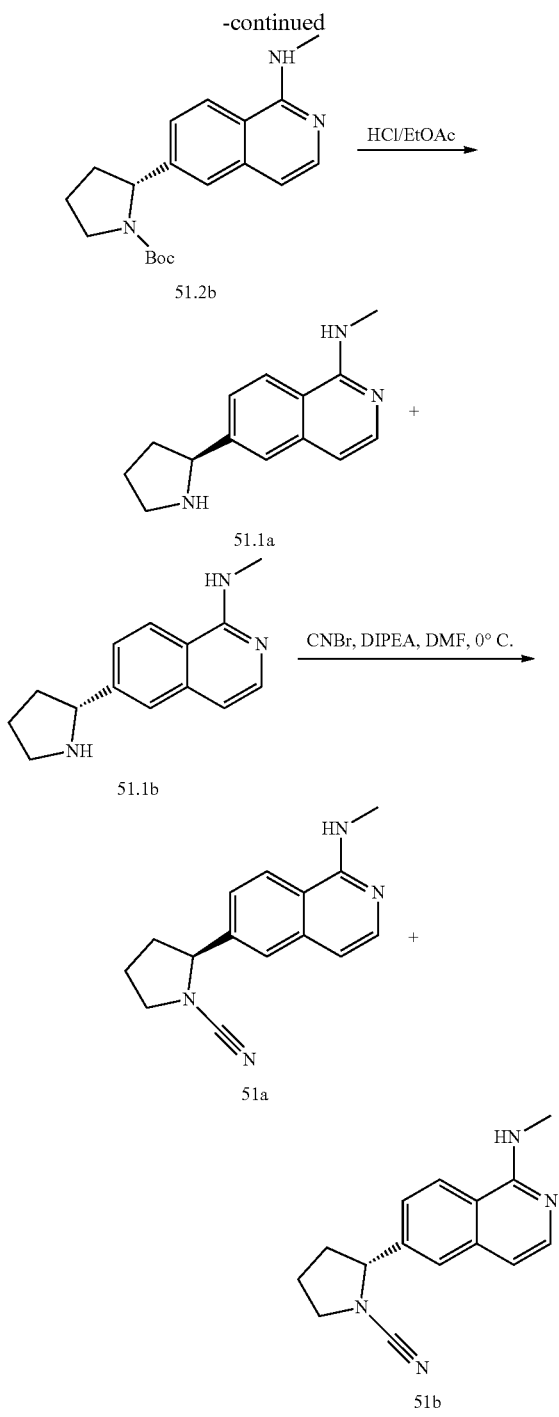

saturated brine (40 mL), dried over Na₂SO₄, filtered and concentrated under reduced pressure to give a residue. The residue was purified by MPLC (SiO₂, petroleum ether/ethyl acetate=10/1 to 1:1) to give compound 51.4 (3.6 g, 11.13 mmol, 98% yield) as a yellow solid. LCMS (ESI) m/z: [M+H] calcd for C₁₉H₂₂N₃O₂: 324; found 324; RT=0.974 min. ¹H NMR (400 MHz, chloroform-d) δ: 8.03 (d, J=5.95 Hz, 1H), 7.62-7.72 (m, 2H), 7.37-7.49 (m, 1H), 7.37-7.49 (m, 1H), 7.37-7.49 (m, 1H), 7.26 (s, 2H), 6.89-6.95 (m, 1H), 6.92 (d, J=5.95 Hz, 1H), 6.23-6.34 (m, 2H), 5.27 (br s, 1H), 3.18 (d, J=4.85 Hz, 3H) and 1.34 (s, 9H) ppm.

To a solution of compound 51.4 (3.60 g, 11.13 mmol, 1 eq) in MeOH (400 mL) was added PtO₂ (252.79 mg, 1.11 mmol, 0.1 eq) under N₂. The suspension was degassed under vacuum and purged with hydrogen gas several times, then was stirred under H₂ (50 psi) at 50° C. for 10 hours. The reaction mixture was filtered; the filtrate was concentrated under reduced pressure to give a residue. The residue was purified by MPLC (SiO₂, petroleum ether/ethyl acetate=10/1 to 1:1) to give compound 51.3 (1.8 g, 4.64 mmol, 38% yield, 84.4% purity) as a white solid. LCMS (ESI) m/z: [M+H] calcd for C₁₉H₂₆N₃O₂: 328; found 328; RT=0.899 min. ¹H NMR (400 MHz, chloroform-d) δ: 8.02 (br d, J=5.38 Hz, 1H), 7.69 (br d, J=8.56 Hz, 1H), 7.43 (d, J=1.34 Hz, 1H), 7.29 (br d, J=1.22 Hz, 1H), 6.88 (d, J=5.87 Hz, 1H), 5.31 (br s, 1H), 4.79-5.12 (m, 1H), 3.69 (br s, 2H), 3.17 (br d, J=4.28 Hz, 3H), 2.39 (br s, 1H), 1.80-2 (m, 4H) and 1.09-1.60 (m, 11H) ppm.

500 mg of compound 51.3 was purified by SFC (column: Chiral Pak IC-H 250×30 5μ; mobile phase: [0.1% NH₃ in H₂O/ETOH]; B %: 40%-40%, 8 min) to give compound 51.2a (188 mg) and compound 51.2b (229 mg) as white solid.

To compound 51.2a (188 mg, 574.18 μmol, 1 eq) was added HCl/EtOAc (4 M, 18.6 mL) the reaction mixture was stirred at 25° C. for 12 h. The reaction mixture was concentrated under reduced pressure to give compound 51.1a (180 mg) as a hydrogen chloride salt. ¹H NMR (400 MHz, METHANOL-d₄) δ: 8.51 (d, J=8.68 Hz, 1H), 8.06 (s, 1H), 7.89 (br d, J=8.44 Hz, 1H), 7.63 (d, J=6.85 Hz, 1H), 7.26 (d, J=6.85 Hz, 1H), 3.45-3.66 (m, 2H), 3.24 (s, 3H), 2.63 (br d, J=8.07 Hz, 1H) and 2.16-2.40 (m, 3H) ppm.

To a solution of 51.1a (30 mg, 113.74 μmol, 1 eq) in DMF (1 mL) was added cyanogen bromide (12.05 mg, 113.74 μmol, 8.37 μL, 1 eq) and DIPEA (29.4 mg, 227.48 mol, 39.62 μL, 2 eq). The mixture was stirred at 0° C. for 1 h. The reaction mixture was filtered, and the organic layers has the desired compound. The residue was purified by semi-preparative scale HPLC (column: Agela Durashell C18 150×25 5μ; mobile phase: [water (10 mM NH₄HCO₃)-ACN]; B %: 20%-60%, 10 min) to give 51a (5 mg, 19.4 μmol, 17% yield, 97.9% purity) as a yellow solid. LCMS (ESI) m/z: [M+H] calcd for C₁₅H₁₇N₄: 253; found 253; RT=2.357 min. ¹H NMR (400 MHz, METHANOL-d₄) δ: 8.10 (d, J=8.60 Hz, 1H), 7.82 (d, J=6.17 Hz, 1H), 7.67 (d, J=1.54 Hz, 1H), 7.48 (dd, J=8.60, 1.76 Hz, 1H), 6.92 (d, J=5.73 Hz, 1H), 4.83-4.88 (m, 1H), 3.81 (dt, J=8.93, 7.22 Hz, 1H), 3.65 (ddd, J=8.93, 7.39, 5.73 Hz, 1H), 3.06 (s, 2H), 2.45 (dq, J=12.43, 6.29 Hz, 1H), 2.04-2.15 (m, 2H) and 1.89-1.99 (m, 1H) ppm.

To compound 51.2b (229 mg, 699.41 μmol, 1 eq) was added HCl/EtOAc (4 M, 22.7 mL) the reaction mixture was stirred at 25° C. for 12 h. The reaction mixture was concentrated under reduced pressure to give compound 51.1b (289 mg) as a hydrogen chloride salt. ¹H NMR (400 MHz, METHANOL-d₄) δ: 8.50 (d, J=8.68 Hz, 1H), 8.05 (d, J=1.47 Hz, 1H), 7.89 (dd, J=8.68, 1.83 Hz, 1H), 7.63 (d, J=6.97 Hz, 1H), 7.26 (d, J=6.97 Hz, 1H), 3.44-3.62 (m, 2H), 3.24 (s, 3H), 2.58-2.67 (m, 1H) and 2.21-2.37 (m, 3H) ppm.

To a solution of compound 51.1b (30 mg, 113.74 μmol, 1 eq) in DMF (1 mL) was added cyanogen bromide (12.05 mg, 113.74 μmol, 8.37 μL, 1 eq) and DIPEA (29.40 mg, 227.48 μmol, 39.62 μL, 2 eq). The mixture was stirred at 0° C. for 1 h. The reaction mixture was filtered, and the organic layers were concentrated. The residue was purified by semi-preparative scale HPLC (column: Agela Durashell C18 150×25 5μ; mobile phase: [water (10 mM NH₄HCO₃)-ACN]; B %: 20%-60%, 10 min) to give 51b (5 mg, 19.7 μmol, 17% yield, 99.4% purity) as a white solid. LCMS (ESI) m/z: [M+H] calcd for C₁₅H₁₇N₄: 253; found 253; RT=2.357 min. ¹H NMR (400 MHz, METHANOL-d4) δ: 8.10 (d, J=8.77 Hz, 1H), 7.82 (d, J=6.14 Hz, 1H), 7.66 (d, J=1.75 Hz, 1H), 7.48 (dd, J=8.77, 1.75 Hz, 1H), 6.92 (d, J=6.14 Hz, 1H), 4.82-4.87 (m, 1H), 3.75-3.86 (m, 1H), 3.60-3.71 (m, 1H), 3.05 (s, 3H), 2.38-2.50 (m, 1H), 2.04-2.17 (m, 2H) and 1.89-1.99 (m, 1H) ppm.

Examples 52a and 52b. Preparation of (S)-2-(1-(dimethylamino)isoquinolin-6-yl)pyrrolidine-1-carbonitrile (52a) and (R)-2-(1-(dimethylamino)isoquinolin-6-yl)pyrrolidine-1-carbonitrile (52b)

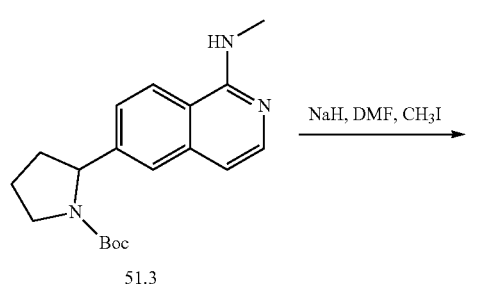

51.3

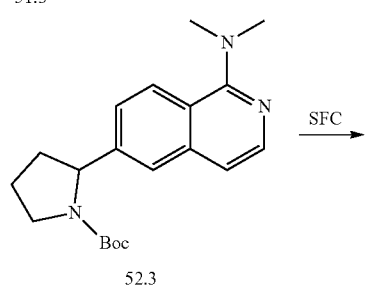

52.3

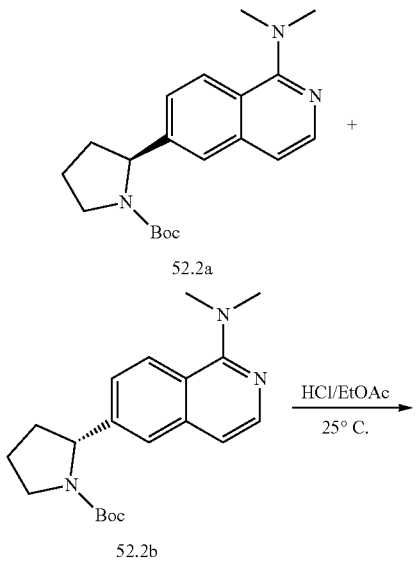

52.2a 52.2b

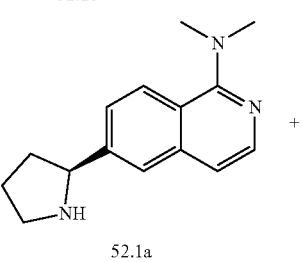

52.1a

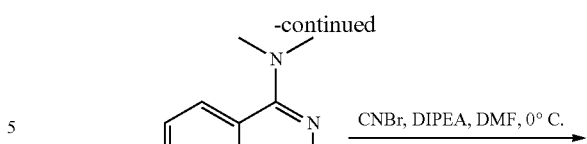

52.1b

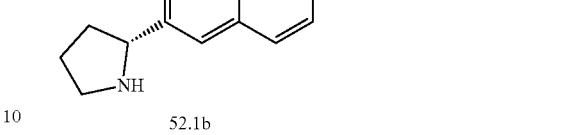

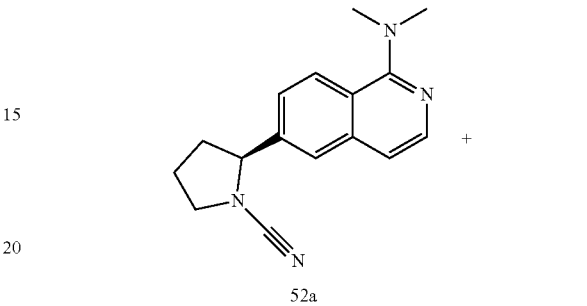

52a

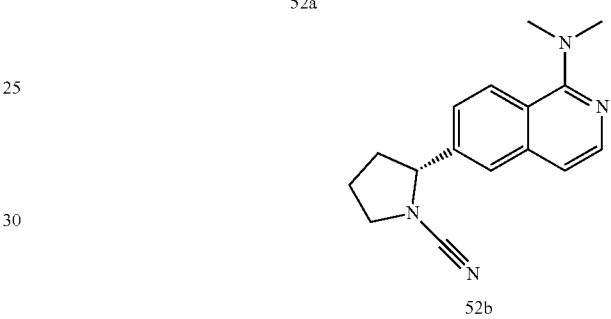

52b

To a solution of compound 51.3 (800 mg, 2.44 mmol, 1 eq) in DMF (8 mL) was added NaH (134.97 mg, 3.37 mmol, 60% purity, 1.38 eq) portion-wise at 0° C. under N$_2$. The mixture was stirred at 0° C. for 30 mins, then to the mixture was added CH$_3$I (478.59 mg, 3.37 mmol, 209.91 μL, 1.38 eq) in one portion, and the mixture was heated to 25° C. and stirred for 15.5 hours. The reaction mixture was quenched by addition H$_2$O (10 mL) and extracted with EtOAc (10 mL×3). The combined organic layers were washed with H$_2$O (10 mL×3), and the combined organic layers were washed with saturated brine (10 mL), dried over Na$_2$SO$_4$, filtered and concentrated under reduced pressure to give a residue. The residue was purified by MPLC (SiO$_2$, petroleum ether/ethyl acetate=10/1 to 1:1) to give compound 52.3 (480 mg, 1.33 mmol, 54% yield, 94.4% purity) as yellow oil. LCMS (ESI) m/z: [M+H] calcd for C$_{20}$H$_{28}$N$_3$O$_2$: 342; found 342; RT=1.170 min. $^1$H NMR (400 MHz, chloroform-d) δ: 8.06 (br d, J=8.60 Hz, 3H), 7.46 (s, 1H), 7.30 (br d, J=8.82 Hz, 2H), 7.10 (d, J=5.73 Hz, 2H), 4.91 (br s, 1H), 3.68 (br s, 3H), 3.09 (br s, 9H), 2.38 (br s, 2H), 1.91 (br t, J=6.06 Hz, 5H), 1.46 (br s, 5H) and 1.13 (br s, 9H) ppm.

Compound 52.3 was purified by SFC (column: Chiral Pak AY-H 250×30 5 t; mobile phase, A: 0.1% NH$_3$H$_2$O in IPA; B: 30%-30%, 5 min) to give compound 52.2a (180 mg) and compound 52.2b (200 mg) as white solid.

To compound 52.2a (180 mg, 527.17 μmol, 1 eq) was added HCl/EtOAc (4 M, 6 mL). The reaction mixture was stirred at 25° C. for 12 h. The reaction mixture was concentrated under reduced pressure to give to give compound 52.1a (189 mg) as a hydrogen chloride salt. $^1$H NMR (400 MHz, METHANOL-d$_4$) δ: 8.62 (d, J=8.80 Hz, 1H), 8.14 (d, J=1.59 Hz, 1H), 7.91 (dd, J=8.86, 1.77 Hz, 1H), 7.71 (d, J=6.85 Hz, 1H), 7.43 (d, J=6.85 Hz, 1H), 3.60 (s, 6H), 3.33 (dt, J=3.24, 1.68 Hz, 2H), 2.60-2.73 (m, 1H), 2.24-2.45 (m, 3H) and 2.04 (s, 1H) ppm.

To a solution of compound 52.1a (30 mg, 108 μmol, 1 eq, HCl) in DMF (1 mL) was added cyanogen bromide (11.44 mg, 108 μmol, 7.94 μL, 1 eq) and DIPEA (27.91 mg, 215.99 μmol, 37.62 μL, 2 eq). The mixture was stirred at 0° C. for 1 h. The reaction mixture was filtered, and the organic layers were concentrated. The residue was purified by semi-preparative scale HPLC (column: Agela Durashell C18 150×25 5μ; mobile phase A: [water (10 mM NH₄HCO₃)-ACN]; B: 25%-65%, 10 min) to give 52a (7 mg, 25.42 μmol, 24% yield, 96.7% purity) as a white solid. LCMS (ESI) m/z: [M+H] calcd for $C_{16}H_{19}N_4$: 267; found 267; RT=2.628 min. ¹H NMR (400 MHz, METHANOL-d₄) δ: 8.21 (d, J=8.82 Hz, 1H), 7.97 (d, J=5.95 Hz, 1H), 7.76 (d, J=1.54 Hz, 1H), 7.53 (dd, J=8.82, 1.76 Hz, 1H), 7.25 (d, J=5.73 Hz, 1H), 4.87-4.90 (m, 1H), 3.81 (dt, J=8.82, 7.28 Hz, 1H), 3.65 (ddd, J=9.04, 7.28, 5.73 Hz, 1H), 3.10 (s, 5H), 3.04-3.14 (m, 1H), 2.39-2.50 (m, 1H), 2.03-2.14 (m, 2H) and 1.94 (dq, J=12.49, 7.60 Hz, 1H) ppm.

To compound 52.2b (200 mg, 585.7 μmol, 1 eq) was added HCl/EtOAc (4 M, 6 mL). The reaction mixture was stirred at 25° C. for 12 h. The reaction mixture was concentrated under reduced pressure to give compound 52.1b (203 mg) as a hydrogen chloride salt. ¹H NMR (400 MHz, METHANOL-d₄) δ: 8.57-8.62 (m, 1H), 8.10-8.13 (m, 1H), 7.85-7.91 (m, 1H), 7.65-7.70 (m, 1H), 7.37-7.43 (m, 1H), 3.57 (s, 6H), 3.34 (s, 1H), 2.56-2.74 (m, 1H) and 2.18-2.42 (m, 3H) ppm.

To a solution of compound 52.1b (30 mg, 108 μmol, 1 eq) in DMF (1 mL) was added cyanogen bromide (11.44 mg, 108 μmol, 7.94 μL, 1 eq) and DIPEA (27.91 mg, 216 mol, 37.62 μL, 2 eq). The mixture was stirred at 0° C. for 1 h. The reaction mixture was filtered, and the organic layers were concentrated to give the residue. The residue was purified by semi-preparative scale HPLC (column: Agela Durashell C18 150×25, 5μ; mobile phase: [water (10 mM NH₄HCO₃)-ACN]; B %: 25%-65%, 10 min) to give 52b (7 mg, 26 μmol, 24% yield, 99.8% purity) as a white solid. LCMS (ESI) m/z: [M+H] calcd for $C_{16}H_{19}N_4$: 267; found 267; RT=2.621 min. ¹H NMR (400 MHz, METHANOL-d₄) δ: 8.22 (d, J=8.77 Hz, 1H), 7.98 (d, J=5.70 Hz, 1H), 7.76 (s, 1H), 7.54 (dd, J=8.55, 1.97 Hz, 1H), 7.26 (d, J=6.14 Hz, 1H), 4.90 (br s, 1H), 3.78-3.86 (m, 1H), 3.61-3.70 (m, 1H), 3.10 (s, 6H), 2.42-2.49 (m, 1H), 2.05-2.15 (m, 1H) and 1.92-2 (m, 1H) ppm.

Example 53. Preparation of N-(1-(6-aminopyridin-3-yl)-3-oxo-4-(2,3,5,6-tetrafluorophenoxy)butan-2-yl)cyclopentanecarboxamide (53)

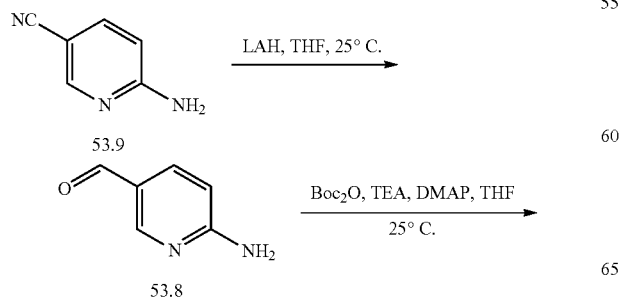

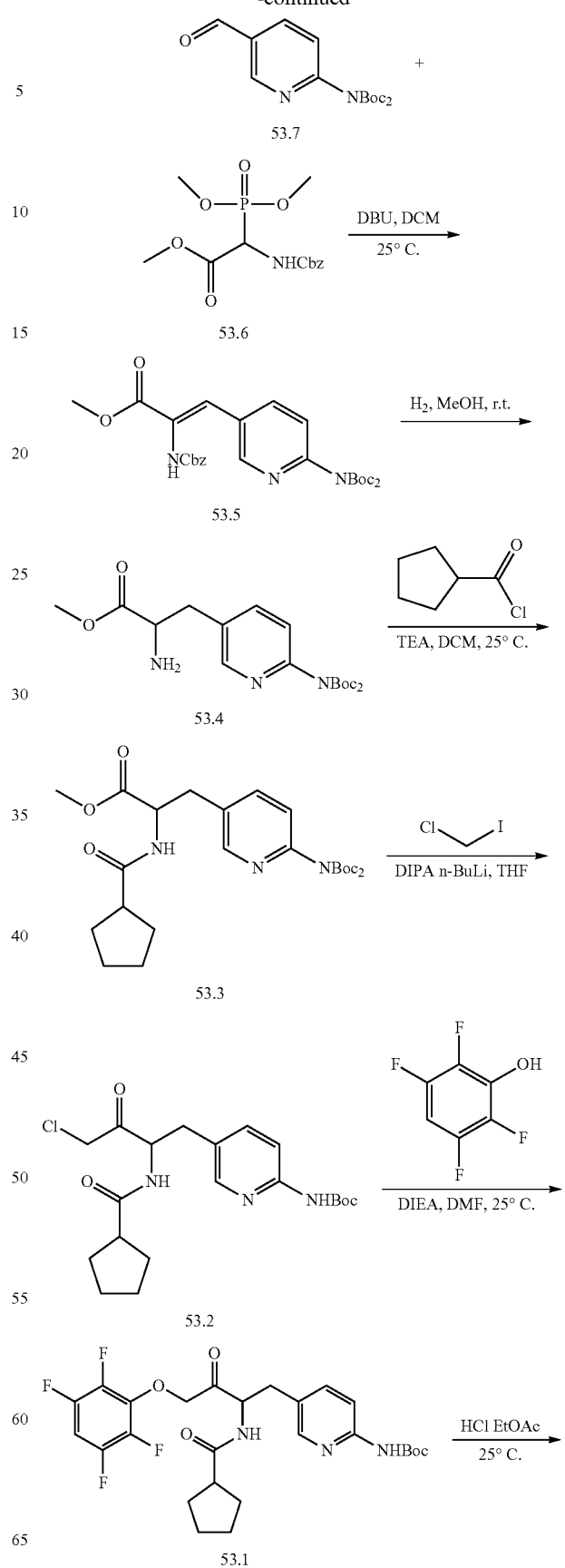

153

-continued

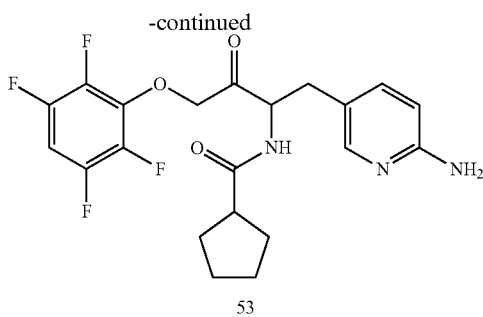

53

To a solution of compound 53.9 (10 g, 83.95 mmol, 1 eq) in THF (150 mL) was added LAH (6.37 g, 167.90 mmol, 2 eq) at 0° C. The mixture was stirred at 0° C. for 1.5 hours. The reaction mixture was quenched by addition saturated sodium sulfate at 0° C. and added 100 ml H$_2$O then extracted with ethyl acetate (100 mL×3). The combined organic layers were washed with saturated brines (30 mL×1), dried over anhydrous sodium sulfate, filtered and concentrated under reduced pressure to give the product compound 53.8 (7.50 g, 61.42 mmol, 73.16% yield) as a yellow oil. LCMS (ESI): m/z: [M+H] called for C$_6$H$_6$N$_2$O: 123; found 123; RT=0.099 min.

To a solution of compound 53.8 (7.50 g, 61.42 mmol, 1 eq) in THF (100 mL) was added TEA (24.86 g, 245.68 mmol, 34.05 mL, 4 eq), Boc$_2$O (40.21 g, 184.26 mmol, 42.33 mL, 3 eq) and DMAP (1.50 g, 12.28 mmol, 0.20 eq). The mixture was stirred at 25° C. for 1.5 hours. The reaction mixture was quenched by addition H$_2$O 100 mL at 25° C. and extracted with ethyl acetate (100 mL×3). The combined organic layers were washed with saturated brines (50 mL×1), dried over anhydrous sodium sulfate, filtered and concentrated under reduced pressure to give a crude product. The residue was purified by column chromatography (SiO$_2$, Petroleum ether/Ethyl acetate=5:1). Compound 53.7 (1.2 g, 3.72 mmol, 6.06% yield) was obtained as a white solid. $^1$H NMR (400 MHz, chloroform-d) δ ppm 1.42-1.61 (m, 21H) 7.66 (d, J=8.38 Hz, 1H) 8.19 (dd, J=8.60, 2.21 Hz, 1H) 8.87 (d, J=2.21 Hz, 1H) 9.98-10.13 (m, 1H).

To a solution of compound 53.7 (1.03 g, 3.10 mmol, 1 eq) in DCM (20 mL) was added DBU (708.40 mg, 4.65 mmol, 701.39 µL, 1.50 eq). The mixture was stirred at 25° C. for 0.5 hr. Then to the mixture was added compound 53.6 (1 g, 3.10 mmol, 1 eq), the mixture was stirred at 25° C. for 0.5 hr. The mixture was concentrated under reduced pressure to give a residue. The residue was purified by column chromatography (SiO$_2$, Petroleum ether/Ethyl acetate=1:1). Compound 53.5 (1 g, 1.90 mmol, 61.15% yield) was obtained as a yellow oil. LCMS (ESI): m/z: [M+H] called for C$_{27}$H$_{33}$N$_3$O$_8$: 528; found 528; RT=0.917 min.

To a solution of compound 53.5 (1 g, 1.90 mmol, 1 eq) in MeOH (10 mL) was added Pd—C (10%, 0.3 g) under N$_2$. The suspension was degassed under vacuum and purged with H$_2$ several times. The mixture was stirred under H$_2$ (50 psi) at 25° C. for 15 hours. The reaction mixture was filtered and the filter was concentrated. Compound 53.4 (1 g, crude) was obtained as a yellow oil. $^1$H NMR (400 MHz, chloroform-d) δ ppm 1.35-1.54 (m, 23H) 2.83-3.13 (m, 2H) 3.70-3.77 (m, 4H) 7.19 (d, J=8.16 Hz, 1H) 7.61 (dd, J=8.16, 2.43 Hz, 1H) 8.33 (d, J=2.21 Hz, 1H). LCMS (ESI): m/z: [M+H] called for C$_{19}$H$_{29}$N$_3$O$_6$: 396; found 396; RT=0.701 min.

To a solution of compound 53.4 (600 mg, 1.52 mmol, 1 eq) in DCM (10 mL) was added TEA (307.06 mg, 3.03

154 mmol, 420.63 µL, 2 eq) and cyclopentanecarbonyl chloride (241.41 mg, 1.82 mmol, 221.48 µL, 1.20 eq). The mixture was stirred at 25° C. for 5 mins. The mixture was concentrated under reduced pressure to give a residue. The residue was purified by column chromatography (SiO$_2$, Petroleum ether/Ethyl acetate=1:1). Compound 53.3 (650 mg, 1.32 mmol, 86.99% yield) was obtained as a yellow oil. LCMS (ESI): m/z: [M+H] called for C$_{25}$H$_{37}$N$_3$O$_7$: 492; found 492; RT=0.866 min.

To a solution of DIPA (349.94 mg, 3.46 mmol, 486.03 µL, 5 eq) in THF (5 mL) was added n-BuLi (2.5 M, 1.38 mL, 5 eq). The mixture was stirred at 0° C. for 0.5 hr under N$_2$. Then the mixture was added to the solution of compound 53.3 (340 mg, 691.0 µmol, 1 eq) and chloroiodomethane (609.96 mg, 3.46 mmol, 251.01 µL, 5 eq) in THF (5 mL) was stirred at −78° C. for 0.5 hr. The reaction mixture was quenched by addition saturated NH$_4$Cl (20 ml) at 25° C. and extracted with ethyl acetate (15 mL×3). The combined organic layers were washed with saturated Na$_2$SO$_3$ (10 mL) and saturated NaHCO$_3$ (10 mL) and saturated brines (10 mL×1), dried over anhydrous sodium sulfate, filtered and concentrated under reduced pressure to give a crude product. Compound 53.2 (500 mg, crude) was obtained as a yellow oil. LCMS (ESI): m/z: [M+H] called for C$_{20}$H$_{28}$N$_3$O$_4$Cl: 410; found 410; RT=0.805 min.

To a solution of compound 53.2 (500 mg, 1.22 mmol, 1 eq) in DMF (5 mL) was added DIEA (472.93 mg, 3.66 mmol, 639.10 µL, 3 eq) and 2, 3, 5, 6-tetrafluorophenol (303.85 mg, 1.83 mmol, 1.50 eq). The mixture was stirred at 25° C. for 15 hours. The reaction mixture was quenched by addition saturated NaHCO$_3$20 mL at 25° C. and extracted with ethyl acetate (20 mL×3). The combined organic layers were washed with saturated brines (10 mL×1), dried over anhydrous sodium sulfate, filtered and concentrated under reduced pressure to give a crude product. The residue was purified by prep-HPLC (TFA condition). Compound 53.1 (50 mg, 74.14 umol, 6.08% yield, 80% purity) was obtained as a yellow solid. LCMS (ESI): m/z: [M+H] called for C$_{26}$H$_{29}$N$_3$O$_5$F$_4$: 540; found 540; RT=1.310 min.

The solution of compound 53.1 (50 mg, 92.67 umol, 1 eq) in HCl/EtOAc (2 mL) was stirred at 25° C. for 15 hours. The mixture was concentrated under reduced pressure to give a residue. The residue was purified by prep-HPLC (TFA condition). Product 53 (5 mg, 11.38 µmol, 12.28% yield) was obtained as a white solid. $^1$H NMR (400 MHz, DMSO-d6) δ ppm 1.31-1.77 (m, 8H) 2.34 (dt, J=3.69, 1.79 Hz, 1H) 2.67-2.71 (m, 1H) 3.01 (dd, J=14.11, 4.41 Hz, 1H) 4.60 (ddd, J=10.20, 8.10, 4.63 Hz, 1H) 5.22 (d, J=2.21 Hz, 2H) 6.89 (d, J=9.04 Hz, 1H) 7.61 (tt, J=10.91, 7.28 Hz, 1H) 7.71 (d, J=1.54 Hz, 1H) 7.79 (br d, J=9.04 Hz, 2H) 8.27 (d, J=8.16 Hz, 1H). LCMS (ESI): m/z: [M+H] called for C$_{21}$H$_{21}$N$_3$O$_3$F$_4$: 440; found 440; RT=2.662 min.

Example 54. Preparation of N-(1-(2-aminopyridin-4-yl)-3-oxo-4-(2,3,5,6-tetrafluorophenoxy)butan-2-yl)cyclopentanecarboxamide (54)

To a solution of compound 54.12 (58 g, 419.92 mmol, 1 eq) in MeOH (600 mL) was added SOCl$_2$ (99.92 g, 839.84 mmol, 60.93 mL, 2 eq) dropwise at 0° C. under N2. The mixture was stirred at 0° C. for 30 mins, then was heated to 18° C. and stirred at 18° C. for 14.5 hours. The reaction mixture was concentrated under reduced pressure to give compound 54.11 (65 g, crude) as a white solid. LCMS (ESI): m/z: [M+H] calcd for C$_1$H$_8$N$_2$O$_2$: 152; found 153; RT=0.100 min.

To a mixture of methyl compound 54.11 (65 g, 427.21 mmol, 1 eq) and DMAP (2.61 g, 21.36 mmol, 0.05 eq) in t-BuOH (500 mL) and ACETONE (150 mL) was added Boc$_2$O (279.72 g, 1.28 mol, 294.44 mL, 3 eq) dropwies at 18° C. under N$_2$. The mixture was stirred at 18° C. for 15 hours. The solution was diluted with pentane (200 ml), cooled in the refrigerator for 3 hours and filtered to obtain compound 54.10 (110 g, 312.16 mmol, 73.07% yield) as a white solid. LCMS (ESI): m/z: [M+H] calcd for C$_{17}$H$_{24}$N$_2$O$_6$: 352; found 353; RT=0.877 min. $^1$H NMR (400 MHz, chloroform-d) δ ppm 1.39-1.50 (m, 19H) 3.97 (s, 3H) 7.77 (dd, J=5.02, 1.38 Hz, 1H) 7.82 (s, 1H) 8.62 (d, J=5.02 Hz, 1H).

To a solution of compound 54.10 (60 g, 170.27 mmol, 1 eq) in THF (1 L) was added LiAlH$_4$ (12.92 g, 340.54 mmol, 2 eq) portionwise at 0° C. under N$_2$. The mixture was stirred at 0° C. for 1 hours, then heated to 18° C. and stirred at 18° C. for 14 hours. The reaction mixture was quenched by addition 8% NaOH (15 ml), filtered and then diluted with H$_2$O 1000 mL and extracted with EtOAc 1500 mL (500 mL×3). The combined organic layers were washed with brine 1000 mL (1000 mL×1), dried over Na$_2$SO$_4$, filtered and concentrated under reduced pressure to give a residue. The residue was purified by column chromatography (SiO2, Petroleum ether/Ethyl acetate=2:1) to give compound 54.9 (15 g, 66.89 mmol, 39.28% yield) as a white solid. LCMS (ESI): m/z: [M+H] calcd for C$_{11}$H$_{16}$N$_2$O$_3$: 293; found 294; RT=0.313 min.

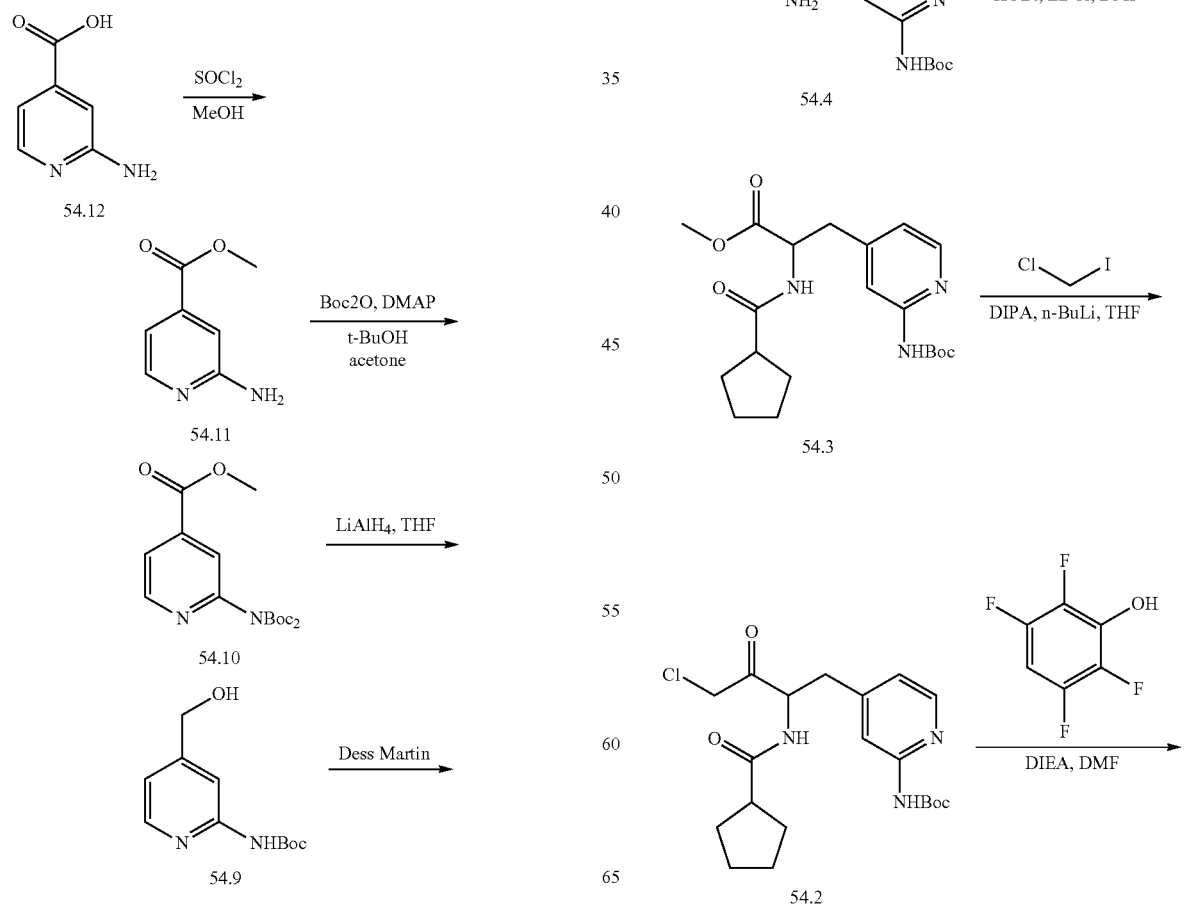

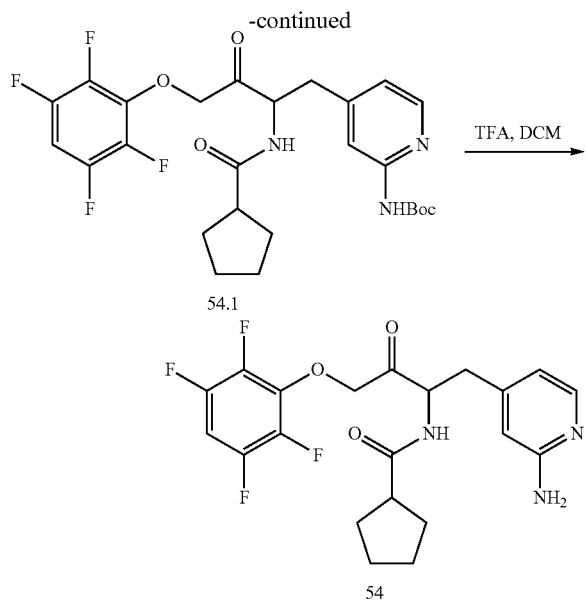

To a solution of compound 54.9 (8 g, 35.67 mmol, 1 eq) in DCM (60 mL) was added Dess-Martin periodinane (18.16 g, 42.81 mmol, 13.25 mL, 1.20 eq) portionwise at 18° C. under $N_2$. The mixture was stirred at 18° C. for 2 hours. The reaction mixture was diluted with $H_2O$ 60 mL and extracted with DCM 150 mL (50 mL×3). The combined organic layers were washed with brine 100 mL (100 mL×1), dried over $Na_2SO_4$, filtered and concentrated under reduced pressure to give a residue. The residue was purified by column chromatography ($SiO_2$, Petroleum ether/Ethyl acetate=5:1) to give compound 54.8 (5.10 g, 22.95 mmol, 64.33% yield) as a white solid. $^1H$ NMR (400 MHz, chloroform-d) δ ppm 1.59 (s, 9H) 7.41 (dd, J=5.08, 1.32 Hz, 1H) 8.48 (s, 1H) 8.52 (d, J=5.15 Hz, 1H) 8.83 (br s, 1H).

To a solution of compound 54.7 (1.49 g, 4.50 mmol, 1 eq) in DCM (15 mL) was added DBU (1.03 g, 6.75 mmol, 1.02 mL, 1.50 eq) in one portion at 18° C. under $N_2$. The mixture was stirred at 18° C. for 0.5 hour, then to the mixture was added compound 54.8 (1 g, 4.50 mmol, 1 eq) in one portion at 18° C., then was stirred at 18° C. for 0.5 hour. The reaction mixture was concentrated under reduced pressure to give a residue. The residue was purified by column chromatography (SiO2, Petroleum ether/Ethyl acetate=1:1) to give compound 54.6 (1.90 g, 4.44 mmol, 98.78% yield) as a white solid.

To a solution compound 54.6 (1 g, 2.34 mmol, 1 eq) in MeOH (50 mL) and THF (50 mL) was added Pd—C (10%, 100 mg) under $N_2$. The suspension was degassed under vacuum and purged with $H_2$ several times. The mixture was stirred under $H_2$ (50 psi) at 20° C. for 15 hours. The reaction mixture was filtered and concentrated under reduced pressure to give compound 54.5 (700 mg, crude) as a white solid. LCMS (ESI): m/z: [M+H] calcd for $C_{14}H_{19}N_3O_4$: 293; found 294; RT=0.638 min.

To a solution of compound 54.5 (600 mg, 2.05 mmol, 1 eq) in MeOH (50 mL) and THF (50 mL) was added Pd—C (10%, 100 mg) under $N_2$. The suspension was degassed under vacuum and purged with $H_2$ several times. The mixture was stirred under $H_2$ (50 psi) at 20° C. for 15 hours. The reaction mixture was filtered and concentrated under reduced pressure to give compound 54.4 (600 mg, crude) as a white solid. LCMS (ESI): m/z: [M+H] calcd for $C_{14}H_{21}N_3O_4$: 295; found 296; RT=0.239 min.

To a mixture of cyclopentanecarboxylic acid (193.24 mg, 1.69 mmol, 184.04 µL, 1 eq) and EDCI (357.01 mg, 1.86 mmol, 1.10 eq) in DMF (10 mL) was added HOBt (251.64 mg, 1.86 mmol, 1.10 eq) in one portion at 0° C. under $N_2$. The mixture was stirred at 0° C. for 1 hour, then the mixture was added dropwise a solution of compound 54.4 (500 mg, 1.69 mmol, 1 eq) in DMF (5 mL), then the mixture was added dropwise DIPEA (656.42 mg, 5.08 mmol, 887.05 µL, 3 eq) and stirred at 0° C. for 1 hour. The reaction mixture was diluted with $H_2O$ 10 mL and extracted with EtOAc 15 mL (5 mL×3). The combined organic layers were washed with brine 15 mL (15 mL×1), dried over $Na_2SO_4$, filtered and concentrated under reduced pressure to give a residue. The residue was purified by column chromatography ($SiO_2$, Petroleum ether/Ethyl acetate=3:1) to give compound 54.3 (600 mg, 1.53 mmol, 90.69% yield) as a white solid. LCMS (ESI): m/z: [M+H] calcd for $C_{20}H_{29}N_3O_5$: 391; found 392; RT=0.681 min. $^1H$ NMR (400 MHz, chloroform-d) δ ppm 1.43-1.62 (m, 9H) 1.66-1.93 (m, 5H) 2.49-2.62 (m, 1H) 3.02-3.12 (m, 1H) 3.14-3.25 (m, 1H) 3.71-3.87 (m, 2H) 4.86-5 (m, 1H) 5.96 (br d, J=7.53 Hz, 1H) 6.72 (d, J=5.02 Hz, 1H) 7.77 (s, 1H) 8 (s, 1H) 8.16 (d, J=5.02 Hz, 1H).

To a solution of DIPA (426.51 mg, 4.21 mmol, 592.38 µL, 5.50 eq) in THF (6 mL) was added n-BuLi (2.5 M, 1.69 mL, 5.50 eq) at 0° C., the mixture was stirred at 0° C. for 30 mins. The mixture was added to a solution of compound 54.3 (300 mg, 766.36 µmol, 1 eq) and chloroiodomethane (675.85 mg, 3.83 mmol, 278.13 µL, 5 eq) in THF (6 mL) at −78° C. The mixture was stirred at −78° C. for 30 mins. The reaction mixture was quenched by addition of saturated aqueous $NH_4Cl$ 5 mL, and then extracted with EtOAc 15 mL (5 mL×3). The combined organic layers were washed with sat. aq. $Na_2SO_3$ 10 mL (10 mL×1), and brine 10 mL (10 mL×1), dried over $Na_2SO_4$, filtered and concentrated under reduced pressure to give compound 54.2 (400 mg, crude) as a white solid.

To a mixture of compound 54.2 (400 mg, 975.82 µmol, 1 eq) and 2,3,5,6-tetrafluorophenol (243.08 mg, 1.46 mmol, 1.50 eq) in DMF (5 mL) was added DIEA (504.46 mg, 3.90 mmol, 681.70 µL, 4 eq) in one portion at 20° C. under $N_2$. The mixture was stirred at 20° C. for 10 hours. The residue was purified by prep-HPLC (neutral condition) to give compound 54.1 (60 mg, 111.21 µmol, 11.40% yield) as a yellow solid. LCMS (ESI): m/z: [M+H] calcd for $C_{26}H_{29}N_3O_5F_4$: 539; found 540; RT=1.306 min.

To a solution of compound 54.1 (60 mg, 111.21 µmol, 1 eq) in DCM (10 mL) was added TFA (3.08 g, 27.01 mmol, 2 mL, 242.90 eq) in one portion at 18° C. under $N_2$. The mixture was stirred at 18 for 15 hours. The reaction mixture was concentrated under reduced pressure to give a residue. The residue was purified by prep-HPLC (TFA condition) to give Product 54 (10 mg, 22.76 µmol, 20.46% yield) as a white solid. LCMS (ESI): m/z: [M+H] calcd for $C_{21}H_{21}N_3O_3F_4$: 439; found 440; RT=2.383 min. $^1H$ NMR (400 MHz, DMSO-d6) ppm 1.40-1.52 (m, 3H) 1.57 (br d, J=6.53 Hz, 3H) 1.63-1.76 (m, 2H) 2.78 (dd, J=13.61, 10.60 Hz, 1H) 3.13 (dd, J=13.61, 4.33 Hz, 1H) 4.65-4.74 (m, 1H) 5.22 (s, 2H) 6.71 (s, 1H) 6.75 (d, J=6.78 Hz, 1H) 7.54-7.70 (m, 1H) 7.88 (br s, 3H) 8.34 (d, J=8.03 Hz, 1H).

Example 55. Preparation of N-(1-(2-aminopyridin-4-yl)-4-(2,6-difluorophenoxy)-3-oxobutan-2-yl)cyclopentanecarboxamide (55)

To a solution of compound 55.12 (58 g, 419.92 mmol, 1 eq) in MeOH (600 mL) was added $SOCl_2$ (99.92 g, 839.84 mmol, 60.93 mL, 2 eq) dropwise at 0° C. under N$_2$. The mixture was stirred at 0° C. for 30 mins, then was heated to 18° C. and stirred at 18° C. for 14.5 hours. The reaction mixture was concentrated under reduced pressure to give compound 55.11 (65 g, crude) as a white solid. LCMS (ESI): m/z: [M+H] calcd for C$_7$H$_8$N$_2$O$_2$: 152; found 153; RT=0.100 min.

To a mixture of compound 55.11 (65 g, 427.21 mmol, 1 eq) and DMAP (2.61 g, 21.36 mmol, 0.05 eq) in t-BuOH (500 mL) and ACETONE (150 mL) was added Boc$_2$O (279.72 g, 1.28 mol, 294.44 mL, 3 eq) dropwies at 18° C. under N$_2$. The mixture was stirred at 18° C. for 15 hours. The solution was diluted with pentane (200 ml), cooled in the refrigerator for 3 hours and filtered to obtain compound 55.10 (110 g, 312.16 mmol, 73.07% yield) as a white solid. LCMS (ESI): m/z: [M+H] calcd for C$_{17}$H$_{24}$N$_2$O$_6$: 352; found 353; RT=0.877 min. $^1$H NMR (400 MHz, chloroform-d) δ ppm 1.39-1.50 (m, 19H) 3.97 (s, 3H) 7.77 (dd, J=5.02, 1.38 Hz, 1H) 7.82 (s, 1H) 8.62 (d, J=5.02 Hz, 1H).

To a solution of compound 55.10 (60 g, 170.27 mmol, 1 eq) in THF (1 L) was added LiAlH$_4$ (12.92 g, 340.54 mmol, 2 eq) portionwise at 0° C. under N$_2$. The mixture was stirred at 0° C. for 1 hour, then heated to 18° C. and stirred at 18° C. for 14 hours. The reaction mixture was quenched by addition 8% NaOH (15 ml), filtered and then diluted with H$_2$O 1000 mL and extracted with EtOAc 1500 mL (500 mL×3). The combined organic layers were washed with brine 1000 mL (1000 mL×1), dried over Na$_2$SO$_4$, filtered and concentrated under reduced pressure to give a residue. The residue was purified by column chromatography (SiO$_2$, Petroleum ether/Ethyl acetate=2:1) to give compound 55.9 (15 g, 66.89 mmol, 39.28% yield) as a white solid. LCMS (ESI): m/z: [M+H] calcd for C$_{11}$H$_{16}$N$_2$O$_3$: 293; found 294; RT=0.313 min.

To a solution of compound 55.9 (8 g, 35.67 mmol, 1 eq) in DCM (60 mL) was added Dess-Martin periodinane (18.16 g, 42.81 mmol, 13.25 mL, 1.20 eq) portionwise at 18° C. under N$_2$. The mixture was stirred at 18° C. for 2 hours. The reaction mixture was diluted with H$_2$O 60 mL and extracted with DCM 150 mL (50 mL×3). The combined organic layers were washed with brine 100 mL (100 mL×1), dried over Na$_2$SO$_4$, filtered and concentrated under reduced pressure to give a residue. The residue was purified by column chromatography (SiO2, Petroleum ether/Ethyl acetate=5:1) to give compound 55.8 (5.10 g, 22.95 mmol, 64.33% yield) as a white solid. $^1$H NMR (400 MHz, chloroform-d) δ ppm 1.59 (s, 9H) 7.41 (dd, J=5.08, 1.32 Hz, 1H) 8.48 (s, 1H) 8.52 (d, J=5.15 Hz, 1H) 8.83 (br s, 1H).

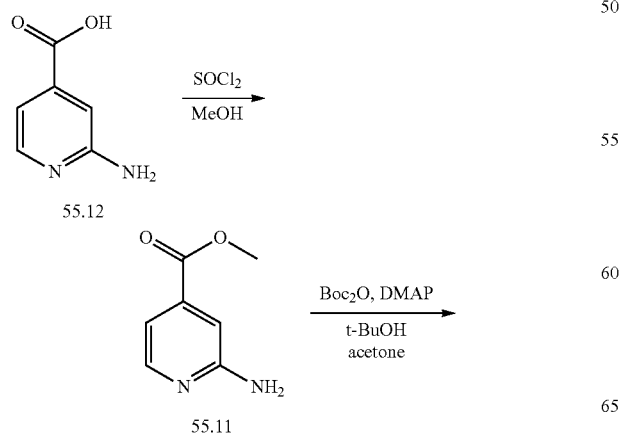

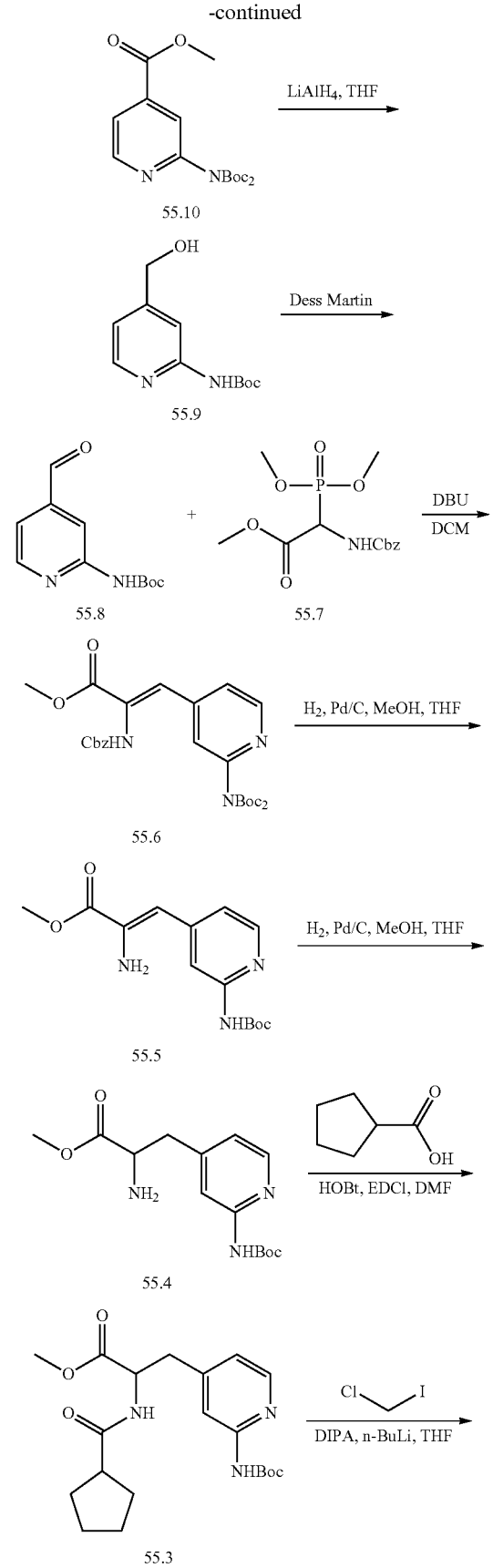

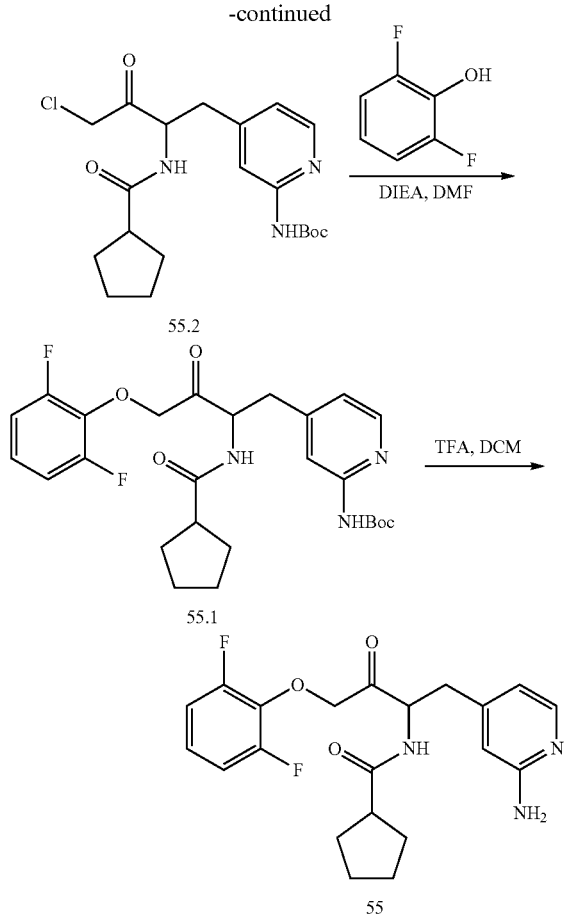

To a solution of compound 55.7 (1.49 g, 4.50 mmol, 1 eq) in DCM (15 mL) was added DBU (1.03 g, 6.75 mmol, 1.02 mL, 1.50 eq) in one portion at 18° C. under $N_2$. The mixture was stirred at 18° C. for 0.5 hour, and then to the mixture was added compound 55.8 (1 g, 4.50 mmol, 1 eq) in one portion at 18° C., then was stirred at 18° C. for 0.5 hour. The reaction mixture was concentrated under reduced pressure to give a residue. The residue was purified by column chromatography ($SiO_2$, Petroleum ether/Ethyl acetate=1:1) to give compound 55.6 (1.90 g, 4.44 mmol, 98.78% yield) as a white solid.

To a solution compound 55.6 (1 g, 2.34 mmol, 1 eq) in MeOH (50 mL) and THF (50 mL) was added Pd—C (10%, 100 mg) under $N_2$. The suspension was degassed under vacuum and purged with $H_2$ several times. The mixture was stirred under $H_2$ (50 psi) at 20° C. for 15 hours. The reaction mixture was filtered and concentrated under reduced pressure to give compound 55.5 (700 mg, crude) as a white solid. LCMS (ESI): m/z: [M+H] calcd for $C_{14}H_{19}N_3O_4$: 293; found 294; RT=0.638 min.

To a solution of compound 55.5 (600 mg, 2.05 mmol, 1 eq) in MeOH (50 mL) and THF (50 mL) was added Pd—C (10%, 100 mg) under $N_2$. The suspension was degassed under vacuum and purged with $H_2$ several times. The mixture was stirred under $H_2$ (50 psi) at 20° C. for 15 hours. The reaction mixture was filtered and concentrated under reduced pressure to give compound 55.4 (600 mg, crude) as a white solid. LCMS (ESI): m/z: [M+H] calcd for $C_{14}H_{21}N_3O_4$: 295; found 296; RT=0.239 min.

To a mixture of cyclopentanecarboxylic acid (193.24 mg, 1.69 mmol, 184.04 μL, 1 eq) and EDCI (357.01 mg, 1.86 mmol, 1.10 eq) in DMF (10 mL) was added HOBt (251.64 mg, 1.86 mmol, 1.10 eq) in one portion at 0° C. under $N_2$. The mixture was stirred at 0° C. for 1 hour, then the mixture was added dropwise a solution of compound 55.4 (500 mg, 1.69 mmol, 1 eq) in DMF (5 mL), then the mixture was added dropwise DIPEA (656.42 mg, 5.08 mmol, 887.05 μL, 3 eq) and stirred at 0° C. for 1 hours. The reaction mixture was diluted with $H_2O$ 10 mL and extracted with EtOAc 15 mL (5 mL×3). The combined organic layers were washed with brine 15 mL (15 mL×1), dried over $Na_2SO_4$, filtered and concentrated under reduced pressure to give a residue. The residue was purified by column chromatography ($SiO_2$, Petroleum ether/Ethyl acetate=3:1) to give compound 55.3 (600 mg, 1.53 mmol, 90.69% yield) as a white solid. LCMS (ESI): m/z: [M+H] calcd for $C_{20}H_{29}N_3O_5$: 391; found 392; RT=0.681 min. $^1$H NMR (400 MHz, chloroform-d) δ ppm 1.43-1.62 (m, 9H) 1.66-1.93 (m, 5H) 2.49-2.62 (m, 1H) 3.02-3.12 (m, 1H) 3.14-3.25 (m, 1H) 3.71-3.87 (m, 2H) 4.86-5 (m, 1H) 5.96 (br d, J=7.53 Hz, 1H) 6.72 (d, J=5.02 Hz, 1H) 7.77 (s, 1H) 8 (s, 1H) 8.16 (d, J=5.02 Hz, 1H).

To a solution of DIPA (426.51 mg, 4.21 mmol, 592.38 μL, 5.50 eq) in THF (10 mL) was added n-BuLi (270.01 mg, 4.21 mmol, 5.50 eq) at 0° C., the mixture was stirred at 0° C. for 30 mins. The mixture was added to a solution of compound 55.3 (300 mg, 766.36 μmol, 1 eq) and chloro(iodo)methane (675.85 mg, 3.83 mmol, 278.13 μL, 5 eq) in THF (10 mL) at −78° C. The mixture was stirred at −78° C. for 30 mins. The reaction mixture was quenched by addition aq sat $NH_4Cl$ 5 mL, and then extracted with EtOAc 15 mL (5 mL×3). The combined organic layers were washed with aq sat $Na_2SO_3$ 10 mL (10 mL×1), and bine 10 mL (10 mL×1), dried over $Na_2SO_4$, filtered and concentrated under reduced pressure to give compound 55.2 (400 mg, crude) as a white solid.

To a mixture of compound 55.2 (400 mg, 975.82 μmol, 1 eq) and 2,6-difluorophenol (126.95 mg, 975.82 μmol, 1 eq) in DMF (5 mL) was added DIEA (504.46 mg, 3.90 mmol, 681.70 μL, 4 eq) in one portion at 20° C. under $N_2$. The mixture was stirred at 20° C. for 10 hours. The residue was purified by prep-HPLC (neutral condition) to give compound 55.1 (60 mg, 119.16 μmol, 12.21% yield) as a white solid. LCMS (ESI): m/z: [M+H] calcd for $C_{26}H_{31}N_3O_5F_2$: 503; found 504; RT=0.804 min.

To a solution of compound 55.1 (60 mg, 119.16 μmol, 1 eq) in DCM (3 mL) was added TFA (1.54 g, 13.51 mmol, 1 mL, 113.35 eq) in one portion at 18° C. under $N_2$. The mixture was stirred at 18° C. for 15 hours. The reaction mixture was concentrated under reduced pressure to give a residue. The residue was purified by prep-HPLC (TFA condition) and SFC (condition: neutral condition) to give product 55 (10 mg, 24.79 μmol, 25% yield) as a white solid. LCMS (ESI): m/z: [M+H] calcd for $C_{21}H_{23}N_3O_3F_2$: 403; found 404; RT=2.518 min. $^1$H NMR (400 MHz, METHANOL-d4) δ ppm 1.46-1.58 (m, 3H) 1.58-1.71 (m, 3H) 1.71-1.85 (m, 2H) 2.56-2.65 (m, 1H) 2.71-2.80 (m, 1H) 3.14 (dd, J=14, 5.40 Hz, 1H) 4.85-5.02 (m, 2H) 6.41-6.55 (m, 2H) 6.93-7.03 (m, 2H) 7.03-7.11 (m, 1H) 7.69-7.79 (m, 1H).

Examples 56, 57, and 58. (S)—N-(1-(6-aminopyridin-3-yl)-3-oxo-4-(2,3,5,6-tetrafluorophenoxy)butan-2-yl)cyclopentanecarboxamide (56); (R)—N-(1-(6-aminopyridin-3-yl)-3-oxo-4-(2,3,5,6-tetrafluorophenoxy)butan-2-yl)cyclopentanecarboxamide (57); and N-(1-(6-aminopyridin-3-yl)-4-(2,6-difluorophenoxy)-3-oxobutan-2-yl)-2-methoxy-2-methylpropanamide (58)

Compounds 56, 57, and 58 were prepared according to the methods described above.

| Compound No. | Structure |
|---|---|
| 56 | 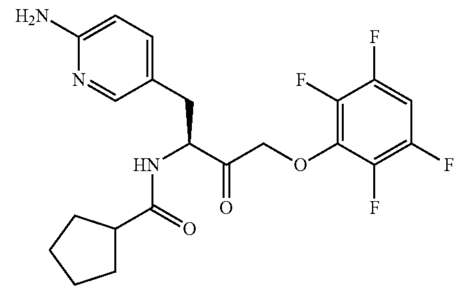 [SMILES: Nc1ccc(C[C@H](NC(=O)C2CCCC2)C(=O)COc2c(F)c(F)cc(F)c2F)cn1] |
| 57 | 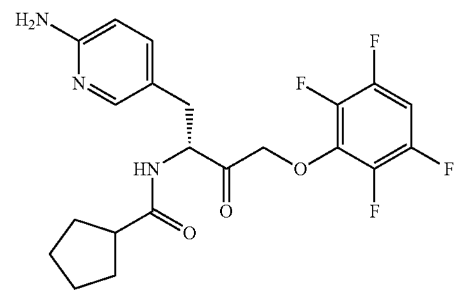 [SMILES: Nc1ccc(C[C@@H](NC(=O)C2CCCC2)C(=O)COc2c(F)c(F)cc(F)c2F)cn1] |
| 58 | 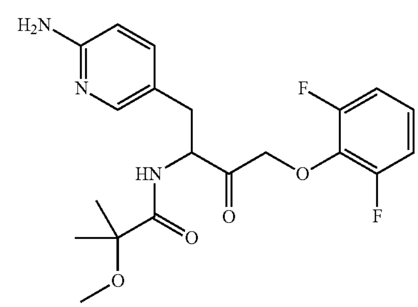 [SMILES: COC(C)(C)C(=O)NC(Cc1ccc(N)nc1)C(=O)COc1c(F)cccc1F] |
Example 59. Preparation of N-(1-(6-aminopyridin-3-yl)-4-(isoxazol-3-yloxy)-3-oxobutan-2-yl)-2-methoxy-2-methylpropanamide (59)
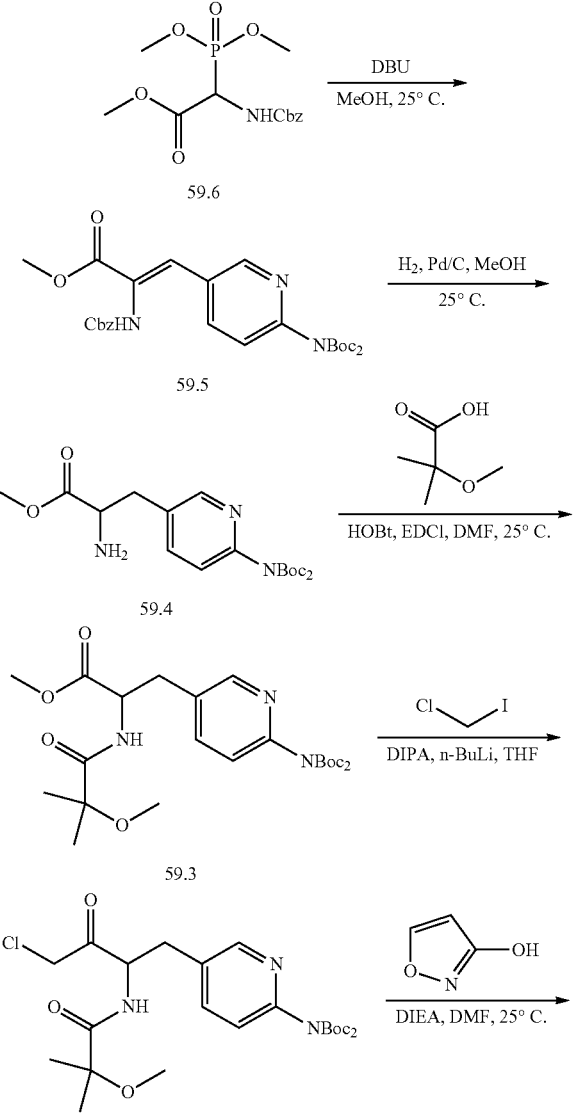
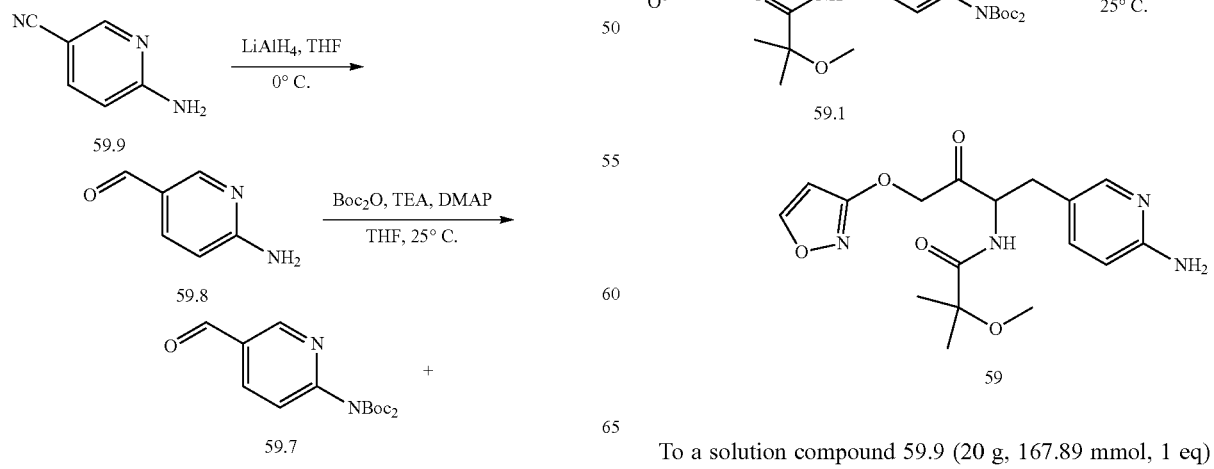
To a solution compound 59.9 (20 g, 167.89 mmol, 1 eq) in THF (500 mL) was added LiAlH$_4$ (12.74 g, 335.78 mmol, 2 eq) portions wise at 0° C. under $N_2$. The mixture was stirred at 0° C. for 2 hours. The reaction mixture was quenched by the addition of $Na_2SO_4.10H_2O$ (30 g) then filtered. The filtrate was diluted with $H_2O$ (200 mL) and extracted with EtOAc (200 mL×3). The combined organic layers were washed with brine (500 mL), dried over $Na_2SO_4$, filtered and concentrated under reduced pressure to give a residue. The residue was purified by column chromatography ($SiO_2$, Petroleum ether/Ethyl acetate=3:1) to give compound 59.8 (10 g, 81.88 mmol, 49% yield) as a yellow solid.

To a mixture of compound 59.8 (10 g, 81.88 mmol, 1 eq) and TEA (33.14 g, 327.53 mmol, 45.59 mL, 4 eq) in THF (150 mL) was added $Boc_2O$ (53.61 g, 245.65 mmol, 56.43 mL, 3 eq) and DMAP (1.60 g, 13.10 mmol, 0.16 eq) in one portion at 25° C. under $N_2$. The mixture was stirred at 25° C. for 10 hours. The reaction mixture was quenched by addition of $Na_2SO_4.10H_2O$ (30 g), then filtered. The filtrate was diluted with $H_2O$ (200 mL) and extracted with EtOAc (200 mL×3). The combined organic layers were washed with brine (500 mL), dried over $Na_2SO_4$, filtered and concentrated under reduced pressure to give a residue. The residue was purified by column chromatography ($SiO_2$, Petroleum ether/Ethyl acetate=2:1) to give compound 59.7 (11 g, 34.12 mmol, 42% yield) as a yellow solid. LCMS (ESI) m/z: [M+H]+ calcd for $C_{16}H_{23}N_2O_5$: 323; found 323; RT=1.537 min. $^1$H NMR (400 MHz, chloroform-d) δ: 1.50 (s, 18H), 7.65 (d, J=8.33 Hz, 1H), 8.18 (dd, J 8.77, 2.19 Hz, 1H), 8.86 (d, J=2.19 Hz, 1H), 10.02-10.10 (m, 1H) ppm.

To a mixture of compound 59.7 (9.5 g, 29.47 mmol, 1 eq) and 59.6 (9.76 g, 29.47 mmol, 1 eq) in DCM (60 mL) was added DBU (8.97 g, 58.94 mmol, 8.88 mL, 2 eq) in one portion at 25° C. under $N_2$. The mixture was stirred at 25° C. for 10 hours. The reaction mixture was quenched by addition $Na_2SO_4.10H_2O$ (30 g), then filtered, and then the filtrate was diluted with $H_2O$ (200 mL) and extracted with EtOAc (200 mL×3). The combined organic layers were washed with brine (500 mL), dried over $Na_2SO_4$, filtered and concentrated under reduced pressure to give a residue. The residue was purified by column chromatography ($SiO_2$, Petroleum ether/Ethyl acetate=2:1) to give compound 59.5 (7 g, 13.27 mmol, 45% yield) as a yellow solid. LCMS (ESI) m/z: [M+H]+ calcd for $C_{27}H_{34}N_3O_8$: 528; found 528; RT=1.60 min.

To a solution of compound 59.5 (7 g, 13.27 mmol, 1 eq) in MeOH (200 mL) was added 10% Pd on carbon catalyst (800 mg) under $N_2$. The suspension was degassed under vacuum and purged with $H_2$ several times. The mixture was stirred under $H_2$ (50 psi) at 25° C. for 10 hours. The reaction mixture was concentrated under reduced pressure to remove solvent. The residue was purified by column chromatography ($SiO_2$, Petroleum ether/Ethyl acetate=3:1) to give compound 59.4 (2.8 g, 7.08 mmol, 53% yield) as a yellow solid. LCMS (ESI) m/z: [M+H]+ calcd for $C_{19}H_{30}N_6O_3$: 396; found 396; RT=1.029 min.

To a mixture of compound 59.4 (836.43 mg, 7.08 mmol, 1 eq) and EDCI (1.63 g, 8.50 mmol, 1.2 eq) in DMF (30 mL) was added HOBt (1.15 g, 8.50 mmol, 1.2 eq) in one portion at 0° C. under $N_2$. The mixture was stirred at 0° C. for 60 min, then the mixture was added 2-methoxy-2-methylpropanoic acid (2.8 g, 7.08 mmol, 1 eq) and DIPEA (2.75 g, 21.24 mmol, 3.70 mL, 3 eq), then the mixture was stirred at 0° C. for 60 mins. The residue was diluted with $H_2O$ (50 mL) and extracted with EtOAc (50 mL×3). The combined organic layers were washed with $H_2O$ (50 mL×3), The combined organic layers were washed with brine (100 mL), dried over $Na_2SO_4$, filtered and concentrated under reduced pressure to give a residue. The residue was purified by column chromatography ($SiO_2$, Petroleum ether/Ethyl acetate=3:1) to give compound 59.3 (3 g, 6.05 mmol, 86% yield) as yellow oil. LCMS (ESI): m/z: [M+H-Boc] calcd for $C_{19}H_{30}N_3O_6$: 496; found 396; RT=1.516 min.

To a solution of DIPA (1.80 g, 17.76 mmol, 2.51 mL, 5.5 eq) in THF (50 mL) was added n-BuLi (2.5 M, 7.10 mL, 5.5 eq) at 0° C., the mixture was stirred at 0° C. for 30 mins. To the mixture was added a solution of compound 59.3 (1.6 g, 3.23 mmol, 1 eq) and chloroiodomethane (3.13 g, 17.76 mmol, 1.29 mL, 5.5 eq) in THF (50 mL) at −78° C., then added DIPA (1.80 g, 17.76 mmol, 2.51 mL, 5.5 eq) at −78° C. The mixture was stirred at −78° C. for 3 h. The residue was diluted with $H_2O$ (50 mL) and extracted with EtOAc (50 mL×3). The combined organic layers were washed with $H_2O$ (50 mL×3), The combined organic layers were washed with brine (100 mL), dried over $Na_2SO_4$, filtered and concentrated under reduced pressure to give a residue. The residue was purified by column chromatography ($SiO_2$, Petroleum ether/Ethyl acetate=3:1) to give compound 59.2 (100 mg, 194.55 μmol, 6% yield) as a white solid. LCMS (ESI) m/z: [M+H]+ calcd for $C_{24}H_{37}N_3O_7Cl$: 514; found 514; RT=1.414 min.

To a mixture of compound 59.2 (100 mg, 194.55 μmol, 1 eq) and isoxazol-3-ol (16.55 mg, 194.55 μmol, 1 eq) in DMF (2 mL) was added DIPEA (75.43 mg, 583.65 μmol, 101.66 μL, 3 eq) in one portion at 25° C. under $N_2$. The mixture was stirred at 25° C. for 10 hours. The residue was diluted with $H_2O$ (50 mL) and extracted with EtOAc (50 mL×3). The combined organic layers were washed with $H_2O$ (50 mL×3); the combined organic layers were washed with brine (100 mL), dried over $Na_2SO_4$, filtered and concentrated under reduced pressure to give a residue. The residue was purified by column chromatography ($SiO_2$, Petroleum ether/Ethyl acetate=3:1) to give compound 59.1 (150 mg) as a white solid. LCMS (ESI) m/z: [M+H-Boc] called for $C_{22}H_{31}N_4O_7$: 563; found 463; RT=0.937 min.

To a solution of compound 59.1 (300 mg, 533.23 μmol, 1 eq) in DCM (5 mL) was added TFA (533.23 μmol, 40 μL, 1 eq) in one portion at 25° C. under $N_2$. The mixture was stirred at 25° C. for 30 mins. The residue was diluted with $H_2O$ (50 mL) and extracted with EtOAc (50 mL×3). The combined organic layers were washed with $H_2O$ (50 mL×3) then washed with brine (100 mL), dried over $Na_2SO_4$, filtered and concentrated under reduced pressure to give a residue. The residue was purified by column chromatography ($SiO_2$, Petroleum ether/Ethyl acetate=3:1) to give 59 (20 mg) as a white solid. LCMS (ESI) m/z: [M+H]+ calcd for $C_{17}H_{23}N_4O_5$: 363; found 363; RT=2.357 min. $^1$H NMR (400 MHz, METHANOL-d4) δ: 1.23 (s, 3H), 1.33 (s, 3H), 2.84 (dd, J 14.55, 9.66 Hz, 1H), 3.21-3.28 (m, 4H), 4.83-4.83 (m, 1H), 5.06 (d, J=1.22 Hz, 2H), 6.18 (d, J=1.83 Hz, 1H), 6.92-6.98 (m, 1H), 7.67 (d, J=1.47 Hz, 1H), 7.88 (dd, J=9.17, 2.08 Hz, 1H) and 8.39 (d, J=1.83 Hz, 1H) ppm.

Example 60. Preparation of N-(1-(6-aminopyridin-3-yl)-3-oxo-4-(2,3,5,6-tetrafluorophenoxy)butan-2-yl)-2-methoxy-2-methylpropanamide (60)

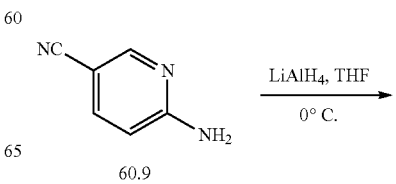

60.9

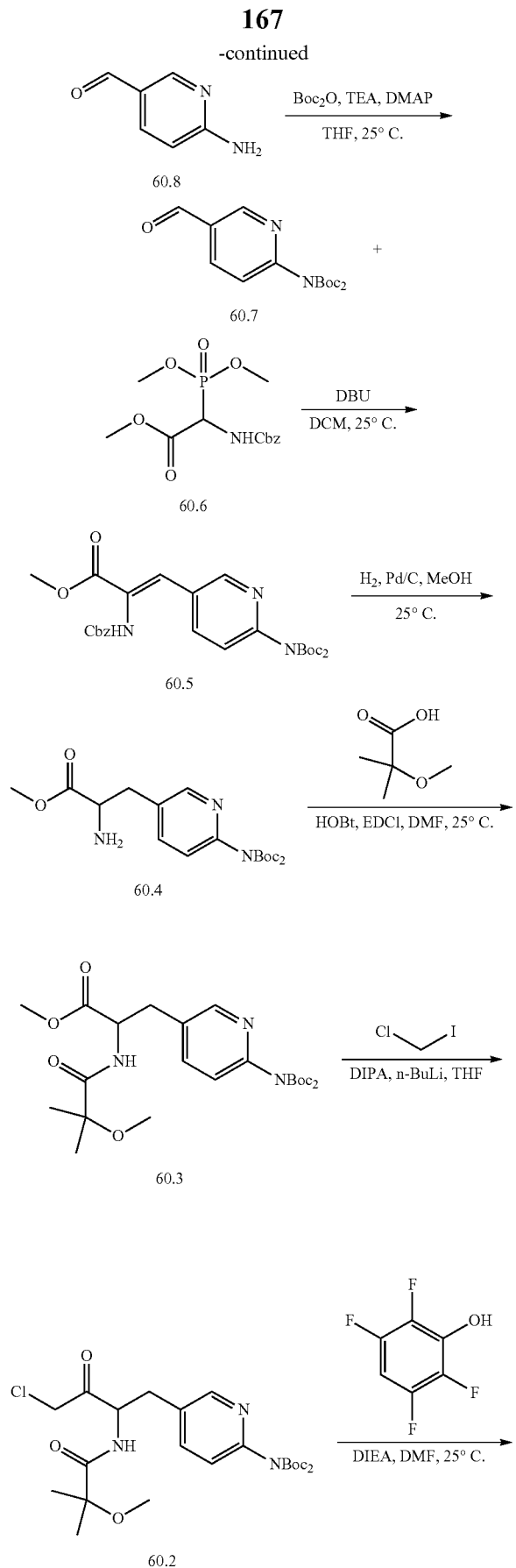

To a solution of compound 60.9 (10 g, 83.95 mmol, 1 eq) in THF (300 mL) was added LAH (6.37 g, 167.9 mmol, 2 eq) at 0° C. The mixture was stirred at 0° C. for 1.5 hour. The reaction mixture was quenched by addition of saturated sodium sulfate at 0° C. and added 300 mL of $H_2O$ then extracted with ethyl acetate (300 mL×3). The combined organic layers were washed with saturated brine (30 mL), dried over anhydrous sodium sulfate, filtered and concentrated under reduced pressure to give compound 60.8 (10 g, crude) as a yellow solid.

To a solution of compound 60.8 (10 g, 81.9 mmol, 1 eq) in THF (200 mL) was added TEA (33.14 g, 327.6 mmol, 45.4 mL, 4 eq), $Boc_2O$ (53.62 g, 245.67 mmol, 56.44 mL, 3 eq) and DMAP (2 g, 16.38 mmol, 0.2 eq). The mixture was stirred at 25° C. for 15 hours. The reaction mixture was quenched by addition $H_2O$ (300 mL) at 25° C. and extracted with ethyl acetate (300 mL×3). The combined organic layers were washed with saturated brine (50 mL), dried over anhydrous sodium sulfate, filtered and concentrated under reduced pressure to give a crude product. The residue was purified by column chromatography ($SiO_2$, Petroleum ether/Ethyl acetate=2:1) to give compound 60.7 (4 g, 12.41 mmol, 15% yield) as a yellow solid. LCMS (ESI) m/z: [M+H]+ calcd for $C_{16}H_{22}N_2O_5$: 323; found 167; RT=1.537 min.

To a solution of compound 60.7 (1 g, 3.1 mmol, 1 eq) in DCM (30 mL) was added DBU (944.53 mg, 6.20 mmol, 935.18 µL, 2 eq) and compound 60.6 (1.03 g, 3.1 mmol, 1 eq). The mixture was stirred at 25° C. for 1 hour. The reaction mixture was quenched by addition $H_2O$ (100 mL) at 25° C. and extracted with ethyl acetate (100 mL×3). The combined organic layers were washed with saturated brines (5 mL), dried over anhydrous sodium sulfate, filtered and concentrated under reduced pressure to give a crude product. The residue was purified by column chromatography ($SiO_2$, Petroleum ether/Ethyl acetate=2:1) to give compound 60.5 (2.6 g, 4.9 mmol, 79% yield) as yellow oil. LCMS (ESI) m/z: [M+H]+ calcd for $C_{27}H_{33}N_3O_8$: 528; found 528; RT=1.612 min.

To a solution of compound 60.5 (2.6 g, 4.93 mmol, 1 eq) in MeOH (200 mL) was added 10% palladium on carbon (1 g) under $N_2$. The suspension was degassed under vacuum and purged with $H_2$ several times. The mixture was stirred under $H_2$ (50 psi) at 25° C. for 15 hours. The reaction mixture was filtered, and the filter was concentrated to give compound 60.4 (900 mg, 2.28 mmol, 46% yield) as yellow oil. LCMS (ESI) m/z: [M+H]+ calcd for $C_{19}H_{29}N_3O_6$: 396; found 396; RT=1.161 min.

To a solution of 2-methoxy-2-methylpropanoic acid (268.85 mg, 2.28 mmol, 1 eq) in DMF (15 mL) was added HOBt (338.3 mg, 2.5 mmol, 1.1 eq) and EDCI (479.9 mg, 2.5 mmol, 1.1 eq). The mixture was stirred at 25° C. for 1 hr. To this mixture was added compound 60.4 (900 mg, 2.28 mmol, 1 eq) and DIPEA (1.18 g, 9.1 mmol, 1.6 mL, 4 eq). The mixture was stirred at 25° C. for 14 hours. The reaction mixture was quenched by addition H₂O (30 mL) at 25° C. and extracted with ethyl acetate (30 mL×3). The combined organic layers were washed with saturated brines (5 mL), dried over anhydrous sodium sulfate, filtered and concentrated under reduced pressure to give a crude product. The residue was purified by column chromatography (SiO₂, Petroleum ether/Ethyl acetate=2:1) to give compound 60.3 (960 mg, 1.94 mmol, 85% yield) as yellow oil. LCMS (ESI) m/z: [M+H]+ calcd for $C_{24}H_{37}N_3O_8$: 496; found 496; RT=1.487 min. ¹H NMR (400 MHz, chloroform-d) δ: 1.35 (d, J=8.38 Hz, 6H), 1.43 (s, 19H), 3.06-3.31 (m, 5H), 3.74 (s, 3H), 4.72-4.97 (m, 1H), 7.09-7.21 (m, 2H), 7.53 (dd, J=8.16, 2.21 Hz, 1H) and 8.24 (d, J=2.20 Hz, 1H) ppm.

To a solution of DIPA (842.3 mg, 8.32 mmol, 1.18 mL, 5.5 eq) in THF (5 mL) was added n-BuLi (2.5 M, 3.33 mL, 5.5 eq) then was stirred at 0° C. for 0.5 hr under N₂. Then to the mixture was added to the solution of compound 60.3 (750 mg, 1.51 mmol, 1 eq) and chloroiodomethane (1.47 g, 8.32 mmol, 604.19 μL, 5.5 eq) in THF (15 mL) was stirred at −78° C. for 2.5 hours. The reaction mixture was quenched by addition of saturated NH₄Cl (20 mL) at 25° C. and extracted with ethyl acetate (15 mL×3). The combined organic layers were washed with saturated Na₂SO₃ (10 mL) and saturated NaHCO₃ (10 mL) and saturated brine (10 mL), dried over anhydrous sodium sulfate, filtered and concentrated under reduced pressure to give a crude product. The residue was purified by column chromatography (SiO2, Petroleum ether/Ethyl acetate=2:1) to give compound 60.2 (50 mg, 97.3 μmol, 6% yield) as yellow oil. LCMS (ESI) m/z: [M+H]+ calcd for $C_{24}H_{36}N_3O_7Cl$: 514; found 414; RT=1.253 min.

To a solution of compound 60.2 (40 mg, 77.8 μmol, 1 eq) in DMF (2 mL) was added DIEA (30.17 mg, 233.5 μmol, 40.7 μL, 3 eq) and 2,3,5,6-tetrafluorophenol (19.4 mg, 116.73 μmol, 1.5 eq). The mixture was stirred at 25° C. for 12 hours. The reaction mixture was quenched by addition H₂O (10 mL) at 25° C. and extracted with ethyl acetate (10 mL×3). The combined organic layers were washed with saturated brine (5 mL), dried over anhydrous sodium sulfate, filtered and concentrated under reduced pressure to give a crude product. The residue was purified by column chromatography (SiO₂, Petroleum ether/Ethyl acetate=1:1) to give compound 60.1 (20 mg, 31.07 μmol, 40% yield) as a white solid. LCMS (ESI) m/z: [M+H]+ calcd for $C_{30}H_{37}N_3O_8F_4$: 644; found 544; RT=1.402 min.

A mixture of compound 60.1 (20 mg, 31.07 μmol, 1 eq) in TFA (1 mL) and DCM (5 mL) was stirred at 25° C. for 15 hours. The mixture was concentrated under reduced pressure to give a residue. The residue was purified by prep-HPLC (neutral condition) to give 60 (10 mg, 22.55 μmol, 73% yield) as a white solid. LCMS (ESI) m/z: [M+H]+* calcd for $C_{20}H_{21}N_3O_4F_4$: 444; found 444; RT=1.68 min. ¹H NMR (400 MHz, METHANOL-d₄) δ: 1.15-1.33 (m, 6H), 2.72-2.90 (m, 1H), 3.04-3.23 (m, 4H), 4.94-5 (m, 1H), 5.02-5.25 (m, 2H), 6.53 (br d, J=8.16 Hz, 1H), 7.12 (br s, 1H), 7.37 (br d, J=7.50 Hz, 1H) and 7.65-7.78 (m, 1H) ppm.

Example 61. Preparation of N-(1-(6-aminopyridin-3-yl)-3-oxo-4-(2,3,6-trifluorophenoxy)butan-2-yl)-2-methoxy-2-methylpropanamide (61)

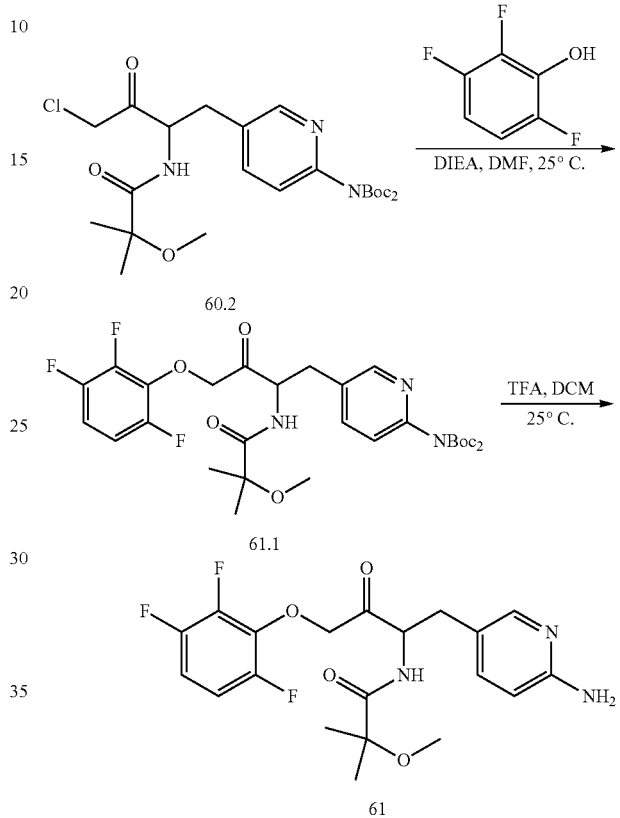

To a solution of compound 60.2 (50 mg, 97.3 μmol, 1 eq) in DMF (3 mL) was added DIEA (37.72 mg, 291.82 μmol, 50.83 μL, 3 eq) and 2,3,6-trifluorophenol (28.81 mg, 194.55 μmol, 2 eq). The mixture was stirred at 25° C. for 15 hours. The reaction mixture was quenched by addition H₂O (10 mL) at 25° C. and extracted with ethyl acetate (10 mL×3). The combined organic layers were washed with saturated brine (5 mL), dried over anhydrous sodium sulfate, filtered and concentrated under reduced pressure to give a crude product. The residue was purified by column chromatography (SiO₂, Petroleum ether/Ethyl acetate=1:1) to give compound 61.1 (15 mg, 24 μmol, 25% yield) as yellow oil. LCMS (ESI) m/z: [M+H]+ calcd for $C_{30}H_{38}Na_3O_8F_8$: 626; found 526; RT=1.389 min.

A mixture of compound 61.1 (40 mg, 63.94 μmol, 1 eq) in TFA (1 mL) and DCM (5 mL) was stirred at 25° C. for 1 hr. The mixture was concentrated under reduced pressure to give a residue. The residue was purified by semi-preparative scale HPLC (TFA condition) to give 61 (3 mg, 7.1 μmol, 11% yield) as a yellow solid. LCMS (ESI) m/z: [M+H]+ calcd for $C_{20}H_{22}N_3O_4F_3$: 426; found 426; RT=1.664 min. ¹H NMR (400 MHz, DMSO-d6) δ: 1.10 (s, 3H), 1.21 (s, 3H), 2.69-2.79 (m, 1H), 2.94 (br dd, J=14.06, 4.16 Hz, 1H), 3.01 (s, 3H), 4.47-4.65 (m, 1H), 4.98-5.30 (m, 2H), 5.70 (s, 2H), 6.32 (d, J=8.31 Hz, 1H), 7.19 (td, J=9.35, 6.72 Hz, 3H), 7.71 (s, 1H) and 8.07 (br d, J=8.31 Hz, 1H) ppm.

171

Example 62. Preparation of N-(1-(6-aminopyridin-3-yl)-3-oxo-4-(2,3,6-trifluorophenoxy)butan-2-yl)-2-methoxy-2-methylpropanamide (62)

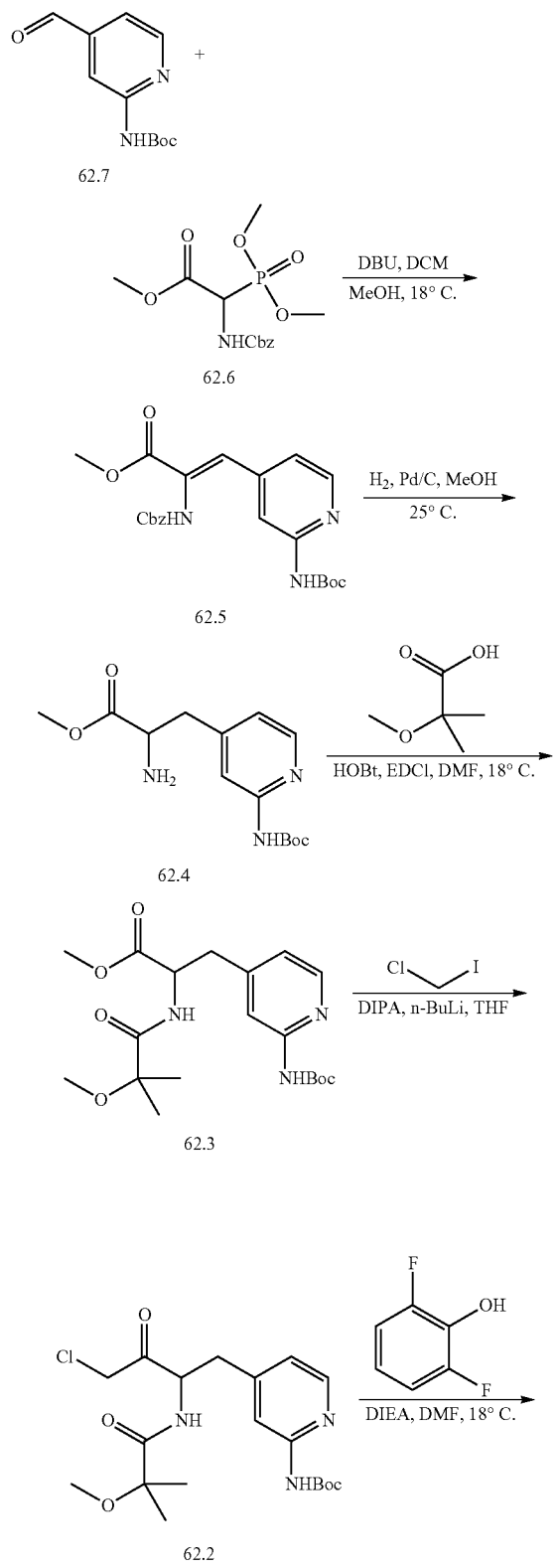

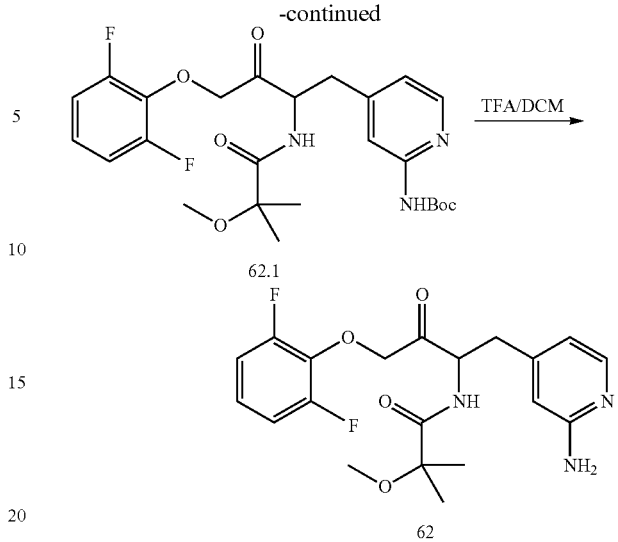

To a mixture of compound 62.7 (1.4 g, 6.3 mmol, 1 eq) and compound 62.6 (2.09 g, 6.3 mmol, 1 eq) in DCM (30 mL) was added DBU (1.92 g, 12.6 mmol, 1.9 mL, 2 eq) in one portion at 18° C. under $N_2$. The mixture was stirred at 18° C. for 1 hour. The reaction mixture was concentrated under reduced pressure to give a residue. This was purified by column chromatography ($SiO_2$, Petroleum ether/Ethyl acetate=2:1) to give compound 62.5 (1.2 g, 2.81 mmol, 44.6% yield) as a white solid.

To a solution of compound 62.5 (1 g, 2.34 mmol, 1 eq) in MeOH (20 mL) was added Pd—C (10% palladium on carbon, 100 mg) under $N_2$. The suspension was degassed under vacuum and purged with $H_2$ several times. The mixture was stirred under $H_2$ (50 psi) at 25° C. for 10 hours. The reaction mixture was filtered and concentrated under reduced pressure to give a residue. The residue was purified by column chromatography ($SiO_2$, Ethyl acetate) to give compound 62.4 (270 mg, 914.2 μmol, 39.1% yield) as a white solid.

To a mixture of 2-methoxy-2-methylpropanoic acid (129.6 mg, 1.1 mmol, 1.2 eq) and EDCI (210.31 mg, 1.1 mmol, 1.2 eq) in DMF (5 mL) was added HOBt (148.24 mg, 1.1 mmol, 1.2 eq) in one portion at 18° C. under $N_2$. The mixture was stirred at 18° C. for 30 mins, then compound 62.4 (270 mg, 914.22 μmol, 1 eq) and DIPEA (354.47 mg, 2.74 mmol, 477.7 μL, 3 eq) were added in one portion, the mixture was stirred at 18° C. for 30 mins. The reaction mixture was diluted with $H_2O$ (5 mL) and extracted with EtOAc (3 mL×3). The combined organic layers were washed with brine (10 mL), dried over $Na_2SO_4$, filtered and concentrated under reduced pressure. This residue was purified by column chromatography ($SiO_2$, Petroleum ether/Ethyl acetate=2:1) to give compound 62.3 (250 mg, 632.2 μmol, 69.2% yield) as a white solid. LCMS (ESI) m/z: [M+H]+ calcd. for $C_{19}H_{29}N_3O_6$: 395; found 396; RT=0.88 min. $^1H$ NMR (400 MHz, DMSO-d6) δ: 1.12 (s, 3H), 1.20 (s, 3H), 1.47 (s, 9H), 3.05 (s, 3H), 3.06-3.15 (m, 2H), 3.66 (s, 3H), 4.49-4.61 (m, 1H), 6.90 (dd, J=5.07, 1.28 Hz, 1H), 7.71 (s, 1H), 8.02-8.16 (m, 2H) and 9.68 (s, 1H) ppm.

To a solution of DIPA (351.8 mg, 3.5 mmol, 491.4 μL, 5.5 eq) in THF (5 mL) was added n-BuLi (2.5 M, 1.4 mL, 5.5 eq) at 0° C., the mixture was stirred at 0° C. for 30 mins. To the mixture was added a solution of compound 62.3 (250 mg, 632.2 μmol, 1 eq) and chloroiodomethane (613.3 mg, 3.48 mmol, 252.4 μL, 5.5 eq) in THF (5 mL) at −78 OC. The mixture was stirred at −78° C. for 30 minutes. The reaction mixture was quenched by addition of aqueous saturated NH$_4$Cl (5 mL) and extracted with EtOAc (2 mL×3). The combined organic layers were washed with aqueous saturated Na$_2$SO$_3$ (3 mL) and brine (5 mL), dried over Na$_2$SO$_4$, filtered and concentrated under reduced pressure to give compound 62.2 (400 mg, crude) as yellow oil. LCMS (ESI) m/z: [M+H]+ calcd. for C$_{19}$H$_{28}$N$_3$O$_5$Cl: 413; found 414; RT=1.2 min.

To a mixture of compound 62.2 (400 mg, 966.4 μmol, 1 eq) and 2,6-difluorophenol (125.7 mg, 966.4 μmol, 1 eq) in DMF (2 mL) was added DIEA (374.71 mg, 2.9 mmol, 505 L, 3 eq) in one portion at 18° C. under N$_2$. The mixture was stirred at 18° C. for 10 hours. The residue was purified by prep-HPLC (neutral condition) to give compound 62.1 (20 mg, 39.4 μmol, 4.1% yield) as a white solid. LCMS (ESI) m/z: [M+H]+ calcd for C$_{25}$H$_{31}$N$_3$O$_6$F$_2$: 507; found 508; RT=1.076 min.

To a solution of compound 62.1 (20 mg, 39.41 μmol, 1 eq) in DCM (5 mL) was added TFA (1 mL) in one portion at 18° C. under N$_2$. The mixture was stirred at 18° C. for 10 hours. The reaction mixture was concentrated under reduced pressure to give 62 (8 mg, 19.6 μmol, 50% yield) as a yellow solid. LCMS (ESI) m/z: [M+H]+ calcd. for C$_{20}$H$_{23}$N$_3$O$_4$F$_2$: 407; found 408; RT=2.41 min. $^1$H NMR (400 MHz, DMSO-d6) δ: 1.11 (s, 3H), 1.21 (s, 3H), 2.84-2.94 (m, 1H), 3.04 (s, 3H), 3.16-3.24 (m, 1H), 4.75-4.85 (m, 1H), 4.97-5.16 (m, 2H), 6.74 (s, 1H), 6.79 (d, J=6.58 Hz, 1H), 7.05-7.18 (m, 3H), 7.85 (d, J=6.58 Hz, 1H), 8.04 (br s, 2H) and 8.35 (d, J=8.77 Hz, 1H) ppm.

Example 63. Preparation of N-(1-(2-aminopyridin-4-yl)-4-(isoxazol-3-yloxy)-3-oxobutan-2-yl)-2-methoxy-2-methylpropanamide (63)

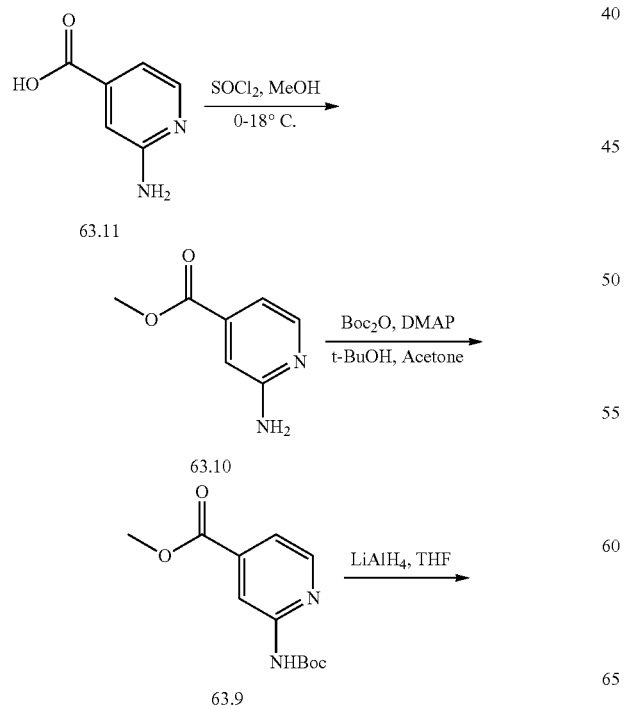

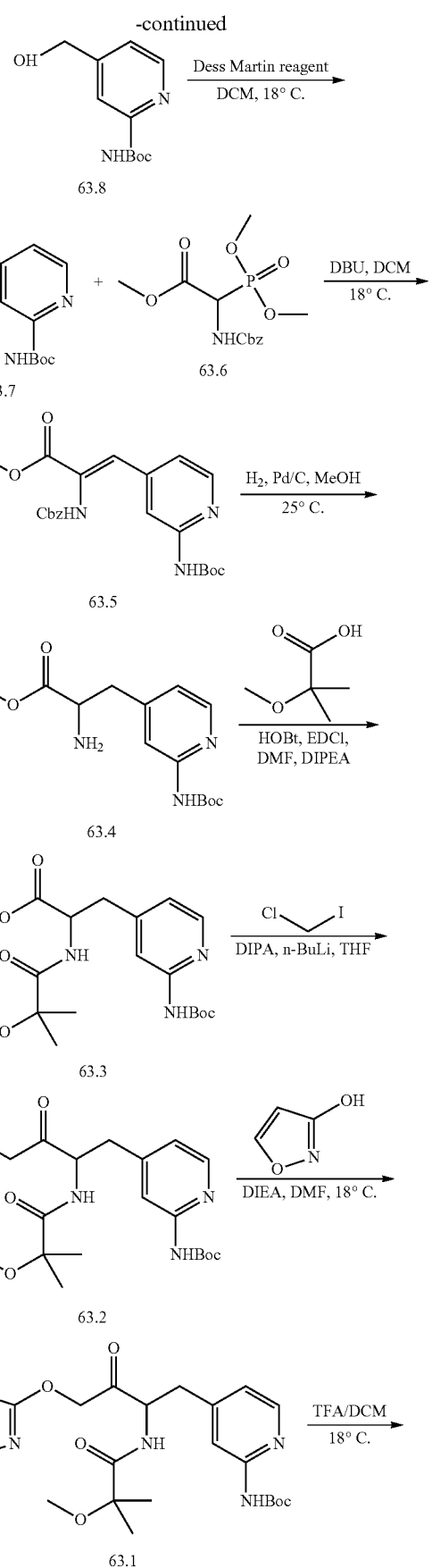

-continued

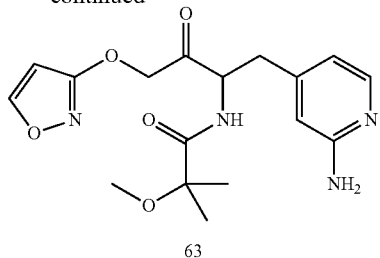

63

To a solution of compound 63.11 (30 g, 217.2 mmol, 1 eq) in MeOH (500 mL) was added SOCl$_2$ (103.4 g, 868.8 mmol, 63 mL, 4 eq) dropwise at 0° C. under N$_2$, then it was stirred at 18° C. for 10 hours. The reaction mixture was concentrated under reduced pressure to give compound 63.10 (33 g, crude) as a white solid. LCMS (ESI): m/z: [M+H]+ calcd for C$_7$H$_9$N$_2$O$_2$: 153; found 153; RT=0.3 min.

To a mixture of compound 63.10 (10 g, 65.72 mmol, 1 eq) and DMAP (401.48 mg, 3.29 mmol, 0.05 eq) in t-BuOH (500 mL) and ACETONE (150 mL) was added Boc$_2$O (43 g, 197.2 mmol, 45.30 mL, 3 eq) dropwise at 18° C. under N$_2$. The mixture was stirred at 18° C. for 15 hours. The solution was diluted with pentane (200 mL), cooled in the refrigerator for 3 hours then filtered to give compound 63.9 (25 g, 99.1 mmol, 50.3% yield) as a white solid. $^1$H NMR (400 MHz, METHANOL-d4) δ: 1.48 (s, 9H), 3.80-3.96 (m, 3H), 7.44 (dd, J=5.07, 1.41 Hz, 1H), 8.33 (s, 1H), 8.43 (d, J=5.01 Hz, 1H) and 10.11 (s, 1H) ppm.

To a solution of compound 63.9 (25 g, 99.1 mmol, 1 eq) in THF (500 mL) was added LiAlH$_4$ (7.52 g, 198.2 mmol, 2 eq) portion-wise at 0° C. under N$_2$. The mixture was stirred at 0° C. for 1 hour, then it was stirred at 18° C. for 14 hours. The reaction mixture was quenched by addition 8% NaOH (15 mL), filtered and then diluted with H$_2$O (1000 mL) and extracted with EtOAc (500 mL×3). The combined organic layers were washed with brine (1000 mL), dried over Na$_2$SO$_4$, filtered and concentrated under reduced pressure. The residue was purified by column chromatography (SiO$_2$, Petroleum ether/Ethyl acetate=2:1) to give compound 63.8 (7 g, 31.21 mmol, 31.5% yield) as a white solid. $^1$H NMR (400 MHz, DMSO-d6) δ: 1.47 (s, 8H), 4.50 (d, J=5.73 Hz, 2H), 5.40 (t, J=5.73 Hz, 1H), 6.94 (dd, J=5.07, 0.66 Hz, 1H), 7.81 (s, 1H), 8.15 (d, J=5.07 Hz, 1H) and 9.70 (br s, 1H) ppm.

To a solution of compound 63.8 (7 g, 31.2 mmol, 1 eq) in DCM (60 mL) was added Dess-Martin periodinane (19.9 g, 46.8 mmol, 14.5 mL, 1.5 eq) portion-wise at 18° C. under N$_2$, then the mixture was stirred at 18° C. for 2 hours. The reaction mixture was diluted with H$_2$O (60 mL) and extracted with DCM (50 mL×3). The combined organic layers were washed with brine (100 mL), dried over Na$_2$SO$_4$, filtered and concentrated under reduced pressure to give a residue. This residue was purified by column chromatography (SiO$_2$, Petroleum ether/Ethyl acetate=5:1) to give compound 63.7 (5.8 g, 26.1 mmol, 83.6% yield) as a white solid. $^1$H NMR (400 MHz, DMSO-d6) δ: 1.49 (s, 9H), 7.42 (dd, J=4.96, 0.99 Hz, 1H), 8.25 (s, 1H), 8.50 (d, J=4.85 Hz, 1H), 10.04 (s, 1H) and 10.12 (s, 1H) ppm.

To a mixture of compound 63.7 (5.8 g, 26.1 mmol, 1 eq) and compound 63.6 (8.65 g, 26.1 mmol, 1 eq) in DCM (60 mL) was added DBU (7.95 g, 52.2 mmol, 7.87 mL, 2 eq) in one portion at 18° C. under N$_2$. The mixture was stirred at 18° C. for 10 hours. The reaction mixture was concentrated under reduced pressure to give a residue, then it was purified by column chromatography (SiO$_2$, Petroleum ether/Ethyl acetate=2:1) to give compound 63.5 (3 g, 7 mmol, 27% yield) as a white solid. LCMS (ESI) m/z: [M+H]+ calcd for C$_{22}$H$_{26}$N$_3$O$_6$: 428; found 428; RT=1.34 min.

To a solution of compound 63.5 (3 g, 7 mmol, 1 eq) in MeOH (20 mL) was added Pd—C (10% palladium on carbon, 100 mg) under N$_2$. The suspension was degassed under vacuum and purged with H$_2$ several times. The mixture was stirred under H$_2$ (50 psi) at 25° C. for 10 hours. The reaction mixture was filtered and concentrated under reduced pressure to give a residue. The residue was purified by column chromatography (SiO$_2$, Ethyl acetate) to give compound 63.4 (1.32 g, 4.47 mmol, 64% yield) as a white solid. LCMS (ESI) m/z: [M+H]+ calcd for C$_{14}$H$_{22}$N$_3$O$_4$: 296; found 296; RT=0.694 min. $^1$H NMR (400 MHz, DMSO-d6) δ: 1.46 (s, 9H), 2.69-2.79 (m, 1H), 2.81-2.91 (m, 1H), 3.54-3.62 (m, 4H), 6.85 (d, J=4.82 Hz, 1H), 7.64 (s, 1H), 8.10 (d, J=4.82 Hz, 1H) and 9.71 (s, 1H) ppm.

To a mixture of 2-methoxy-2-methylpropanoic acid (633.6 mg, 5.36 mmol, 1.2 eq) and EDCI (1.03 g, 5.36 mmol, 1.2 eq) in DMF (15 mL) was added HOBt (724.72 mg, 5.36 mmol, 1.2 eq) in one portion at 18° C. under N$_2$. The mixture was stirred at 18° C. for 30 mins, then was added compound 63.4 (1.32 g, 4.47 mmol, 1 eq) and DIPEA (1.73 g, 13.41 mmol, 2.34 mL, 3 eq) in one portion, the mixture was stirred at 18° C. for 30 mins. The reaction mixture was diluted with H$_2$O (10 mL) and extracted with EtOAc (10 mL×3). The combined organic layers were washed with brine (10 mL), dried over Na$_2$SO$_4$, filtered and concentrated under reduced pressure to give a residue. The residue was purified by column chromatography (SiO$_2$, Petroleum ether/Ethyl acetate=2:1) to give compound 63.3 (1.5 g, 3.79 mmol, 85% yield) as a white solid. LCMS (ESI) m/z: [M+H]+ calcd for C$_{19}$H$_{30}$N$_3$O$_6$: 396; found 396; RT=0.892 min. $^1$H NMR (400 MHz, METHANOL-d4) δ: 1.31 (s, 3H), 1.37 (s, 3H), 1.56-1.64 (m, 9H), 3.16 (dd, J=13.89, 9.26 Hz, 1H), 3.25 (s, 3H), 3.34 (dd, J=13.89, 4.85 Hz, 1H), 3.84 (s, 3H), 4.82 (dd, J=9.15, 4.96 Hz, 1H), 6.96 (dd, J=5.07, 1.32 Hz, 1H), 7.78-7.89 (m, 1H) and 8.18 (d, J=5.07 Hz, 1H) ppm.

To a solution of DIPA (281.48 mg, 2.78 mmol, 393.12 µL, 5.5 eq) in THF (5 mL) was added n-BuLi (2.5 M, 1.11 mL, 5.5 eq) at 0° C., the mixture was stirred at 0° C. for 30 mins. The mixture was added a solution of compound 63.3 (0.2 g, 505.75 µmol, 1 eq) and chloroiodomethane (490.64 mg, 2.78 mmol, 201.9 µL, 5.5 eq) in THF (5 mL) at −78° C. The mixture was stirred at −78° C. for 30 mins. The reaction mixture was quenched by addition aqueous saturated NH$_4$Cl (5 mL) and then extracted with EtOAc (5 mL×3). The combined organic layers were washed with aqueous saturated Na$_2$SO$_3$ (10 mL), and brine (50 mL), dried over Na$_2$SO$_4$, filtered and concentrated under reduced pressure to give compound 63.2 (200 mg, crude) as yellow oil.

To a mixture of compound 63.2 (100 mg, 241.6 µmol, 1 eq) and isoxazol-3-ol (20.55 mg, 241.6 µmol, 1 eq) in DMF (2 mL) was added DIEA (93.7 mg, 724.8 µmol, 126.25 L, 3 eq) in one portion at 18° C. under N$_2$. The mixture was stirred at 18° C. for 10 hours. The reaction mixture was diluted with H$_2$O (2 mL) and extracted with EtOAc (2 mL×3). The combined organic layers were washed with brine (5 mL), dried over Na$_2$SO$_4$, filtered and concentrated under reduced pressure to give a residue. The residue was purified by column chromatography (SiO$_2$, Petroleum ether/Ethyl acetate=1:1) to give compound 63.1 (20 mg, 43.24 µmol, 18% yield) as a white solid. LCMS (ESI) m/z: [M+H]+ calcd for C$_{22}$H$_{31}$N$_4$O$_7$: 463; found 463; RT=1.203 min.

To a solution of compound 63.1 (20 mg, 43.24 μmol, 1 eq) in DCM (5 mL) was added TFA (1 mL) in one portion at 18° C. under $N_2$. The mixture was stirred at 18° C. for 10 mins. The reaction mixture was concentrated under reduced pressure to give a residue. The residue was purified by prep-HPLC (TFA condition) to give 63 (5 mg, 13.8 μmol, 32% yield) as a white solid. LCMS (ESI) m/z: [M+H]+ calcd for $C_{17}H_{23}N_4O_5$: 363; found 363; RT=2.688 min. $^1$H NMR (400 MHz, METHANOL-d4) δ: 1.24 (s, 3H), 1.33 (s, 3H), 2.96 (dd, J=14.11, 10.14 Hz, 1H), 3.23 (s, 3H), 3.37 (dd, J=14.11, 4.63 Hz, 1H), 4.95 (dd, J=9.92, 4.63 Hz, 1H), 5.06 (s, 2H), 6.18 (d, J=1.54 Hz, 1H), 6.82-6.86 (m, 2H), 7.74 (d, J=7.06 Hz, 1H) and 8.39 (d, J=1.76 Hz, 1H) ppm.

Example 64. Preparation of N-(1-(2-aminopyridin-4-yl)-3-oxo-4-(2,3,6-trifluorophenoxy)butan-2-yl)-2-methoxy-2-methylpropanamide (64)

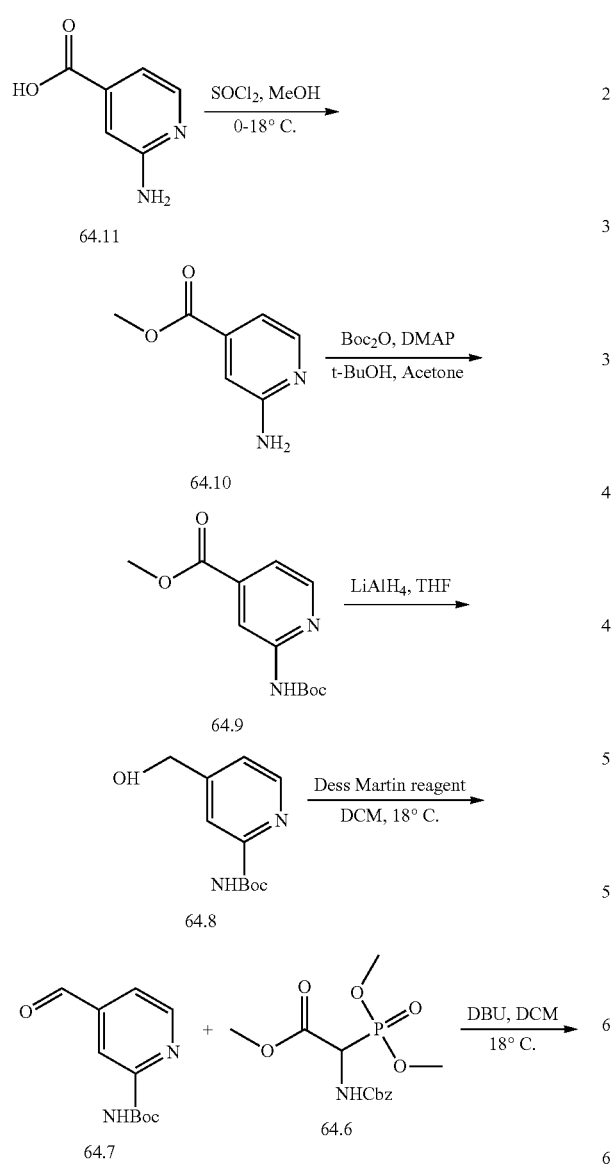

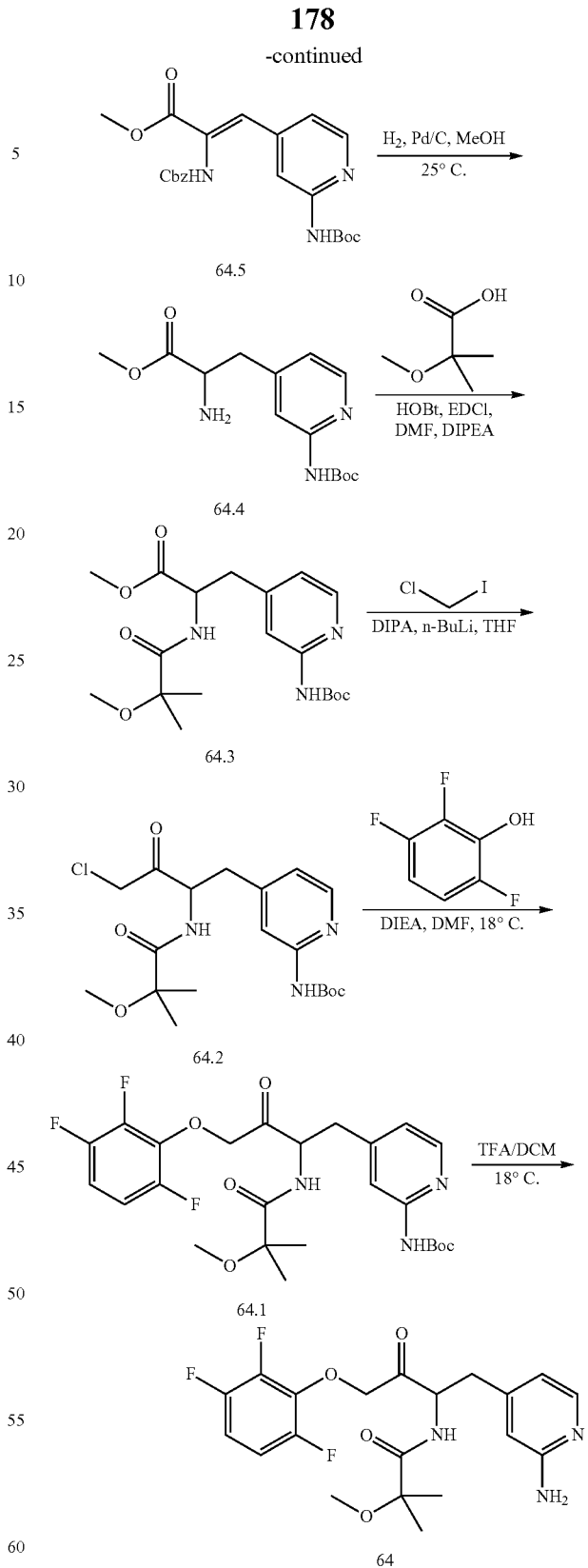

To a solution of compound 64.11 (30 g, 217.2 mmol, 1 eq) in MeOH (500 mL) was added $SOCl_2$ (103.4 g, 868.8 mmol, 63 mL, 4 eq) dropwise at 0° C. under $N_2$, then heated to 18° C. and stirred for 10 hours. The reaction mixture was concentrated under reduced pressure to give compound 64.10 (33 g, crude) as a white solid. LCMS (ESI): m/z: [M+H]+ calcd for $C_7H_9N_2O_2$: 153; found 153; RT=0.3 min.

To a mixture of compound 64.10 (10 g, 65.72 mmol, 1 eq) and DMAP (401.48 mg, 3.29 mmol, 0.05 eq) in t-BuOH (500 mL) and ACETONE (150 mL) was added $Boc_2O$ (43.03 g, 197.17 mmol, 45.3 mL, 3 eq) dropwise at 18° C. under $N_2$. The mixture was stirred at 18° C. for 15 hours. The solution was diluted with pentane (200 mL), cooled in the refrigerator for 3 hours and filtered to give compound 64.9 (25 g, 99.1 mmol, 50% yield) as a white solid. $^1$H NMR (400 MHz, METHANOL-d4) δ: 1.48 (s, 9H), 3.80-3.96 (m, 3H), 7.44 (dd, J=5.07, 1.41 Hz, 1H), 8.33 (s, 1H), 8.43 (d, J=5.01 Hz, 1H) and 10.11 (s, 1H) ppm.

To a solution of compound 64.9 (25 g, 99.1 mmol, 1 eq) in THF (500 mL) was added $LiAlH_4$ (7.52 g, 198.2 mmol, 2 eq) portion-wise at 0° C. under $N_2$. The mixture was stirred at 0° C. for 1 hour, then heated to 18° C. and stirred at 18° C. for 14 hours. The reaction mixture was quenched by addition 8% NaOH (15 mL), filtered and then diluted with $H_2O$ (1000 mL) and extracted with EtOAc (500 mL×3). The combined organic layers were washed with brine (1000 mL), dried over $Na_2SO_4$, filtered and concentrated under reduced pressure. The residue was purified by column chromatography ($SiO_2$, Petroleum ether/Ethyl acetate=2:1) to give compound 64.8 (7 g, 31.21 mmol, 32% yield) as a white solid. $^1$H NMR (400 MHz, DMSO-d6) δ: 1.47 (s, 8H), 4.50 (d, J=5.73 Hz, 2H), 5.40 (t, J=5.73 Hz, 1H), 6.94 (dd, J=5.07, 0.66 Hz, 1H), 7.81 (s, 1H), 8.15 (d, J=5.07 Hz, 1H) and 9.70 (br s, 1H) ppm.

To a solution of compound 64.8 (7 g, 31.21 mmol, 1 eq) in DCM (60 mL) was added Dess-Martin periodinane (19.9 g, 46.8 mmol, 14.5 mL, 1.5 eq) portion-wise at 18° C. under $N_2$. The mixture was stirred at 18° C. for 2 hours. The reaction mixture was diluted with $H_2O$ (60 mL) and extracted with DCM (50 mL×3). The combined organic layers were washed with brine (100 mL×1), dried over $Na_2SO_4$, filtered and concentrated under reduced pressure to give a residue. The residue was purified by column chromatography ($SiO_2$, Petroleum ether/Ethyl acetate=5:1) to give compound 64.7 (5.8 g, 26.1 mmol, 84% yield) as a white solid. $^1$H NMR (400 MHz, DMSO-d6) δ: 1.49 (s, 9H), 7.42 (dd, J=4.96, 0.99 Hz, 1H), 8.25 (s, 1H), 8.50 (d, J=4.85 Hz, 1H), 10.04 (s, 1H) and 10.12 (s, 1H) ppm.

To a mixture of compound 64.7 (5.8 g, 26.1 mmol, 1 eq) and compound 64.6 (8.65 g, 26.1 mmol, 1 eq) in DCM (60 mL) was added DBU (7.95 g, 52.20 mmol, 7.87 mL, 2 eq) in one portion at 18° C. under $N_2$. The mixture was stirred at 18° C. for 10 hours. The reaction mixture was concentrated under reduced pressure to give a residue. The residue was purified by column chromatography ($SiO_2$, Petroleum ether/Ethyl acetate=2:1) to give compound 64.5 (3 g, 7.02 mmol, 27% yield) as a white solid. LCMS (ESI) m/z: [M+H]+ calcd for $C_{22}H_{26}N_3O_6$: 428; found 428; RT=1.343 min.

To a solution of compound 64.5 (3 g, 7.02 mmol, 1 eq) in MeOH (20 mL) was added 10% palladium on carbon catalyst (100 mg) under $N_2$. The suspension was degassed under vacuum and purged with $H_2$ several times. The mixture was stirred under $H_2$ (50 psi) at 25° C. for 10 hours. The reaction mixture was filtered and concentrated under reduced pressure to give a residue. The residue was purified by column chromatography ($SiO_2$, Ethyl acetate) to give compound 64.4 (1.32 g, 4.47 mmol, 64% yield) as a white solid. LCMS (ESI) m/z: [M+H]+ calcd for $C_{14}H_{22}N_3O_4$: 296; found 296; RT=0.694 min. $^1$H NMR (400 MHz, DMSO-d6) δ: 1.46 (s, 9H), 2.69-2.79 (m, 1H), 2.81-2.91 (m, 1H), 3.54-3.62 (m, 4H), 6.85 (d, J=4.82 Hz, 1H), 7.64 (s, 1H), 8.10 (d, J=4.82 Hz, 1H) and 9.71 (s, 1H) ppm.

To a mixture of 2-methoxy-2-methylpropanoic acid (633.59 mg, 5.36 mmol, 1.2 eq) and EDCI (1.03 g, 5.36 mmol, 1.2 eq) in DMF (15 mL) was added HOBt (724.72 mg, 5.36 mmol, 1.2 eq) in one portion at 18° C. under $N_2$. The mixture was stirred at 18° C. for 30 mins, and then was added compound 64.4 (1.32 g, 4.47 mmol, 1 eq) and DIPEA (1.73 g, 13.41 mmol, 2.34 mL, 3 eq) in one portion, the mixture was stirred at 18° C. for 30 mins. The reaction mixture was diluted with $H_2O$ (10 mL) and extracted with EtOAc (10 mL×3). The combined organic layers were washed with brine (10 mL), dried over $Na_2SO_4$, filtered and concentrated under reduced pressure to give a residue. The residue was purified by column chromatography ($SiO_2$, Petroleum ether/Ethyl acetate=2:1) to give compound 64.3 (1.5 g, 3.8 mmol, 85% yield) as a white solid. LCMS (ESI) m/z: [M+H]+ calcd for $C_{19}H_{30}N_3O_6$: 396; found 396; RT=0.892 min. $^1$H NMR (400 MHz, METHANOL-d4) δ: 1.31 (s, 3H), 1.37 (s, 3H), 1.56-1.64 (m, 9H), 3.16 (dd, J=13.89, 9.26 Hz, 1H), 3.25 (s, 3H), 3.34 (dd, J=13.89, 4.85 Hz, 1H), 3.84 (s, 3H), 4.82 (dd, J=9.15, 4.96 Hz, 1H), 6.96 (dd, J=5.07, 1.32 Hz, 1H), 7.78-7.89 (m, 1H) and 8.18 (d, J=5.07 Hz, 1H) ppm.

To a solution of DIPA (1.41 g, 13.91 mmol, 1.97 mL, 5.5 eq) in THF (20 mL) was added n-BuLi (2.5 M, 5.56 mL, 5.5 eq) at 0° C., the mixture was stirred at 0° C. for 30 mins. The mixture was added a solution of compound 64.3 (1 g, 2.53 mmol, 1 eq) and chloroiodomethane (2.45 g, 13.91 mmol, 1.01 mL, 5.5 eq) in THF (20 mL) at −78° C. The mixture was stirred at −78° C. for 30 mins. The reaction mixture was quenched by addition aqueous saturated $NH_4Cl$ (20 mL) and then extracted with EtOAc (20 mL×3). The combined organic layers were washed with aqueous saturated $Na_2SO_3$ (30 mL), and brine (50 mL), dried over $Na_2SO_4$, filtered and concentrated under reduced pressure to give compound 64.2 (2 g) as yellow oil.

To a mixture of compound 64.2 (650 mg, 1.57 mmol, 1 eq) and 2,3,6-trifluorophenol (232.49 mg, 1.57 mmol, 1 eq) in DMF (2 mL) was added DIEA (608.89 mg, 4.71 mmol, 820.61 µL, 3 eq) in one portion at 18° C. under $N_2$. The mixture was stirred at 18° C. for 10 hours. The residue was purified by prep-HPLC (TFA condition) to give compound 64.1 (30 mg, 57.1 µmol, 4% yield) as a white solid. LCMS (ESI) m/z: [M+H]+ calcd for $C_{25}H_{31}N_3O_6F_3$: 526; found 526; RT=1.353 min. $^1$H NMR (400 MHz, METHANOL-d4) δ: 1.22 (s, 3H), 1.31 (s, 2H), 1.56-1.61 (m, 9H), 3.06 (dd, J=14.11, 9.92 Hz, 1H), 3.20 (s, 2H), 3.43-3.53 (m, 1H), 5-5.13 (m, 2H), 6.94-7.07 (m, 3H), 7.21-7.33 (m, 2H) and 8.11-8.20 (m, 1H) ppm.

To a solution of compound 64.1 (30 mg, 57.1 µmol, 1 eq) in DCM (5 mL) was added TFA (1 mL) in one portion at 18° C. under $N_2$. The mixture was stirred at 18° C. for 10 mins. The residue was purified by prep-HPLC (TFA condition) to give 64 (10 mg, 23.51 mol, 41% yield) as a white solid. LCMS (ESI) m/z: [M+H]+ calcd for $C_{20}H_{23}N_3O_4F_3$: 426; found 426; RT=2.646 min. $^1$H NMR (400 MHz, DMSO-d6) δ: 1.15 (s, 3H), 1.22 (s, 3H), 2.91 (dd, J=14, 10.03 Hz, 1H), 3.07 (s, 3H), 3.19 (dd, J=14, 4.30 Hz, 1H), 4.77 (td, J=9.32, 4.52 Hz, 1H), 5.09 (q, J=17.35 Hz, 2H), 6.71 (br d, J=4.19 Hz, 2H), 7.08-7.16 (m, 2H), 7.78-7.82 (m, 1H) and 8.07 (br d, J=8.82 Hz, 1H) ppm.

Example 65. Preparation of N-(1-(2-aminopyridin-4-yl)-3-oxo-4-(2,3,5,6-tetrafluorophenoxy)butan-2-yl)-2-methoxy-2-methylpropanamide (65)

To a solution of compound 65.11 (30 g, 217.2 mmol, 1 eq) in MeOH (500 mL) was added $SOCl_2$ (103.36 g, 868.8 mmol, 63.02 mL, 4 eq) dropwise at 0° C. under N₂, then heated to 18° C. and stirred for 10 hours. The reaction mixture was concentrated under reduced pressure to give compound 65.10 (33 g, crude) as a white solid. LCMS (ESI) m/z: [M+H]+ calcd for $C_7H_9N_2O_2$: 153; found 153; RT=0.298 min.

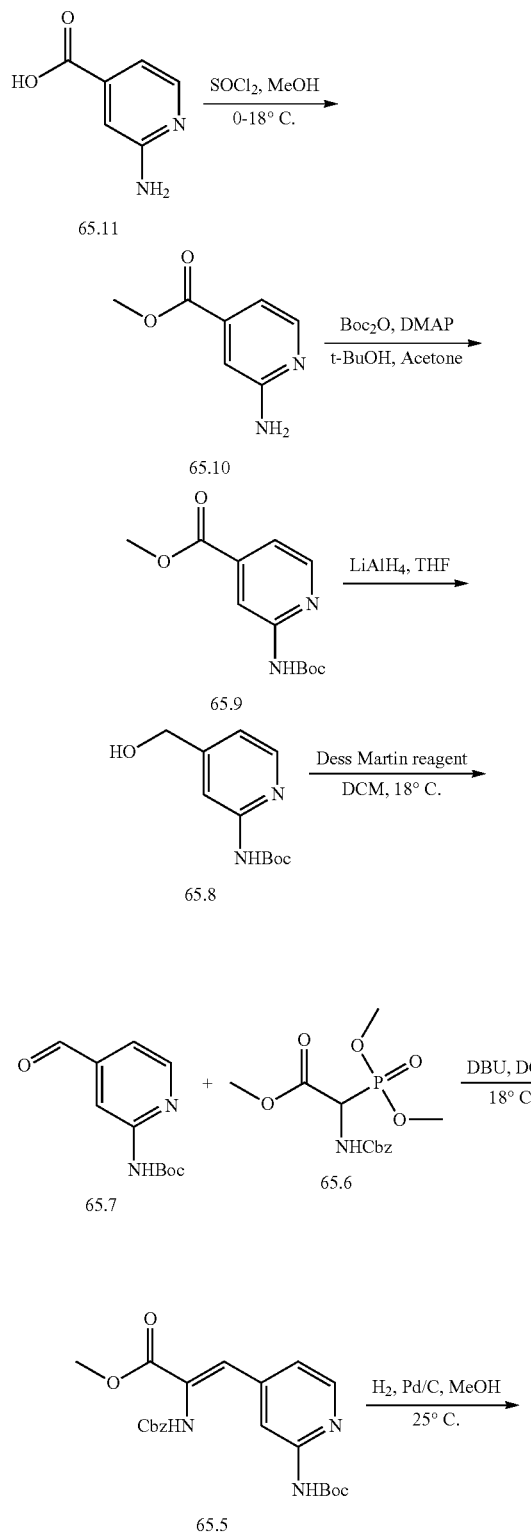

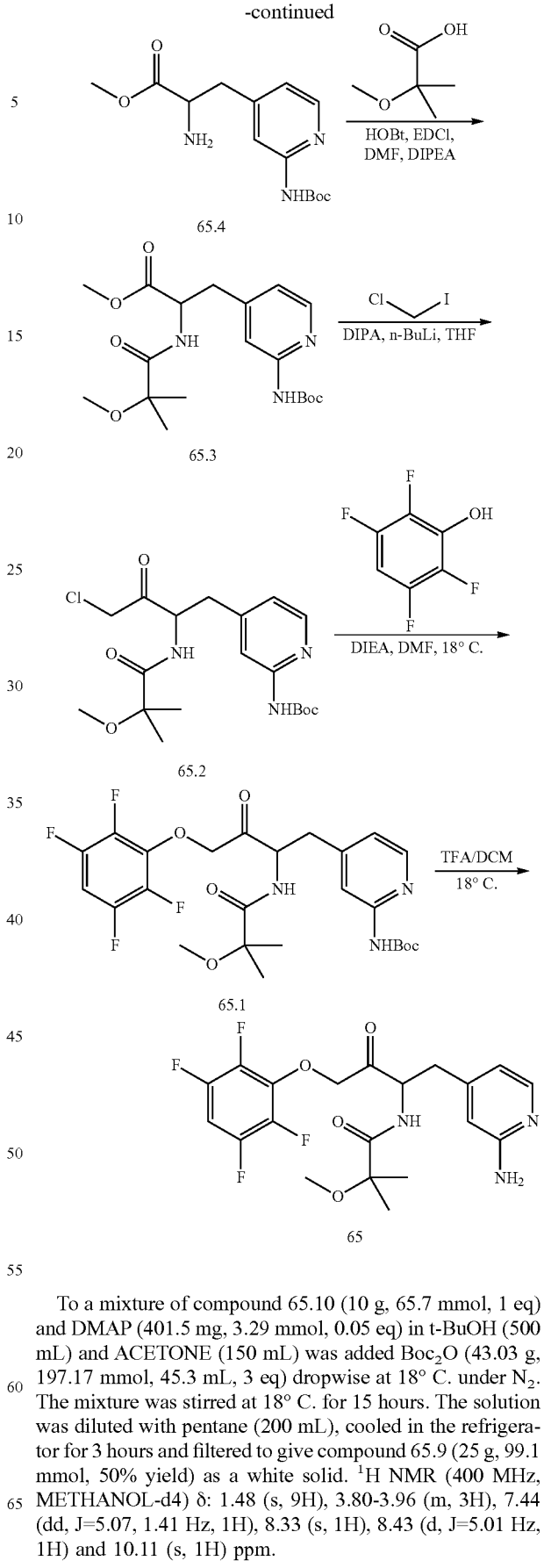

To a mixture of compound 65.10 (10 g, 65.7 mmol, 1 eq) and DMAP (401.5 mg, 3.29 mmol, 0.05 eq) in t-BuOH (500 mL) and ACETONE (150 mL) was added Boc₂O (43.03 g, 197.17 mmol, 45.3 mL, 3 eq) dropwise at 18° C. under N₂. The mixture was stirred at 18° C. for 15 hours. The solution was diluted with pentane (200 mL), cooled in the refrigerator for 3 hours and filtered to give compound 65.9 (25 g, 99.1 mmol, 50% yield) as a white solid. ¹H NMR (400 MHz, METHANOL-d4) δ: 1.48 (s, 9H), 3.80-3.96 (m, 3H), 7.44 (dd, J=5.07, 1.41 Hz, 1H), 8.33 (s, 1H), 8.43 (d, J=5.01 Hz, 1H) and 10.11 (s, 1H) ppm.

To a solution of compound 65.9 (25 g, 99.1 mmol, 1 eq) in THF (500 mL) was added LiAlH₄ (7.52 g, 198.2 mmol, 2 eq) portion-wise at 0° C. under N₂. The mixture was stirred at 0° C. for 1 hour, then heated to 18° C. and stirred at 18° C. for 14 hours. The reaction mixture was quenched by addition 8% NaOH (15 mL), filtered and then diluted with H₂O (1000 mL) and extracted with EtOAc (500 mL×3). The combined organic layers were washed with brine (1000 mL), dried over Na₂SO₄, filtered and concentrated under reduced pressure to give a residue. The residue was purified by column chromatography (SiO₂, Petroleum ether/Ethyl acetate=2:1) to give compound 65.8 (7 g, 31.2 mmol, 32% yield) as a white solid. ¹H NMR (400 MHz, DMSO-d6) δ: 1.47 (s, 8H), 4.50 (d, J=5.73 Hz, 2H), 5.40 (t, J=5.73 Hz, 1H), 6.94 (dd, J=5.07, 0.66 Hz, 1H), 7.81 (s, 1H), 8.15 (d, J=5.07 Hz, 1H) and 9.70 (br s, 1H) ppm.

To a solution of compound 65.8 (7 g, 31.21 mmol, 1 eq) in DCM (60 mL) was added Dess-Martin periodinane (19.86 g, 46.82 mmol, 14.50 mL, 1.5 eq) portion-wise at 18° C. under N₂. The mixture was stirred at 18° C. for 2 hours. The reaction mixture was diluted with H₂O (60 mL) and extracted with DCM (50 mL×3). The combined organic layers were washed with brine (100 mL), dried over Na₂SO₄, filtered and concentrated under reduced pressure to give a residue. The residue was purified by column chromatography (SiO₂, Petroleum ether/Ethyl acetate=5:1) to give compound 65.7 (5.8 g, 26.1 mmol, 84% yield) as a white solid. ¹H NMR (400 MHz, DMSO-d6) δ: 1.49 (s, 9H), 7.42 (dd, J=4.96, 0.99 Hz, 1H), 8.25 (s, 1H), 8.50 (d, J=4.85 Hz, 1H), 10.04 (s, 1H) and 10.12 (s, 1H) ppm.

To a mixture of compound 65.7 (5.8 g, 26.1 mmol, 1 eq) and compound 65.6 (8.65 g, 26.1 mmol, 1 eq) in DCM (60 mL) was added DBU (7.95 g, 52.2 mmol, 7.87 mL, 2 eq) in one portion at 18° C. under N₂. The mixture was stirred at 18° C. for 10 hours. The reaction mixture was concentrated under reduced pressure to give a residue. The residue was purified by column chromatography (SiO₂, Petroleum ether/Ethyl acetate=2:1) to give compound 65.5 (3 g, 7.02 mmol, 27% yield) as a white solid. LCMS (ESI) m/z: [M+H]+ calcd for $C_{22}H_{26}N_3O_6$: 428; found 428; RT=1.343 min.

To a solution of compound 65.5 (3 g, 7.02 mmol, 1 eq) in MeOH (20 mL) was added 10% palladium on carbon catalyst (100 mg) under N₂. The suspension was degassed under vacuum and purged with H₂ several times. The mixture was stirred under H₂ (50 psi) at 25° C. for 10 hours. The reaction mixture was filtered and concentrated under reduced pressure to give a residue. The residue was purified by column chromatography (SiO₂, Ethyl acetate) to give compound 65.4 (1.32 g, 4.47 mmol, 64% yield) as a white solid. LCMS (ESI) m/z: [M+H]+ calcd for $C_{14}H_{22}N_3O_4$: 296; found 296; RT=0.694 min. ¹H NMR (400 MHz, DMSO-d6) δ: 1.46 (s, 9H), 2.69-2.79 (m, 1H), 2.81-2.91 (m, 1H), 3.54-3.62 (m, 4H), 6.85 (d, J=4.82 Hz, 1H), 7.64 (s, 1H), 8.10 (d, J=4.82 Hz, 1H) and 9.71 (s, 1H) ppm.

To a mixture of 2-methoxy-2-methylpropanoic acid (633.59 mg, 5.36 mmol, 1.2 eq) and EDCI (1.03 g, 5.36 mmol, 1.2 eq) in DMF (15 mL) was added HOBt (724.7 mg, 5.36 mmol, 1.2 eq) in one portion at 18° C. under N₂. The mixture was stirred at 18° C. for 30 mins, and then was added compound 65.4 (1.32 g, 4.47 mmol, 1 eq) and DIPEA (1.73 g, 13.41 mmol, 2.34 mL, 3 eq) in one portion, the mixture was stirred at 18° C. for 30 mins. The reaction mixture was diluted with H₂O (10 mL) and extracted with EtOAc (10 mL×3). The combined organic layers were washed with brine (10 mL), dried over Na₂SO₄, filtered and concentrated under reduced pressure. The residue was purified by column chromatography (SiO₂, Petroleum ether/Ethyl acetate=2:1) to give compound 65.3 (1.5 g, 3.79 mmol, 85% yield) as a white solid. LCMS (ESI) m/z: [M+H]+ calcd for $C_{19}H_{30}N_3O_6$: 396; found 396; RT=0.892 min. ¹H NMR (400 MHz, METHANOL-d4) δ: 1.31 (s, 3H), 1.37 (s, 3H), 1.56-1.64 (m, 9H), 3.16 (dd, J=13.89, 9.26 Hz, 1H), 3.25 (s, 3H), 3.34 (dd, J=13.89, 4.85 Hz, 1H), 3.84 (s, 3H), 4.82 (dd, J=9.15, 4.96 Hz, 1H), 6.96 (dd, J=5.07, 1.32 Hz, 1H), 7.78-7.89 (m, 1H) and 8.18 (d, J=5.07 Hz, 1H) ppm.

To a solution of DIPA (281.48 mg, 2.78 mmol, 393.12 µL, 5.5 eq) in THF (10 mL) was added n-BuLi (2.5 M, 1.11 mL, 5.5 eq) at 0° C., the mixture was stirred at 0° C. for 30 mins. To the mixture was added a solution of compound 65.3 (200 mg, 505.75 µmol, 1 eq) and chloroiodomethane (490.64 mg, 2.78 mmol, 201.91 µL, 5.5 eq) in THF (10 mL) at −78° C. The mixture was stirred at −78° C. for 30 mins. The reaction mixture was quenched by addition aqueous saturated NH₄Cl (20 mL), and then extracted with EtOAc (20 mL×3). The combined organic layers were washed with aqueous saturated Na₂SO₃ (30 mL), and brine (50 mL), dried over Na₂SO₄, filtered and concentrated under reduced pressure to give compound 65.2 (300 mg, crude) as yellow oil.

To a mixture of compound 65.2 (300 mg, 724.8 µmol, 1 eq) and 2,3,5,6-tetrafluorophenol (120.37 mg, 724.8 µmol, 1 eq) in DMF (2 mL) was added DIEA (281.03 mg, 2.17 mmol, 378.74 µL, 3 eq) in one portion at 18° C. under N₂. The mixture was stirred at 18° C. for 10 hours. The reaction mixture was diluted with H₂O (4 mL) and extracted with EtOAc (4 mL×3). The combined organic layers were washed with brine (5 mL), dried over Na₂SO₄, filtered and concentrated under reduced pressure to give a residue. The residue was purified by column chromatography (SiO₂, Petroleum ether/Ethyl acetate=1:1) to give compound 65.1 (20 mg, 36.8 µmol, 5% yield) as a white solid. LCMS (ESI) m/z: [M+H]+ calcd for $C_{25}H_{30}N_3O_6F_4$: 544; found 544; RT=1.366 min.

To a solution of compound 65.1 (20 mg, 36.80 µmol, 1 eq) in DCM (5 mL) was added TFA (1 mL) in one portion at 18° C. under N₂. The mixture was stirred at 18° C. for 10 mins. The reaction mixture was concentrated under reduced pressure to give a residue. The residue was purified by prep-HPLC (basic condition) to give 65 (4 mg, 9 µmol, 25% yield) as a white solid. LCMS (ESI) m/z: [M+H]+ calcd for $C_{20}H_{22}N_3O_4F_4$: 444; found 444; RT=2.460 min. ¹H NMR (400 MHz, METHANOL-d4) δ: 1.02-1.35 (m, 6H), 2.84 (br dd, J=13.89, 10.58 Hz, 1H), 3.06-3.26 (m, 4H), 4.61 (br d, J=9.04 Hz, 1H), 5.04-5.23 (m, 2H), 6.41-6.47 (m, 1H), 6.48-6.55 (m, 1H), 7.07-7.21 (m, 1H) and 7.70-7.80 (m, 1H) ppm.

Example 66. Preparation of N-(1-(6-aminopyridin-3-yl)-3-oxo-4-(2,3,6-trifluorophenoxy)butan-2-yl)cyclopentanecarboxamide (66)

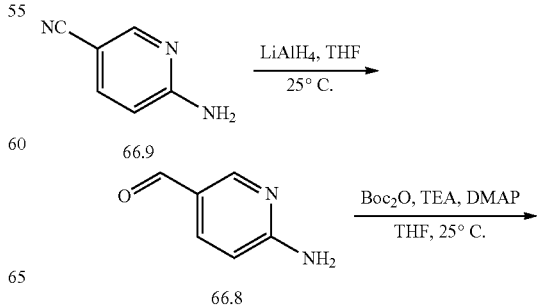

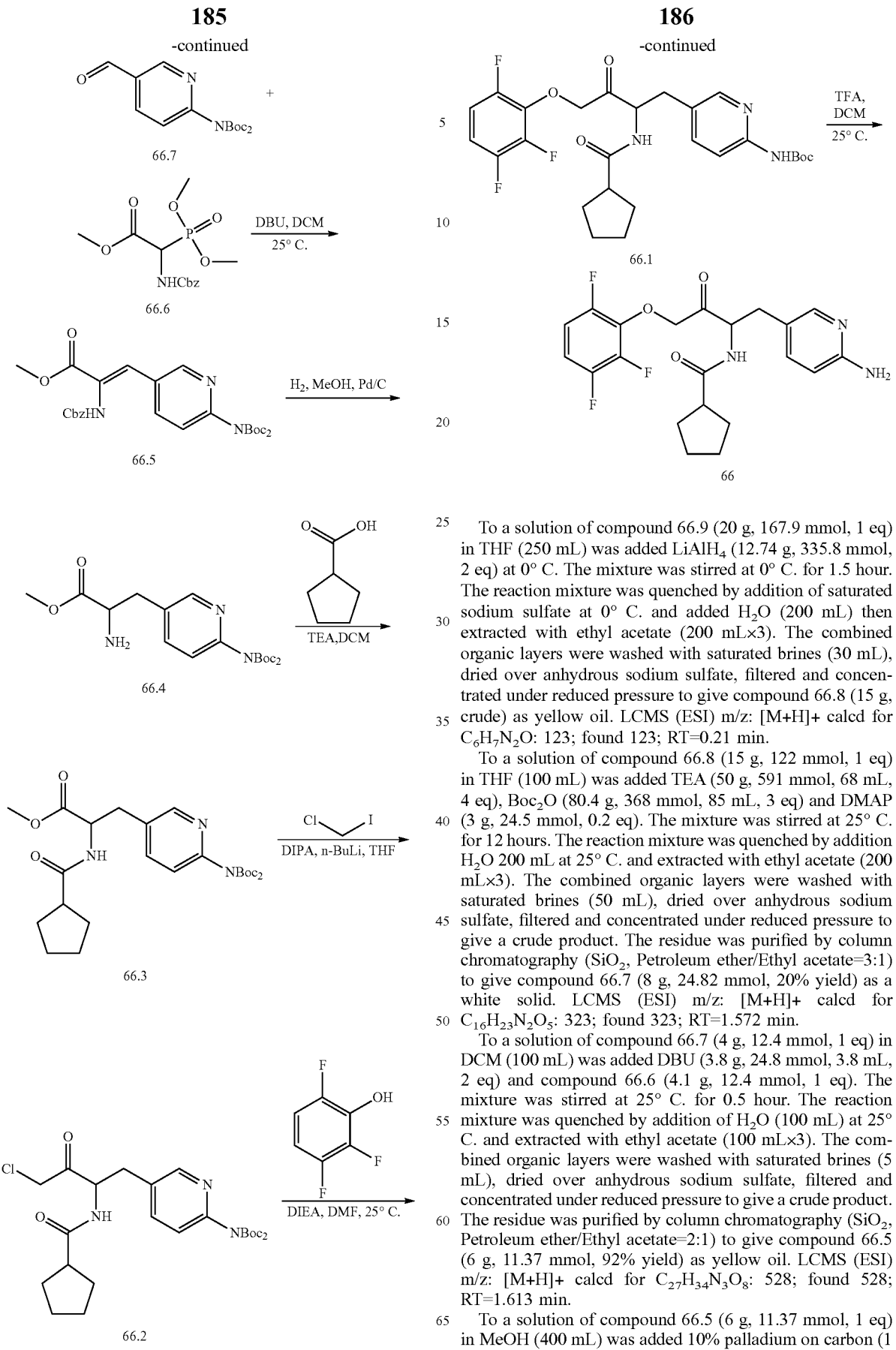

To a solution of compound 66.9 (20 g, 167.9 mmol, 1 eq) in THF (250 mL) was added LiAlH$_4$ (12.74 g, 335.8 mmol, 2 eq) at 0° C. The mixture was stirred at 0° C. for 1.5 hour. The reaction mixture was quenched by addition of saturated sodium sulfate at 0° C. and added H$_2$O (200 mL) then extracted with ethyl acetate (200 mL×3). The combined organic layers were washed with saturated brines (30 mL), dried over anhydrous sodium sulfate, filtered and concentrated under reduced pressure to give compound 66.8 (15 g, crude) as yellow oil. LCMS (ESI) m/z: [M+H]+ calcd for C$_6$H$_7$N$_2$O: 123; found 123; RT=0.21 min.

To a solution of compound 66.8 (15 g, 122 mmol, 1 eq) in THF (100 mL) was added TEA (50 g, 591 mmol, 68 mL, 4 eq), Boc$_2$O (80.4 g, 368 mmol, 85 mL, 3 eq) and DMAP (3 g, 24.5 mmol, 0.2 eq). The mixture was stirred at 25° C. for 12 hours. The reaction mixture was quenched by addition H$_2$O 200 mL at 25° C. and extracted with ethyl acetate (200 mL×3). The combined organic layers were washed with saturated brines (50 mL), dried over anhydrous sodium sulfate, filtered and concentrated under reduced pressure to give a crude product. The residue was purified by column chromatography (SiO$_2$, Petroleum ether/Ethyl acetate=3:1) to give compound 66.7 (8 g, 24.82 mmol, 20% yield) as a white solid. LCMS (ESI) m/z: [M+H]+ calcd for C$_{16}$H$_{23}$N$_2$O$_5$: 323; found 323; RT=1.572 min.

To a solution of compound 66.7 (4 g, 12.4 mmol, 1 eq) in DCM (100 mL) was added DBU (3.8 g, 24.8 mmol, 3.8 mL, 2 eq) and compound 66.6 (4.1 g, 12.4 mmol, 1 eq). The mixture was stirred at 25° C. for 0.5 hour. The reaction mixture was quenched by addition of H$_2$O (100 mL) at 25° C. and extracted with ethyl acetate (100 mL×3). The combined organic layers were washed with saturated brines (5 mL), dried over anhydrous sodium sulfate, filtered and concentrated under reduced pressure to give a crude product. The residue was purified by column chromatography (SiO$_2$, Petroleum ether/Ethyl acetate=2:1) to give compound 66.5 (6 g, 11.37 mmol, 92% yield) as yellow oil. LCMS (ESI) m/z: [M+H]+ calcd for C$_{27}$H$_{34}$N$_3$O$_8$: 528; found 528; RT=1.613 min.

To a solution of compound 66.5 (6 g, 11.37 mmol, 1 eq) in MeOH (400 mL) was added 10% palladium on carbon (1 g) under N$_2$. The suspension was degassed under vacuum and purged with H₂ several times. The mixture was stirred under H₂ (50 psi) at 25° C. for 15 hours. The reaction mixture was filtered, and the filter was concentrated to give compound 66.4 (3.3 g, crude) as yellow oil. LCMS (ESI) m/z: [M+H]+ calcd for $C_{19}H_{30}N_3O_6$: 396; found 396; RT=1.1445 min. ¹H NMR (400 MHz, chloroform-d) δ: 1.44 (s, 25H), 2.83-2.97 (m, 1H), 3.07 (dd, J=13.89, 5.51 Hz, 1H), 3.68-3.78 (m, 4H), 7.18 (d, J=8.16 Hz, 1H), 7.60 (dd, J=8.16, 2.20 Hz, 1H) and 8.32 (d, J=1.98 Hz, 1H) ppm.

To a solution of compound 66.4 (2 g, 5.06 mmol, 1 eq) in DCM (30 mL) was added TEA (1.02 g, 10.12 mmol, 1.4 mL, 2 eq) and cyclopentane carbonyl chloride (804.68 mg, 6.07 mmol, 738.24 µL, 1.20 eq). The mixture was stirred at 25° C. for 5 min. The mixture was concentrated under reduced pressure to give a residue. The residue was purified by column chromatography (SiO₂, Petroleum ether/Ethyl acetate=1:1) to give compound 66.3 (1.8 g, 3.66 mmol, 72% yield) as yellow oil. LCMS (ESI) m/z: [M+H]+ calcd for $C_{25}H_{38}N_3O_7$: 492; found 492; RT=1.552 min.

To a solution of DIPA (1.03 g, 10.17 mmol, 1.43 mL, 5 eq) in THF (10 mL) was added n-BuLi (2.5 M, 4.07 mL, 5 eq). The mixture was stirred at 0° C. for 0.5 hr under N₂. Then the mixture was added to the solution of compound 66.3 (1 g, 2.03 mmol, 1 eq) and chloroiodomethane (1.79 g, 10.17 mmol, 738.3 µL, 5 eq) in THF (10 mL) was stirred at −78° C. for 2.5 hours. The reaction mixture was quenched by addition saturated NH₄Cl (20 mL) at 25° C. and extracted with ethyl acetate (15 mL×3). The combined organic layers were washed with saturated Na₂SO₃ (10 mL) and saturated NaHCO₃ (10 mL) and saturated brines (10 mL), dried over anhydrous sodium sulfate, filtered and concentrated under reduced pressure to give compound 66.2 (1.6 g) as yellow oil.

To a solution of compound 66.2 (500 mg, 1.22 mmol, 1 eq) in DMF (5 mL) was added DIEA (472.93 mg, 3.66 mmol, 637.37 µL, 3 eq) and 2,3,6-trifluorophenol (271 mg, 1.83 mmol, 1.5 eq). The mixture was stirred at 25° C. for 15 hours. The reaction mixture was quenched by addition saturated NaHCO₃ 20 mL at 25° C. and extracted with ethyl acetate (20 mL×3). The combined organic layers were washed with saturated brines (10 mL), dried over anhydrous sodium sulfate, filtered and concentrated under reduced pressure to give a crude product. The residue was purified by column chromatography (SiO₂, Petroleum ether/Ethyl acetate=1:1) to give compound 66.1 (30 mg, 57.52 µmol, 5% yield) as yellow oil. LCMS (ESI) m/z: [M+H]+ calcd for $C_{26}H_{31}N_3O_5F_3$: 522; found 522; RT=1.175 min.

To a solution of compound 66.1 (30 mg, 57.52 µmol, 1 eq) in DCM (5 mL) was added TFA (1 mL). The mixture was stirred at 25° C. for 15 hours. The reaction mixture was quenched by addition saturated NaHCO₃ (20 mL) at 25° C. and extracted with ethyl acetate (20 mL×3). The combined organic layers were washed with saturated brines (10 mL), dried over anhydrous sodium sulfate, filtered and concentrated under reduced pressure to give a crude product. The residue was purified by prep-HPLC (TFA condition) to give 66 (4 mg, 9.5 mol, 17% yield) was obtained as a yellow solid. LCMS (ESI) m/z: [M+H]+ calcd for $C_{21}H_{23}N_3O_3F_3$: 422; found 422; RT=1.472 min. ¹H NMR (400 MHz, METHANOL-d₄) δ: 1.41-1.90 (m, 8H), 2.63 (quin, J=7.66 Hz, 1H), 2.77 (dd, J=14.33, 9.70 Hz, 1H), 3.11-3.24 (m, 1H), 4.86 (br s, 1H), 4.97-5.14 (m, 2H), 6.87-7.06 (m, 3H), 7.66 (s, 1H) and 7.85 (dd, J=9.15, 1.87 Hz, 1H) ppm.

Example 67. Preparation of N-(1-(6-aminopyridin-3-yl)-4-(2,6-difluorophenoxy)-3-oxobutan-2-yl)cyclopentanecarboxamide (67)

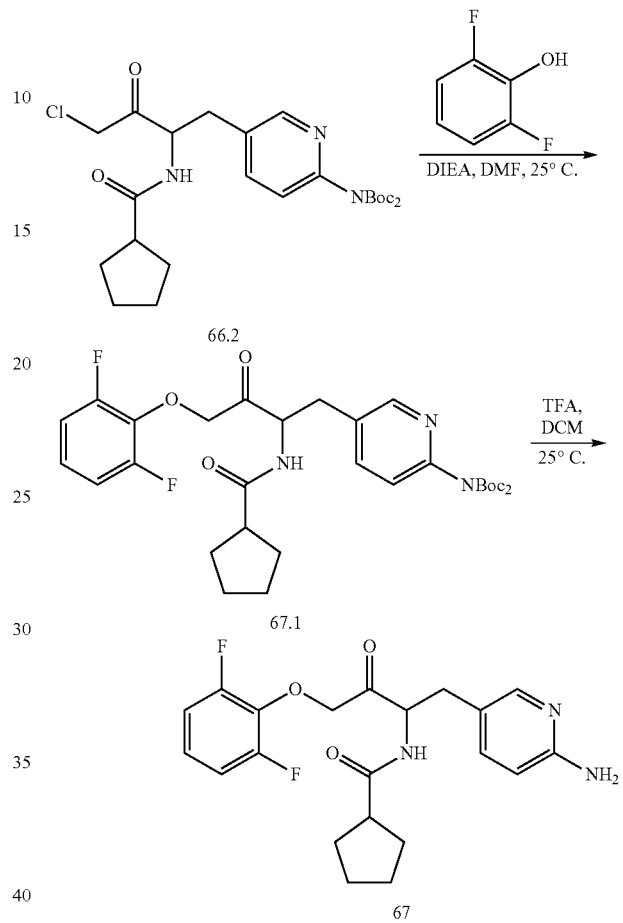

To a solution of compound 66.2 (500 mg, 1.22 mmol, 1 eq) in DMF (5 mL) was added DIEA (472.93 mg, 3.66 mmol, 637.37 µL, 3 eq) and 2,6-difluorophenol (238.07 mg, 1.83 mmol, 1.5 eq). The mixture was stirred at 25° C. for 15 hours. The reaction mixture was quenched by addition of saturated NaHCO₃ (20 mL) at 25° C. and extracted with ethyl acetate (20 mL×3). The combined organic layers were washed with saturated brines (10 mL), dried over anhydrous sodium sulfate, filtered and concentrated under reduced pressure to give a crude product. The residue was purified by column chromatography (SiO₂, Petroleum ether/Ethyl acetate=1:1) to give compound 67.1 (30 mg, 59.6 µmol, 5% yield) as yellow oil. LCMS (ESI) m/z: [M+H]+ calcd for $C_{26}H_{32}N_3O_5F_2$: 504; found 504; RT=1.112 min.

To a solution of compound 67.1 (30 mg, 59.58 µmol, 1 eq) in DCM (5 mL) was added TFA (1 mL). The mixture was stirred at 25° C. for 15 hours. The reaction mixture was quenched by addition saturated NaHCO₃ (20 mL) at 25° C. and extracted with ethyl acetate (20 mL×3). The combined organic layers were washed with saturated brines (10 mL), dried over anhydrous sodium sulfate, filtered and concentrated under reduced pressure to give a crude product. The residue was purified by prep-HPLC (TFA condition) to give 67 (4 mg, 9.92 µmol, 17% yield) as a yellow solid. LCMS (ESI) m/z: [M+H]+ calcd for $C_{21}H_{24}N_3O_3F_2$: 404; found 404; RT=1.422 min. $^1$H NMR (400 MHz, METHANOL-d4) δ: 1.42-1.94 (m, 8H), 2.52-2.69 (m, 1H), 2.76 (dd, J=14.44, 9.81 Hz, 1H), 3.09-3.25 (m, 1H), 4.90-5.04 (m, 3H), 6.87-7.13 (m, 4H), 7.65 (s, 1H) and 7.85 (dd, J=9.26, 1.98 Hz, 1H) ppm.

Example 68. Preparation of N-(1-(6-aminopyridin-3-yl)-4-(isoxazol-3-yloxy)-3-oxobutan-2-yl)cyclopentanecarboxamide (68)

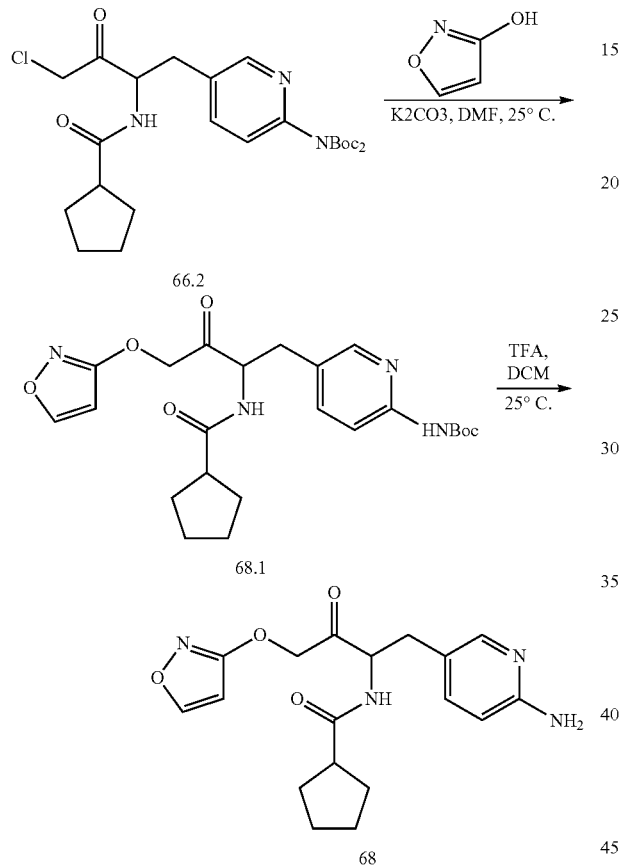

To a solution of compound 66.2 (400 mg, 975.83 μmol, 1 eq) in DMF (5 mL) was added $K_2CO_3$ (404.6 mg, 2.93 mmol, 3 eq) and isoxazol-3-ol (124.51 mg, 1.46 mmol, 1.5 eq). The mixture was stirred at 25° C. for 15 hours. The reaction mixture was quenched by addition saturated NaHCO$_3$20 mL at 25° C. and extracted with ethyl acetate (20 mL×3). The combined organic layers were washed with saturated brines (10 mL), dried over anhydrous sodium sulfate, filtered and concentrated under reduced pressure to give a crude product. The residue was purified by column chromatography (SiO$_2$, Petroleum ether/Ethyl acetate=1:1) to give compound 68.1 (50 mg) as yellow oil.

A mixture of compound 68.1 (100 mg, 65.43 μmol, 1 eq) in TFA (1 mL) and DCM (5 mL) was stirred at 25° C. for 12 hours. The mixture was concentrated in vacuum. The residue was purified by preparative scale-HPLC (TFA condition) to give 68 (2 mg, 5.58 mol, 9% yield) as a white solid. LCMS (ESI) m/z: [M+H]+ calcd for $C_{18}H_{23}N_4O_4$: 359; found 359; RT=1.169 min. $^1$H NMR (400 MHz, METHANOL-d4) δ: 1.43-1.91 (m, 10H), 2.56-2.72 (m, 1H), 2.79 (dd, J=14.44, 9.37 Hz, 1H), 3.09-3.23 (m, 1H), 4.81 (dd, J=9.37, 5.40 Hz, 1H), 5.05 (d, J=2.43 Hz, 2H), 6.17 (d, J=1.76 Hz, 1H), 6.93 (d, J=9.04 Hz, 1H), 7.67 (s, 1H), 7.84 (dd, J=9.15, 1.87 Hz, 1H) and 8.39 (d, J=1.76 Hz, 1H) ppm.

Example 69. Preparation of N-(1-(2-aminopyridin-4-yl)-3-oxo-4-(2,3,6-trifluorophenoxy)butan-2-yl)cyclopentanecarboxamide (69)

To a solution of compound 69.11 (50 g, 362 mmol, 1 eq) in MeOH (600 mL) was added SOCl$_2$ (172.27 g, 1.45 mol, 105.04 mL, 4 eq) dropwise at 0° C. under N$_2$, then heated to 18° C. and stirred for 10 hours. The reaction mixture was concentrated under reduced

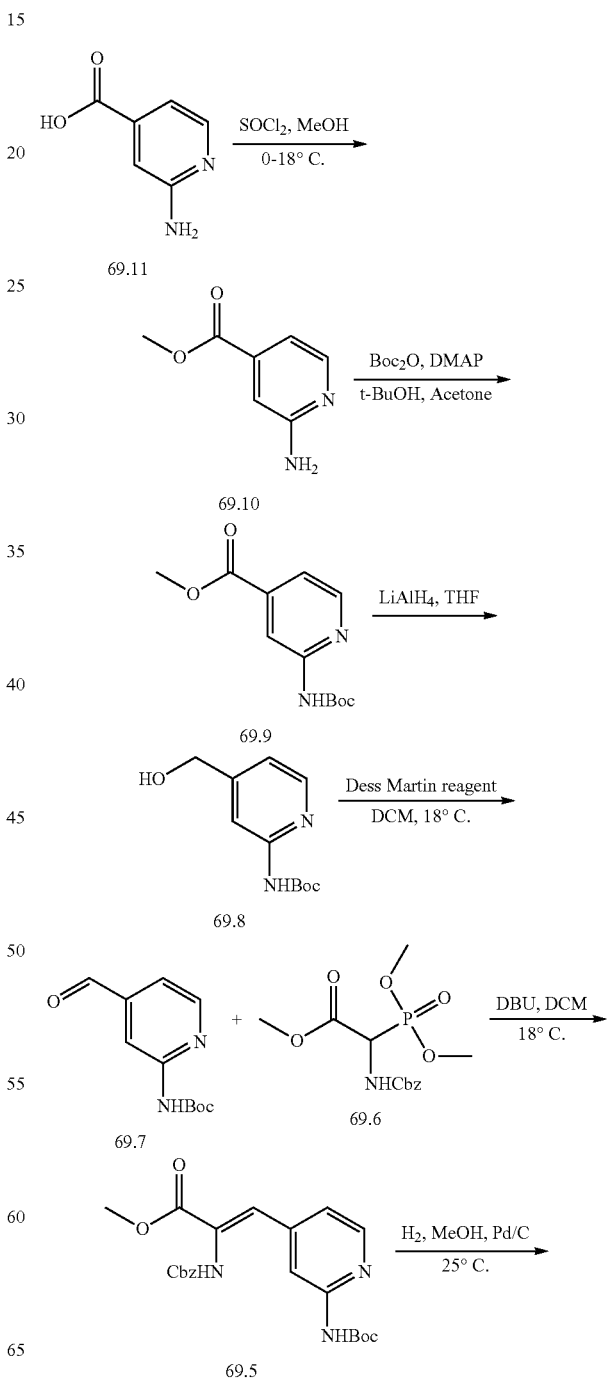

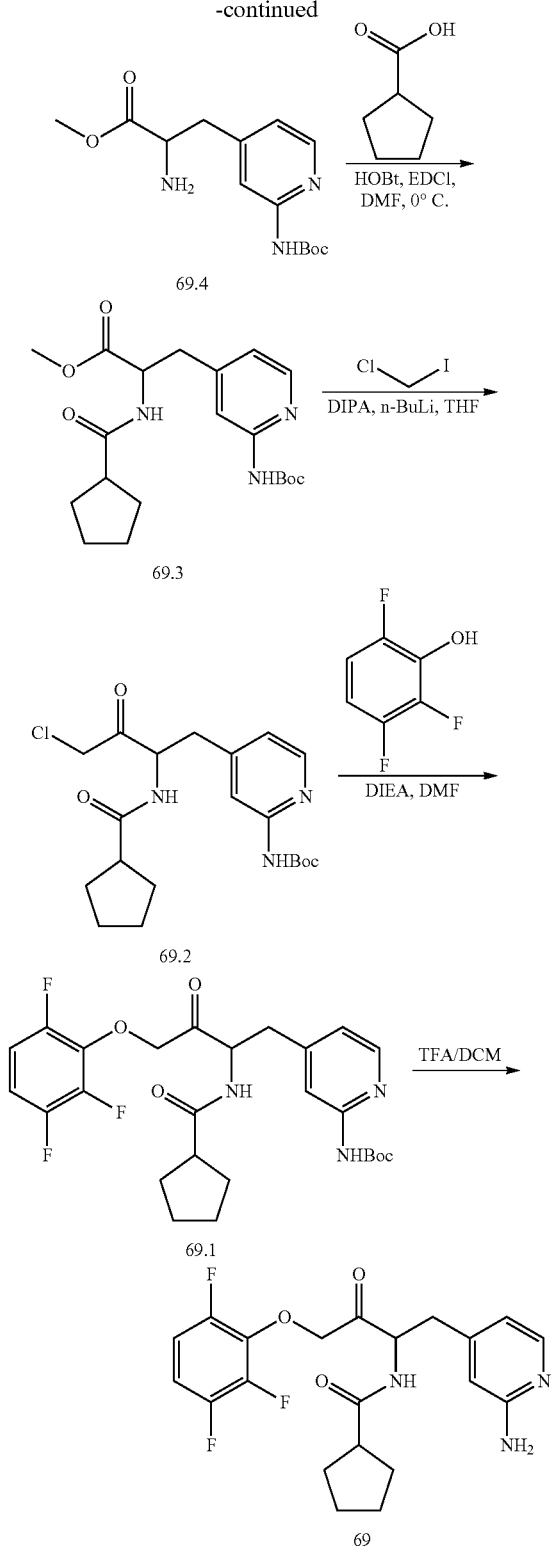

pressure to give compound 69.10 (60 g, crude) as a white solid. LCMS (ESI) m/z: [M+H]+ calcd for $C_7H_8N_2O_2$: 152; found 153; RT=0.214 min.

To a mixture of compound 69.10 (60 g, 394.35 mmol, 1 eq) and DMAP (2.41 g, 19.72 mmol, 0.05 eq) in t-BuOH (600 mL) and ACETONE (200 mL) was added $Boc_2O$ (344.26 g, 1.58 mol, 362.38 mL, 4 eq) dropwise at 18° C.

under $N_2$. The mixture was stirred at 18° C. for 15 hours. The solution was diluted with pentane (200 mL), cooled in the refrigerator for 3 hours and filtered to obtain compound 69.9 (42 g, 166.5 mmol, 42% yield) as a white solid. $^1$H NMR (400 MHz, DMSO-d6) δ: 1.38-1.54 (m, 9H), 3.82-3.96 (m, 3H), 7.44 (dd, J=5.07, 1.41 Hz, 1H), 8.32 (s, 1H), 8.42 (d, J=5.14 Hz, 1H) and 10.11 (s, 1H) ppm.

To a solution of compound 69.9 (42 g, 166.5 mmol, 1 eq) in THF (800 mL) was added $LiAlH_4$ (12.64 g, 333 mmol, 2 eq) portion-wise at 0° C. under $N_2$. The mixture was stirred at 0° C. for 1 hour, then heated to 18° C. and stirred at 18° C. for 14 hours. The reaction mixture was quenched by addition of 8% NaOH (15 mL), filtered and then diluted with $H_2O$ (1000 mL) and extracted with EtOAc (500 mL×3). The combined organic layers were washed with brine (1000 mL), dried over $Na_2SO_4$, filtered and concentrated under reduced pressure to give a residue. The residue was purified by column chromatography ($SiO_2$, Petroleum ether/Ethyl acetate=2:1) to give compound 69.8 (15 g, 67 mmol, 40% yield) as a white solid. $^1$H NMR (400 MHz, DMSO-d6) δ: 1.47 (s, 9H), 4.50 (d, J=5.70 Hz, 2H), 5.40 (t, J=5.92 Hz, 1H), 6.89-6.99 (m, 1H), 7.81 (s, 1H), 8.14 (d, J=5.70 Hz, 1H) and 9.71 (s, 1H) ppm.

To a solution of compound 69.8 (15 g, 67 mmol, 1 eq) in DCM (150 mL) was added Dess-Martin periodinane (42.55 g, 100.33 mmol, 31.06 mL, 1.5 eq) portion-wise at 18° C. under $N_2$. The mixture was stirred at 18° C. for 2 hours. The reaction mixture was diluted with $H_2O$ (60 mL) and extracted with DCM (50 mL×3). The combined organic layers were washed with brine (100 mL), dried over $Na_2SO_4$, filtered and concentrated under reduced pressure to give a residue. The residue was purified by column chromatography ($SiO_2$, Petroleum ether/Ethyl acetate=5:1) to give compound 69.7 (9 g, 40.5 mmol, 60% yield) as a white solid. $^1$H NMR (400 MHz, chloroform-d) δ ppm 1.55-1.62 (m, 9H), 7.40 (dd, J=5.26, 1.32 Hz, 1H), 8.44-8.57 (m, 2H), 9.38 (s, 1H) and 10.01-10.11 (m, 1H) ppm.

To a mixture of compound 69.7 (5 g, 22.5 mmol, 1 eq) and compound 69.6 (7.45 g, 22.5 mmol, 1 eq) in DCM (60 mL) was added 2,3,4,6,7,8,9,10-octahydropyrimido[1,2-a]azepine (DBU) (6.85 g, 45 mmol, 6.78 mL, 2 eq) in one portion at 18° C. under $N_2$. The mixture was stirred at 18° C. for 10 hours. The reaction mixture was concentrated under reduced pressure to give a residue. The residue was purified by column chromatography ($SiO_2$, Petroleum ether/Ethyl acetate=2:1) to give compound 69.5 (5.7 g, 13.33 mmol, 59% yield) as a white solid.

To a solution of compound 69.5 (5.7 g, 13.33 mmol, 1 eq) in MeOH (20 mL) was added 10% palladium on carbon catalyst (100 mg) under $N_2$. The suspension was degassed under vacuum and purged with $H_2$ several times. The mixture was stirred under $H_2$ (50 psi) at 25° C. for 10 hours. The reaction mixture was filtered and concentrated under reduced pressure to give a residue. The residue was purified by column chromatography ($SiO_2$, Ethyl acetate) to give compound 69.4 (2.8 g, 9.48 mmol, 71% yield) as a white solid.

To a mixture of cyclopentanecarboxylic acid (680.21 mg, 5.96 mmol, 647.82 μL, 1 eq) and EDCI (1.26 g, 6.56 mmol, 1.1 eq) in DMF (20 mL) was added HOBt (885.75 mg, 6.56 mmol, 1.1 eq) in one portion at 0° C. under $N_2$. The mixture was stirred at 0° C. for 1 hour, then the mixture was added dropwise a solution of compound 69.4 (1.76 g, 5.96 mmol, 1 eq) in DMF (5 mL), then the mixture was added dropwise DIPEA (2.31 g, 17.88 mmol, 3.12 mL, 3 eq) and stirred at 0° C. for 1 hour. The reaction mixture was diluted with $H_2O$ (10 mL) and extracted with EtOAc (10 mL×3). The combined organic layers were washed with brine (15 mL), dried over $Na_2SO_4$, filtered and concentrated under reduced pressure to give a residue. The residue was purified by column chromatography ($SiO_2$, Petroleum ether/Ethyl acetate=3:1) to give compound 69.3 (1.8 g, 4.6 mmol, 77% yield) as a white solid.

To a solution of DIPA (1.42 g, 14.05 mmol, 1.99 mL, 5.5 eq) in THF (40 mL) was added n-BuLi (2.5 M, 5.62 mL, 5.5 eq) at 0° C., the mixture was stirred at 0° C. for 30 mins. The mixture was added a solution of compound 69.3 (1 g, 2.55 mmol, 1 eq) and chloroiodomethane (2.48 g, 14.05 mmol, 1.02 mL, 5.5 eq) in THF (40 mL) at −78° C. The mixture was stirred at −78° C. for 30 mins. The reaction mixture was quenched by addition aqueous saturated $NH_4Cl$ (40 mL) and then extracted with EtOAc (50 mL×3). The combined organic layers were washed with aqueous saturated $Na_2SO_3$ (80 mL), and brine (50 mL), dried over $Na_2SO_4$, filtered and concentrated under reduced pressure to give compound 69.2 (1.4 g) as yellow oil.

To a mixture of compound 69.2 (300 mg, 731.87 μmol, 1 eq) and 2,3,6-trifluorophenol (108.38 mg, 731.87 μmol, 1 eq) in DMF (2 mL) was added DIEA (283.76 mg, 2.2 mmol, 382.43 μL, 3 eq) in one portion at 18° C. under $N_2$. The mixture was stirred at 18° C. for 10 hours. The mixture was purified by semi-preparative HPLC (TFA condition) to give compound 69.1 (80 mg, 153.4 μmol, 21% yield) as a white solid. LCMS (ESI) m/z: [M+H]+ calcd for $C_{26}H_{30}N_3O_5F_3$: 522; found 522; RT=1.366 min.

To a solution of compound 69.1 (80 mg, 153.4 μmol, 1 eq) in DCM (5 mL) was added TFA (1 mL) in one portion at 18° C. under $N_2$. The mixture was stirred at 18° C. for 1 hour. The reaction mixture was concentrated under reduced pressure to give a residue. The residue was purified by semi-preparative HPLC (TFA condition) to give 69 (40 mg, 95 μmol, 62% yield) as a white solid. LCMS (ESI) m/z: [M+H]+ calcd for $C_{21}H_{23}N_3O_3F_3$: 442; found 442; RT=1.581 min. $^1H$ NMR (400 MHz, DMSO-d6) δ: 1.34-1.49 (m, 3H), 1.49-1.59 (m, 3H), 1.60-1.73 (m, 2H), 2.51 (br s, 1H), 2.75 (dd, J=13.67, 10.58 Hz, 1H), 3.10 (br dd, J=13.78, 4.08 Hz, 1H), 4.61-4.74 (m, 1H), 5.11 (d, J=1.54 Hz, 2H), 6.70 (s, 1H), 6.74 (d, J=6.61 Hz, 1H), 7.08-7.26 (m, 2H), 7.84 (d, J=6.62 Hz, 1H), 7.96 (br s, 2H) and 8.32 (d, J=8.16 Hz, 1H) ppm.

Example 70. Preparation of N-(1-(2-aminopyridin-4-yl)-4-(isoxazol-3-yloxy)-3-oxobutan-2-yl)cyclopentanecarboxamide (70)

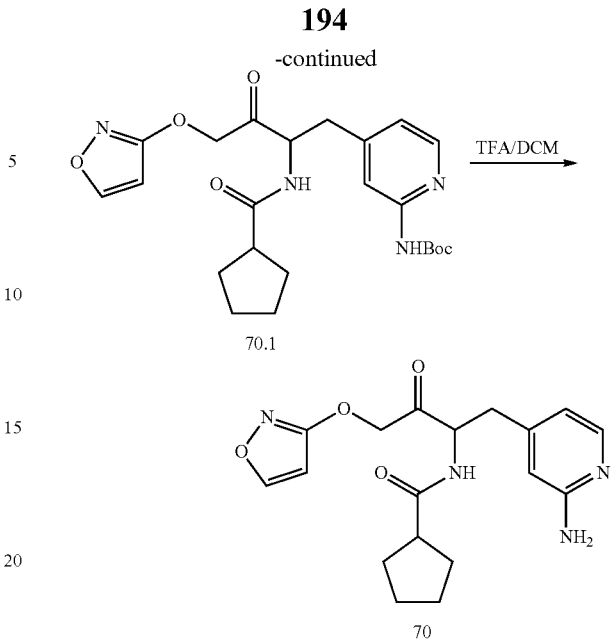

To a mixture of compound 69.2 (300 mg, 732 μmol, 1 eq) and isoxazol-3-ol (62.25 mg, 732 μmol, 1 eq) in DMF (2 mL) was added DIEA (378.35 mg, 2.93 mmol, 510 μL, 4 eq) in one portion at 18° C. under $N_2$. The mixture was stirred at 18° C. for 10 hours. The mixture was purified by semi-preparative scale HPLC (TFA condition) to give compound 70.1 (50 mg, 109 μmol, 15% yield) as a white solid. LCMS (ESI) m/z: [M+H]+ calcd for $C_{23}H_{31}N_4O_6$: 459; found 459; RT=1.233 min.

To a solution of compound 70.1 (50 mg, 109 μmol, 1 eq) in DCM (5 mL) was added TFA (1 mL) in one portion at 18° C. under $N_2$. The mixture was stirred at 18° C. for 1 hour. The reaction mixture was concentrated under reduced pressure to give a residue. The residue was purified by semi-preparative scale HPLC (TFA condition) to give 70 (15 mg, 41.85 μmol, 38% yield) as a white solid. LCMS (ESI) m/z: [M+H]+ calcd for $C_{18}H_{23}N_4O_4$: 359; found 359; RT=1.765 min. $^1H$ NMR (400 MHz, DMSO-d6) δ: 1.39-1.51 (m, 2H), 1.52-1.62 (m, 2H), 1.63-1.77 (m, 2H), 2.53-2.59 (m, 1H), 2.78 (br dd, J=13.56, 10.47 Hz, 1H), 3.15 (br dd, J=13.89, 3.97 Hz, 1H), 4.66-4.76 (m, 1H), 5.09 (s, 1H), 6.38 (d, J=1.76 Hz, 1H), 6.73 (s, 1H), 6.78 (d, J=6.61 Hz, 1H), 7.85 (d, J=6.61 Hz, 1H), 7.89 (br s, 1H), 8.36 (br d, J=8.38 Hz, 1H) and 8.68 (d, J=1.76 Hz, 1H) ppm.

Example 71. Preparation of N-(5-(2-aminopyridin-4-yl)-1-(isoxazol-3-yloxy)-2-oxopentan-3-yl)cyclopentanecarboxamide (71)

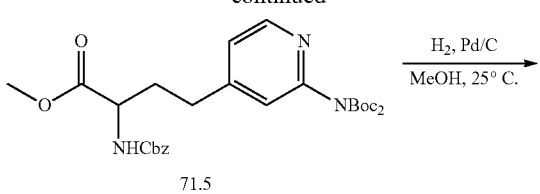

71.5

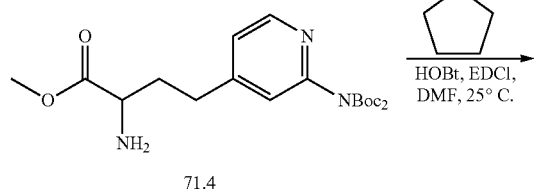

71.4

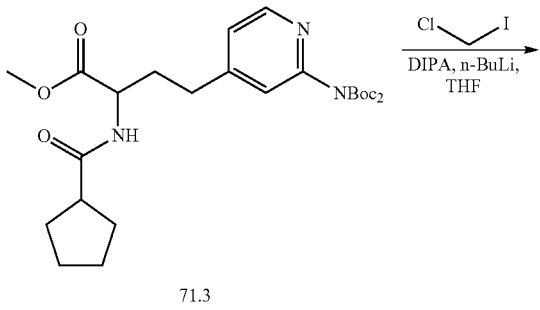

71.3

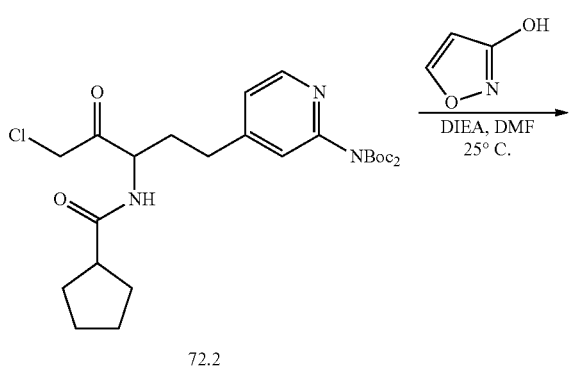

72.2

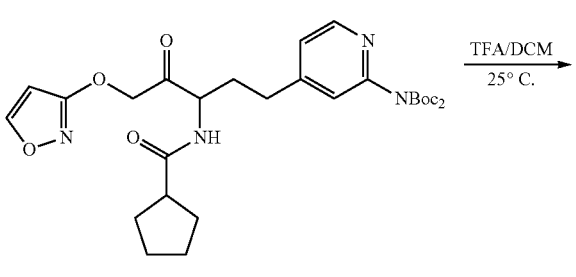

71.1

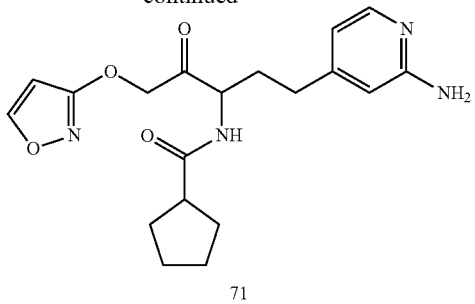

71

To a mixture of compound 71.8 (5 g, 28.9 mmol, 1 eq) and Boc$_2$O (25.23 g, 115.6 mmol, 26.6 mL, 4 eq) in DMF (50 mL) was added TEA (14.62 g, 144.5 mmol, 20.1 mL, 5 eq) and DMAP (353.1 mg, 2.89 mmol, 0.1 eq) in one portion at 25° C. under N$_2$. The mixture was stirred at 25° C. for 10 hours. The reaction mixture was diluted with H$_2$O (50 mL) and extracted with EtOAc (50 mL×3). The combined organic layers were washed with brine (100 mL), dried over Na$_2$SO$_4$, filtered and concentrated under reduced pressure to give a residue. The residue was purified by column chromatography (SiO$_2$, Petroleum ether/Ethyl acetate=3:1) to give compound 71.7 (2.7 g, 7.23 mmol, 25% yield) as a white solid. $^1$H NMR (400 MHz, DMSO-d6) δ: 7.41 (d, J=8.93 Hz, 1H), 8.12 (dd, J=8.56, 2.45 Hz, 1H), 8.59 (d, J=2.20 Hz, 1H) and 1.39 (s, 17H) ppm.

To a solution of compound 71.6 in dioxane (20 mL) was added 9-BBN (0.5 M, 15.9 mL, 2.2 eq) in one portion at 80° C. under N$_2$. The mixture was stirred at 80° C. for 2 hours, then to the mixture was added Pd(dppf)Cl$_2$ (264.20 mg, 361.07 μmol, 0.1 eq), CsF (1.65 g, 10.83 mmol, 399.36 μL, 3 eq) and compound 71.7 (1.62 g, 4.33 mmol, 1.2 eq). This was stirred at 80° C. for 8 hours. The reaction mixture was diluted with H$_2$O (20 mL) and extracted with EtOAc (20 mL×3). The combined organic layers were washed with brine (20 mL), dried over Na$_2$SO$_4$, filtered and concentrated under reduced pressure to give a residue. The residue was purified by column chromatography (SiO$_2$, Petroleum ether/Ethyl acetate=2:1) to give compound 71.5 (1 g, 1.84 mmol, 51% yield) as a white solid. LCMS (ESI) m/z: [M+H]+ calcd for C$_{28}$H$_{38}$N$_3$O$_8$: 544; found 544; RT=1.615 min.

To a solution of compound 71.5 (1 g, 1.84 mmol, 1 eq) in MeOH (50 mL) was added 10% Pd on carbon catalyst (100 mg) under N$_2$. The suspension was degassed under vacuum and purged with H$_2$ several times. The mixture was stirred under H$_2$ atmosphere (50 psi) at 25° C. for 10 hours. The reaction mixture was filtered and concentrated under reduced pressure to give a residue. The residue was purified by column chromatography (SiO$_2$, Ethyl acetate) to give compound 71.4 (400 mg, 977 μmol, 53% yield) as a white solid. $^1$H NMR (400 MHz, METHANOL-d4) δ: 0.99 (s, 18H), 1.44-1.56 (m, 1H), 1.58-1.70 (m, 1H), 2.38 (t, J=7.95 Hz, 2H), 2.87-2.94 (m, 2H), 2.89-2.92 (m, 1H), 3.03 (dd, J=7.21, 5.75 Hz, 1H), 6.86 (d, J=8.19 Hz, 1H), 7.40 (dd, J=8.19, 2.45 Hz, 1H) and 7.92 (d, J=2.08 Hz, 1H) ppm.

To a mixture of cyclopentanecarboxylic acid (111.50 mg, 0.977 μmol, 106.2 μL, 1 eq) and EDCI (224.72 mg, 1.17 mmol, 1.2 eq) in DMF (10 mL) was added HOBt (158.39 mg, 1.17 mmol, 1.2 eq) in one portion at 18° C. under N$_2$. The mixture was stirred at 25° C. for 30 mins, then compound 71.4 (400 mg, 976.86 μmol, 1 eq) and DIPEA (378.76 mg, 2.93 mmol, 510.45 μL, 3 eq) were added in one portion. This mixture was stirred at 25° C. for 30 mins. The reaction was diluted with H$_2$O (10 mL) and extracted with EtOAc (10 mL×3). The combined organic layers were washed with brine (10 mL), dried over Na₂SO₄, filtered and concentrated under reduced pressure to give a residue. The residue was purified by column chromatography (SiO₂, Petroleum ether/ Ethyl acetate=2:1) to give compound 71.3 (600 mg) as a white solid. LCMS (ESI) m/z: [M+H]+ calcd for $C_{26}H_{40}O_7N_3$: 506; found 506; RT=1.316 min.

To a solution of DIPA (600.41 mg, 5.93 mmol, 838.6 µL, 5 eq) in THF (10 mL) was added n-BuLi (2.5 M, 2.37 mL, 5 eq) at 0° C.; the mixture was stirred at 0° C. for 30 mins. The mixture was added a solution of chloroiodomethane (1.05 g, 5.93 mmol, 430.69 µL, 5 eq) and compound 71.3 (600 mg, 1.19 mmol, 1 eq) in THF (10 mL) at −78° C. This was stirred at −78° C. for 30 mins. The reaction mixture was quenched by addition of saturated aqueous NH₄Cl (20 mL) and then extracted with EtOAc (20 mL×3). The combined organic layers were washed with saturated aqueous Na₂SO₃ (30 mL), and brine (50 mL), dried over Na₂SO₄, filtered and concentrated under reduced pressure. The residue was purified by semi-preparative scale HPLC (TFA condition) to give compound 71.2 (100 mg, 190.8 µmol, 16% yield) as a white solid.

To a mixture of compound 71.2 (70 mg, 133.6 µmol, 1 eq) and isoxazol-3-ol (11.36 mg, 133.6 µmol, 1 eq) in DMF (2 mL) was added DIEA (17.26 mg, 133.6 µmol, 23.3 µL, 1 eq) in one portion at 25° C. under N₂. The mixture was stirred at 25° C. for 10 hours. The reaction mixture was diluted with H₂O (10 mL) and extracted with EtOAc (10 mL×3). The combined organic layers were washed with brine (20 mL), dried over Na₂SO₄, filtered and concentrated under reduced pressure to give compound 71.1 (80 mg) as a yellow oil.

To a solution of compound 71.1 (79.73 mg, 139.2 µmol, 1 eq) in DCM (5 mL) was added TFA (139.2 µmol, 10.31 µL, 1 eq) in one portion at 25° C. under N₂. The mixture was stirred at 25° C. for 1 hour. The reaction mixture was concentrated under reduced pressure; the residue was purified by semi-preparative scale HPLC (neutral condition) to give 71 (2 mg, 5.13 µmol, 4% yield, 95.5% purity) as a white solid. LCMS (ESI) m/z: [M+H]+ calcd for $C_{19}H_{24}N_4O_4$: 373; found 373; RT=5.70 min. ¹H NMR (400 MHz, METHANOL-d4) δ: 1.72 (m, 2H), 1.74 (m, 4H), 1.87 (m, 3H), 2.10 (m, 1H), 2.53 (m, 2H), 2.61 (m, 1H), 4.46 (dd, J=9.60, 4.40 Hz, 1H), 4.97-5.07 (m, 1H), 6.13 (s, 1H), 6.57 (d, J=8.40 Hz, 1H), 7.40 (dd, J=8.40, 2.45 Hz, 1H), 7.72 (s, 1H) and 8.36 (dd, J=5.20, 1.60 Hz, 1H) ppm.

Example 72. Preparation of N-(1-(6-aminopyridin-3-yl)-4-((1,1,1,3,3,3-hexafluoropropan-2-yl)oxy)-3-oxobutan-2-yl)-2-methoxy-2-methylpropanamide (72)

To a solution of compound 72.9 (10 g, 83.9 mmol, 1 eq) in THF (250 mL) was added LAH (6.37 g, 167.9 mmol, 2 eq) at 0° C. The mixture was stirred at 0° C. for 1.5 hour. The reaction mixture was quenched by addition saturated sodium sulfate at 0° C. and H₂O (200 mL) was added; then this was extracted with ethyl acetate (200 mL×3). The combined organic layers were washed with saturated brine (30 mL), dried over anhydrous sodium sulfate, filtered and concentrated under reduced pressure to give the product compound 72.8 (6 g, crude) as a yellow solid. LCMS (ESI): m/z: [M+H]+ calcd for $C_6H_7N_2O$: 123; found 123; RT=0.276 min.

To a solution of compound 72.8 (6 g, 49.14 mmol, 1 eq) in THF (100 mL) was added TEA (19.89 g, 196.53 mmol, 4 eq), Boc₂O (32.16 g, 147.39 mmol, 3 eq) and DMAP

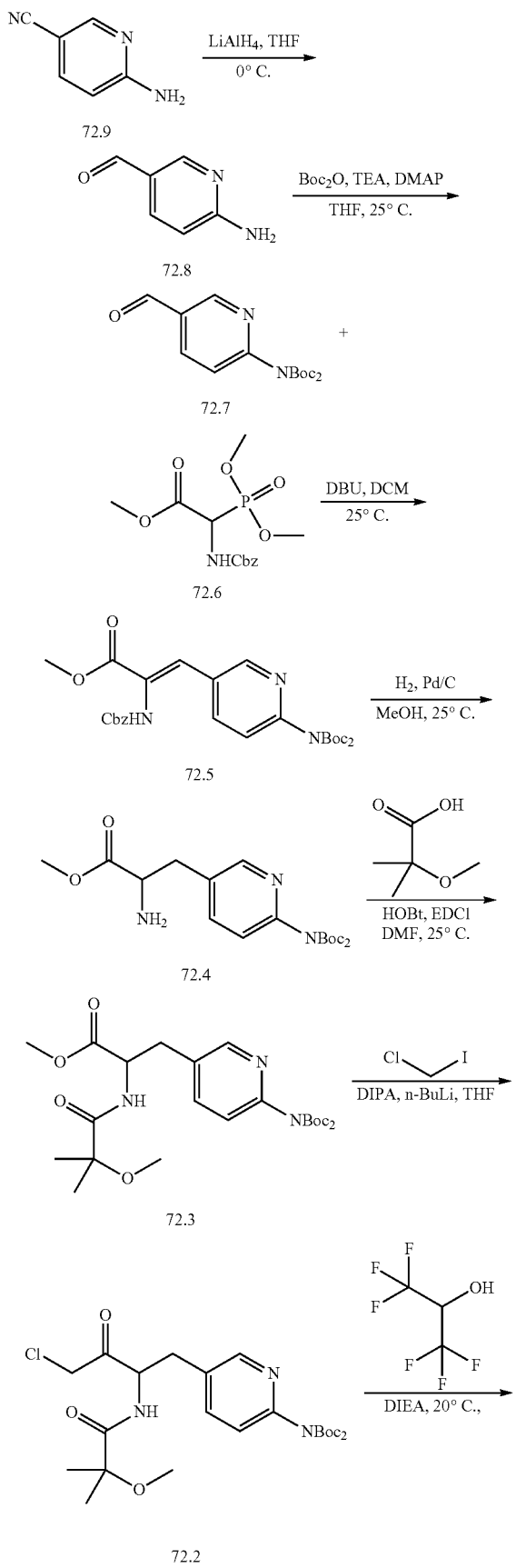

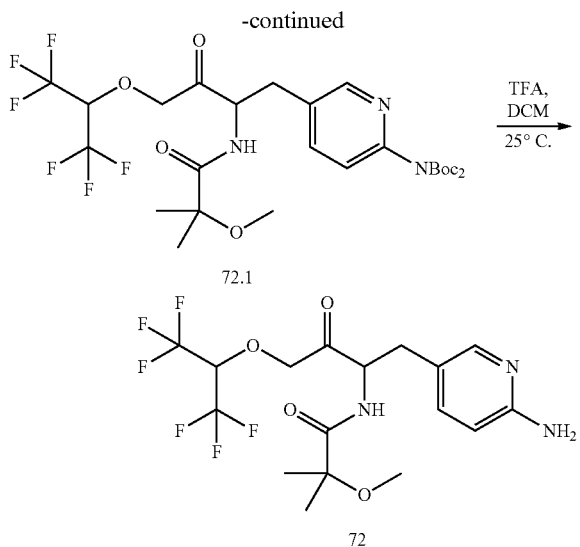

(1.2 g, 9.9 mmol, 0.2 eq). The mixture was stirred at 25° C. for 12 hours. The reaction mixture was quenched by addition of H$_2$O (200 mL) at 25° C. and extracted with ethyl acetate (200 mL×3). The combined organic layers were washed with saturated brines (50 mL), dried over anhydrous sodium sulfate, filtered and concentrated under reduced pressure to give a crude product. The residue was purified by column chromatography (SiO$_2$, Petroleum ether/Ethyl acetate=3:1) to give compound 72.7 (5 g, 15.51 mmol, 32% yield) as yellow solid. LCMS (ESI) m/z: [M+H]+ calcd for C$_{16}$H$_{23}$N$_2$O$_5$: 323; found 323; RT=1.532 min. $^1$H NMR (400 MHz, chloroform-d) δ: 1.52 (br d, J=3.97 Hz, 28H), 7.59-7.74 (m, 1H), 8.10-8.28 (m, 1H), 8.87 (br s, 1H), 10.07 (br d, J=3.97 Hz, 1H) ppm.

To a solution of compound 72.7 (5 g, 15.5 mmol, 1 eq) in DCM (60 mL) was added DBU (4.7 g, 30.4 mmol, 2 eq) and compound 72.6 (5.1 g, 15.5 mmol, 1 eq). The mixture was stirred at 25° C. for 2 hours. The reaction mixture was quenched by addition of H$_2$O (100 mL) at 25° C. and extracted with ethyl acetate (100 mL×3). The combined organic layers were washed with brine (5 mL), dried over anhydrous sodium sulfate, filtered and concentrated under reduced pressure to give a crude product. The residue was purified by column chromatography (SiO$_2$, Petroleum ether/Ethyl acetate=2:1) to give compound 72.5 (3 g, 5.7 mmol, 37% yield) as yellow oil. LCMS (ESI) m/z: [M+H]+ calcd for C$_{27}$H$_{34}$N$_3$O$_8$: 528; found 528; RT=1.604 min.

To a solution of compound 72.5 (3 g, 5.69 mmol, 1 eq) in MeOH (400 mL) was added 10% Pd on carbon catalyst (1 g) under N$_2$. The suspension was degassed under vacuum and purged with H$_2$ several times. The mixture was stirred under H$_2$ (50 psi) at 25° C. for 15 hours. The reaction mixture was filtered, and the filtrate was concentrated. compound 76.4 (1.5 g) was obtained as yellow oil. LCMS (ESI) m/z: [M+H]+ calcd for C$_{19}$H$_{30}$N$_3$O$_6$: 396; found 396; RT=1.084 min.

To a solution of 2-methoxy-2-methylpropanoic acid (448.09 mg, 3.79 mmol, 1 eq) in DMF (20 mL) was added HOBt (563.78 mg, 4.17 mmol, 1.1 eq) and EDCI (799.86 mg, 4.17 mmol, 1.1 eq). The mixture was stirred at 25° C. for 1 hr. To the mixture was added compound 72.4 (1.5 g, 3.79 mmol, 1 eq) and DIPEA (1.96 g, 15.17 mmol, 2.64 mL, 4 eq). The mixture was stirred at 25° C. for 14 hrs. The reaction mixture was quenched by addition of H$_2$O (30 mL) and was extracted with ethyl acetate (30 mL×3). The combined organic layers were washed with brine (5 mL), dried over anhydrous sodium sulfate, filtered and concentrated under reduced pressure. The residue was purified by column chromatography (SiO$_2$, Petroleum ether/Ethyl acetate=2:1) to give compound 72.3 (1.25 g, 2.52 mmol, 67% yield) as yellow oil. LCMS (ESI) m/z: [M+H]+ calcd for C$_{24}$H$_{38}$N$_3$O$_8$: 496; found 496; RT=1.260 min.

To a solution of DIPA (1.40 g, 13.87 mmol, 1.96 mL, 5.5 eq) in THF (10 mL) was added n-BuLi (2.5 M, 5.55 mL, 5.5 eq). The mixture was stirred at 0° C. for 0.5 hr under N$_2$. The mixture was added to compound 72.3 (1.25 g, 2.52 mmol, 1 eq) and chloroiodomethane (2.45 g, 13.87 mmol, 1.01 mL, 5.5 eq) in THF (10 mL) was stirred at -78° C. for 2.5 hrs. The reaction mixture was quenched by addition of saturated NH$_4$Cl (20 ml) at 25° C. and extracted with ethyl acetate (15 mL×3). The combined organic layers were washed with saturated Na$_2$SO$_3$ (10 mL) and saturated NaHCO$_3$ (10 mL) and brine (10 mL), dried over anhydrous sodium sulfate, filtered and concentrated under reduced pressure. The residue was purified by column chromatography (SiO$_2$, Petroleum ether/Ethyl acetate=0:1) to give compound 72.2 (100 mg, 194.55 µmol, 8% yield) as yellow oil. LCMS (ESI) m/z: [M+H]+ calcd for C$_{24}$H$_{37}$N$_3$O$_7$Cl: 514; found 514; RT=0.971 min.

To a solution of compound 72.2 (40 mg, 77.82 µmol, 1 eq) in 1,1,1,3,3,3-hexafluoropropan-2-ol (800 mg, 4.76 mmol, 100 µL, 61.18 eq) was added DIEA (60.35 mg, 466.92 µmol, 81.33 µL, 6 eq). The mixture was stirred at 25° C. for 12 hrs. The reaction mixture was purified by column chromatography (SiO$_2$, Petroleum ether/Ethyl acetate=1:1) to give compound 72.1 (20 mg, 31 µmol, 40% yield) as yellow oil. LCMS (ESI) m/z: [M+H]+ calcd for C$_{22}$H$_{30}$N$_3$O$_6$F$_6$: found 546; RT=1.301 min.

Compound 72.1 was added into DCM (5 mL) and TFA (1 mL), the mixture was stirred at 25° C. for 1 hour. The mixture was concentrated under reduced pressure to give a residue. The residue was purified by semi-preparative scale HPLC (TFA condition) to give 72 (2 mg, 3.58 µmol, 12% yield, TFA) as a white solid. LCMS (ESI) m/z: [M+H]+ calcd for C$_{17}$H$_{22}$N$_3$O$_7$F$_6$: 446; found 446; RT=0.925 min. $^1$H NMR (400 MHz, METHANOL-d4) δ: 1.34 (d, J=9.54 Hz, 6H), 2.23 (s, 3H), 3.32-3.34 (m, 3H), 4.91-4.95 (m, 3H), 5.17 (dq, J=11.95, 6.04 Hz, 1H), 6.92 (d, J=9.17 Hz, 1H), 7.63 (s, 1H) and 7.69 (dd, J=9.23, 2.02 Hz, 1H) ppm.

Example 73. Preparation of N-(1-(2-aminopyridin-4-yl)-4-((1,1,1,3,3,3-hexafluoropropan-2-yl)oxy)-3-oxobutan-2-yl)-2-methoxy-2-methylpropanamide (73)

To a solution of compound 73.11 (50 g, 362 mmol, 1 eq) in MeOH (600 mL) was added SOCl$_2$ (172.27 g, 1.45 mol, 105.04 mL, 4 eq) drop wise at 0° C. under N$_2$, then stirred at 18° C. for 10 hours. The reaction mixture was concentrated under reduced pressure to give compound 73.10 (60 g, crude) as a white solid. LCMS (ESI) m/z: [M+H]+ calcd for C$_7$H$_9$N$_2$O$_2$: 153; found 153; RT=0.214 min.

To a mixture of compound 73.10 (60 g, 394.35 mmol, 1 eq) and DMAP (2.41 g, 19.72 mmol, 0.05 eq) in t-BuOH (600 mL) and ACETONE (200 mL) was added Boc$_2$O (344.26 g, 1.58 mol, 362.38 mL, 4 eq) dropwise. The mixture was stirred for 15 hours. The solution was diluted with pentane (200 ml), cooled in the refrigerator for 3 hours then filtered to give compound 73.9 (42 g, 166.49 mmol, 42% yield) as a white solid. LCMS (ESI) m/z: [M+H]+ calcd for C$_{12}$H$_{17}$N$_2$O$_4$: 253; found 253; RT=1.562 min.

To a solution of compound 73.9 (42 g, 166.49 mmol, 1 eq) in THF (800 mL) was added LiAlH₄ (12.64 g, 332.98 mmol, 2 eq) portion wise at 0° C. under N₂. The mixture was

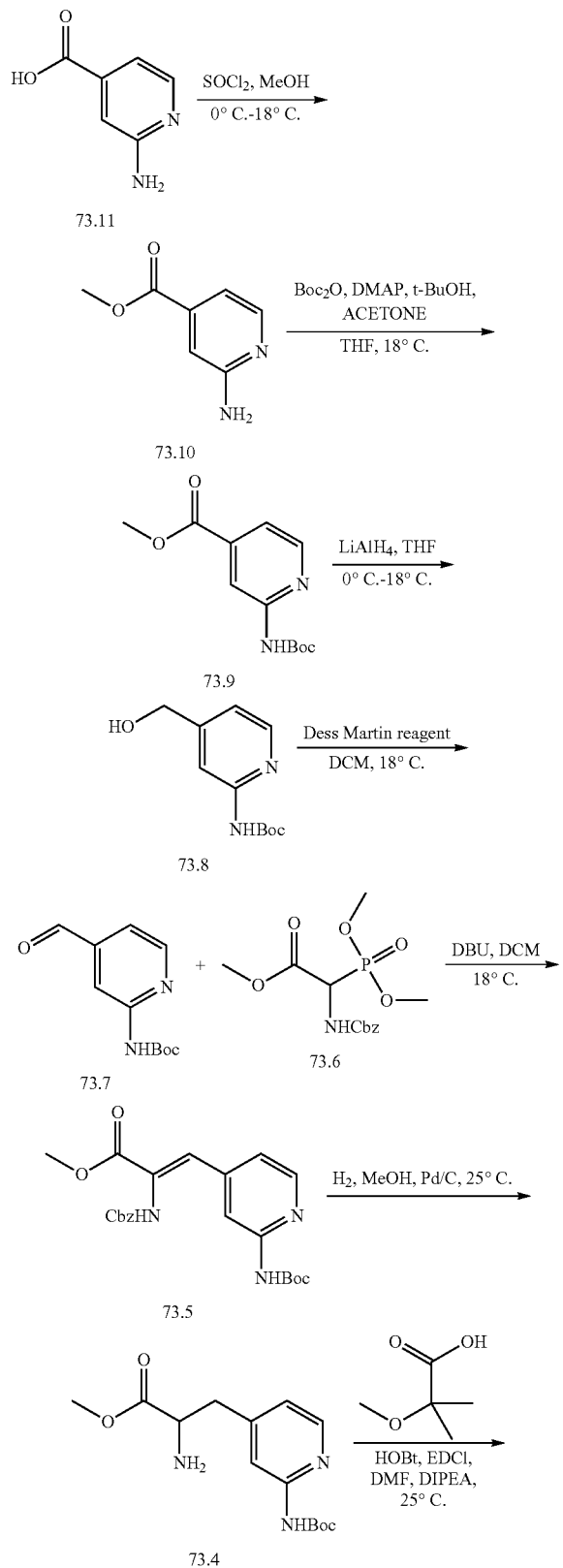

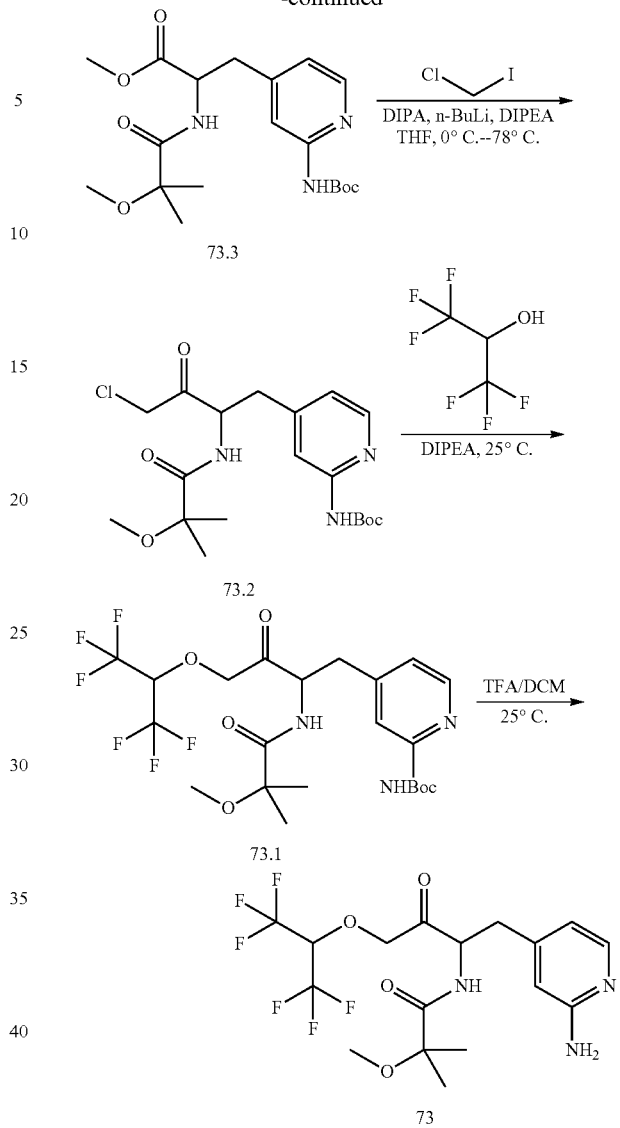

stirred at 0° C. for 1 hours, then stirred for 14 hours. The reaction mixture was quenched by addition 8% NaOH (15 ml), filtered and then diluted with H₂O (1000 mL) and extracted with EtOAc (500 mL×3). The combined organic layers were washed with brine (1000 mL), dried over Na₂SO₄, filtered and concentrated under reduced pressure to give a residue. The residue was purified by column chromatography (SiO2, Petroleum ether/Ethyl acetate=2:1) to give compound 73.8 (15 g, 66.89 mmol, 40% yield) as a white solid. LCMS (ESI) m/z: [M+H]+ calcd for $C_{11}H_{17}N_2O_3$: 225; found 225; RT=0.833 min.

To a solution of compound 73.8 (15 g, 66.89 mmol, 1 eq) in DCM (150 mL) was added Dess-Martin periodinane (42.55 g, 100.33 mmol, 31.06 mL, 1.5 eq) portion-wise at 18° C. under N₂. The mixture was stirred for 2 hours. The reaction mixture was diluted with H₂O (60 mL) and extracted with DCM 150 mL (50 mL×3). The combined organic layers were washed with brine (100 mL) (100 mL), dried over Na₂SO₄, filtered and concentrated under reduced pressure to give a residue. The residue was purified by column chromatography (SiO₂, Petroleum ether/Ethyl acetate=5:1) to give compound 73.7 (9 g, 40.5 mmol, 61% yield) as a white solid.

To a mixture of compound 5 (2 g, 9 mmol, 1 eq) and compound 73.6 (2.98 g, 9 mmol, 1 eq) in DCM (20 mL) was added DBU (2.74 g, 18 mmol, 2.71 mL, 2 eq) in one portion. The mixture was stirred at 18° C. for 10 hours. The reaction mixture was filtered and concentrated under reduced pressure to give a residue. The residue was purified by MPLC (SiO$_2$, Petroleum ether/Ethyl acetate=10/1 to 0:1) to give compound 73.5 (3 g, 7.02 mmol, 78% yield) as a white solid. $^1$H NMR (400 MHz, chloroform-d) δ: 8.41-8.47 (m, 1H), 8.39-8.49 (m, 1H), 8.26-8.33 (m, 1H), 8.25-8.33 (m, 1H), 8.10 (br d, J=14.77 Hz, 1H), 8.06-8.14 (m, 1H), 7.32-7.50 (m, 5H), 7.04-7.10 (m, 1H), 7 (d, J=5.29 Hz, 1H), 6.97-7.10 (m, 1H), 6.85 (br d, J=4.41 Hz, 1H), 6.76-6.91 (m, 1H), 6.38 (s, 1H), 5.17 (s, 1H), 3.91 (s, 2H), 3.95 (s, 1H), 1.59 (s, 5H) and 1.61 (s, 3H) ppm.

To a solution of compound 73.5 (3 g, 7.02 mmol, 1 eq) in MeOH (300 mL) was added 10% palladium on carbon catalyst Pd/C (300 mg) under N$_2$. The suspension was degassed under vacuum and purged with H$_2$ several times. The mixture was shaken under H$_2$ (50 psi) at 25° C. for 20 hours. The reaction mixture was filtered. The filtrate was concentrated under reduced pressure to give a residue. The residue was purified by MPLC (SiO$_2$, Petroleum ether/Ethyl acetate=10/1 to 1:1) to give compound 73.4 (1.4 g, 4.74 mmol, 68% yield) as a white solid. LCMS (ESI) m/z: [M+H]+ calcd for C$_{14}$H$_{22}$N$_3$O$_4$: 296; found 296; RT=0.654 min.

To a mixture of 2-methoxy-2-methylpropanoic acid (560 mg, 4.74 mmol, 1 eq) and HOBt (704.6 mg, 5.21 mmol, 1.1 eq) in DMF (20 mL) was added EDCI (999.6 mg, 5.21 mmol, 1.1 eq) in one portion at 25° C. under N$_2$. The mixture was stirred at 25° C. for 1 hour, then to the mixture was added compound 73.4 (1.4 g, 4.74 mmol, 1 eq) and DIPEA (1.84 g, 14.22 mmol, 2.48 mL, 3 eq) in one portion, and stirred at 25° C. for 9 hours. The reaction mixture was quenched by addition of H$_2$O (20 mL) and then extracted with EtOAc 60 mL (20 mL×3). The combined organic layers were washed with H$_2$O (20 mL×3) and brine (20 mL) then dried over Na$_2$SO$_4$, filtered and concentrated. The residue was purified by MPLC (SiO$_2$, Petroleum ether/Ethyl acetate=10/1 to 0:1) to give compound 73.3 (1.2 g, 3.03 mmol, 64% yield) as a white solid. $^1$H NMR (400 MHz, chloroform-d) δ: 8.57 (s, 1H), 8.18 (d, J=5.14 Hz, 1H), 7.82 (s, 1H), 7.09 (br d, J=8.19 Hz, 1H), 6.74 (dd, J=5.26, 1.47 Hz, 1H), 4.83-4.90 (m, 1H), 3.77 (s, 3H), 3.20 (s, 3H), 3.17 (d, J=5.38 Hz, 1H), 3.01-3.09 (m, 1H), 1.52 (s, 9H), 1.34 (s, 3H) and 1.31 (s, 3H) ppm.

To a solution of DIPA (633.32 mg, 6.26 mmol, 884.52 μL, 5.5 eq) in THF (20 mL) was added n-BuLi (2.5 M, 2.5 mL, 5.5 eq) at 0° C., the mixture was stirred at 0° C. for 30 mins. To the mixture was added a solution of compound 73.3 (0.45 g, 1.14 mmol, 1 eq) and chloroiodomethane (1.10 g, 6.26 mmol, 454.29 μL, 5.5 eq) in THF (20 mL) at −78° C. The mixture was stirred at −78° C. for 1.5 h. The reaction mixture was quenched by addition of NH$_4$Cl (20 mL) and extracted with EtOAc (20 mL×3). The combined organic layers were washed with saturated brines (20 mL), dried over Na$_2$SO$_4$, filtered and concentrated under reduced pressure to give a residue. The residue was purified by column chromatography (SiO$_2$, Petroleum ether/Ethyl acetate=1:1) to give compound 73.2 (100 mg, 241.61 μmol, 21% yield) as a white solid.

To a solution of compound 73.2 (40 mg, 96.64 μmol, 1 eq) in 1,1,1,3,3,3-hexafluoropropan-2-ol (64.96 mg, 386.57 μmol, 100 μL, 4 eq) was added DIPEA (0.5 M, 193.29 μL, 1 eq) in one portion at 25° C. under N$_2$. The mixture was stirred at 25° C. for 20 min. The residue was purified by semi-preparative scale HPLC (TFA condition) to give compound 73.1 (5 mg, 9.17 μmol, 10% yield) as a white solid.

To a solution of compound 73.1 (5 mg, 9.17 μmol, 1 eq) in DCM (2 mL) was added TFA (0.5 mL) in one portion at 25° C. under N$_2$. The mixture was stirred at 25° C. for 1 min. Then the reaction mixture was concentrated under reduced pressure to give 73 (2 mg, 4.49 mol, 50% yield) as a white solid. LCMS (ESI) m/z: [M+H]+ calcd for C$_{17}$H$_{22}$F$_6$N$_3$O$_4$: 446; found 446; RT=2.635 min. $^1$H NMR (400 MHz, METHANOL-d$_4$) δ: 1.24-1.45 (m, 6H), 2.29 (s, 2H), 3.31-3.32 (m, 3H), 3.39-3.53 (m, 2H), 5.14-5.25 (m, 1H), 6.71 (dd, J=6.72, 1.71 Hz, 1H), 6.81 (s, 1H) and 7.77 (d, J=6.72 Hz, 1H) ppm.

Example 74. Preparation of N-(5-(6-aminopyridin-3-yl)-1-(isoxazol-3-yloxy)-2-oxopentan-3-yl)cyclo-pentanecarboxamide (74)

To a mixture of compound 74.8 (5 g, 28.9 mmol, 1 eq) and TEA (11.7 g, 115.6 mmol, 16.09 mL, 4 eq) in DMF (100 mL) was added Boc$_2$O (18.92 g, 86.7 mmol, 19.92 mL, 3 eq) in one portion at 25° C. under N$_2$. The mixture was stirred at 25° C. for 10 hours. The reaction mixture was diluted with H$_2$O (100 mL) then was extracted with EtOAc (100 mL×3). The combined organic layers were washed with brine (200 mL), dried over Na$_2$SO$_4$, filtered and concentrated under reduced pressure. The residue that remained was purified by column chromatography (SiO$_2$, Petroleum ether/Ethyl acetate=5:1) to give compound 74.7

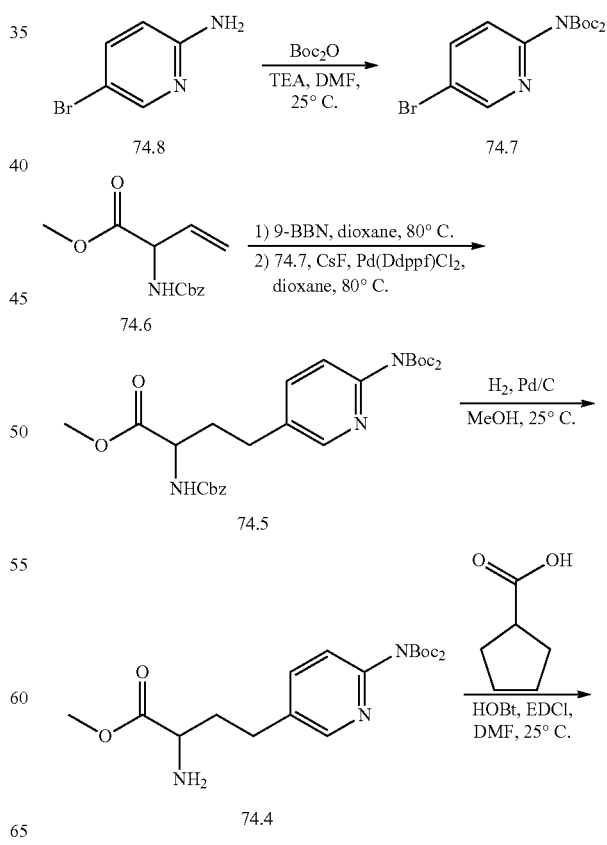

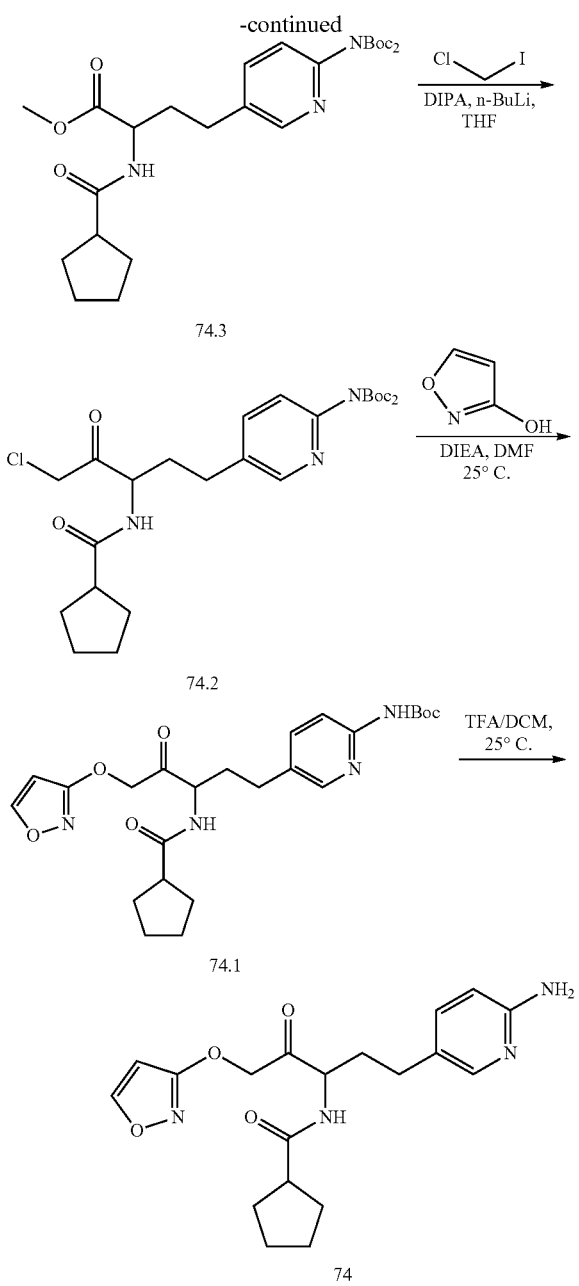

$^1$H NMR (400 MHz, chloroform-d) δ: 1.44 (s, 18H), 1.90-2.03 (m, 2H), 2.11-2.26 (m, 1H), 2.55-2.76 (m, 3H), 3.66-3.80 (m, 4H), 4.37-4.50 (m, 1H), 5.08-5.18 (m, 2H), 5.36-5.49 (m, 1H), 7.14 (d, J=7.89 Hz, 1H), 7.31-7.42 (m, 6H), 7.55 (br d, J=8.33 Hz, 1H) and 8.30 (s, 1H) ppm.

To a solution of compound 74.5 (3.8 g, 6.99 mmol, 1 eq) in MeOH (100 mL) was added 10% Pd on carbon catalyst (400 mg) under $N_2$. The suspension was degassed under vacuum and purged with $H_2$ several times. The mixture was stirred under $H_2$ atmosphere (50 psi) at 25° C. for 0.5 hour. The reaction mixture was purged with $N_2$ gas, filtered through a Celite pad and was concentrated under reduced pressure to give a residue. The residue was purified by column chromatography ($SiO_2$, Petroleum ether/Ethyl acetate=10:1 to 1:1) to give compound 74.4 (2 g, 4.88 mmol, 70% yield) as a yellow solid.

To a mixture of cyclopentanecarboxylic acid (111.5 mg, 976.86 μmol, 106.19 μL, 1 eq) and EDCI (206 mg, 1.07 mmol, 1.1 eq) in DMF (25 mL) was added HOBt (145.19 mg, 1.07 mmol, 1.1 eq) in one portion at 0° C. under $N_2$. The mixture was stirred at 0° C. for 1 hour. After this time, to the mixture was added dropwise a solution of compound 74.4 (400 mg, 976.86 μmol, 1 eq) in DMF (5 mL), then there was added dropwise DIPEA (378.75 mg, 2.93 mmol, 510.44 μL, 3 eq). This was stirred at 0° C. for 1 hour; then the reaction mixture was diluted with $H_2O$ (10 mL) and extracted with EtOAc (10 mL×3). The combined organic layers were washed with brine (15 mL), dried over $Na_2SO_4$, filtered and concentrated under reduced pressure to give a residue. The residue was purified by column chromatography ($SiO_2$, Petroleum ether/Ethyl acetate=3:1) to give compound 74.3 (2 g, 3.96 mmol, 81% yield) as a white solid. $^1$H NMR (400 MHz, chloroform-d) δ: 1.44 (s, 15H), 1.59 (br d, J=6.11 Hz, 2H), 1.67-2 (m, 8H), 2.12-2.28 (m, 1H), 2.50-2.77 (m, 3H), 3.66-3.82 (m, 3H), 4.63-4.75 (m, 1H), 6-6.12 (m, 1H), 7.15 (d, J=8.07 Hz, 1H), 7.51-7.61 (m, 1H) and 8.29 (s, 1H) ppm.

To a solution of DIPA (2.20 g, 21.76 mmol, 3.07 mL, 5.5 eq) in THF (10 mL) was added n-BuLi (2.5 M, 8.70 mL, 5.5 eq) at 0° C., the mixture was stirred at 0° C. for 30 mins. To this mixture was added a solution of chloroiodomethane (3.84 g, 21.76 mmol, 1.58 mL, 5.5 eq) and compound 74.3 (2 g, 3.96 mmol, 1 eq) in THF (10 mL) at −78° C. The mixture was stirred at −78° C. for 30 mins. The reaction mixture was quenched by addition of $NH_4Cl$ (20 mL) and then extracted with EtOAc 60 mL (20 mL×3). The combined organic layers were washed with saturated aqueous $Na_2SO_3$ (30 mL), and brine (50 mL), dried over $Na_2SO_4$, filtered and concentrated under reduced pressure to give a residue. The residue was purified by column chromatography ($SiO_2$, Petroleum ether/Ethyl acetate=2:1) to give compound 74.2 (500 mg, 954.11 μmol, 24% yield) as yellow oil. LCMS (ESI) m/z: [M+H]+ calcd for $C_{26}H_{39}N_3O_6Cl$: 525; found 525; RT=1.33 min.

To a mixture of compound 74.2 (500 mg, 954.11 μmol, 1 eq) and isoxazol-3-ol (81.16 mg, 954.11 μmol, 1 eq) in DMF (4 mL) was added DIEA (369.93 mg, 2.86 mmol, 498.56 μL, 3 eq) in one portion at 25° C. under $N_2$. The mixture was stirred at 25° C. for 10 hours. The reaction was purified by prep-HPLC (TFA condition) to give compound 74.1 (100 mg, 211.63 μmol, 22% yield) as yellow oil. $^1$H NMR (400 MHz, chloroform-d) δ: 1.56 (s, 10 H), 1.62 (br s, 2H), 1.70-1.83 (m, 4H), 1.85-1.97 (m, 3H), 2.24-2.36 (m, 1H), 2.56-2.66 (m, 1H), 2.70 (br t, J=7.95 Hz, 2H), 4.82-4.89 (m, 1H), 4.92-5.07 (m, 2H), 6.08 (s, 1H), 6.22 (br d, J=7.70 Hz, 1H), 7.92 (br d, J=9.29 Hz, 1H), 7.99 (s, 1H), 8.17 (s, 1H) and 8.35 (d, J=8.68 Hz, 1H) ppm.

(20 g, 53.58 mmol, 46% yield) as a white solid. $^1$H NMR (400 MHz, chloroform-d) δ: 1.45 (s, 20H), 7.18 (d, J=8.44 Hz, 1H), 7.81-7.91 (m, 1H), 7.81-7.91 (m, 1H) and 8.54 (d, J=2.20 Hz, 1H) ppm.

To a solution of compound 74.6 (3 g, 12.04 mmol, 1 eq) in dioxane (30 mL) was added 9-BBN (0.5 M, 53 mL, 2.2 eq) in one portion at 80° C. under $N_2$. The mixture was stirred at 80° C. for 30 mins, then there was added CsF (5.48 g, 36.11 mmol, 1.33 mL, 3 eq), Pd(dppf)Cl$_2$ (880.65 mg, 1.2 mmol, 0.1 eq) and compound 74.7 (5.39 g, 14.44 mmol, 1.2 eq). This mixture was stirred at 80° C. for 9.5 hours; then the reaction was diluted with $H_2O$ (20 mL) and extracted with EtOAc (20 mL×3). The combined organic layers were washed with brine (20 mL), dried over $Na_2SO_4$, filtered and concentrated. The residue was purified by column chromatography ($SiO_2$, Petroleum ether/Ethyl acetate=2:1) to give compound 74.5 (4 g, 7.36 mmol, 61% yield) as yellow oil.

To a solution of compound 74.1 (100 mg, 211.63 µmol, 1 eq) in DCM (5 mL) was added TFA (211.63 µmol, 15.67 µL, 1 eq) in one portion at 25° C. under $N_2$. The mixture was stirred at 25° C. for 1 hour. The reaction mixture was concentrated under reduced pressure to give a residue. The residue was purified by semi-preparative scale HPLC (TFA condition) to give 74 (40 mg, 107.41 µmol, 51% yield) as colorless oil. LCMS (ESI) m/z: [M+H]+ calcd for $C_{19}H_{25}N_4O_4$: 373; found 373; RT=2.046 min. $^1$H NMR (400 MHz, METHANOL-d4) δ: 1.56-1.67 (m, 2H), 1.69-1.81 (m, 4H), 1.84-1.97 (m, 3H), 2.14-2.25 (m, 1H), 2.53-2.81 (m, 3H), 4.49 (dd, J=9.17, 4.77 Hz, 1H), 4.95-5.11 (m, 2H), 6.15 (d, J=1.83 Hz, 1H), 6.99 (d, J=9.17 Hz, 1H), 7.65 (d, J=1.34 Hz, 1H), 7.88 (dd, J=9.17, 2.20 Hz, 1H) and 8.37 (d, J=1.83 Hz, 1H) ppm.

Example 75. Inhibition of Arginine Gingipain by the Aminopyridinecyanamide Compounds of the Invention The capacities of compounds of the present invention to inhibit the activity of RgpB were measured in a fluorogenic assay similar to those described in Barret *Biochemical Journal*. 1980, 187(3), 909. The specific assay conditions were as follows. Buffer: pH=7.5, 100 mM Tris-HCl, 75 mM NaCl, 2.5 mM $CaCl_2$, 10 mM cysteine, 1% DMSO after all additions. Protein: 0.02 nM RgpB, isolated from culture of *Porphyromonas gingivalis*, as described in Pike et al. *J. Biol. Chem.* 1994, 269(1), 406, and Potempa and Nguyen. *Current Protocols in Protein Scienc.* 2007, 21.20.1-21.20.27. Fluorogenic substrate: 10 µM Boc-Phe-Ser-Arg-MCA. Time=90 minutes. Temperature=37° C. Each compound: 10 concentrations, starting at either 100 µM or 100 nM, with lower concentrations generated by serial 3-fold dilutions. By testing a range of concentrations for each compound, the concentration required to inhibit the activity of RgpB by 50% (the "$IC_{50}$") was determined. RgpB inhibitory activity is summarized in the following table.

| No. | Activity |
|---|---|
| 1 | + |
| 2 | ++++ |
| 3 | ++++ |
| 4 | ++ |
| 5 | ++ |
| 6 | ++ |
| 7 | + |
| 8 | + |
| 9 | ++++ |
| 10 | + |
| 11 | + |
| 12 | ++++ |
| 13 | ++++ |
| 14 | ++++ |
| 15 | ++++ |
| 16 | ++ |
| 17 | +++ |
| 18 | ++ |
| 19 | +++++ |
| 20 | +++ |
| 21 | ++++ |
| 22 | ++++ |
| 23 | ++ |
| 24 | ++ |
| 25 | ++++ |
| 26 | ++++ |
| 27 | + |
| 28 | +++ |
| 29 | ++ |
| 30 | ++ |
| 31 | + |
| 32 | ++++ |
| 33 | +++ |
| 34 | +++ |
| 35 | +++ |
| 36 | +++ |
| 37 | ++++ |
| 38 | ++ |
| 39 | ++ |
| 40 | ++ |
| 41 | ++ |
| 42 | ++ |
| 43 | +++++ |
| 44 | ++++ |
| 45 | +++++ |
| 46 | +++ |
| 47 | +++ |
| 48 | ++++ |
| 49 | +++++ |
| 50a | +++++ |
| 50b | +++++ |
| 51a | ++ |
| 51b | ++ |
| 52a | >1 µM[a] |
| 52b | >1 µM[a] |
| 53 | +++++ |
| 54 | +++++ |
| 55 | +++++ |
| 56 | +++++ |
| 57 | +++++ |
| 58 | ++++ |
| 59 | ++++ |
| 60 | +++++ |
| 61 | +++++ |
| 62 | ++++ |
| 63 | +++ |
| 64 | ++++ |
| 65 | +++++ |
| 66 | +++++ |
| 67 | +++++ |
| 68 | +++++ |
| 69 | +++++ |
| 70 | ++++ |
| 71 | ++++ |
| 72 | >1 µM[a] |
| 73 | >1 µM[a] |
| 74 | +++++ |

+++++: RgpB $IC_{50}$ < 100 nm
++++: 100 nM ≤ RgpB $IC_{50}$ < 1 µM
+++: 1 µM ≤ RgpB $IC_{50}$ < 10 µM
++: 10 µM ≤ RgpB $IC_{50}$ < 100 µM
+: 100 µM ≤ RgpB $IC_{50}$
[a]compound not tested above 1 µM Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound according to Formula I:

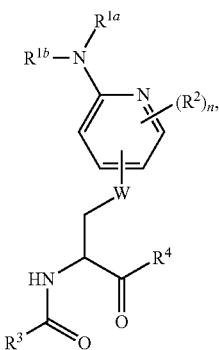

or a pharmaceutically acceptable salt thereof, wherein
W is selected from the group consisting of a bond, CH$_2$, and O;
R$^{1a}$ and R$^{1b}$ are independently selected from the group consisting of H and C$_{1-6}$ alkyl;
R$^2$ is selected from the group consisting of C$_{1-6}$ alkyl and halogen;
subscript n is 0 or 1;
R$^3$ is selected from the group consisting of C$_{3-8}$ cycloalkyl, C$_{3-8}$ alkyl,
C$_{3-12}$ heterocyclyl, C$_{6-10}$ aryl, and C$_{5-12}$ heteroaryl wherein R$^3$ is optionally substituted with one or more R$^{3a}$ substituents;
each R$^{3a}$ is independently selected from the group consisting of halogen, —CN, —NO$_2$, —N$_3$, —OH, C$_{1-4}$ alkyl, C$_{1-4}$ haloalkyl, C$_{1-4}$ alkoxy,
C$_{1-4}$ haloalkoxy, —N(R$^c$)$_2$, —(CH$_2$)$_k$C(O)R$^b$, —NR$^c$(CH$_2$)$_u$C(O)R$^b$, —O(CH$_2$)$_u$C(O)R$^b$, —(CH$_2$)$_k$CONR$^c$R$^c$, —(CH$_2$)$_k$NR$^c$C(O)R$^b$, —NR$^c$(CH$_2$)$_u$CONR$^c$R$^c$, —NR$^c$(CH$_2$)$_u$NR$^c$C—(O)R$^b$, —O(CH$_2$)$_u$CONR$^c$R$^c$, and —O(CH$_2$)$_u$NR$^c$C(O)R$^b$, and optionally substituted triazolyl;
each R$^b$ is independently selected from the group consisting of C$_{1-4}$ alkyl, C$_{1-4}$ haloalkyl, and C$_{1-4}$ deuteroalkyl;
each R$^c$ is independently selected from the group consisting of hydrogen and C$_{1-8}$ alkyl;
each subscript k is independently selected from 0, 1, 2, 3, 4, 5, and 6;
each subscript u is independently selected from 1, 2, 3, 4, 5, and 6;
R$^4$ is selected from the group consisting of —CH$_2$R$^{4a}$ and C$_{1-6}$ haloalkyl;
R$^{4a}$ is selected from the group consisting of —O—R$^5$, —S—R$^6$, —SO—R$^6$, —SO$_2$—R$^6$, —N(R$^7$)$_2$, and C$_{5-12}$ heteroaryl;
R$^5$ is selected from the group consisting of phenyl, C$_{1-6}$ alkyl, C$_{1-6}$ haloalkyl, and
C$_{5-12}$ heteroaryl, wherein phenyl is substituted with 1-5 halogens, and wherein
C$_{5-12}$ heteroaryl is optionally substituted with halogen or C$_{1-3}$ haloalkyl;
R$^6$ is selected from the group consisting of phenyl, C$_{1-6}$ alkyl, C$_{1-6}$ haloalkyl, and
C$_{5-12}$ heteroaryl, wherein phenyl is optionally substituted with 1-5 halogens, and
wherein C$_{5-12}$ heteroaryl is optionally substituted with halogen or C$_{1-3}$ haloalkyl; and
each R$^7$ is independently selected C$_{1-6}$ alkyl.

2. The compound of claim 1, or a pharmaceutically acceptable salt thereof, having a structure according to Formula IIa:

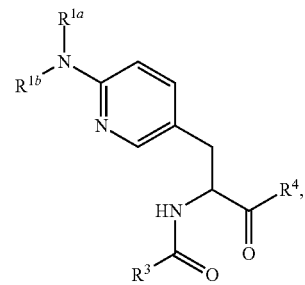

or
a structure according to Formula IIb:

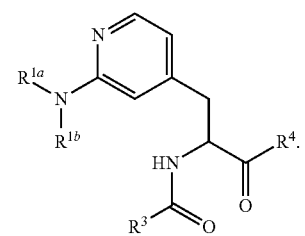

3. The compound of claim 1, or a pharmaceutically acceptable salt thereof, wherein R$^3$ is selected from the group consisting of C$_{3-8}$ cycloalkyl and C$_{3-8}$ alkyl, each of which is optionally substituted with one or more R$^{3a}$ substituents.

4. The compound of claim 1, or a pharmaceutically acceptable salt thereof, wherein R$^4$ is —CH$_2$—O—R$^5$ and wherein R$^5$ is phenyl substituted with 1-5 halogens.

5. The compound of claim 1, or a pharmaceutically acceptable salt thereof, wherein R$^4$ is —CH$_2$—O—R$^5$ and R$^5$ is selected from the group consisting of 1,1,1,3,3,3-hexafluoroprop-2-yl, isoxazolyl, and phenyl, wherein phenyl is substituted with 1-5 halogens.

6. The compound of claim 1, which is selected from the group consisting of

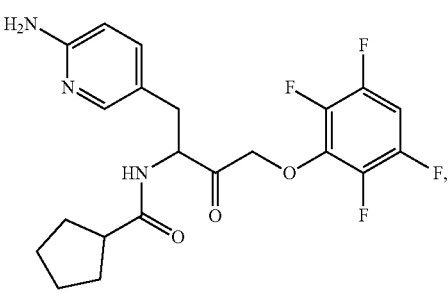

211
-continued
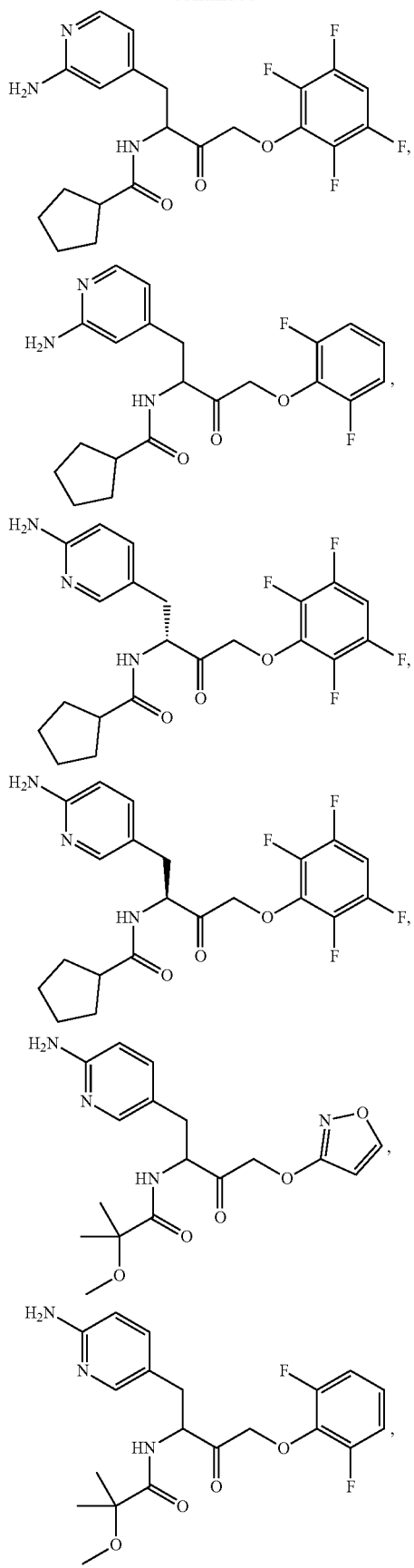
212
-continued
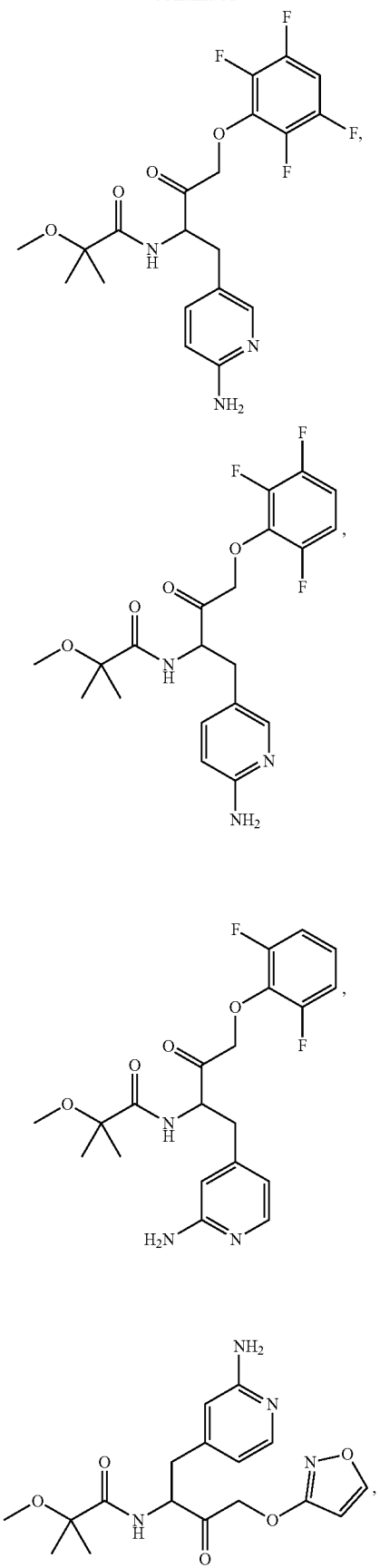

213
-continued
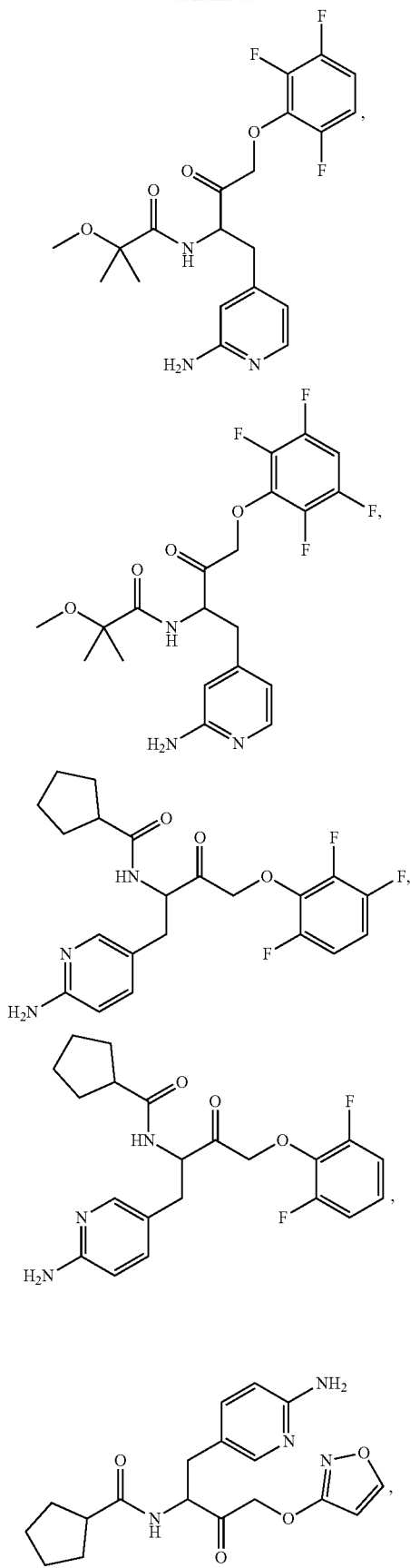
214
-continued
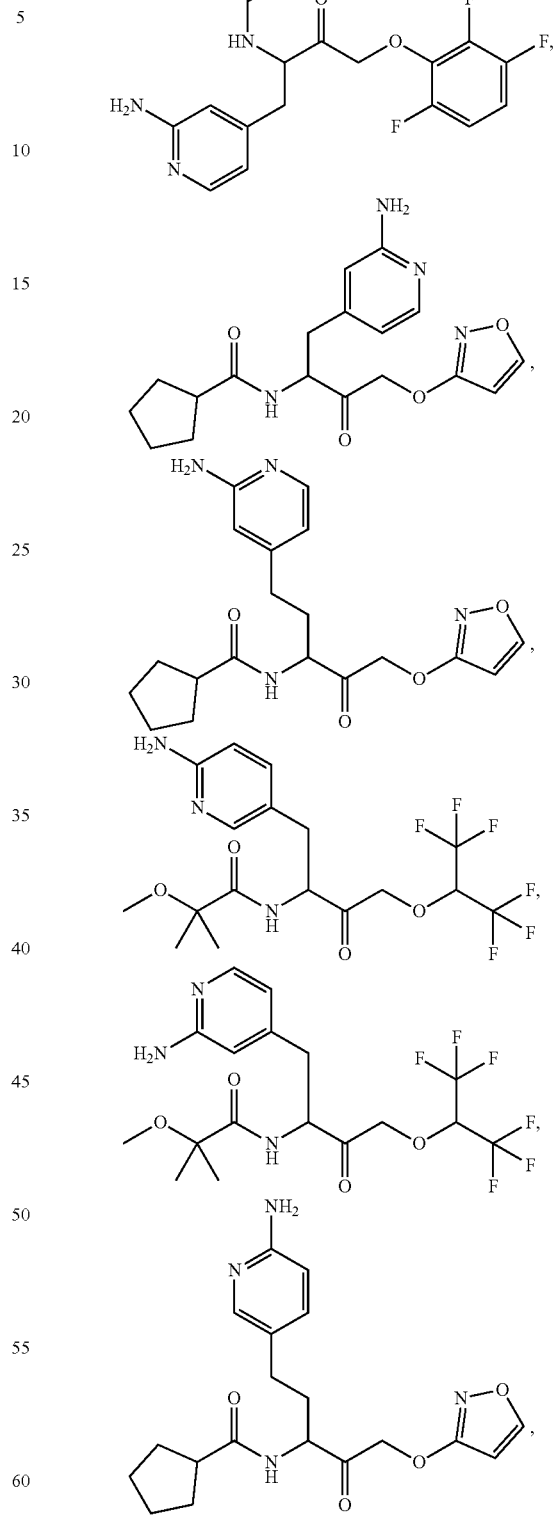
and pharmaceutically acceptable salts thereof.
7. A pharmaceutical composition comprising a compound of claim 1, or a pharmaceutically acceptable salt thereof, and a pharmaceutically acceptable excipient.

8. A compound according to Formula III:

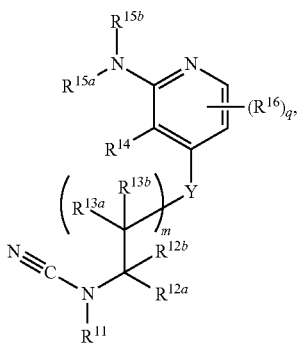

(III)

or a pharmaceutically acceptable salt thereof, wherein:
$R^{11}$ is selected from the group consisting of $C_{1-6}$ alkyl and $C_{3-8}$ cycloalkyl;
$R^{12a}$ and $R^{12b}$ are independently selected from the group consisting of H, $C_{1-6}$ alkyl, and $C_{6-10}$ aryl, or
$R^{12a}$ and $R^{12b}$ are taken together to form $C_{3-6}$ cycloalkyl, or
$R^{12a}$ and $R^{12b}$ are taken together to form 4- to 10-membered heterocyclyl which is optionally substituted with one or more $R^{17}$;
each $R^{13a}$ and each $R^{13b}$ is independently selected from the group consisting of H, —OH, and $C_{1-6}$ alkyl, or
one $R^{13a}$ and $R^{11}$ are taken together to form 4- to 10-membered heterocyclyl, or
one $R^{13b}$ and $R^{12b}$ are taken together to form a 5- or 6-membered ring;
$R^{14}$ is selected from the group consisting of H and halogen, or
$R^{14}$, $R^{12a}$, and $R^{12b}$ are taken together to form a 6- to 8-membered ring, which is optionally substituted with one or more $R^{18}$, or
$R^{14}$ and one $R^{13a}$ are taken together to form a 5- to 8-membered ring, which is optionally substituted with one or more $R^{18}$, or
$R^{14}$ is taken together with one $R^{13a}$ and one $R^{13b}$ on the same carbon atom to form a 5- to 8-membered ring, which is optionally substituted with one or more $R^{18}$, or
$R^{14}$, $R^{11}$, and $R^{12a}$ are taken together to form a 6- to 10-membered bicyclic ring, which is optionally substituted with one or more $R^{18}$;
$R^{15a}$ and $R^{15b}$ are independently selected from the group consisting of H and $C_{1-6}$ alkyl;
$R^{16}$ is independently selected from the group consisting of $C_{1-6}$ alkyl and halogen;
each $R^{17}$ is independently selected from the group consisting of $C_{1-6}$ alkyl, $C_{1-6}$ alkoxy, $C_{1-6}$ haloalkyl, $C_{1-6}$ haloalkoxy, —OH, and —N($R^{17a}$)$_2$, wherein each $R^{17a}$ is independently selected from the group consisting of H and $C_{1-6}$ alkyl;
each $R^{18}$ is independently selected from the group consisting of $C_{1-6}$ alkyl and halogen;
Y is selected from the group consisting of O, S, C($R^{19a}$)$_2$, and NR$^{19b}$;

each $R^{19a}$ is selected from the group consisting of H and $C_{1-6}$ alkyl, or
one $R^{19a}$ and one $R^{13b}$ on adjacent atoms are taken together to form a double bond;
$R^{19b}$ is selected from the group consisting of H and $C_{1-6}$ alkyl, or
$R^{19b}$ and $R^{11}$ are taken together to form a 4- to 6-membered ring;
subscript m is 0, 1, 2, or 3; and
subscript q is 0 or 1.

9. The compound of claim 8, or a pharmaceutically acceptable salt thereof, having a structure according to Formula IVa:

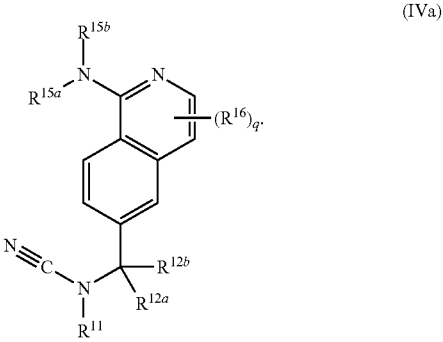

(IVa)

10. The compound of claim 8, or a pharmaceutically acceptable salt thereof, having a structure according to Formula V:

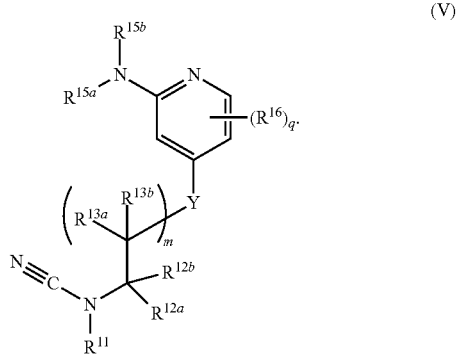

(V)

11. The compound of claim 10, or a pharmaceutically acceptable salt thereof, wherein Y is NR$^{19b}$.

12. The compound of claim 8, or a pharmaceutically acceptable salt thereof, wherein $R^{12a}$ and $R^{11}$ are taken together to form 4- to 10-membered heterocyclyl.

13. The compound of claim 8, or a pharmaceutically acceptable salt thereof, wherein $R^{12a}$ is H and $R^{12b}$ is selected from the group consisting of H, $C_{1-6}$ alkyl, and $C_{6-10}$ aryl.

14. The compound of claim 8, or a pharmaceutically acceptable salt thereof, wherein $R^{15a}$ and $R^{15b}$ are H.

15. The compound of claim 8, or a pharmaceutically acceptable salt thereof, wherein subscript q is 0.

16. The compound of claim 8, which is selected from the group consisting of:
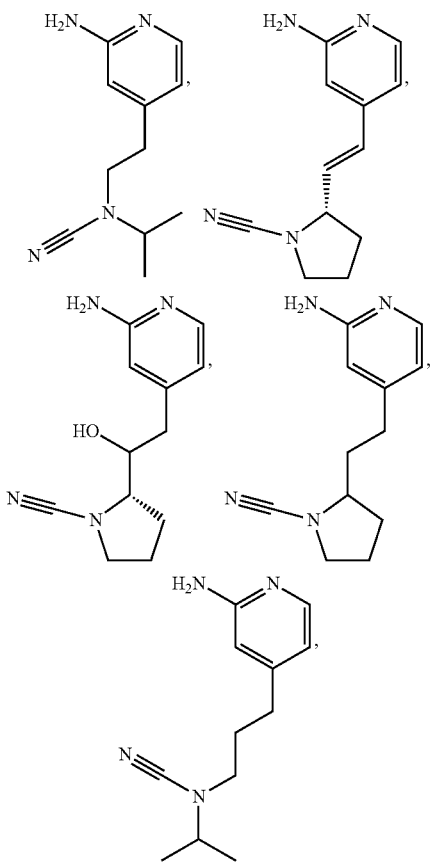
and pharmaceutically acceptable salts thereof.
17. The compound of claim 8, which is selected from the group consisting of:
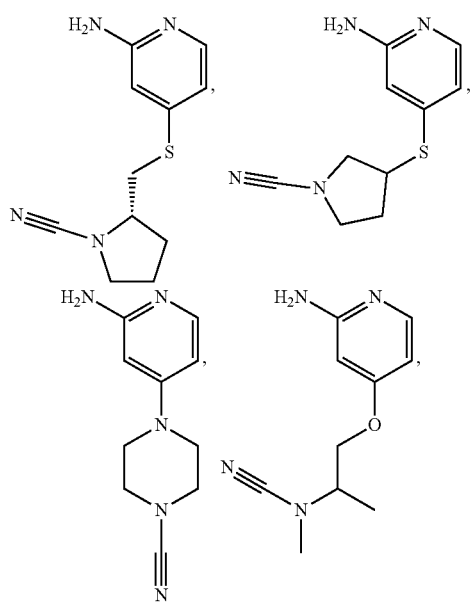
-continued
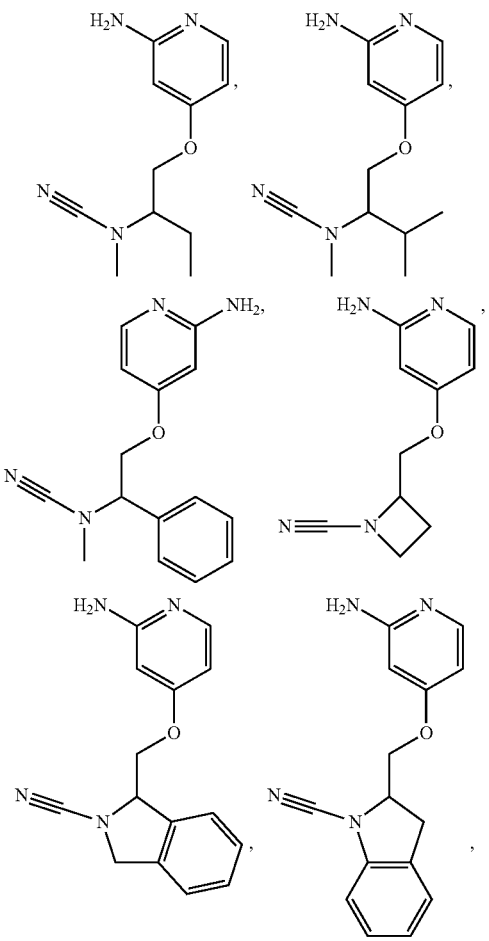
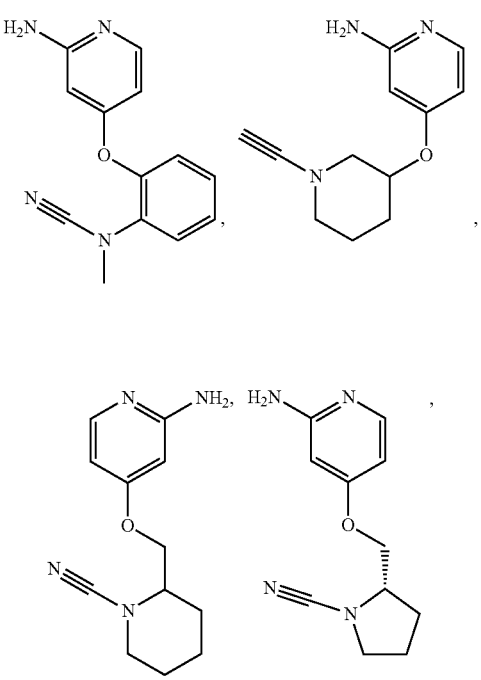

219
-continued
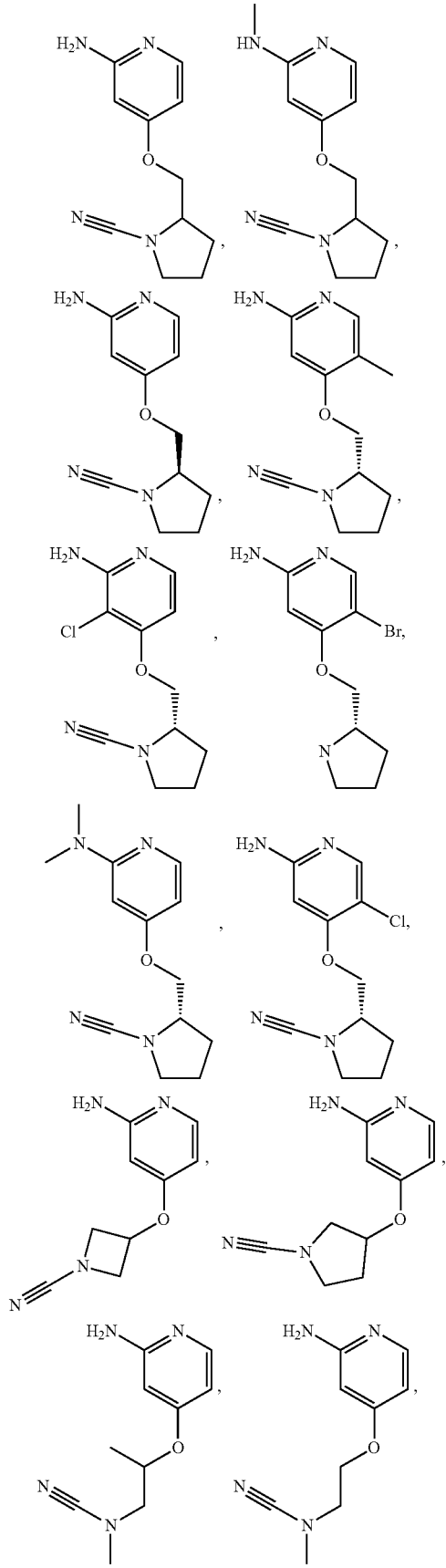
220
-continued
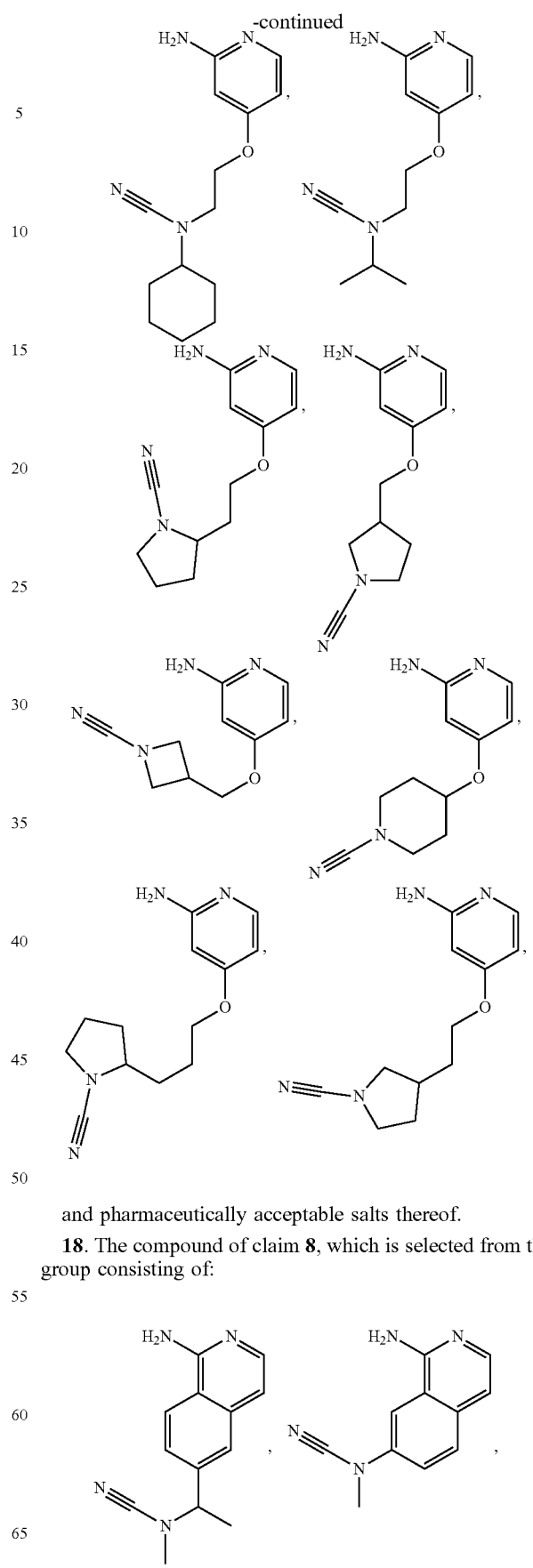
and pharmaceutically acceptable salts thereof.
18. The compound of claim 8, which is selected from the group consisting of:

221
-continued

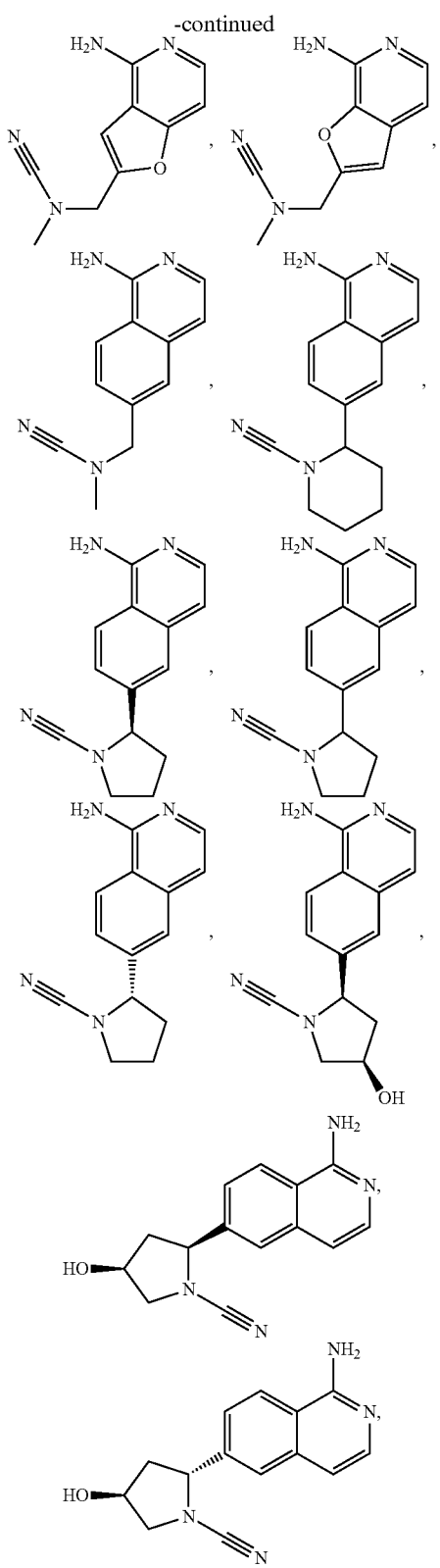

222
-continued

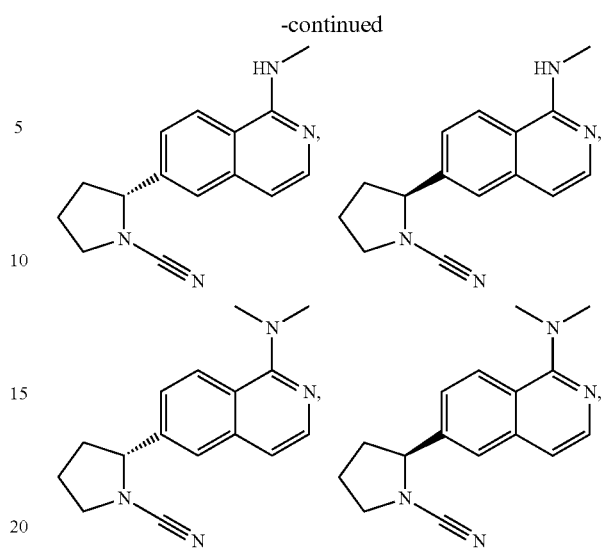

and pharmaceutically acceptable salts thereof.

19. A method of treating a disease or condition associated with *P. gingivalis* infection, the method comprising administering to a subject in need thereof an effective amount of a compound according to claim 1, or a pharmaceutically acceptable salt thereof.

20. The method of claim 19, wherein the disease or condition is selected from the group consisting of a brain disorder, periodontal disease, diabetes, a cardiovascular disease, arthritis, rheumatoid arthritis, osteoarthritis, infectious arthritis, psoriatic arthritis, elevated risk of preterm birth, pneumonia, cancer, a kidney disease, a liver disease, a retinal disorder, and glaucoma.

21. The method of claim 20, wherein the brain disorder is selected from the group consisting of Alzheimer's disease, Down's syndrome, epilepsy, autism, Parkinson's disease, essential tremor, fronto-temporal dementia, progressive supranuclear palsy, amyotrophic lateral sclerosis, Huntington's disease, multiple sclerosis, mild cognitive impairment, age associated memory impairment, chronic traumatic encephalopathy, stroke, cerebrovascular disease, Lewy Body disease, multiple system atrophy, schizophrenia, and depression.

22. The method of claim 21, wherein the brain disorder is Alzheimer's disease.

23. The method of claim 22, further comprising administering to the subject one or more active agents selected from the group consisting of a cholinesterase inhibitor, a serotonin modulator, an NMDA modulator, an Aβ targeted therapy, an ApoE targeted therapy, a microglia targeted therapy, a blood brain barrier targeted therapy, a tau targeted therapy, a complement targeted therapy, and an anti-inflammatory.

* * * * *